United States Patent
Hartman et al.

(10) Patent No.: US 11,723,884 B2
(45) Date of Patent: Aug. 15, 2023

(54) EPINEPHRINE SPRAY FORMULATIONS

(71) Applicant: Bryn Pharma, LLC, Raleigh, NC (US)

(72) Inventors: Steven Hartman, Beverly Hills, CA (US); Michelle Lobel, Beverly Hills, CA (US); Matthew P. Robben, Pittsford, NY (US); Kenneth L. Dretchen, Gaithersburg, MD (US); Michael Mesa, Boyds, MD (US)

(73) Assignee: Bryn Pharma, LLC, Raleigh, NC (US)

( * ) Notice: Subject to any disclaimer, the term of this patent is extended or adjusted under 35 U.S.C. 154(b) by 0 days.

(21) Appl. No.: 16/930,408

(22) Filed: Jul. 16, 2020

(65) Prior Publication Data
US 2020/0345629 A1 Nov. 5, 2020

Related U.S. Application Data

(63) Continuation of application No. 16/864,183, filed on May 1, 2020, now Pat. No. 10,925,841, which is a
(Continued)

(51) Int. Cl.
*A61K 31/137* (2006.01)
*A61K 9/00* (2006.01)
(Continued)

(52) U.S. Cl.
CPC .......... *A61K 31/137* (2013.01); *A61K 9/0043* (2013.01); *A61K 9/0078* (2013.01);
(Continued)

(58) Field of Classification Search
CPC .......... A61M 15/0033; A61M 15/0035; A61M 15/0036; A61M 15/0038; A61M 15/0041;
(Continued)

(56) References Cited

U.S. PATENT DOCUMENTS

| 4,959,358 A | * | 9/1990 | Carey .................. A61K 31/137 |
| | | | 514/37 |
| 5,922,341 A | | 7/1999 | Smith et al. |

(Continued)

FOREIGN PATENT DOCUMENTS

| CN | 102335125 A | 2/2012 |
| EP | 1163909 A2 | 12/2001 |

(Continued)

OTHER PUBLICATIONS

Parish et al, Ann Allergy Asthma Immunol 117 (2016) 79e87, "A systematic review of epinephrine degradation with exposure to excessive heat or cold".*

(Continued)

*Primary Examiner* — Tu A Vo
(74) *Attorney, Agent, or Firm* — Honigman LLP; Andrew N. Weber; Jonathan P. O'Brien

(57) ABSTRACT

Provided herein are epinephrine spray formulations and methods of administering the same. Also provided herein are methods of treating anaphylaxis by administering epinephrine spray formulations to subjects in need of such treatment. The spray formulations contain epinephrine or a pharmaceutically acceptable salt thereof, one or more of an antioxidant, an antimicrobial preservative, an isotonicity agent, an absorption enhancer, a viscosity modifier, and/or a buffering agent.

28 Claims, 14 Drawing Sheets

Related U.S. Application Data continuation of application No. 16/355,525, filed on Mar. 15, 2019, now Pat. No. 10,688,044.

(60) Provisional application No. 62/810,261, filed on Feb. 25, 2019, provisional application No. 62/747,048, filed on Oct. 17, 2018, provisional application No. 62/712,678, filed on Jul. 31, 2018, provisional application No. 62/663,100, filed on Apr. 26, 2018, provisional application No. 62/644,834, filed on Mar. 19, 2018.

(51) Int. Cl.
| | | |
|---|---|---|
| *A61P 37/08* | (2006.01) | |
| *A61K 47/02* | (2006.01) | |
| *A61K 47/10* | (2017.01) | |
| *A61K 47/12* | (2006.01) | |
| *A61K 47/38* | (2006.01) | |
| *A61M 11/00* | (2006.01) | |
| *A61K 9/08* | (2006.01) | |
| *A61K 9/12* | (2006.01) | |
| *A61M 15/08* | (2006.01) | |
| *A61K 47/20* | (2006.01) | |

(52) U.S. Cl.
CPC ............ *A61K 9/08* (2013.01); *A61K 9/12* (2013.01); *A61K 47/02* (2013.01); *A61K 47/10* (2013.01); *A61K 47/12* (2013.01); *A61K 47/20* (2013.01); *A61K 47/38* (2013.01); *A61M 11/007* (2014.02); *A61P 37/08* (2018.01); *A61M 15/08* (2013.01); *A61M 2205/3553* (2013.01)

(58) Field of Classification Search
CPC ........ A61M 11/007; A61M 2205/3553; A61M 11/00; A61M 11/001; A61M 11/006; A61M 11/008; A61M 11/04; A61M 11/02; A61M 11/08; A61M 15/00; A61M 15/0001; A61M 15/0028; A61M 15/003; A61M 15/004; A61M 15/006; A61M 15/0053; A61M 15/0061; A61M 15/08; A61K 9/0043; A61K 31/137; A61K 9/0078; A61K 9/08; A61K 9/12; A61K 47/02; A61K 47/10; A61K 47/12; A61K 47/38; A61P 37/08

See application file for complete search history.

(56) References Cited

U.S. PATENT DOCUMENTS

| | | |
|---|---|---|
| 6,179,164 B1 | 1/2001 | Fuchs et al. |
| 6,209,760 B1 | 4/2001 | Fuchs et al. |
| 6,244,472 B1 | 6/2001 | Hennemann et al. |
| 6,284,765 B1 | 9/2001 | Caffrey |
| 6,290,104 B1 | 9/2001 | Bougamont et al. |
| 6,413,499 B1 * | 7/2002 | Clay .................. A61K 31/5375 424/49 |
| 6,513,684 B1 | 2/2003 | Bougamont et al. |
| 6,645,181 B1 | 11/2003 | Lavi et al. |
| 6,708,852 B2 | 3/2004 | Blake et al. |
| 7,029,249 B2 | 4/2006 | Bougamont et al. |
| 7,066,359 B2 | 6/2006 | Greiner-Perth et al. |
| 7,182,226 B2 | 2/2007 | Mbonyumuhire et al. |
| 7,201,296 B2 | 4/2007 | Graf et al. |
| 7,297,136 B2 | 11/2007 | Wyrick et al. |
| 7,299,949 B2 | 11/2007 | Greiner-Perth et al. |
| 7,416,194 B2 | 8/2008 | Splain et al. |
| 7,416,540 B2 | 8/2008 | Edwards et al. |
| 7,449,012 B2 | 11/2008 | Young et al. |
| 7,717,299 B2 | 5/2010 | Greiner-Perth et al. |
| 7,726,522 B2 | 6/2010 | Greiner-Perth et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,767,429 B2 | 8/2010 | Bookbinder et al. |
| 7,780,044 B2 | 8/2010 | Leuliet et al. |
| 7,794,432 B2 | 9/2010 | Young et al. |
| 7,845,521 B2 | 12/2010 | Blake et al. |
| 7,866,513 B2 | 1/2011 | Leuliet et al. |
| 7,882,988 B2 | 2/2011 | Nicolle et al. |
| 7,905,352 B2 | 3/2011 | Wyrick et al. |
| 7,918,823 B2 | 4/2011 | Edwards et al. |
| 7,947,017 B2 | 5/2011 | Edwards et al. |
| 8,016,788 B2 | 9/2011 | Edwards et al. |
| 8,021,344 B2 | 9/2011 | Edwards et al. |
| 8,048,035 B2 | 11/2011 | Mesa et al. |
| 8,083,159 B2 | 12/2011 | Leuliet et al. |
| 8,163,764 B2 | 4/2012 | Chung et al. |
| 8,172,082 B2 | 5/2012 | Edwards et al. |
| 8,206,360 B2 | 6/2012 | Edwards et al. |
| 8,226,610 B2 | 7/2012 | Edwards et al. |
| 8,231,573 B2 | 7/2012 | Edwards et al. |
| 8,263,581 B2 | 9/2012 | Du |
| 8,292,131 B2 | 10/2012 | Pruvot et al. |
| 8,313,466 B2 | 11/2012 | Edwards et al. |
| 8,314,083 B2 | 11/2012 | Chung et al. |
| 8,337,817 B2 | 12/2012 | Nagata et al. |
| 8,361,029 B2 | 1/2013 | Edwards et al. |
| 8,365,961 B2 | 2/2013 | Donnette et al. |
| 8,365,966 B2 | 2/2013 | Nicolle et al. |
| 8,367,734 B1 | 2/2013 | Gao et al. |
| 8,425,462 B2 | 4/2013 | Edwards et al. |
| 8,517,220 B2 | 8/2013 | Julia et al. |
| 8,608,698 B2 | 12/2013 | Edwards et al. |
| 8,628,805 B2 | 1/2014 | Baillie et al. |
| 8,734,392 B2 | 5/2014 | Stadelhofer et al. |
| 8,863,993 B2 | 10/2014 | Donnette et al. |
| 8,870,827 B2 | 10/2014 | Young et al. |
| 8,920,377 B2 | 12/2014 | Edwards et al. |
| 8,926,594 B2 | 1/2015 | Edwards et al. |
| 8,978,937 B2 | 3/2015 | Chambers et al. |
| 9,022,980 B2 | 5/2015 | Edwards et al. |
| 9,056,170 B2 | 6/2015 | Edwards et al. |
| 9,101,539 B2 | 8/2015 | Nagata et al. |
| 9,101,730 B2 | 8/2015 | Greiner-Perth et al. |
| 9,119,771 B2 | 9/2015 | Du |
| 9,119,876 B1 | 9/2015 | Kannan et al. |
| 9,149,579 B2 | 10/2015 | Edwards et al. |
| 9,151,281 B2 | 10/2015 | Donnette et al. |
| 9,155,694 B2 | 10/2015 | Baillie et al. |
| 9,186,471 B2 | 11/2015 | Pardonge et al. |
| 9,199,037 B2 | 12/2015 | Buchine et al. |
| 9,227,017 B2 | 1/2016 | Buchine et al. |
| 9,238,108 B2 | 1/2016 | Edwards et al. |
| 9,259,539 B2 | 2/2016 | Edwards et al. |
| 9,278,069 B2 | 3/2016 | Berkland et al. |
| 9,278,182 B2 | 3/2016 | Edwards et al. |
| 9,283,197 B1 | 3/2016 | Taneja et al. |
| 9,295,657 B1 | 3/2016 | Kannan et al. |
| 9,549,897 B2 | 1/2017 | Mccarty |
| 9,555,950 B2 | 1/2017 | Le Maner et al. |
| 9,586,010 B2 | 3/2017 | Mesa et al. |
| 9,707,360 B2 | 7/2017 | Bacon et al. |
| 9,707,581 B2 | 7/2017 | Petit et al. |
| 9,724,471 B2 | 8/2017 | Edwards et al. |
| 9,737,669 B2 | 8/2017 | Edwards et al. |
| 9,789,071 B2 | 10/2017 | Fleming et al. |
| 9,827,315 B2 | 11/2017 | Patel et al. |
| 9,895,444 B2 | 2/2018 | Maggio et al. |
| 9,907,910 B2 | 3/2018 | Constantineau et al. |
| 9,907,911 B2 | 3/2018 | Constantineau et al. |
| 10,039,710 B2 | 8/2018 | Potta et al. |
| 10,039,728 B1 | 8/2018 | Taneja et al. |
| 10,688,044 B2 | 6/2020 | Hartman et al. |
| 10,925,841 B2 | 2/2021 | Hartman et al. |
| 2001/0007327 A1 * | 7/2001 | Ritsche ............ A61M 15/0036 222/82 |
| 2001/0053775 A1 | 12/2001 | Seidel et al. |
| 2002/0048587 A1 | 4/2002 | Aucouturier et al. |

(56) References Cited

U.S. PATENT DOCUMENTS

| | | |
|---|---|---|
| 2002/0056890 A1 | 5/2002 | Advocate et al. |
| 2003/0216329 A1 | 11/2003 | Robinson et al. |
| 2004/0002647 A1 | 1/2004 | Desai |
| 2004/0045546 A1* | 3/2004 | Hirsh ............... A61M 15/00 128/200.14 |
| 2004/0076588 A1 | 4/2004 | Batycky et al. |
| 2005/0070487 A1 | 3/2005 | Nyce |
| 2005/0249831 A1* | 11/2005 | Arora ............... A61P 25/08 514/33 |
| 2005/0260186 A1 | 11/2005 | Bookbinder et al. |
| 2007/0071806 A1 | 3/2007 | Mccarty |
| 2007/0225379 A1* | 9/2007 | Carrara ............... A61K 31/439 514/756 |
| 2007/0286813 A1 | 12/2007 | Toutounghi |
| 2008/0269347 A1 | 10/2008 | Bruss et al. |
| 2009/0163597 A1* | 6/2009 | Goto ............... A61P 29/00 514/626 |
| 2009/0202467 A1 | 8/2009 | Bock |
| 2009/0312724 A1 | 12/2009 | Pipkin et al. |
| 2010/0003237 A1 | 1/2010 | Keller et al. |
| 2010/0215728 A1 | 8/2010 | Chung et al. |
| 2011/0003015 A1 | 1/2011 | Baillie et al. |
| 2011/0151012 A1 | 6/2011 | Desai et al. |
| 2011/0223203 A1 | 9/2011 | Berkland et al. |
| 2011/0226646 A1 | 9/2011 | Wyrick et al. |
| 2012/0269772 A1 | 10/2012 | Thuresson et al. |
| 2012/0289489 A1 | 11/2012 | Du |
| 2012/0315265 A1 | 12/2012 | Lai et al. |
| 2012/0322884 A1 | 12/2012 | Rawas-Qalaji et al. |
| 2013/0029951 A1 | 1/2013 | Lulla et al. |
| 2013/0041418 A1 | 2/2013 | Rubin et al. |
| 2013/0095145 A1 | 4/2013 | Nagata et al. |
| 2013/0143797 A1 | 6/2013 | Tisdale et al. |
| 2013/0209566 A1 | 8/2013 | Jablonski et al. |
| 2014/0066881 A1* | 3/2014 | Freeman ............... A61K 9/0073 514/12.4 |
| 2014/0107145 A1 | 4/2014 | Maggio et al. |
| 2014/0162965 A1 | 6/2014 | Maggio et al. |
| 2014/0193347 A1 | 7/2014 | Thuresson et al. |
| 2014/0243749 A1* | 8/2014 | Edwards ............ A61M 15/0001 604/187 |
| 2014/0348903 A1 | 11/2014 | Tiberg et al. |
| 2015/0005356 A1* | 1/2015 | Fleming ............... A61K 31/137 514/521 |
| 2015/0057325 A1 | 2/2015 | Johansson et al. |
| 2015/0119440 A1 | 4/2015 | Karolchyk et al. |
| 2015/0231334 A1 | 8/2015 | Buchine et al. |
| 2015/0238525 A1 | 8/2015 | Gavard |
| 2015/0265535 A1 | 9/2015 | Yu et al. |
| 2015/0359738 A1 | 12/2015 | Mulvahill |
| 2015/0374832 A1 | 12/2015 | Surakitbanharn |
| 2016/0030339 A1 | 2/2016 | Muhlen-Bartmer et al. |
| 2016/0058830 A1* | 3/2016 | McGregor ............... A61P 25/32 530/315 |
| 2016/0175408 A1 | 6/2016 | Chang et al. |
| 2016/0220489 A1* | 8/2016 | Fleming ............... A61K 31/137 |
| 2016/0243060 A1 | 8/2016 | Standley et al. |
| 2016/0374979 A1* | 12/2016 | Yamamoto ............... A61P 43/00 514/546 |
| 2017/0079907 A1* | 3/2017 | Potta ............... A61K 47/20 |
| 2017/0136477 A1 | 5/2017 | Heldt et al. |
| 2017/0144177 A1 | 5/2017 | Heldt et al. |
| 2017/0216199 A1* | 8/2017 | Potta ............... A61K 9/0043 |
| 2017/0259285 A1 | 9/2017 | Petit et al. |
| 2017/0296758 A1 | 10/2017 | Petit et al. |
| 2018/0000942 A1 | 1/2018 | Cunningham et al. |
| 2018/0028671 A1 | 2/2018 | Surakitbanharn |
| 2018/0104344 A1 | 4/2018 | Maggio et al. |
| 2018/0169247 A1 | 6/2018 | Maggio et al. |
| 2018/0207146 A1 | 7/2018 | Ahn et al. |
| 2018/0221489 A1 | 8/2018 | Maggio et al. |
| 2018/0289617 A1 | 10/2018 | Potta et al. |
| 2018/0289639 A1 | 10/2018 | Potta et al. |
| 2018/0318215 A1 | 11/2018 | Potta et al. |
| 2019/0254962 A1 | 8/2019 | Lhartman et al. |
| 2019/0269782 A1 | 9/2019 | Lowenthal et al. |
| 2019/0282496 A1 | 9/2019 | Hartman et al. |
| 2019/0282497 A1 | 9/2019 | Hartman et al. |
| 2019/0282518 A1 | 9/2019 | Hartman et al. |
| 2019/0350881 A1* | 11/2019 | Surakitbanharn .... A61K 31/198 |
| 2020/0253866 A1 | 8/2020 | Hartman et al. |
| 2020/0397722 A1 | 12/2020 | Hartman et al. |

FOREIGN PATENT DOCUMENTS

| | | | |
|---|---|---|---|
| EP | 1768650 B1 | 7/2008 | |
| EP | 2085071 A1 | 8/2009 | |
| EP | 2437781 B1 | 7/2013 | |
| EP | 3400930 A1 | 11/2018 | |
| WO | 1999/039713 A1 | 8/1999 | |
| WO | 2001/034088 A2 | 5/2001 | |
| WO | 2001/035926 A2 | 5/2001 | |
| WO | 2002/085297 A2 | 10/2002 | |
| WO | 2002/085309 A2 | 10/2002 | |
| WO | 2004/002551 A2 | 1/2004 | |
| WO | 2004/004709 A1 | 1/2004 | |
| WO | 2004/014293 A2 | 2/2004 | |
| WO | 2005/117830 A1 | 12/2005 | |
| WO | 2006/077309 A1 | 7/2006 | |
| WO | 2009/097277 A1 | 8/2009 | |
| WO | 2009/100435 A2 | 8/2009 | |
| WO | 2009/111083 A2 | 9/2009 | |
| WO | 2010/139751 A2 | 12/2010 | |
| WO | 2010/139752 A2 | 12/2010 | |
| WO | 2011/161427 A2 | 12/2011 | |
| WO | 2012/064766 A2 | 5/2012 | |
| WO | 2013/083460 A1 | 6/2013 | |
| WO | WO-2013099861 A1 * | 7/2013 | ........... A61M 11/008 |
| WO | WO-2013123033 A1 * | 8/2013 | ........... A61K 31/428 |
| WO | 2013/143548 A1 | 10/2013 | |
| WO | 2014/031693 A1 | 2/2014 | |
| WO | 2014/056722 A2 | 4/2014 | |
| WO | 2014/056723 A1 | 4/2014 | |
| WO | 2014/057365 A1 | 4/2014 | |
| WO | 2014/104784 A1 | 7/2014 | |
| WO | 2014/104784 A4 | 7/2014 | |
| WO | 2014/127015 A1 | 8/2014 | |
| WO | 2014/127018 A1 | 8/2014 | |
| WO | 2014/127020 A1 | 8/2014 | |
| WO | 2014/127367 A1 | 8/2014 | |
| WO | 2014/161837 A1 | 10/2014 | |
| WO | 2015/020982 A2 | 2/2015 | |
| WO | 2015/051264 A1 | 4/2015 | |
| WO | 2015/095389 A1 | 6/2015 | |
| WO | 2016/013829 A1 | 1/2016 | |
| WO | 2017/094027 A1 | 6/2017 | |
| WO | WO-2017094027 A1 * | 6/2017 | ............ B05B 11/02 |
| WO | 2017/218918 A1 | 12/2017 | |
| WO | 2017/220901 A2 | 12/2017 | |
| WO | 2018/053029 A1 | 3/2018 | |
| WO | 2019/067505 A1 | 4/2019 | |
| WO | 2019/182745 A1 | 9/2019 | |
| WO | 2019/182908 A1 | 9/2019 | |
| WO | 2021/026330 A1 | 2/2021 | |

OTHER PUBLICATIONS

Carr et al, Can J Hosp Pharm. 2014;67(3): 197-202, "Stability of Epinephrine at Standard Concentrations".*

Definition of chlorobutanol hemihydrate, Drugbank Online, captured on Mar. 10, 2022.*

Definition of chlorobutanol hemihydrate, PubChem, captured on Mar. 10, 2022.*

Definition of chlorobutanol hemihydrate, NIH Inxight databases, captured on Mar. 12, 2022.*

Definition of "hemihydrate", dictionary.com, captured on Jul. 5, 2022.*

Definition of "hemihydrate", collinsdicitonary.com, captured on Jul. 5, 2022.*

Definition of "hemihydrate", thefreedictionary.com, captured on Jul. 5, 2022.*

(56) References Cited

OTHER PUBLICATIONS

Definition of "hemihydrate", lexico.com, captured on Jul. 5, 2022.*
Definition of "hemihydrate", Oxford Direcitonary of English, captured on Jul. 5, 2022.*
Berge, Stephen M. et al., "Pharmaceutical Salts", Journal of Pharmaceutical Sciences, vol. 66, No. 1, Jan. 1977, pp. 1-19.
Bleske, Barry E. et al., "Effect of Dose on the Nasal Absorption of Epinephrine During Cardiopulmonary Resuscitation", American Journal of Emergency Medicine, vol. 14, No. 2, Mar. 1996, pp. 133-138.
Carr, Roxane R. et al., "Stability of Epinephrine at Standard Concentrations", Can J Hosp Pharm, vol. 67, No. 3, 2014, pp. 197-202.
CoChen et al., "An Open-Label, 5-Treatment, Crossover, Single-Dose Pharmacokinetic Study of Epinephrine Nasal Spray in Comparison to EpiPen® Intramuscular Injection in Healthy Adults With Seasonal Allergies", Poster presented at the 2019 AAAAI Annual Meeting; San Francisco, CA, USA Feb. 22-25, 2019.
Co-pending US patent application No. US201916355484, filed on Mar. 15, 2019.
Co-pending US patent application No. US201916355511, filed on Mar. 15, 2019.
Co-pending US patent application No. US201916355518, filed on Mar. 15, 2019.
Co-pending US patent application No. US201916355525, filed on Mar. 15, 2019.
Edwards, Eric S. et al., "Bioavailability of epinephrine from Auvi-Q compared with EpiPen", Ann Allergy Asthma Immunol 111, 2013, pp. 132-137.
EpiPen Prescribing Information published 2012. (Year: 2012).
FDA (https://www.accessdata.fda.gov/drugsatfda_docs/label/2016/020800s034lbl.pdf), accessed Jul. 8, 2019, published May 2016 (Year: 2016).
International Search Report and Written Opinion from International Application No. PCT/US2019/020360 dated May 16, 2019.
International Search Report and Written Opinion from International Application No. PCT/US2019/022557 dated May 24, 2019.
Parish, Hannah G. et al., "A systematic review of epinephrine degradation with exposure to excessive heat or cold". Elsevier, Ann Allergy Asthma Immunol, vol. 117, 2006, pp. 79-87.
RxResource (https://www.rxresource.org/prescription-information/Epinephrine-Hospira-Inc.html, published 2012 (Year: 2012).
Srisawat, Chatchawan et al., "A preliminary study of intranasal epinephrine administration as a potential route for anaphylaxis treatment", Asian Pac J Allergy Immunol, 2016, vol. 34, pp. 38-43.
Co-pending US patent application No. US202016864183, Filed on May 1, 2020.
Co-pending US patent application No. US202016930386, Filed on Jul. 16, 2020.
Co-pending US patent application No. US202016981859, Filed on Sep. 17, 2020.
International Preliminary Report on Patentability from International Application No. PCT/US2019/020360 dated Oct. 1, 2020.
International Preliminary Report on Patentability from International Application No. PCT/US2019/022557 dated Oct. 1, 2020.
International Search Report and Written Opinion from International Application No. PCT/US2020/045165 dated Dec. 9, 2020.

* cited by examiner

EPINEPHRINE SPRAY FORMULATIONS

CROSS-REFERENCE

This application is a continuation of U.S. Ser. No. 16/864,183, filed on May 1, 2020, which is a continuation of U.S. application Ser. No. 16/355,525, filed on Mar. 15, 2019, which claims the benefit of U.S. Provisional Application No. 62/644,834, filed Mar. 19, 2018, U.S. Provisional Application No. 62/663,100, filed Apr. 26, 2018, U.S. Provisional Application No. 62/712,678, filed Jul. 31, 2018, U.S. Provisional Application No. 62/747,048, filed Oct. 17, 2018, and U.S. Provisional Application No. 62/810,261, filed Feb. 25, 2019, which applications are incorporated herein in their entirety by reference.

BACKGROUND OF THE INVENTION

Epinephrine is a catecholamine that stimulates the α- and β-adrenergic receptors of the sympathetic nervous system. Epinephrine binds to these adrenergic receptors leading to relief of many life-threatening symptoms of anaphylaxis (e.g., relaxation of the smooth muscle in the bronchi of the lungs thereby opening up constricted airways, constriction of the blood vessels leading to decreased swelling of the tongue and throat and increasing blood pressure, and increased heart rate thereby preventing or reversing cardiovascular collapse).

BRIEF SUMMARY OF THE INVENTION

In an aspect provided herein, is a pharmaceutical spray formulation. In some embodiments, the pharmaceutical spray formulation includes from about 0.5% to about 25% w/w of epinephrine, or a pharmaceutically acceptable salt of epinephrine, in water, wherein the pH of the formulation is from about 4.0 to about 6.5. In some embodiments, the pharmaceutical spray formulation includes from about 0.5% to about 25% w/w of epinephrine, or a pharmaceutically acceptable salt of epinephrine, in water, ethanol, propylene glycol, or a combination thereof. In some embodiments, the pharmaceutical spray formulation includes from about 0.5% to about 25% w/w of epinephrine, or a pharmaceutically acceptable salt of epinephrine, in water, ethanol, propylene glycol, or a combination thereof. In some embodiments, the pharmaceutical spray formulation includes from about 0.5% to about 10% w/w of epinephrine, or a pharmaceutically acceptable salt of epinephrine, in water, ethanol, propylene glycol, or a combination thereof. In some embodiments, the pH of the pharmaceutical spray formulation is from about 4.0 to about 6.5.

In one aspect, disclosed herein is a pharmaceutical spray formulation comprising from about 0.5% to about 25% w/w of epinephrine, or a pharmaceutically acceptable salt of epinephrine, in water, wherein the pH of the formulation is from about 4.0 to about 6.5. In some embodiments, the pharmaceutical spray formulation comprises from about 0.5% to about 10% w/w of epinephrine, or a pharmaceutically acceptable salt thereof. In some embodiments, the pharmaceutical spray formulation comprises from about 2% to about 5% w/w of epinephrine. In some embodiments, the pharmaceutical spray formulation comprises about 2% w/w of epinephrine. In some embodiments, the pharmaceutical spray formulation comprises about 5% w/w of epinephrine. In some embodiments, the pharmaceutical spray formulation further comprises one or more of an antioxidant, an antimicrobial preservative, an isotonicity agent, an absorption enhancer, a viscosity modifier, or a buffering agent. In some embodiments, the pharmaceutical spray formulation comprises an antioxidant, an antimicrobial preservative, an isotonicity agent, an absorption enhancer, a viscosity modifier, and a buffering agent. In some embodiments, the pharmaceutical spray formulation comprises an antioxidant. In some embodiments, the pharmaceutical spray formulation comprises the antioxidant comprises sodium bisulfite or sodium metabisulfite. In some embodiments, the pharmaceutical spray formulation comprises the antioxidant at a concentration from about 0.0001% (w/w) to about 0.1% (w/w). In some embodiments, the pharmaceutical spray formulation comprises the antioxidant at a concentration from about 0.001% (w/w) to about 0.1% (w/w). In some embodiments, the pharmaceutical spray formulation comprises the antioxidant at a concentration from about 0.01% (w/w) to about 0.1% (w/w). In some embodiments, the pharmaceutical spray formulation comprises the antioxidant at a concentration of about 0.05% (w/w). In some embodiments, the pharmaceutical spray formulation comprises an antimicrobial preservative. In some embodiments, the pharmaceutical spray formulation comprises the antimicrobial preservative comprises chlorobutanol. In some embodiments, the pharmaceutical spray formulation comprises the antimicrobial preservative at a concentration from about 0.005% (w/v) to about 1% (w/v). In some embodiments, the pharmaceutical spray formulation comprises the antimicrobial preservative at a concentration from about 0.01% (w/v) to about 1% (w/v). In some embodiments, the pharmaceutical spray formulation comprises the antimicrobial preservative at a concentration from about 0.1% (w/v) to about 1% (w/v). In some embodiments, the pharmaceutical spray formulation comprises the antimicrobial preservative at a concentration of about 0.21% (w/v). In some embodiments, the pharmaceutical spray formulation comprises an isotonicity agent. In some embodiments, the pharmaceutical spray formulation comprises an isotonicity agent comprises sodium chloride. In some embodiments, the pharmaceutical spray formulation comprises an isotonicity agent at a concentration from about 0.1% to about 5%. In some embodiments, the pharmaceutical spray formulation comprises an isotonicity agent at a concentration from about 0.1% to about 1%. In some embodiments, the pharmaceutical spray formulation comprises an isotonicity agent at a concentration of about 0.4%. In some embodiments, the pharmaceutical spray formulation comprises an absorption enhancer. In some embodiments, the pharmaceutical spray formulation comprises the absorption enhancer comprises diethylene glycol monoethyl ether. In some embodiments, the pharmaceutical spray formulation comprises the absorption enhancer at a concentration from about 0.05% to about 15%. In some embodiments, the pharmaceutical spray formulation comprises the absorption enhancer at a concentration from about 0.1% to about 5%. In some embodiments, the pharmaceutical spray formulation comprises the absorption enhancer at a concentration of about 1%. In some embodiments, the pharmaceutical spray formulation comprises a viscosity modifier. In some embodiments, the pharmaceutical spray formulation comprises the viscosity modifier comprises hypromellose. In some embodiments, the pharmaceutical spray formulation comprises the viscosity modifier at a concentration from about 0.001% to about 0.5%. In some embodiments, the pharmaceutical spray formulation comprises the viscosity modifier at a concentration from about 0.01% to about 0.2%. In some embodiments, the pharmaceutical spray formulation comprises the viscosity modifier at a concentration of about 0.1%. In some embodiments, the pharmaceutical spray formulation comprises a buffering agent. In some embodiments, the pharmaceutical spray formulation comprises the buffering agent comprises citric acid or citric acid monohydrate. In some embodiments, the pharmaceutical spray formulation comprises the buffering agent at a concentration from about 0.01% to about 2%. In some embodiments, the pharmaceutical spray formulation comprises the buffering agent at a concentration from about 0.1% to about 1%. In some embodiments, the pharmaceutical spray formulation comprises the buffering agent at a concentration of about 0.42%. In some embodiments, the pharmaceutical spray formulation comprises sodium metabisulfite, sodium chloride, hypromellose, citric acid monohydrate, and diethylene glycol monoethyl ether. In some embodiments, the pharmaceutical spray formulation comprises from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. In some embodiments, the pharmaceutical spray formulation comprises from about 1% to about 20% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. In some embodiments, the pharmaceutical spray formulation comprises about 2% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. In some embodiments, the pharmaceutical spray formulation comprises about 2% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. In some embodiments, the pharmaceutical spray formulation comprises about 2% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. In some embodiments, the pharmaceutical spray formulation comprises about 5% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. In some embodiments, the pharmaceutical spray formulation comprises about 5% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. In some embodiments, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. In some embodiments, the pharmaceutical spray formulation comprises about 10% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. In some embodiments, the pharmaceutical spray formulation comprises about 10% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. In some embodiments, the pharmaceutical spray formulation comprises about 10% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. In some embodiments, the pharmaceutical spray formulation comprises about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. In some embodiments, the pharmaceutical spray formulation comprises about 20% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. In some embodiments, the pharmaceutical spray formulation comprises about 20% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. In some embodiments, the pharmaceutical spray formulation comprises chlorobutanol at a concentration of from about 0.005% (w/v) to about 10% (w/v). In some embodiments, the pharmaceutical spray formulation comprises chlorobutanol at a concentration of from about 0.01% (w/v) to about 10% (w/v). In some embodiments, the pharmaceutical spray formulation comprises chlorobutanol at a concentration of from about 0.1% (w/v) to about 1% (w/v). In some embodiments, the pharmaceutical spray formulation comprises chlorobutanol at a concentration about 0.21% (w/v). In another aspect, disclosed herein is a spray, comprising droplets, wherein the droplets comprise a pharmaceutical spray formulation described herein. In another aspect, disclosed herein is a method of treating anaphylaxis, anaphylactic shock, a severe allergic reaction, and/or bronchial constriction, comprising delivering a spray of a pharmaceutical solution from a pre-primed device into a nostril of a subject in need thereof, wherein: the device is adapted for nasal delivery; a volume of from about 20 μL to about 250 μL of spray is delivered; and the pharmaceutical solution comprises a pharmaceutical spray formulation described herein. In another aspect, disclosed herein is a method of treating anaphylaxis- or anaphylactic shock-induced respiratory depression or distress, comprising delivering a spray of a pharmaceutical solution from a pre-primed device into a nostril of a subject in need thereof in a manner that delivers the pharmaceutical solution in a round spray plume with an ovality ratio less than about 2.0 when measured at a distance of from about 1 to about 10 cm from the pre-primed device, wherein: the device is adapted for nasal delivery; a volume of from about 20 µL to about 250 µL of spray is delivered; and the pharmaceutical solution comprises a pharmaceutical spray formulation described herein. In another aspect, disclosed herein is a method for treating at least one symptom of anaphylaxis or anaphylactic shock, comprising delivering a spray of a pharmaceutical solution from a device into a nostril of a subject in need thereof, wherein: the device is adapted for nasal delivery; a volume of from about 20 µL to about 250 µL of spray is delivered; and the pharmaceutical solution comprises a pharmaceutical spray formulation described herein. In some embodiments, a therapeutic plasma concentration of epinephrine in the subject is achieved in less than 20 minutes following administration to the subject. In some embodiments, the therapeutic plasma concentration of epinephrine in the subject is about 0.5 ng/mL of epinephrine. In some embodiments, the subject has a maximum plasma concentration ($C_{max}$) of from about 0.1 ng/mL to about 1 ng/mL of epinephrine. In some embodiments, the area under a plasma concentration-time curve of epinephrine in the subject is from about 0.1 ng·h/mL to about 5 ng·h/mL. In some embodiments, the plasma concentration versus time curve of epinephrine in the subject has a $t_{max}$ of less than from about 10 minutes to about 120 minutes In some embodiments, the device is a single-dose device. In some embodiments, the device is a bi-dose device. In some embodiments, the device delivers two sprays of the pharmaceutical solution from a single reservoir. In some embodiments, the device has a first reservoir containing from about 50 µL to about 250 µL of the pharmaceutical solution and a second reservoir containing from about 50 µL to about 250 µL of the pharmaceutical solution. In some embodiments, less than about 20% of the formulation leaves the nasal cavity via drainage into the nasopharynx or externally. In some embodiments, a single spray in a nostril of the subject yields a plasma concentration of at least 0.2 ng/mL within 2 minutes in the subject. In another aspect, disclosed herein is a stable pharmaceutical spray formulation, comprising: from about 1% to about 25% w/w of epinephrine, or a pharmaceutically acceptable salt thereof, in water; and one or more excipients, vehicles, emulsifiers, stabilizing agents, preservatives, mucosal adhesives, antibacterial agents, buffers, and/or other additives, wherein the formulation is stable at a temperature of at least about 20° C. and at a relative humidity of at least about 30%, and wherein the formulation is stable for a period of at least about two months, wherein the stable pharmaceutical formulation is a pharmaceutical spray formulation disclosed herein.

In an aspect provided herein, is a method of treating anaphylaxis, anaphylactic shock, a severe allergic reaction, and/or bronchial constriction, comprising administering to a subject in need thereof a therapeutically effective amount of a pharmaceutical spray formulation described herein. In some embodiments, the subject is an adult. In some embodiments, the subject is a child. In some embodiments, the child weighs from about 10 lbs to about 80 lbs.

In an aspect provided herein, is a spray including droplets. In the spray, the droplets include in aggregate from about 0.5 mg to about 100 mg of epinephrine, or a pharmaceutically acceptable salt thereof, an isotonicity agent, and benzalkonium chloride or chlorobutanol. In some embodiments, the spray contains from about 0.005% to about 10% (w/v) of benzalkonium chloride or from about 0.005% to about 10% (w/v) chlorobutanol. In some embodiments provided herein, is a spray, comprising droplets, wherein the droplets comprise in aggregate from about 0.5 mg to about 100 mg of epinephrine, or a pharmaceutically acceptable salt thereof, an isotonicity agent, and from about 0.005% (w/v) to about 10% (w/v) of benzalkonium chloride or from about 0.005% (w/v) to about 10% (w/v) chlorobutanol. In some embodiments, the spray is delivered from a device. In some embodiments, the device is a single-dose device. In some embodiments, the device is a bi-dose device. In some embodiments, the device has a single reservoir containing from about 125 µL to about 250 µL of the pharmaceutical formulation. In some embodiments, the bi-dose device has a first reservoir containing from about 50 µL to about 250 µL of the pharmaceutical formulation and a second reservoir containing from about 50 µL to about 250 µL of the pharmaceutical formulation. In some embodiments, the spray is delivered from a device, wherein the device is pre-primed. In some embodiments, the isotonicity agent is present in a concentration from about 0.1% (w/v) to about 5% (w/v). In some embodiments, the isotonicity agent is sodium chloride. In some embodiments, the spray takes the shape of a round plume with an ovality ratio less than about 2.0. In some embodiments, the spray takes the shape of a round plume with an ovality ratio less than about 1.5. In some embodiments, the spray takes the shape of a round plume with an ovality ratio less than about 1.3. In some embodiments, the spray takes the shape of a round plume with an ovality ratio less than about 1.2. In some embodiments, the spray takes the shape of a round plume with an ovality ratio less than about 1.1. In some embodiments, the ovality ratio is measured at a distance of from about 1 cm to about 10 cm from the device. In some embodiments, the ovality ratio is measured at a distance of from about 1 cm to about 5 cm from the device. In some embodiments, the ovality ratio is measured at a distance of about 3 cm from the device. In some embodiments, the epinephrine is at least 10% bioavailable. In some embodiments, the epinephrine is at least 40% bioavailable. In some embodiments, the epinephrine is at least 50% bioavailable. In some embodiments, the epinephrine is at least 60% bioavailable. In some embodiments, the median droplet size is from about 10 µm to about 120 µm. In some embodiments, no more than about 10% of the droplets have a diameter less than about 10 µm. In some embodiments, no more than approximately 5% of the droplets have a diameter less than about 10 µm. In some embodiments, no more than approximately 2% of the droplets have a diameter less than about 10 µm. In some embodiments, approximately 50% of the droplets have a diameter of from about 10 µm to about 120 µm. In some embodiments, approximately 50% of the droplets have a diameter of from about 10 µm to about 60 µm. In some embodiments, approximately 90% of the droplets have a diameter less than about 120 µm. In some embodiments, the spray further comprises a stabilizing agent and an acid. In some embodiments, the spray further comprises a stabilizing agent and an acid, wherein the stabilizing agent is disodium edetate. In some embodiments, the spray further comprises a stabilizing agent and an acid. In some embodiments, the spray further comprises a stabilizing agent and an acid, wherein the acid is hydrochloric acid or citric acid, or a combination thereof. In some embodiments, the epinephrine, or a pharmaceutically acceptable salt thereof, is dissolved in water, ethanol, or propylene glycol, or a combination thereof. In some embodiments, the spray further comprises sodium bisulfite at a concentration of from about 0.0001% (w/w) to about 0.1% (w/w) or sodium metabisulfite at a concentration of from about 0.0001% (w/w) to about 0.1% (w/w). In some embodiments, the spray further comprises sodium bisulfite at a concentration of from about 0.0001% (w/w) to about 0.05% (w/w) or sodium metabisulfite at a concentration of from about 0.0001% (w/w) to about 0.05% (w/w). In some embodiments, the spray further comprises sodium bisulfite at a concentration of from about 0.0001% (w/w) to about 0.1% (w/w) or sodium metabisulfite at a concentration of from about 0.0001% (w/w) to about 0.1% (w/w). In some embodiments, the spray further comprises sodium bisulfite at a concentration of from about 0.01% (w/w) to about 0.1% (w/w) or sodium metabisulfite at a concentration of from about 0.01% (w/w) to about 0.1% (w/w). In some embodiments, the spray further comprises chlorobutanol at a concentration of from about 0.005% (w/w) to about 1% (w/w). In some embodiments, the spray further comprises a vasodilator. In some embodiments, the spray further comprises a vasodilator, wherein the vasodilator is nitroprusside, phentolamine, or nifedipine. In some embodiments, the spray further comprises a permeability enhancer. In some embodiments, the spray further comprises a permeability enhancer, wherein the permeability enhancer is diethylene glycol monoethyl ether. In some embodiments, the spray further comprises a viscosity modifier. In some embodiments, the spray further comprises a permeability enhancer, wherein the viscosity modifier is polyethylene glycol, methylcellulose, or hypromellose. In some embodiments, the spray further comprises trisodium citrate or citric acid monohydrate. In some embodiments, the spray is delivered from a device, wherein the device comprises at least one oxygen absorber or scavenger. In some embodiments, the spray is delivered from a device, wherein the device comprises at least one oxygen absorber or scavenger, and wherein the at least one oxygen absorber or scavenger is iron, ferrous carbonate, ascorbate, or sodium bicarbonate, or a combination thereof. In some embodiments, the spray comprises per 100 μL of solution: from about 0.5 mg to about 100 mg of epinephrine, or a pharmaceutically acceptable salt thereof from about 0.1 mg to about 2 mg sodium chloride; from about 0.01 mg to about 1 mg benzalkonium chloride; from about 0.1 mg to about 2 mg disodium edetate; and hydrochloric acid or citric acid, or a combination thereof sufficient to achieve a pH of from about 3.5 to about 6.5. In some embodiments, the spray is delivered from a spray nozzle of a pre-primed device, and wherein no more than about 10% of the droplets have a diameter less than 10 In some embodiments, the spray is measured by laser diffraction with beams measuring at both 3 cm and 6 cm from the spray nozzle.

In another aspect provided herein, is a stable pharmaceutical spray formulation where the pharmaceutical spray formulation is stable for a period of at least about two months at a temperature of at least about 20° C. and at a relative humidity of at least about 30%. The stable pharmaceutical spray formulation includes:

(i) from about 1% to about 25% w/w of epinephrine, or a pharmaceutically acceptable salt thereof, in water, ethanol, propylene glycol, or a combination thereof and (ii) one or more excipients, vehicles, emulsifiers, stabilizing agents, preservatives, mucosal adhesives, antibacterial agents, buffers, and/or other additives, wherein the formulation is stable at a temperature of at least about 20° C. and at a relative humidity of at least about 30%, and wherein the formulation is stable for a period of at least about two months. In some embodiments, the pharmaceutical spray formulation comprises from about 1% to about 10% w/w of epinephrine, or a pharmaceutically acceptable salt thereof. In some embodiments, the pharmaceutical spray formulation is stable at a temperature of at least about 25° C. In some embodiments, the pharmaceutical spray formulation is stable at a temperature of at least about 30° C. In some embodiments, the pharmaceutical spray formulation is stable at a temperature of at least about 35° C. In some embodiments, the pharmaceutical spray formulation is stable at a temperature of at least about 40° C. In some embodiments, the pharmaceutical spray formulation is stable at a temperature of at least about 45° C. In some embodiments, the pharmaceutical spray formulation is stable at a relative humidity of at least about 40%. In some embodiments, the pharmaceutical spray formulation is stable at a relative humidity of at least about 50%. In some embodiments, the pharmaceutical spray formulation is stable at a relative humidity of at least about 60%. In some embodiments, the pharmaceutical spray formulation is stable at a relative humidity of at least about 70%. In some embodiments, the pharmaceutical spray formulation is stable at a relative humidity of at least about 80%. In some embodiments, the pharmaceutical spray formulation is stable for a period of at least about six months. In some embodiments, the pharmaceutical spray formulation is stable for a period of at least about 12 months. In some embodiments, the pharmaceutical spray formulation is stable for a period of at least about 18 months. In some embodiments, the pharmaceutical spray formulation is stable for a period of at least about 24 months. In some embodiments, the pharmaceutical spray formulation is stable for a period of at least about 36 months. In some embodiments, the pharmaceutical spray formulation has a viscosity of from about 100 to about 2,500 cP. In some embodiments, the pharmaceutical spray formulation is adapted for parenteral dosing. In some embodiments, the pharmaceutical spray formulation is adapted for dosing by inhalation. In some embodiments, the pharmaceutical spray formulation is adapted for intranasal dosing. In some embodiments, the pharmaceutical spray formulation further comprises an isotonicity agent present in a concentration from about 0.1% (w/w) to about 5% (w/w). In some embodiments, the pharmaceutical spray formulation further comprises an isotonicity agent present in a concentration from about 0.1% (w/w) to about 5% (w/w), wherein the isotonicity agent is sodium chloride. In some embodiments, the pharmaceutical spray formulation comprises a stabilizing agent. In some embodiments, the pharmaceutical spray formulation comprises a stabilizing agent, wherein the stabilizing agent is disodium edetate. In some embodiments, the pharmaceutical spray formulation further comprises an acid sufficient to achieve a pH of from about 3.5 to about 6.5. In some embodiments, the pharmaceutical spray formulation further comprises an acid sufficient to achieve a pH of from about 3.5 to about 6.5, wherein the acid is hydrochloric acid or citric acid, or a combination thereof. In some embodiments, the spray further comprises sodium bisulfite at a concentration of from about 0.0001% (w/w) to about 0.1% (w/w) or sodium metabisulfite at a concentration of from about 0.0001% (w/w) to about 0.1% (w/w). In some embodiments, the pharmaceutical spray formulation further comprises sodium bisulfite at a concentration of from about 0.0001% (w/w) to about 0.05% (w/w) or sodium metabisulfite at a concentration of from about 0.0001% (w/w) to about 0.05% (w/w). In some embodiments, the spray further comprises sodium bisulfite at a concentration of from about 0.0001% (w/w) to about 0.1% (w/w) or sodium metabisulfite at a concentration of from about 0.0001% (w/w) to about 0.1% (w/w). In some embodiments, the spray further comprises sodium bisulfite at a concentration of from about 0.01% (w/w) to about 0.1% (w/w) or sodium metabisulfite at a concentration of from about 0.01% (w/w) to about 0.1% (w/w). In some embodiments, the pharmaceutical spray formulation further comprises chlorobutanol at a concentration of from about 0.005% (w/v) to about 1% (w/v). In some embodiments, the pharmaceutical spray formulation further comprises a vasodilator. In some embodiments, the pharmaceutical spray formulation further comprises a vasodilator, wherein the vasodilator is nitroprusside, phentolamine, or nifedipine. In some embodiments, the pharmaceutical spray formulation further comprises a permeability enhancer. In some embodiments, the pharmaceutical spray formulation further comprises a permeability enhancer, wherein the permeability enhancer is diethylene glycol monoethyl ether. In some embodiments, the pharmaceutical spray formulation further comprises a viscosity modifier. In some embodiments, the pharmaceutical spray formulation further comprises a viscosity modifier, wherein the viscosity modifier is polyethylene glycol, methylcellulose, or hypromellose. In some embodiments, the pharmaceutical spray formulation further comprises trisodium citrate or citric acid monohydrate. In some embodiments, the pharmaceutical spray formulation comprises from about 1% to about 20% w/w of epinephrine, or a pharmaceutically acceptable salt thereof, from about 0.0001% (w/w) to about 0.05% (w/w) of sodium metabisulfite, from about 0.1% to about 5% sodium chloride, from about 0.001% to about 0.5% hypromellose, from about 0.01% to about 2.0% trisodium citrate, and from about 0.05% to about 15% diethylene glycol monoethyl ether. In some embodiments, the pharmaceutical spray formulation comprises from about 1% to about 5% w/w of epinephrine, or a pharmaceutically acceptable salt thereof, from about 0.01% (w/w) to about 0.05% (w/w) of sodium metabisulfite, from about 0.1% to about 1.0% sodium chloride, from about 0.01% to about 0.2% hypromellose, from about 0.1% to about 1.0% trisodium citrate, and from about 0.1% to about 2.0% diethylene glycol monoethyl ether. In some embodiments, the pharmaceutical spray formulation comprises from about 5% to about 20% w/w of epinephrine, or a pharmaceutically acceptable salt thereof, from about 0.01% (w/w) to about 0.05% (w/w) of sodium metabisulfite, from about 0.1% to about 1.0% sodium chloride, from about 0.05% to about 0.5% hypromellose, from about 0.1% to about 1.0% trisodium citrate, and from about 0.5% to about 5% diethylene glycol monoethyl ether In some embodiments, the pharmaceutical spray formulation comprises about 2.4% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. In some embodiments, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. In some embodiments, the pharmaceutical spray formulation comprises about 10% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. In some embodiments, the pharmaceutical spray formulation comprises about 20% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. In some embodiments, the pharmaceutical spray formulation comprises from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2.0% citric acid monohydrate, and from about 0.05% to about 15% diethylene glycol monoethyl ether. In some embodiments, the pharmaceutical spray formulation comprises about 2% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. In some embodiments, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. In some embodiments, the pharmaceutical spray formulation further comprises chlorobutanol at a concentration of from about 0.05% (w/v) to about 1% (w/v). In some embodiments, the pharmaceutical spray formulation is delivered from a device. In some embodiments, the device is a single-dose device. In some embodiments, the device is a bi-dose device. In some embodiments, the device has a single reservoir containing from about 125 µL to about 250 µL of the pharmaceutical formulation. In some embodiments, the device delivers two sprays of the pharmaceutical solution from a single reservoir. In some embodiments, the bi-dose device has a first reservoir containing from about 50 µL to about 250 µL of the pharmaceutical formulation and a second reservoir containing from about 50 µL to about 250 µL of the pharmaceutical formulation. In some embodiments, the device delivers one spray of the pharmaceutical solution from the first reservoir and one spray of the pharmaceutical solution from the second reservoir. In some embodiments, the pharmaceutical spray formulation is delivered from a device, wherein the device is pre-primed. In some embodiments, the pharmaceutical spray formulation is delivered from a device, wherein the device is suitable for delivering the formulation into the nostril of a subject. In some embodiments, the pharmaceutical spray formulation is delivered from a device, wherein the device comprises at least one oxygen absorber or scavenger. In some embodiments, the pharmaceutical spray formulation is delivered from a device, wherein the device comprises at least one oxygen absorber or scavenger, and wherein the at least one oxygen absorber or scavenger is iron, ferrous carbonate, ascorbate, or sodium bicarbonate, or a combination thereof. In some embodiments, the pharmaceutical spray formulation is delivered as a spray. In some embodiments, the spray takes the shape of a round plume with an ovality ratio less than about 2.0. In some embodiments, the spray takes the shape of a round plume with an ovality ratio less than about 1.5. In some embodiments, the spray takes the shape of a round plume with an ovality ratio less than about 1.3. In some embodiments, the spray takes the shape of a round plume with an ovality ratio less than about 1.2. In some embodiments, the spray takes the shape of a round plume with an ovality ratio less than about 1.1. In some embodiments, the ovality ratio is measured at a distance of from about 1 cm to about 10 cm from the device. In some embodiments, the ovality ratio is measured at a distance of from about 1 cm to about 5 cm from the device. In some embodiments, the ovality ratio is measured at a distance of about 3 cm from the device. In some embodiments, the epinephrine is at least 10% bioavailable. In some embodiments, the epinephrine is at least 40% bioavailable. In some embodiments, the epinephrine is at least 50% bioavailable. In some embodiments, the epinephrine is at least 60% bioavailable. In some embodiments, the median droplet size is from about 10 µm to about 120 µm. In some embodiments, no more than about 10% of the droplets have a diameter less than about 10 µm. In some embodiments, no more than approximately 5% of the droplets have a diameter less than about 10 µm. In some embodiments, no more than approximately 2% of the droplets have a diameter less than about 10 µm. In some embodiments, approximately 50% of the droplets have a diameter of from about 10 µm to about 120 µm. In some embodiments, approximately 50% of the droplets have a diameter of from about 10 µm to about 60 In some embodiments, approximately 90% of the droplets have a diameter less than about 120 µm.

Provided herein is a method of treating anaphylaxis, anaphylactic shock, a severe allergic reaction, and/or bronchial constriction. The method includes delivering a spray of a pharmaceutical solution from device into a nostril of a subject in need thereof where:

(i) the device is adapted for nasal delivery;
(ii) a volume of from about 20 µL to about 250 µL of spray is delivered; and
(iii) the pharmaceutical solution comprises from about 0.5 mg to about 100 mg of epinephrine, or a pharmaceutically acceptable salt thereof, an isotonicity agent, and from about 0.005% (w/v) to about 1% (w/v) of benzalkonium chloride.

In some embodiments, the device is a single-dose device. In some embodiments, the device is a bi-dose device. In some embodiments, the device has a single reservoir containing from about 125 µL to about 250 µL of the pharmaceutical formulation. In some embodiments, the device delivers two sprays of the pharmaceutical solution from a single reservoir. In some embodiments, the bi-dose device has a first reservoir containing from about 50 µL to about 250 µL of the pharmaceutical formulation and a second reservoir containing from about 50 µL to about 250 µL of the pharmaceutical formulation. In some embodiments, the device delivers one spray of the pharmaceutical solution from the first reservoir and one spray of the pharmaceutical solution from the second reservoir. In some embodiments, the epinephrine, or a pharmaceutically acceptable salt thereof, is dissolved in water, ethanol, propylene glycol, or a combination thereof. In some embodiments, the isotonicity agent is present in a concentration of from about 0.2% (w/v) to about 1.2% (w/v). In some embodiments, the pharmaceutical solution further comprises from about 0.1% (w/v) to about 0.5% (w/v) of a stabilizing agent. In some embodiments, the pharmaceutical solution further comprises an amount of an acid sufficient to achieve a pH of from about 3.5 to about 6.5. In some embodiments, the pharmaceutical solution further comprises an amount of an acid sufficient to achieve a pH of from about 3.5 to about 6.5, wherein the acid is hydrochloric acid or citric acid, or a combination thereof. In some embodiments, the isotonicity agent is sodium chloride, the stabilizing agent is disodium edetate, and the acid is hydrochloric acid or citric acid, or a combination thereof. In some embodiments, the plasma concentration versus time curve of epinephrine in the subject has a $t_{max}$ of less than from about 10 minutes to about 120 minutes. In some embodiments, a therapeutic plasma concentration of epinephrine in the subject is achieved in less than 20 minutes following administration to the subject. In some embodiments, a therapeutic plasma concentration of epinephrine in the subject is achieved in less than 15 minutes following administration to the subject. In some embodiments, a therapeutic plasma concentration of epinephrine in the subject is achieved in less than 10 minutes following administration to the subject. In some embodiments, a therapeutic plasma concentration of epinephrine in the subject is achieved in less than 5 minutes following administration to the subject. In some embodiments, the therapeutic plasma concentration of epinephrine in the subject is about 500 pg/mL of epinephrine. In some embodiments, the therapeutic plasma concentration of epinephrine in the subject is about 450 pg/mL of epinephrine. In some embodiments, the therapeutic plasma concentration of epinephrine in the subject is about 400 pg/mL of epinephrine. In some embodiments, the therapeutic plasma concentration of epinephrine in the subject is about 350 pg/mL of epinephrine. In some embodiments, the therapeutic plasma concentration of epinephrine in the subject is about 300 pg/mL of epinephrine. In some embodiments, the subject has a maximum plasma concentration ($C_{max}$) of from about 50 pg/mL to about 500 pg/mL of epinephrine. In some embodiments, the area under a plasma concentration-time curve of epinephrine in the subject is from about 5 ng/minute/mL to about 50 ng/minute/mL. In some embodiments, the device comprises a plunger that houses a container closure comprising:

(i) a vial comprising an opening;
(ii) a cannula; and
(iii) a rubber stopper;

wherein the stopper is configured to occlude the opening of the vial, and wherein the cannula is configured such that the cannula can pierce the stopper when the plunger applies sufficient force to the cannula. In some embodiments, the spray delivers from about 0.5 mg to about 100 mg of epinephrine, or a pharmaceutically acceptable salt thereof. In some embodiments, the pre-primed device is actuatable with one hand. In some embodiments, the pre-primed device has a single reservoir containing approximately 125 µL of the pharmaceutical solution. In some embodiments, approximately 100 µL of the pharmaceutical solution is delivered by one actuation of the device. In some embodiments, the volume of the reservoir is not more than about 140 µL. In some embodiments, delivery time of the pharmaceutical solution is less than about 25 seconds. In some embodiments, delivery time of the pharmaceutical solution is less than about 20 seconds. In some embodiments, less than about 20% of the pharmaceutical solution leaves the nasal cavity via drainage into the nasopharynx or externally. In some embodiments, less than about 10% of the pharmaceutical solution leaves the nasal cavity via drainage into the nasopharynx or externally. In some embodiments, less than about 5% of the pharmaceutical solution leaves the nasal cavity via drainage into the nasopharynx or externally. In some embodiments, the subject is suffering from a severe allergic reaction from exposure or suspected exposure to an allergen. In some embodiments, the allergen is food, medication, or an insect bite or sting. In some embodiments, the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, and vomiting. In some embodiments, the subject exhibits respiratory depression or distress, or cardiovascular depression. In some embodiments, the subject is free from respiratory depression or distress for at least about 1 hour following treatment comprising delivery of the therapeutically effective amount of the epinephrine, or a pharmaceutically acceptable salt thereof. In some embodiments, the subject is free from respiratory depression or distress for at least about 2 hours following treatment comprising delivery of the therapeutically effective amount of the epinephrine, or a pharmaceutically acceptable salt thereof. In some embodiments, the subject is free from respiratory depression or distress for at least about 4 hours following treatment comprising delivery of the therapeutically effective amount of the epinephrine, or a pharmaceutically acceptable salt thereof. In some embodiments, the subject is free from respiratory depression or distress for at least about 6 hours following treatment comprising delivery of the therapeutically effective amount of the epinephrine, or a pharmaceutically acceptable salt thereof. In some embodiments, the subject is in a lying, supine, or recovery position. In some embodiments, a single spray in the nostril yields a plasma concentration of ≥1 ng/mL within 2.5 minutes in the subject. In some embodiments, a single spray in the nostril yields a plasma concentration of ≥1 ng/mL within 5 minutes in the subject. In some embodiments, a single spray in the nostril yields a plasma concentration of ≥1 ng/mL within 10 minutes in the subject.

In an aspect provided herein, is a method of treating anaphylaxis- or anaphylactic shock-induced respiratory depression or distress, comprising delivering a spray of a pharmaceutical solution from a pre-primed device into a nostril of a subject in need thereof in a manner that delivers the pharmaceutical solution in a round spray plume with an ovality ratio less than about 2.0 when measured at a distance of from about 1 to about 10 cm from the pre-primed device, wherein:
(i) the device is adapted for nasal delivery;
(ii) a volume of from about 20 µL to about 250 µL of spray is delivered; and
(iii) the pharmaceutical solution comprises from about 0.5 mg to about 100 mg of epinephrine, or a pharmaceutically acceptable salt thereof, an isotonicity agent, and from about 0.005% (w/v) to about 1% (w/v) of benzalkonium chloride. In some embodiments, the device is a single-dose device. In some embodiments, the device is a bi-dose device. In some embodiments, the device has a single reservoir containing from about 125 µL to about 250 µL of the pharmaceutical formulation. In some embodiments, the device delivers two sprays of the pharmaceutical solution from a single reservoir. In some embodiments, the bi-dose device has a first reservoir containing from about 50 µL to about 250 µL of the pharmaceutical formulation and a second reservoir containing from about 50 µL to about 250 µL of the pharmaceutical formulation. In some embodiments, the device delivers one spray of the pharmaceutical solution from the first reservoir and one spray of the pharmaceutical solution from the second reservoir. In some embodiments, the ovality ratio is less than about 1.5. In some embodiments, the ovality ratio is less than about 1.3. In some embodiments, the ovality ratio is less than about 1.2. In some embodiments, the ovality ratio is less than about 1.1. In some embodiments, the ovality ratio of the spray is measured at a distance from about 1 cm to about 5 cm from the device.

In another aspect provided herein, is a method for treating at least one symptom of anaphylaxis or anaphylactic shock comprising delivering a spray of a pharmaceutical solution into a nostril of a subject in need thereof, wherein:
(i) the device is adapted for nasal delivery;
(ii) a volume of from about 20 µL to about 250 µL of spray is delivered; and
the pharmaceutical solution comprises from about 0.5 mg to about 100 mg of epinephrine, or a pharmaceutically acceptable salt thereof, an isotonicity agent, and from about 0.005% (w/v) to about 1% (w/v) of benzalkonium chloride. In some embodiments, the device is a single-dose device. In some embodiments, the device is a bi-dose device. In some embodiments, the device has a single reservoir containing from about 125 µL to about 250 µL of the pharmaceutical formulation. In some embodiments, the device delivers two sprays of the pharmaceutical solution from a single reservoir. In some embodiments, the bi-dose device has a first reservoir containing from about 50 µL to about 250 µL of the pharmaceutical formulation and a second reservoir containing from about 50 µL to about 250 µL of the pharmaceutical formulation. In some embodiments, the device delivers one spray of the pharmaceutical solution from the first reservoir and one spray of the pharmaceutical solution from the second reservoir. In some embodiments, the subject is an adult. In some embodiments, the subject is a child. In some embodiments, the child weighs from about 10 lbs to about 80 lbs.

In another aspect provided herein, is a method of treating anaphylaxis, anaphylactic shock, a severe allergic reaction, and/or bronchial constriction, comprising administering or delivering to a subject in need thereof a pharmaceutical spray formulation described herein. In some embodiments, the pharmaceutical spray formulation is administered or delivered into a nostril of the subject from a pre-primed device adapted for nasal delivery. In some embodiments, a volume of from about 20 µL to about 250 µL of spray is delivered. In some embodiments, the plasma concentration versus time curve of epinephrine in the subject has a $t_{max}$ of less than from about 10 minutes to about 120 minutes. In some embodiments, the subject has a maximum plasma concentration ($C_{max}$) of from about 50 pg/mL to about 500 pg/mL of epinephrine. In some embodiments, the area under a plasma concentration-time curve of epinephrine in the subject is from about 5 ng/minute/mL to about 50 ng/minute/mL. In some embodiments, the pre-primed device is actuatable with one hand. In some embodiments, the pre-primed device has a single reservoir containing from about 125 µL to about 250 µL of the pharmaceutical solution. In some embodiments, approximately 100 µL of the pharmaceutical solution is delivered by one actuation of the device. In some embodiments, the volume of the reservoir is not more than about 140 µL. In some embodiments, delivery time of the pharmaceutical solution is less than about 25 seconds. In some embodiments, delivery time of the pharmaceutical solution is less than about 20 seconds. In some embodiments, less than about 20% of the pharmaceutical solution leaves the nasal cavity via drainage into the nasopharynx or externally. In some embodiments, less than about 10% of the pharmaceutical solution leaves the nasal cavity via drainage into the nasopharynx or externally. In some embodiments, less than about 5% of the pharmaceutical solution leaves the nasal cavity via drainage into the nasopharynx or externally. In some embodiments, the subject is suffering from a severe allergic reaction from exposure or suspected exposure to an allergen. In some embodiments, the allergen is food, medication, or an insect bite or sting. In some embodiments, the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, and vomiting. In some embodiments, the subject exhibits respiratory depression or distress, or cardiovascular depression. In some embodiments, the subject is free from respiratory depression or distress for at least about 1 hour following treatment comprising delivery of the therapeutically effective amount of the epinephrine, or a pharmaceutically acceptable salt thereof. In some embodiments, the subject is free from respiratory depression or distress for at least about 2 hours following treatment comprising delivery of the therapeutically effective amount of the epinephrine, or a pharmaceutically acceptable salt thereof. In some embodiments, the subject is free from respiratory depression or distress for at least about 4 hours following treatment comprising delivery of the therapeutically effective amount of the epinephrine, or a pharmaceutically acceptable salt thereof. In some embodiments, the subject is free from respiratory depression or distress for at least about 6 hours following treatment comprising delivery of the therapeutically effective amount of the epinephrine, or a pharmaceutically acceptable salt thereof. In some embodiments, the subject is in a lying, supine, or recovery position. In some embodiments, a single spray in the nostril yields a plasma concentration of ≥1 ng/mL within 2.5 minutes in the subject. In some embodiments, a single spray in the nostril yields a plasma concentration of ≥1 ng/mL within 5 minutes in the subject. In some embodiments, a single spray in the nostril yields a plasma concentration of ng/mL within 10 minutes in the subject.

In another aspect provided herein, is a method of treating anaphylaxis- or anaphylactic shock-induced respiratory depression or distress, comprising administering or delivering to a subject in need thereof a spray formulation described herein from a pre-primed device into a nostril of the subject in a manner that delivers the formulation in a round spray plume with an ovality ratio less than about 2.0 when measured at a distance of from about 1 to about 10 cm from the pre-primed device, wherein:
(i) the device is adapted for nasal delivery; and
(ii) a volume of from about 20 μL to about 250 μL of spray is delivered.

In some embodiments, the ovality ratio is less than about 1.5. In some embodiments, the ovality ratio is less than about 1.3. In some embodiments, the ovality ratio is less than about 1.2. In some embodiments, the ovality ratio is less than about 1.1. In some embodiments, the ovality ratio of the spray is measured at a distance from about 1 cm to about 5 cm from the device.

In another aspect provided herein, is a method for treating at least one symptom of anaphylaxis or anaphylactic shock, comprising administering or delivering to a subject in need thereof the pharmaceutical spray formulation described herein from a device into a nostril of the subject, wherein:
(iii) the device is adapted for nasal delivery; and
(iv) a volume of from about 20 μL to about 250 μL of spray is delivered.

In some embodiments, the subject is an adult. In some embodiments, the subject is a child. In some embodiments, the child weighs from about 10 lbs to about 80 lbs.

In another aspect provided herein, is a device as described herein, wherein the device comprises: at least one processor, an operating system configured to perform executable instructions, a memory, and a computer program including instructions executable by the digital processing device to create an application comprising:
a) a software module sending a first notification to a portable device of a user when the device has been triggered for formulation administration;
b) a software module sending a second notification to a second device of a designated third party when the device has been triggered for formulation administration;
c) a software module sending a third notification to the portable device of the user when the device is outside a predetermined range from the portable device;
d) a software module sending a fourth notification to the second device of the designated third party when the device is outside the predetermined range from the portable device;
e) a software module collecting geographic data of the device when the device is in administration to the user or a second user;
f) a software module saving geographic data of the device to a remote or cloud database; and
g) a software module allowing the user or the second user to order a new device using the device or the portable device of the user.

In some embodiments, the portable device or the second device comprises one or more of: a computer, a notebook computer, a handheld computer, a mobile smartphones, a tablet computer, and a personal digital assistant. In some embodiments, the device further comprises a communications element configured to allow two-way data communication with the portable device of the user and a digital processing device using a wireless data transfer protocol. In some embodiments, the first, second, third, or fourth notification is sent within the application. In some embodiments, the first, second, third, or fourth notification is automatic. In some embodiments, the first, second, third, or fourth notification comprises one or more of: text, graphic information, sound, and vibration.

In another aspect of the methods described herein, the method comprises;
a) sending a first notification to a portable device of a user when the device has been triggered for formulation administration;
b) sending a second notification to a second device of a designated third party when the device has been triggered for formulation administration;
c) sending a third notification to the portable device of the user when the device is outside a predetermined range from the portable device;
d) sending a fourth notification to the second device of the designated third party when the device is outside the predetermined range from the portable device;
e) collecting geographic data of the device when the device is in administration to the user or a second user;
f) saving geographic data of the device to a remote or cloud database; and
g) allowing the user or the second user to order a new device using the device or the portable device of the user.

In another aspect provided herein, is a method of treating anaphylaxis, anaphylactic shock, a severe allergic reaction, and/or bronchial constriction, comprising delivering a spray of a pharmaceutical solution from a pre-primed device into a nostril of a subject in need thereof, wherein: the device is adapted for nasal delivery, a volume of from about 20 µL to about 250 µL of spray is delivered, and the pharmaceutical solution comprises the pharmaceutical spray formulation described herein.

In another aspect provided herein, is a method of treating anaphylaxis, anaphylactic shock, a severe allergic reaction, and/or bronchial constriction, comprising delivering a spray of a pharmaceutical solution from a pre-primed device into a nostril of a subject in need thereof, wherein: the device is adapted for nasal delivery, a volume of from about 20 µL to about 250 µL of spray is delivered, and the pharmaceutical solution comprises the pharmaceutical spray formulation described herein.

In an aspect provided herein, is a method of treating anaphylaxis- or anaphylactic shock-induced respiratory depression or distress, comprising delivering a spray of a pharmaceutical solution from a pre-primed device into a nostril of a subject in need thereof in a manner that delivers the pharmaceutical solution in a round spray plume with an ovality ratio less than about 2.0 when measured at a distance of from about 1 to about 10 cm from the pre-primed device, wherein: the device is adapted for nasal delivery, a volume of from about 20 µL to about 250 µL of spray is delivered, and the pharmaceutical solution comprise the pharmaceutical spray formulation described herein.

In another aspect provided herein, is a method for treating at least one symptom of anaphylaxis or anaphylactic shock, comprising delivering a spray of a pharmaceutical solution from a device into a nostril of a subject in need thereof, wherein: the device is adapted for nasal delivery, a volume of from about 20 µL to about 250 µL of spray is delivered, and the pharmaceutical solution comprise the pharmaceutical spray formulation described herein.

In an aspect provided herein, is a stable pharmaceutical spray formulation, comprising: from about 1% to about 25% w/w of epinephrine, or a pharmaceutically acceptable salt thereof, in water; and one or more excipients, vehicles, emulsifiers, stabilizing agents, preservatives, mucosal adhesives, antibacterial agents, buffers, and/or other additives, wherein the formulation is stable at a temperature of at least about 20° C. and at a relative humidity of at least about 30%, and wherein the formulation is stable for a period of at least about two months, wherein the stable pharmaceutical formulation is the pharmaceutical spray formulation described herein.

In another aspect, disclosed herein is a pharmaceutical spray formulation, comprising: (i) from about 1% to about 25% (w/w) of epinephrine, or a pharmaceutically acceptable salt thereof, in water, ethanol, propylene glycol, or a combination thereof; and (ii) one or more of an antioxidant, an antimicrobial preservative, an isotonicity agent, an absorption enhancer, a viscosity modifier, or a buffering agent; wherein the formulation is configured to be administered into a nostril of a subject as a nasal spray that yields a plasma concentration of at least 0.5 ng/mL within 1 minute of administration. In some embodiments, the pH of the formulation is from about 4.0 to about 6.5. In some embodiments, the antioxidant comprises sodium bisulfite or sodium metabisulfite at a concentration from about 0.01% to about 0.1% (w/w). In some embodiments, the antimicrobial preservative comprises chlorobutanol or chlorobutanol hemihydrate at a concentration from about 0.1% to about 1% (w/w). In some embodiments, the isotonicity agent comprises sodium chloride at a concentration from about 0.1% to about 1% (w/w). In some embodiments, the viscosity modifier comprises hypromellose at a concentration from about 0.01% to about 0.2% (w/w). In some embodiments, the buffering agent comprises citric acid or citric acid monohydrate at a concentration from about 0.1% to about 1% (w/w). In some embodiments, the pharmaceutical spray formulation comprises about 2% or about 5% (w/w) of epinephrine, or a pharmaceutically acceptable salt thereof. In some embodiments, the pharmaceutical spray formulation comprises sodium metabisulfite, sodium chloride, hypromellose, citric acid monohydrate, diethylene glycol monoethyl ether, and chlorobutanol hemihydrate. In some embodiments, the pharmaceutical spray formulation comprises from about 1% to about 10% (w/w) of epinephrine, or a pharmaceutically acceptable salt thereof, from about 0.01% to about 0.1% (w/w) of sodium metabisulfite, from about 0.1% to about 1% (w/w) sodium chloride, from about 0.01% to about 0.2% (w/w) hypromellose, from about 0.1% to about 1% (w/w) citric acid monohydrate, from about 0.1% to about 5% (w/w) diethylene glycol monoethyl ether, and from about 0.1% to about 1% (w/w) chlorobutanol hemihydrate. In another aspect, disclosed herein is a stable pharmaceutical spray formulation, comprising: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the formulation is stable for a period of at least about one month at a temperature of at least about 20° C. In some embodiments, the formulation is stable for a period of at least one month at a temperature of at least about 40° C. In some embodiments, the formulation has no more than about 2% total impurities after storage for a period of at least about one month at a temperature of at least about 40° C. In some embodiments, the antioxidant comprises sodium bisulfite or sodium metabisulfite at a concentration from about 0.01% to about 0.1% (w/w). In some embodiments, the antimicrobial preservative comprises chlorobutanol or chlorobutanol hemihydrate at a concentration from about 0.1% to about 1% (w/w). In some embodiments, the isotonicity agent comprises sodium chloride at a concentration from about 0.1% to about 1% (w/w). In some embodiments, the buffering agent comprises citric acid or citric acid monohydrate at a concentration from about 0.1% to about 1% (w/w). In another aspect, disclosed herein is a pharmaceutical spray formulation, comprising: (i) from about 1% to about 25% (w/w) of epinephrine, or a pharmaceutically acceptable salt thereof, in water, ethanol, propylene glycol, or a combination thereof; and (ii) one or more of an antioxidant, an antimicrobial preservative, an isotonicity agent, an absorption enhancer, a viscosity modifier, or a buffering agent; wherein the absorption enhancer is diethylene glycol monoethyl ether. In some embodiments, the formulation comprises diethylene glycol monoethyl ether at a concentration from about 0.1% to about 5% (w/w). In some embodiments, the absorption enhancer comprises diethylene glycol monoethyl ether at a concentration of about 1% (w/w).

In another aspect, disclosed herein is a method for treating at least one symptom of anaphylaxis or anaphylactic shock, comprising delivering a spray of a pharmaceutical spray formulation from a nasal spray device into a nostril of a subject in need thereof, wherein the pharmaceutical spray formulation comprises: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the formulation is configured to be administered into a nostril of a subject as a nasal spray that yields a plasma concentration of at least 0.5 ng/mL within 1 minute of administration. In some embodiments, the subject is suffering from a severe allergic reaction from exposure or suspected exposure to an allergen. In some embodiments, the allergen is food, medication, or an insect bite or sting. In some embodiments, the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, and vomiting. In some embodiments, the subject exhibits respiratory depression or distress, or cardiovascular depression. In some embodiments, the subject is free from respiratory depression or distress for at least about 1 hour following delivery of the pharmaceutical spray formulation. In some embodiments, the antioxidant comprises sodium bisulfite or sodium metabisulfite at a concentration from about 0.01% to about 0.1% (w/w). In some embodiments, the antimicrobial preservative comprises chlorobutanol or chlorobutanol hemihydrate at a concentration from about 0.1% to about 1% (w/w). In some embodiments, the isotonicity agent comprises sodium chloride at a concentration from about 0.1% to about 1% (w/w). In some embodiments, the viscosity modifier comprises hypromellose at a concentration from about 0.01% to about 0.2% (w/w). In some embodiments, the buffering agent comprises citric acid or citric acid monohydrate at a concentration from about 0.1% to about 1% (w/w). In some embodiments, the pharmaceutical spray formulation comprises about 2% or about 5% (w/w) of epinephrine, or a pharmaceutically acceptable salt thereof. In some embodiments, the pharmaceutical spray formulation comprises sodium metabisulfite, sodium chloride, hypromellose, citric acid monohydrate, diethylene glycol monoethyl ether, and chlorobutanol hemihydrate. In another aspect, disclosed herein is a method of treating at least one of anaphylaxis, anaphylactic shock, a severe allergic reaction, or bronchial constriction, comprising administering or delivering to a subject in need thereof a stable pharmaceutical spray formulation, wherein the stable pharmaceutical spray formulation comprises: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the formulation is stable for a period of at least about one month at a temperature of at least about 20° C. In some embodiments, the formulation is stable for a period of at least one month at a temperature of at least about 40° C. In some embodiments, the formulation comprises no more than 2% total impurities after storage for a period of at least about one month at a temperature of at least about 40° C. In another aspect, disclosed herein is a method of treating at least one of anaphylaxis, anaphylactic shock, a severe allergic reaction, or bronchial constriction, comprising administering or delivering to a subject in need thereof the pharmaceutical spray formulation, wherein the pharmaceutical spray formulation comprises: (c) from about 1% to about 25% (w/w) of epinephrine, or a pharmaceutically acceptable salt thereof, in water, ethanol, propylene glycol, or a combination thereof; and (d) one or more of an antioxidant, an antimicrobial preservative, an isotonicity agent, an absorption enhancer, a viscosity modifier, or a buffering agent; wherein a therapeutic plasma concentration of epinephrine in the subject is achieved in less than 15 minutes following administration to the subject. In some embodiments, the absorption enhancer is diethylene glycol monoethyl ether. In some embodiments, the formulation comprises diethylene glycol monoethyl ether at a concentration from about 0.1% to about 5% (w/w). In some embodiments, the formulation comprises diethylene glycol monoethyl ether at a concentration of about 1% (w/w).

In another aspect, disclosed herein is a bi-dose nasal delivery device adapted for delivery of a pharmaceutical solution into a nostril of a subject, comprising: (a) the pharmaceutical solution configured as a pharmaceutical spray formulation comprising from about 1% to about 25% (w/w) of epinephrine, or a pharmaceutically acceptable salt thereof, in water, ethanol, propylene glycol, or a combination thereof; (b) a reservoir containing from about 125 μL to about 250 μL of the pharmaceutical solution; and wherein the bi-dose device is configured to administer the pharmaceutical solution into a nostril of a subject as two nasal sprays. In some embodiments, the device is a pre-primed device that is configured to be actuatable with one hand. In some embodiments, the device is configured to deliver about 100 μL of the pharmaceutical solution from the reservoir upon each actuation of the device. In some embodiments, the pH of the pharmaceutical solution is from about 4.0 to about 6.5. In some embodiments, one or more sprays take the shape of a round plume with an ovality ratio less than about 2.0. In some embodiments, the pharmaceutical solution comprises an antioxidant. In some embodiments, the antioxidant comprises sodium bisulfite or sodium metabisulfite at a concentration from about 0.01% to about 0.1% (w/w). In some embodiments, the pharmaceutical solution comprises an antimicrobial preservative. In some embodiments, the antimicrobial preservative comprises chlorobutanol or chlorobutanol hemihydrate at a concentration from about 0.1% to about 1% (w/w). In some embodiments, the pharmaceutical solution comprises an isotonicity agent. In some embodiments, the isotonicity agent comprises sodium chloride at a concentration from about 0.1% to about 1% (w/w). In some embodiments, the pharmaceutical solution comprises a viscosity modifier. In some embodiments, the viscosity modifier comprises hypromellose at a concentration from about 0.01% to about 0.2% (w/w). In some embodiments, the pharmaceutical solution comprises a buffering agent. In some embodiments, wherein the buffering agent comprises citric acid or citric acid monohydrate at a concentration from about 0.1% to about 1% (w/w). In some embodiments, the pharmaceutical solution comprises about 2% or about 5% (w/w) of epinephrine, or a pharmaceutically acceptable salt thereof. In another aspect, disclosed herein is a pre-primed device adapted for delivery of a pharmaceutical solution into one or both nostrils of a subject, comprising a reservoir containing from about 125 μL to about 250 μL of the pharmaceutical solution, wherein the pharmaceutical solution comprises: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the pre-primed device is configured to administer the pharmaceutical solution as one or more sprays into one or both nostrils of the subject. In some embodiments, the formulation comprises diethylene glycol monoethyl ether at a concentration from about 0.1% to about 5% (w/w). In another aspect, disclosed herein is a bi-dose device adapted for delivery of a pharmaceutical solution into one or both nostrils of a subject, comprising a reservoir containing from about 125 µL to about 250 µL of the pharmaceutical solution, wherein the pharmaceutical solution comprises: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the pharmaceutical solution is stable for a period of at least about one month at a temperature of at least about 20° C. In some embodiments, the pharmaceutical solution is stable for a period of at least about three months at a temperature of at least about 20° C.

In another aspect, disclosed herein is a method of administering a pharmaceutical solution, comprising delivering a spray of the pharmaceutical solution from a device into a nostril of a subject in need thereof in a manner that delivers the pharmaceutical solution in a round spray plume with an ovality ratio less than about 1.4 when measured at a distance of from about 1 to about 10 cm from the device, wherein: (i) the device is adapted for nasal delivery; (ii) a volume of from about 20 µL to about 250 µL of spray is delivered; and (iii) the pharmaceutical solution comprises from about 0.5 mg to about 100 mg of epinephrine, or a pharmaceutically acceptable salt thereof. In some embodiments, the spray plume has a particle size distribution with a span of no more than about 2.2 when measured at a distance of from about 1 to about 10 cm from the device. In some embodiments, the spray plume has a Dmax of less than about 28 mm when measured at a distance of from about 1 to about 10 cm from the device. In some embodiments, the device is a bi-dose device configured to deliver two sprays of the pharmaceutical solution. In some embodiments, the device has a single reservoir containing from about 125 µL to about 250 µL of the pharmaceutical solution. In some embodiments, the device comprises a plunger that houses a container closure comprising: (i) a vial comprising an opening; (ii) a cannula; and (iii) a rubber stopper; wherein the stopper is configured to occlude the opening of the vial, and wherein the cannula is configured such that the cannula can pierce the stopper when the plunger applies sufficient force to the cannula. In some embodiments, the device is a pre-primed device that is configured to be actuatable with one hand. In some embodiments, a delivery time of the pharmaceutical solution is less than about 25 seconds. In some embodiments, the subject is suffering from a severe allergic reaction from exposure or suspected exposure to an allergen. In some embodiments, the allergen is food, medication, or an insect bite or sting. In some embodiments, the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, or vomiting. In some embodiments, the subject exhibits respiratory depression or distress, or cardiovascular depression. In some embodiments, the subject is free from respiratory depression or distress for at least about 1 hour following treatment comprising delivery of a therapeutically effective amount of the epinephrine, or a pharmaceutically acceptable salt thereof.

In another aspect, disclosed herein is a method of administering a pharmaceutical solution, comprising delivering a spray of the pharmaceutical solution from a device into a nostril of a subject in need thereof in a manner that delivers the pharmaceutical solution in a spray plume with a particle size distribution having a span of no more than about 2.2 when measured at a distance of from about 1 to about 10 cm from the device, wherein: (i) the device is adapted for nasal delivery; (ii) a volume of from about 20 µL to about 250 µL of spray is delivered; and (iii) the pharmaceutical solution comprises from about 0.5 mg to about 100 mg of epinephrine, or a pharmaceutically acceptable salt thereof. In some embodiments, the particle size distribution has a span of no more than about 2.0 when measured at a distance of from about 1 to about 10 cm from the device. In some embodiments, the device has a single reservoir containing from about 125 µL to about 250 µL of the pharmaceutical solution. In some embodiments, the device is a bi-dose device configured to deliver two sprays of the pharmaceutical solution from a single reservoir. In another aspect, disclosed herein is a method for administering a pharmaceutical solution, comprising delivering a spray of the pharmaceutical solution from a device into a nostril of a subject in need thereof in a manner that delivers the pharmaceutical solution in a spray plume with a Dmax of less than about 28 mm when measured at a distance of from about 1 to about 10 cm from the device, wherein: (i) the device is adapted for nasal delivery; (ii) a volume of from about 20 µL to about 250 µL of spray is delivered; and (iii) the pharmaceutical solution comprises from about 0.5 mg to about 100 mg of epinephrine, or a pharmaceutically acceptable salt thereof. In some embodiments, the device is a bi-dose device configured to deliver two sprays of the pharmaceutical solution. In some embodiments, the Dmax is less than about 26 mm when measured at a distance of from about 1 to about 10 cm from the device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present subject matter will be obtained by reference to the following detailed description that sets forth illustrative embodiments and the accompanying drawings.

DETAILED DESCRIPTION

Figure 1:
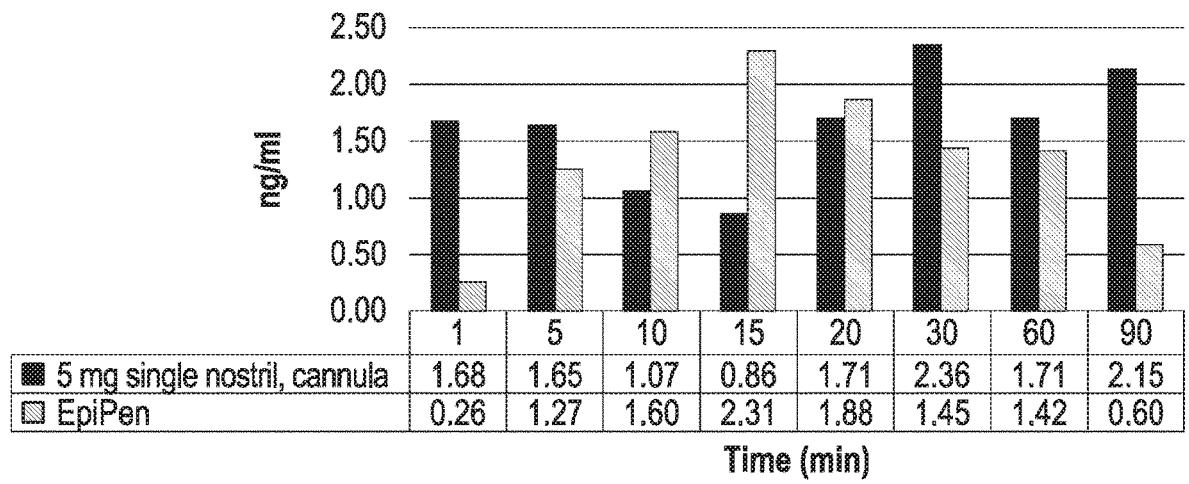
FIG. 1 depicts plasma concentrations of epinephrine in dogs dosed with 5 mg in a single nostril of a formulation described in Example 3 (Formulation 2) versus plasma concentrations of epinephrine in dogs dosed with EpiPen Adult (0.3 mg/mL).

Provided herein are, for example, pharmaceutical spray formulations of epinephrine for treating anaphylaxis. Also provided herein are, for example, methods of treating anaphylaxis, anaphylactic shock, and/or a severe allergic reaction, or at least one symptom thereof.

I. Definitions

The abbreviations used herein have their conventional meaning within the chemical and biological arts. The chemical structures and formulae set forth herein are constructed according to the standard rules of chemical valency known in the chemical arts.

The terms "about" or "approximately" as used herein, when referring to a numerical value or range, allow for a degree of variability in the value or range, for example, within 10%, or within 5% of a stated value or of a stated limit of a range.

The term "actuation," as used herein, refers to operation of the device such that the pharmaceutical composition is delivered therefrom.

The term "AUC," as used herein, refers to the area under the drug (e.g., epinephrine) plasma concentration-time curve. The term "$AUG_{0-t}$," as used herein, refers to the area under the drug plasma concentration-time curve from t=0 to the last measurable concentration. The term "$AUG_{0-\infty}$," as used herein, refers to the area under the drug plasma concentration-time curve extrapolated to $\infty$.

The term "bioavailability (F)," as used herein, refers to the fraction of a dose of drug (e.g., epinephrine) that is absorbed from its site of administration and reaches, in an unchanged form, the systemic circulation. The term "absolute bioavailability" is used when the fraction of absorbed drug is related to its I.V. bioavailability. It may be calculated using the following formula:

$$F = \frac{AUC_{extravascular}}{AUC_{intravenous}} \times \frac{Dose_{intravenous}}{Dose_{extravascular}}$$

The term relative bioavailability ($F_{rel}$) is used to compare two different extravascular routes of drug administration and it may be calculated using the following formula:

$$F_{rel} = \frac{AUC_{extravascular\ 1}}{AUC_{extravascular\ 2}} \times \frac{Dose_{extravascular\ 2}}{Dose_{Extravascular\ 1}}$$

The term "clearance (CL)," as used herein, refers to the rate at which a drug is eliminated divided by its plasma concentration, giving a volume of plasma from which drug is completely removed per unit of time. CL is equal to the elimination rate constant ($\lambda$) multiplied by the volume of distribution ($V_d$), wherein "$V_d$" is the fluid volume that would be required to contain the amount of drug present in the body at the same concentration as in the plasma. The term "apparent clearance (CL/F)," as used herein, refers to clearance that does not take into account the bioavailability of the drug. It is the ratio of the dose over the AUC.

The term "$C_{max}$," as used herein, refers to the maximum observed plasma concentration.

The term "coefficient of variation (CV)," as used herein, refers to the ratio of the sample standard deviation to the sample mean. It is often expressed as a percentage.

The term "confidence interval," as used herein, refers to a range of values which will include the true average value of a parameter a specified percentage of the time.

The term "device," as used herein, refers to an apparatus capable of delivering a drug to patient in need thereof.

The term "delivery time," as used herein, refers to the amount of time that elapses between a determination made by a healthcare professional, or an untrained individual that an individual is in need of nasal delivery of epinephrine and completion of the delivery.

The term "elimination rate constant ($\lambda$)," as used herein, refers to the fractional rate of drug removal from the body. This rate is constant in first-order kinetics and is independent of drug concentration in the body. $\lambda$ is the slope of the plasma concentration-time line (on a logarithmic y scale). The term "$\lambda_z$," as used herein, refers to the terminal phase elimination rate constant, wherein the "terminal phase" of the drug plasma concentration-time curve is a straight line when plotted on a semi-logarithmic graph. The terminal phase is often called the "elimination phase" because the primary mechanism for decreasing drug concentration during the terminal phase is drug elimination from the body. The distinguishing characteristic of the terminal elimination phase is that the relative proportion of drug in the plasma and peripheral volumes of distribution remains constant. During this "terminal phase" drug returns from the rapid and slow distribution volumes to the plasma, and is permanently removed from the plasma by metabolism or renal excretion.

The term "epinephrine," as used herein, refers to a compound of the following structure:

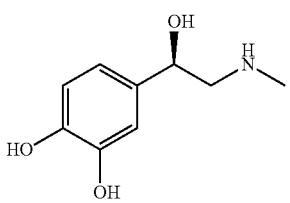

or a pharmaceutically acceptable salt, hydrate, or solvate thereof. The CAS registry number for epinephrine is 51-43-4. Other names for epinephrine include, but are not limited to, (R)-4-(1-hydroxy-2-(methylamino)ethyl)benzene-1,2-diol and adrenaline.

The term "nostril," as used herein, is synonymous with "naris."

The terms "permeation enhancer", "permeability enhancer", "absorption enhancer", and "penetration enhancer," as disclosed herein, are intended to be equivalent, all four referring to an agent which aids in delivering and/or increasing bioavailability and $C_{max}$ of a compound through a mucosal barrier, such as through the nasal mucosa. Permeation or absorption enhancers suitable for use in the present invention include, but are not limited to, caprylic acid, oleic acid, polysorbate 80, menthol, EDTA, sodium edetate, cetylpyridinium chloride, sodium lauryl sulfate, citric acid, sodium desoxycholate, sodium deoxyglycolate, glyceryl oleate, L-lysine, diethylene glycol monoethyl ether, α- β- or γ-cyclodextrin, hydroxypropyl β-cyclodextrin, phosphatidylcholine, and combinations thereof. In some cases, the absorption enhancer comprises diethylene glycol monoethyl ether. In some cases, use of absorption enhancers can reduce $T_{max}$. In some cases, use of absorption enhancers decreases the time within which a given plasma concentration of the active ingredient is achieved following administration. Absorption enhancers may be used to increase the AUC of the active ingredient.

The term "stabilizer" and "stabilizing agent" are intended to be equivalent and refer to a chemical that is used to prevent degradation. Examples of stabilizers or stabilizing agents include, but are not limited to, butylated hydroxyanisole (BHA), butylated hydroxytoluene (BHT), ascorbic acid, methionine, sodium ascorbate, sodium thiosulfate, sodium bisulfite, sodium metabisulfite, ascorbyl palmitate, thioglycerol, alpha tocopherol (vitamin E), cysteine hydrochloride, citric acid, ethylenediaminetetraacetic acid ("EDTA"), sodium citrate, propyl gallate, 8-hydroxyquinoline, boric acid, histidine, vitamin A, and combinations thereof.

The term "viscosity modifier" refers to a product or combination of products designed to change the thickness or texture of pharmaceutical ingredients or formulations. Viscosity modifiers can include such products as thickeners, texturizers, gelation agents and stiffening agents. Examples of viscosity modifiers include, but are not limited to, polyethylene glycol, methylcellulose, hypromellose, polyvinylpyrrolidone, carboxymethyl cellulose, hydroxypropylmethyl cellulose ("HPMC"), methyl cellulose, hydroxyethyl cellulose, glycerin, polyvinyl alcohol, xanthan gum, chitosan, alginate, and combinations thereof.

Solvents suitable for use in the present invention include, but are not limited to, water, ethanol, glycerin, propylene glycol, polyethylene glycol 400 and combinations thereof.

The term "pre-primed," as used herein, refers to a device, such as a nasal spray which is capable of delivering a pharmaceutical composition to a patient in need thereof with the first actuation of the spray pump, i.e., without the need to prime the pump prior to dosing, such as by actuating the pump one or more times until a spray appears.

The term "recovery position," as used herein, means a position of the human body in which a patient lies on his/her side, with a leg or knee out in front (e.g., to prevent rolling onto his/her stomach) and at least one hand supporting the head (e.g., to elevate the face to facilitate breathing and prevent inhalation of vomit).

The term "storage-stable," as used herein, refers to a pharmaceutical composition in which at least about 95%—for example at least about 99.5%—of the active ingredient remains in an undegraded state after storage of the pharmaceutical composition at specified temperature and humidity for a specified time, for example, for 12 months at 25° C. and 60% relative humidity.

The term "supine," as used herein, refers to a patient who is lying face up.

The term "$t_{1/2}$" or "half-life," as used herein, refers to the amount of time required for half of a drug to be eliminated from the body or the time required for a drug concentration to decline by half.

The terms "tonicity agent" and "isotonicity agent" as used herein are interchangeable and refer to a compound which modifies the osmolality of a formulation, for example, to render it isotonic. Tonicity agents include, but are not limited to, dextrose, lactose, sodium chloride, calcium chloride, magnesium chloride, sorbitol, sucrose, mannitol, trehalose, raffinose, polyethylene glycol, hydroxyethyl starch, glycine and the like.

The term "$t_{max}$," as used herein, refers to the time from administration of the pharmaceutical compositions described herein to maximum drug plasma concentration.

Liquid nasal formulations are mainly aqueous solutions, but suspensions and emulsions can also be delivered. In traditional spray pump systems, antimicrobial preservatives are typically required to maintain microbiological stability in liquid formulations.

The droplet size distribution of a nasal spray influences the in vivo deposition of the drug in the nasal cavity. The droplet size is influenced by the actuation parameters of the device and the formulation. In some embodiments, the median droplet size is from about 30 to about 100 If the droplets are too large (e.g., greater than about 120 μm), deposition takes place mainly in the anterior parts of the nose, and if the droplets are too small (e.g., less than about 10 μm), they can possibly be inhaled and reach the lungs.

Spray characterization (e.g., plume geometry, spray pattern, pump delivery, droplet size distribution, DSD) of the delivered plume subsequent to spraying may be measured under specified experimental and instrumental conditions by appropriate and validated and/or calibrated analytical procedures known in the art. These include photography, laser diffraction, and impaction systems (cascade impaction, next generation impaction (NGI), etc.). Droplet size distribution can be controlled in terms of ranges for the D10, D50, D90, span [(D90-D10)/D50], and percentage of droplets less than 10 mm. In some embodiments, the formulation will have a narrow DSD. In some embodiments, the formulation will have a Dv(50) of 30-70 μm and a Dv(90)<120 The particle diameter "(D)" designations refer to the representative diameter where 10% (D10), 50% (D50) and 90% (D90) of the total volume of the liquid sprayed is made up of droplets with diameters smaller than or equal to the stated value. The spray characteristics can refer to a mean (average) or median value collected for a plurality of sprays. The plurality of sprays can be at least 2, 3, 4, 5, 6, 7, 8, 9 or 10 or more sprays.

All percent compositions are given as weight-percentages, unless otherwise stated.

All average molecular weights of polymers are weight-average molecular weights, unless otherwise specified.

As used herein, "subject" or "patient" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds. Terms "subject" and "patient" are synonymous and refer, but are not limited to, a person that is experiencing type I allergies including anaphylaxis. "Patient" or "subject in need thereof" refers to a living organism suffering from or prone to a disease or condition that can be treated by administration of a pharmaceutical composition as provided herein. In some embodiments, a patient is human.

The terms "disease," "disorder," or "condition" are used interchangeably and refer to a state of being or health status of a patient or subject capable of being treated with the compounds or methods provided herein. The disease may be anaphylaxis. The disease may be a severe allergic reaction, and the like. The disease may be a cancer. The disease may be an autoimmune disease. The disease may be an inflammatory disease. The disease may be an infectious disease.

As used herein, "type I reactions," type I allergies," and "severe allergic reactions" are used interchangeably (i.e., immediate hypersensitivity reactions) and refer to the involvement of immunoglobulin E (IgE)-mediated release of histamine and other mediators from mast cells and basophils. Examples include, but are not limited to, anaphylaxis, an anaphylactic reaction, anaphylactic shock and allergic rhinoconjunctivitis. Severe allergic reactions are caused by allergens. Non-limiting examples of allergens include an insect bite (for example a bee sting), medication (for example an antibiotic such as a penicillin), food (such as eggs, nuts, or shellfish), and a chemical (for example latex).

As used herein, "free of propellant" refers to a formulation that is not administered using compressed gas.

The terms "spray" and "mist" are used interchangeably herein and refer to liquid (e.g., a formulation for intranasal administration) that is blown or driven through the air in the form of drops or droplets.

As used herein, all numerical values relating to amounts, weights, and the like, that are defined as "about" or "approximately" each particular value is plus or minus 10%. For example, the phrase "about 10% w/w" is to be understood as "9% w/w to 11% w/w." Therefore, amounts within 10% of the claimed value are encompassed by the scope of the claims.

As used herein "% w/w" and "percent w/w" refer to the percent weight of the total formulation.

As used herein the term "effective amount" refers to the amount necessary to treat a patient in need thereof.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In some embodiments, treating is preventing. In some embodiments, treating does not include preventing. In some embodiments, "treat," "treating," or "treatment" refer to ameliorating or inhibiting symptoms of type I allergies including anaphylaxis.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., throat or tongue swelling, itchy rash, shortness of breath, low blood pressure, inflammation, bronchoconstriction, etc.), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In some embodiments, prevent refers to slowing the progression of the disease, disorder or condition or inhibiting progression thereof to a harmful or otherwise undesired state.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means administration by inhalation or intranasal administration. The term "intranasal" refers to administration of the composition to any portion of the nasal epithelium.

Administering may also mean oral administration, administration as a suppository, topical contact, intravenous, parenteral, intraperitoneal, intramuscular, intralesional, intrathecal, intracranial, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-inflammatory agent). The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation). Liquid form preparations include solutions, suspensions, and emulsions. In some embodiments, the compositions are water or water/propylene glycol solutions. The compositions of the present invention may additionally include components to provide sustained release and/or comfort.

By "co-administer" it is meant that a composition described herein is administered at the same time, just prior to, or just after the administration of one or more additional therapies. The compounds of the disclosure can be administered alone or can be co-administered to the patient. Co-administration is meant to include simultaneous or sequential administration of the compounds individually or in combination (more than one compound).

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

"Anti-inflammatory agent" is used in accordance with its plain ordinary meaning and refers to a composition (e.g. compound, drug, antagonist, inhibitor, modulator) used in any way to reduce inflammation or swelling. In some embodiments, an anti-inflammatory agent is an agent identified herein having utility in methods of treating an inflammatory disease or disorder. In some embodiments, an anti-inflammatory agent is an agent approved by the FDA or similar regulatory agency of a country other than the USA, for reducing swelling and inflammation.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

As used herein the term "anaphylaxis" refers to an allergic reaction involving multiple organ systems in a subject upon contact with an allergen whether or not that allergen is identifiable.

As used herein the term "allergen" refers to any chemical capable of causing an immune system response in a subject including, but not limited to, chemicals found in drugs, food, plants, insect bites, and insect stings.

As used herein the term "pharmaceutically acceptable" refers to ingredients that are not biologically or otherwise undesirable for administration to a living subject.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In some embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

In some embodiments, epinephrine salts may include citrate, hydrochloride, sulfate, tartrate, phosphate, acetate, malate, maleate, succinate, ascorbate, carbonate, mesylate, and lactate salts. One of skill in the art could use other pharmaceutically acceptable epinephrine salts in the formulations disclosed herein.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of a compound to and absorption by a subject and can be included in the compositions of the present disclosure without causing a significant adverse toxicological effect on the patient. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure. Examples of preservatives include, but are not limited to, butyl paraben, methyl paraben, ethyl paraben, propyl paraben, sodium benzoate, chlorobutanol, benzalkonium chloride, benzoic acid and combinations thereof.

It is understood that the examples and embodiments described herein are for illustrative purposes only and that various modifications or changes in light thereof will be suggested to persons skilled in the art and are to be included within the spirit and purview of this application and scope of the appended claims.

II. Compositions

In an aspect provided herein, is a pharmaceutical spray formulation. In some embodiments, the pharmaceutical spray formulation comprises epinephrine, or a pharmaceutically acceptable salt of epinephrine, in water, ethanol, propylene glycol, or a combination thereof. In some embodiments, the pH of the pharmaceutical spray formulation is about 3.5 to about 6.5.

In some aspects, the pharmaceutical spray formulation comprises an active ingredient. In some embodiments, the active ingredient is epinephrine. In some embodiments, the pharmaceutical spray formulation comprises from about 0.5% to about 25% w/w of epinephrine. In some embodiments, the pharmaceutical spray formulation comprises from about 0.5% to about 20% w/w of epinephrine. In some embodiments, the pharmaceutical spray formulation comprises from about 0.5% to about 10% w/w of epinephrine. In some embodiments, the pharmaceutical spray formulation comprises from about 1.0% to about 25% w/w of epinephrine. In some embodiments, the pharmaceutical spray formulation comprises from about 1.0% to about 20% w/w of epinephrine. In some embodiments, the pharmaceutical spray formulation comprises from about 1.0% to about 10% w/w of epinephrine. In some embodiments, the pharmaceutical spray formulation comprises from about 2.0% to about 25% w/w of epinephrine. In some embodiments, the pharmaceutical spray formulation comprises from about 2.0% to about 20% w/w of epinephrine. In some embodiments, the pharmaceutical spray formulation comprises from about 2.0% to about 10% w/w of epinephrine. In some embodiments, the pharmaceutical spray formulation comprises from about 3.0% to about 25% w/w of epinephrine. In some embodiments, the pharmaceutical spray formulation comprises from about 3.0% to about 20% w/w of epinephrine. In some embodiments, the pharmaceutical spray formulation comprises from about 3.0% to about 10% w/w of epinephrine. In some embodiments, the pharmaceutical spray formulation comprises from about 4.0% to about 25% w/w of epinephrine. In some embodiments, the pharmaceutical spray formulation comprises from about 4.0% to about 20% w/w of epinephrine. In some embodiments, the pharmaceutical spray formulation comprises from about 4.0% to about 25% w/w of epinephrine. In some embodiments, the pharmaceutical spray formulation comprises from about 4.0% to about 20% w/w of epinephrine. In some embodiments, the pharmaceutical spray formulation comprises from about 4.0% to about 10% w/w of epinephrine. In some embodiments, the pharmaceutical spray formulation comprises from about 5.0% to about 25% w/w of epinephrine. In some embodiments, the pharmaceutical spray formulation comprises from about 5.0% to about 20% w/w of epinephrine. In some embodiments, the pharmaceutical spray formulation comprises from about 5.0% to about 10% w/w of epinephrine. In some embodiments, the pharmaceutical spray formulation comprises from about 0.5% to about 5% w/w of epinephrine. In some embodiments, the pharmaceutical spray formulation comprises from about 1.0% to about 5% w/w of epinephrine. In some embodiments, the pharmaceutical spray formulation comprises from about 2.0% to about 5% w/w of epinephrine. In some embodiments, the pharmaceutical spray formulation comprises about 0.5% w/w of epinephrine. In some embodiments, the pharmaceutical spray formulation comprises about 0.5% w/w of epinephrine. In some embodiments, the pharmaceutical spray formulation comprises about 1% w/w of epinephrine. In some embodiments, the pharmaceutical spray formulation comprises about 1.5% w/w of epinephrine. In some embodiments, the pharmaceutical spray formulation comprises about 2% w/w of epinephrine. In some embodiments, the pharmaceutical spray formulation comprises about 2.5% w/w of epinephrine. In some embodiments, the pharmaceutical spray formulation comprises about 3% w/w of epinephrine. In some embodiments, the pharmaceutical spray formulation comprises about 3.5% w/w of epinephrine. In some embodiments, the pharmaceutical spray formulation comprises about 4% w/w of epinephrine. In some embodiments, the pharmaceutical spray formulation comprises about 4.5% w/w of epinephrine. In some embodiments, the pharmaceutical spray formulation comprises about 5% w/w of epinephrine. In some embodiments, the pharmaceutical spray formulation comprises about 6.5% w/w of epinephrine. In some embodiments, the pharmaceutical spray formulation comprises about 7% w/w of epinephrine. In some embodiments, the pharmaceutical spray formulation comprises about 7.5% w/w of epinephrine. In some embodiments, the pharmaceutical spray formulation comprises about 8% w/w of epinephrine. In some embodiments, the pharmaceutical spray formulation comprises about 8.5% w/w of epinephrine. In some embodiments, the pharmaceutical spray formulation comprises about 9% w/w of epinephrine. In some embodiments, the pharmaceutical spray formulation comprises about 9.5% w/w of epinephrine. In some embodiments, the pharmaceutical spray formulation comprises about 10% w/w of epinephrine. In some embodiments, the pharmaceutical spray formulation comprises about 10.5% w/w of epinephrine. In some embodiments, the pharmaceutical spray formulation comprises about 11% w/w of epinephrine. In some embodiments, the pharmaceutical spray formulation comprises about 11.5% w/w of epinephrine. In some embodiments, the pharmaceutical spray formulation comprises about 12% w/w of epinephrine. In some embodiments, the pharmaceutical spray formulation comprises about 12.5% w/w of epinephrine. In some embodiments, the pharmaceutical spray formulation comprises about 13% w/w of epinephrine. In some embodiments, the pharmaceutical spray formulation comprises about 13.5% w/w of epinephrine. In some embodiments, the pharmaceutical spray formulation comprises about 14% w/w of epinephrine. In some embodiments, the pharmaceutical spray formulation comprises about 14.5% w/w of epinephrine. In some embodiments, the pharmaceutical spray formulation comprises about 15% w/w of epinephrine. In some embodiments, the pharmaceutical spray formulation comprises about 15.5% w/w of epinephrine. In some embodiments, the pharmaceutical spray formulation comprises about 16% w/w of epinephrine. In some embodiments, the pharmaceutical spray formulation comprises about 16.5% w/w of epinephrine. In some embodiments, the pharmaceutical spray formulation comprises about 17% w/w of epinephrine. In some embodiments, the pharmaceutical spray formulation comprises about 17.5% w/w of epinephrine. In some embodiments, the pharmaceutical spray formulation comprises about 18% w/w of epinephrine. In some embodiments, the pharmaceutical spray formulation comprises about 18.5% w/w of epinephrine. In some embodiments, the pharmaceutical spray formulation comprises about 19% w/w of epinephrine. In some embodiments, the pharmaceutical spray formulation comprises about 19.5% w/w of epinephrine. In some embodiments, the pharmaceutical spray formulation comprises about 20% w/w of epinephrine. In some embodiments, the pharmaceutical spray formulation comprises about 21% w/w of epinephrine. In some embodiments, the pharmaceutical spray formulation comprises about 22% w/w of epinephrine. In some embodiments, the pharmaceutical spray formulation comprises about 23% w/w of epinephrine. In some embodiments, the pharmaceutical spray formulation comprises about 24% w/w of epinephrine. In some embodiments, the pharmaceutical spray formulation comprises about 25% w/w of epinephrine.

In an aspect provided herein, is a stable pharmaceutical spray formulation, comprising:
(i) from about 1% to about 25% w/w of epinephrine, or a pharmaceutically acceptable salt thereof, in water, ethanol, propylene glycol, or a combination thereof; and
(ii) one or more excipients, vehicles, emulsifiers, stabilizing agents, preservatives, mucosal adhesives, antibacterial agents, buffers, and/or other additives, wherein the formulation is stable at a temperature of at least about 20° C. and at a relative humidity of at least about 30%, and wherein the formulation is stable for a period of at least about two months.

In an aspect provided herein, is a stable pharmaceutical spray formulation, comprising:
(iii) from about 1% to about 10% w/w of epinephrine, or a pharmaceutically acceptable salt thereof, in water, ethanol, propylene glycol, or a combination thereof; and
(iv) one or more excipients, vehicles, emulsifiers, stabilizing agents, preservatives, mucosal adhesives, antibacterial agents, buffers, and/or other additives, wherein the formulation is stable at a temperature of at least about 20° C. and at a relative humidity of at least about 30%, and wherein the formulation is stable for a period of at least about two months.

In some embodiments, the pharmaceutical spray formulation is stable at a temperature of at least about 25° C. In some embodiments, the pharmaceutical spray formulation is stable at a temperature of at least about 30° C. In some embodiments, the pharmaceutical spray formulation is stable at a temperature of at least about 35° C. In some embodiments, the pharmaceutical spray formulation is stable at a temperature of at least about 40° C. In some embodiments, the pharmaceutical spray formulation is stable at a temperature of at least about 45° C.

In some embodiments, the pharmaceutical spray formulation is stable at a relative humidity of at least about 40%. In some embodiments, the pharmaceutical spray formulation is stable at a relative humidity of at least about 50%. In some embodiments, the pharmaceutical spray formulation is stable at a relative humidity of at least about 60%. In some embodiments, the pharmaceutical spray formulation is stable at a relative humidity of at least about 70%. In some embodiments, the pharmaceutical spray formulation is stable at a relative humidity of at least about 80%.

In some embodiments, the pharmaceutical spray formulation is stable for a period of at least about six months. In some embodiments, the pharmaceutical spray formulation is stable for a period of at least about 12 months. In some embodiments, the pharmaceutical spray formulation is stable for a period of at least about 18 months. In some embodiments, the pharmaceutical spray formulation is stable for a period of at least about 24 months. In some embodiments, the pharmaceutical spray formulation is stable for a period of at least about 30 months. In some embodiments, the pharmaceutical spray formulation is stable for a period of at least about 36 months.

Viscosity Modifiers

In some embodiments, the pharmaceutical spray formulation comprises a viscosity modifier. Viscosity modifiers can include such products as thickeners, texturizers, gelation agents and stiffening agents. In some embodiments, the viscosity modifier is polyethylene glycol, methylcellulose, hypromellose, polyvinylpyrrolidone, carboxymethyl cellulose, hydroxypropylmethyl cellulose ("HPMC"), methyl cellulose, hydroxyethyl cellulose, glycerin, polyvinyl alcohol, xanthan gum, chitosan, alginate, or any combinations thereof. In some embodiments, the viscosity modifier is polyethylene glycol. In some embodiments, the viscosity modifier is methylcellulose. In some embodiments, the viscosity modifier is hypromellose. In some embodiments, the viscosity modifier is polyvinylpyrrolidone. In some embodiments, the viscosity modifier is carboxymethyl cellulose. In some embodiments, the viscosity modifier is hydroxypropylmethyl cellulose. In some embodiments, the viscosity modifier is methyl cellulose. In some embodiments, the viscosity modifier is hydroxyethyl cellulose. In some embodiments, the viscosity modifier is glycerin. In some embodiments, the viscosity modifier is polyvinyl alcohol. In some embodiments, the viscosity modifier is xanthan gum. In some embodiments, the viscosity modifier is chitosan. In some embodiments, the viscosity modifier is alginate.

In some embodiments, the pharmaceutical spray formulation comprises about 0.001% (w/w) to about 1% (w/w) of a viscosity modifier. In some embodiments, the pharmaceutical spray formulation comprises about 0.001% (w/w) to about 0.5% (w/w) of a viscosity modifier. In some embodiments, the pharmaceutical spray formulation comprises about 0.001% (w/w) to about 1% (w/w) of a viscosity modifier. In some embodiments, the pharmaceutical spray formulation comprises about 0.01% (w/w) to about 1% (w/w) of a viscosity modifier. In some embodiments, the pharmaceutical spray formulation comprises about 0.01% (w/w) to about 0.5% (w/w) of a viscosity modifier. In some embodiments, the pharmaceutical spray formulation comprises about 0.1% (w/w) of a viscosity modifier. In some embodiments, the pharmaceutical spray formulation comprises at least about 0.001% (w/w), at least about 0.01% (w/w), or at least about 0.1% (w/w), and/or no more than about 5% (w/w), no more than about 1% (w/w), no more than about 0.5% (w/w), no more than about 0.4% (w/w), no more than about 0.3% (w/w), no more than about 0.2% (w/w), or no more than about 0.1% (w/w) of a viscosity modifier.

In some embodiments, the pharmaceutical spray formulation comprises a viscosity modifier at a concentration of about 0.001% (w/w) to about 2% (w/w). In some embodiments, the pharmaceutical spray formulation comprises a viscosity modifier at a concentration of at least about 0.001% (w/w). In some embodiments, the pharmaceutical spray formulation comprises a viscosity modifier at a concentration of at most about 2% (w/w). In some embodiments, the pharmaceutical spray formulation comprises a viscosity modifier at a concentration of about 0.001% (w/w) to about 0.01% (w/w), about 0.001% (w/w) to about 0.05% (w/w), about 0.001% (w/w) to about 0.06% (w/w), about 0.001% (w/w) to about 0.07% (w/w), about 0.001% (w/w) to about 0.08% (w/w), about 0.001% (w/w) to about 0.09% (w/w), about 0.001% (w/w) to about 0.1% (w/w), about 0.001% (w/w) to about 0.5% (w/w), about 0.001% (w/w) to about 1% (w/w), about 0.001% (w/w) to about 1.5% (w/w), about 0.001% (w/w) to about 2% (w/w), about 0.01% (w/w) to about 0.05% (w/w), about 0.01% (w/w) to about 0.06% (w/w), about 0.01% (w/w) to about 0.07% (w/w), about 0.01% (w/w) to about 0.08% (w/w), about 0.01% (w/w) to about 0.09% (w/w), about 0.01% (w/w) to about 0.1% (w/w), about 0.01% (w/w) to about 0.5% (w/w), about 0.01% (w/w) to about 1% (w/w), about 0.01% (w/w) to about 1.5% (w/w), about 0.01% (w/w) to about 2% (w/w), about 0.05% (w/w) to about 0.06% (w/w), about 0.05% (w/w) to about 0.07% (w/w), about 0.05% (w/w) to about 0.08% (w/w), about 0.05% (w/w) to about 0.09% (w/w), about 0.05% (w/w) to about 0.1% (w/w), about 0.05% (w/w) to about 0.5% (w/w), about 0.05% (w/w) to about 1% (w/w), about 0.05% (w/w) to about 1.5% (w/w), about 0.05% (w/w) to about 2% (w/w), about 0.06% (w/w) to about 0.07% (w/w), about 0.06% (w/w) to about 0.08% (w/w), about 0.06% (w/w) to about 0.09% (w/w), about 0.06% (w/w) to about 0.1% (w/w), about 0.06% (w/w) to about 0.5% (w/w), about 0.06% (w/w) to about 1% (w/w), about 0.06% (w/w) to about 1.5% (w/w), about 0.06% (w/w) to about 2% (w/w), about 0.07% (w/w) to about 0.08% (w/w), about 0.07% (w/w) to about 0.09% (w/w), about 0.07% (w/w) to about 0.1% (w/w), about 0.07% (w/w) to about 0.5% (w/w), about 0.07% (w/w) to about 1% (w/w), about 0.07% (w/w) to about 1.5% (w/w), about 0.07% (w/w) to about 2% (w/w), about 0.08% (w/w) to about 0.09% (w/w), about 0.08% (w/w) to about 0.1% (w/w), about 0.08% (w/w) to about 0.5% (w/w), about 0.08% (w/w) to about 1% (w/w), about 0.08% (w/w) to about 1.5% (w/w), about 0.08% (w/w) to about 2% (w/w), about 0.09% (w/w) to about 0.1% (w/w), about 0.09% (w/w) to about 0.5% (w/w), about 0.09% (w/w) to about 1% (w/w), about 0.09% (w/w) to about 1.5% (w/w), about 0.09% (w/w) to about 2% (w/w), about 0.1% (w/w) to about 0.5% (w/w), about 0.1% (w/w) to about 1% (w/w), about 0.1% (w/w) to about 1.5% (w/w), about 0.1% (w/w) to about 2% (w/w), about 0.5% (w/w) to about 1% (w/w), about 0.5% (w/w) to about 1.5% (w/w), about 0.5% (w/w) to about 2% (w/w), about 1% (w/w) to about 1.5% (w/w), about 1% (w/w) to about 2% (w/w), or about 1.5% (w/w) to about 2% (w/w). In some embodiments, the pharmaceutical spray formulation comprises a viscosity modifier at a concentration of about 0.001% (w/w), about 0.01% (w/w), about 0.05% (w/w), about 0.06% (w/w), about 0.07% (w/w), about 0.08% (w/w), about 0.09% (w/w), about 0.1% (w/w), about 0.5% (w/w), about 1% (w/w), about 1.5% (w/w), or about 2% (w/w). In some embodiments, the viscosity modifier is hypromellose.

In some embodiments, the pharmaceutical spray formulation has a viscosity of at least about 100 cP, at least about 250 cP, at least about 500 cP, at least about 750 cP, at least about 1000 cP, at least about 1250 cP, at least about 1500 cP, at least about 1750 cP, at least about 2000 cP, at least about 2250 cP, or at least about 2500 cP, and/or no more than about 100 cP, no more than about 250 cP, no more than about 500 cP, no more than about 750 cP, no more than about 1000 cP, no more than about 1250 cP, no more than about 1500 cP, no more than about 1750 cP, no more than about 2000 cP, no more than about 2250 cP, or no more than about 2500 cP.

In some embodiments, the pharmaceutical spray formulation has a viscosity of about 100 cP to about 2,500 cP. In some embodiments, the pharmaceutical spray formulation has a viscosity of at least about 100 cP. In some embodiments, the pharmaceutical spray formulation has a viscosity of at most about 2,500 cP. In some embodiments, the pharmaceutical spray formulation has a viscosity of about 100 cP to about 250 cP, about 100 cP to about 500 cP, about 100 cP to about 750 cP, about 100 cP to about 1,000 cP, about 100 cP to about 1,250 cP, about 100 cP to about 1,500 cP, about 100 cP to about 1,750 cP, about 100 cP to about 2,000 cP, about 100 cP to about 2,250 cP, about 100 cP to about 2,500 cP, about 250 cP to about 500 cP, about 250 cP to about 750 cP, about 250 cP to about 1,000 cP, about 250 cP to about 1,250 cP, about 250 cP to about 1,500 cP, about 250 cP to about 1,750 cP, about 250 cP to about 2,000 cP, about 250 cP to about 2,250 cP, about 250 cP to about 2,500 cP, about 500 cP to about 750 cP, about 500 cP to about 1,000 cP, about 500 cP to about 1,250 cP, about 500 cP to about 1,500 cP, about 500 cP to about 1,750 cP, about 500 cP to about 2,000 cP, about 500 cP to about 2,250 cP, about 500 cP to about 2,500 cP, about 750 cP to about 1,000 cP, about 750 cP to about 1,250 cP, about 750 cP to about 1,500 cP, about 750 cP to about 1,750 cP, about 750 cP to about 2,000 cP, about 750 cP to about 2,250 cP, about 750 cP to about 2,500 cP, about 1,000 cP to about 1,250 cP, about 1,000 cP to about 1,500 cP, about 1,000 cP to about 1,750 cP, about 1,000 cP to about 2,000 cP, about 1,000 cP to about 2,250 cP, about 1,000 cP to about 2,500 cP, about 1,250 cP to about 1,500 cP, about 1,250 cP to about 1,750 cP, about 1,250 cP to about 2,000 cP, about 1,250 cP to about 2,250 cP, about 1,250 cP to about 2,500 cP, about 1,500 cP to about 1,750 cP, about 1,500 cP to about 2,000 cP, about 1,500 cP to about 2,250 cP, about 1,500 cP to about 2,500 cP, about 1,750 cP to about 2,000 cP, about 1,750 cP to about 2,250 cP, about 1,750 cP to about 2,500 cP, about 2,000 cP to about 2,250 cP, about 2,000 cP to about 2,500 cP, or about 2,250 cP to about 2,500 cP. In some embodiments, the pharmaceutical spray formulation has a viscosity of about 100 cP, about 250 cP, about 500 cP, about 750 cP, about 1,000 cP, about 1,250 cP, about 1,500 cP, about 1,750 cP, about 2,000 cP, about 2,250 cP, or about 2,500 cP.

In an aspect provided herein, the pharmaceutical spray formulation further comprises a viscosity modifier. In some embodiments, the viscosity modifier is polyethylene glycol, methylcellulose, or hypromellose.

In some embodiments, the pharmaceutical spray formulation further comprises polyethylene glycol. In some embodiments, the pharmaceutical spray formulation further comprises from about 0.5% to about 50% polyethylene glycol.

In some embodiments, the pharmaceutical spray formulation further comprises methylcellulose. In some embodiments, the pharmaceutical spray formulation further comprises from about 0.001% to about 5% methylcellulose.

In some embodiments, the pharmaceutical spray formulation further comprises hypromellose. In some embodiments, the pharmaceutical spray formulation further comprises from about 0.001% to about 0.5% hypromellose. In some embodiments, the pharmaceutical spray formulation further comprises from about 0.05% to about 0.5% hypromellose. In some embodiments, the pharmaceutical spray formulation further comprises from about 0.05% to about 0.4% hypromellose. In some embodiments, the pharmaceutical spray formulation further comprises from about 0.05% to about 0.3% hypromellose. In some embodiments, the pharmaceutical spray formulation further comprises from about 0.05% to about 0.3% hypromellose. In some embodiments, the pharmaceutical spray formulation further comprises about 0.1% hypromellose.

Buffering Agents

In some embodiments, the pharmaceutical spray formulation comprises a buffering agent. In some embodiments, the buffering agent is citric acid, citrate, citric acid monohydrate, or any combination thereof. In some embodiments, the buffering agent is sodium phosphate or sodium citrate.

In some embodiments, the pH of the pharmaceutical spray formulation is about 3.5 to about 6.5. In some embodiments, the pH of the pharmaceutical spray formulation is about 3.5 to about 5.5. In some embodiments, the pH of the pharmaceutical spray formulation is about 3.5 to about 4.5. In some embodiments, the pH of the pharmaceutical spray formulation is about 4.0 to about 5.0. In some embodiments, the pH of the pharmaceutical spray formulation is about 4.5 to about 5.5. In some embodiments, the pH of the pharmaceutical spray formulation is about 4.5 to about 6.5. In some embodiments, the pH of the pharmaceutical spray formulation is about 5.5 to about 6.5. In some embodiments, the pH of the pharmaceutical spray formulation is about 3.5. In some embodiments, the pH of the pharmaceutical spray formulation is about 4. In some embodiments, the pH of the pharmaceutical spray formulation is about 4.5. In some embodiments, the pH of the pharmaceutical spray formulation is about 4.7. In some embodiments, the pH of the pharmaceutical spray formulation is about 5. In some embodiments, the pH of the pharmaceutical spray formulation is about 5.5. In some embodiments, the pH of the pharmaceutical spray formulation is about 6. In some embodiments, the pH of the pharmaceutical spray formulation is about 6.5. In some embodiments, the pH of the pharmaceutical spray formulation is at least about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or about 6.0 and/or no more than about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or about 6.0. In some embodiments, the pH of the pharmaceutical spray formulation is about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or about 6.0.

In some embodiments, the pharmaceutical spray formulation has a pH of about 3.5 to about 7.5. In some embodiments, the pharmaceutical spray formulation has a pH of at least about 3.5. In some embodiments, the pharmaceutical spray formulation has a pH of at most about 7.5. In some embodiments, the pharmaceutical spray formulation has a pH of about 3.5 to about 4, about 3.5 to about 4.5, about 3.5 to about 5, about 3.5 to about 5.5, about 3.5 to about 6, about 3.5 to about 6.5, about 3.5 to about 7, about 3.5 to about 7.5, about 4 to about 4.5, about 4 to about 5, about 4 to about 5.5, about 4 to about 6, about 4 to about 6.5, about 4 to about 7, about 4 to about 7.5, about 4.5 to about 5, about 4.5 to about 5.5, about 4.5 to about 6, about 4.5 to about 6.5, about 4.5 to about 7, about 4.5 to about 7.5, about 5 to about 5.5, about 5 to about 6, about 5 to about 6.5, about 5 to about 7, about 5 to about 7.5, about 5.5 to about 6, about 5.5 to about 6.5, about 5.5 to about 7, about 5.5 to about 7.5, about 6 to about 6.5, about 6 to about 7, about 6 to about 7.5, about 6.5 to about 7, about 6.5 to about 7.5, or about 7 to about 7.5. In some embodiments, the pharmaceutical spray formulation has a pH of about 3.5, about 4, about 4.5, about 5, about 5.5, about 6, about 6.5, about 7, or about 7.5.

In some embodiments, the pH is controlled by the addition of hydrochloric acid, citric acid, citrate, citric acid monohydrate, or a combination thereof. In some embodiments, the pH is controlled by the addition of hydrochloric acid. In some embodiments, the pH is controlled by the addition of citric acid. In some embodiments, the pH is controlled by the addition of citrate. In some embodiments, the pH is controlled by the addition of citric acid monohydrate. In some embodiments, the pH is controlled by the addition of a combination of hydrochloric acid and any of citric acid, citrate, of citric acid monohydrate In some embodiments, the pharmaceutical spray formulation comprises a buffering agent at a concentration of about 0.01% (w/w) to about 2% (w/w). In some embodiments, the pharmaceutical spray formulation comprises a buffering agent at a concentration of at least about 0.01% (w/w). In some embodiments, the pharmaceutical spray formulation comprises a buffering agent at a concentration of at most about 2% (w/w). In some embodiments, the pharmaceutical spray formulation comprises a buffering agent at a concentration of about 0.01% (w/w) to about 0.1% (w/w), about 0.01% (w/w) to about 0.2% (w/w), about 0.01% (w/w) to about 0.3% (w/w), about 0.01% (w/w) to about 0.4% (w/w), about 0.01% (w/w) to about 0.5% (w/w), about 0.01% (w/w) to about 0.6% (w/w), about 0.01% (w/w) to about 0.7% (w/w), about 0.01% (w/w) to about 0.8% (w/w), about 0.01% (w/w) to about 0.9% (w/w), about 0.01% (w/w) to about 1% (w/w), about 0.01% (w/w) to about 2% (w/w), about 0.1% (w/w) to about 0.2% (w/w), about 0.1% (w/w) to about 0.3% (w/w), about 0.1% (w/w) to about 0.4% (w/w), about 0.1% (w/w) to about 0.5% (w/w), about 0.1% (w/w) to about 0.6% (w/w), about 0.1% (w/w) to about 0.7% (w/w), about 0.1% (w/w) to about 0.8% (w/w), about 0.1% (w/w) to about 0.9% (w/w), about 0.1% (w/w) to about 1% (w/w), about 0.1% (w/w) to about 2% (w/w), about 0.2% (w/w) to about 0.3% (w/w), about 0.2% (w/w) to about 0.4% (w/w), about 0.2% (w/w) to about 0.5% (w/w), about 0.2% (w/w) to about 0.6% (w/w), about 0.2% (w/w) to about 0.7% (w/w), about 0.2% (w/w) to about 0.8% (w/w), about 0.2% (w/w) to about 0.9% (w/w), about 0.2% (w/w) to about 1% (w/w), about 0.2% (w/w) to about 2% (w/w), about 0.3% (w/w) to about 0.4% (w/w), about 0.3% (w/w) to about 0.5% (w/w), about 0.3% (w/w) to about 0.6% (w/w), about 0.3% (w/w) to about 0.7% (w/w), about 0.3% (w/w) to about 0.8% (w/w), about 0.3% (w/w) to about 0.9% (w/w), about 0.3% (w/w) to about 1% (w/w), about 0.3% (w/w) to about 2% (w/w), about 0.4% (w/w) to about 0.5% (w/w), about 0.4% (w/w) to about 0.6% (w/w), about 0.4% (w/w) to about 0.7% (w/w), about 0.4% (w/w) to about 0.8% (w/w), about 0.4% (w/w) to about 0.9% (w/w), about 0.4% (w/w) to about 1% (w/w), about 0.4% (w/w) to about 2% (w/w), about 0.5% (w/w) to about 0.6% (w/w), about 0.5%

(w/w) to about 0.7% (w/w), about 0.5% (w/w) to about 0.8% (w/w), about 0.5% (w/w) to about 0.9% (w/w), about 0.5% (w/w) to about 1% (w/w), about 0.5% (w/w) to about 2% (w/w), about 0.6% (w/w) to about 0.7% (w/w), about 0.6% (w/w) to about 0.8% (w/w), about 0.6% (w/w) to about 0.9% (w/w), about 0.6% (w/w) to about 1% (w/w), about 0.6% (w/w) to about 2% (w/w), about 0.7% (w/w) to about 0.8% (w/w), about 0.7% (w/w) to about 0.9% (w/w), about 0.7% (w/w) to about 1% (w/w), about 0.7% (w/w) to about 2% (w/w), about 0.8% (w/w) to about 0.9% (w/w), about 0.8% (w/w) to about 1% (w/w), about 0.8% (w/w) to about 2% (w/w), about 0.9% (w/w) to about 1% (w/w), about 0.9% (w/w) to about 2% (w/w), or about 1% (w/w) to about 2% (w/w). In some embodiments, the pharmaceutical spray formulation comprises a buffering agent at a concentration of about 0.01% (w/w), about 0.1% (w/w), about 0.2% (w/w), about 0.3% (w/w), about 0.4% (w/w), about 0.5% (w/w), about 0.6% (w/w), about 0.7% (w/w), about 0.8% (w/w), about 0.9% (w/w), about 1% (w/w), or about 2% (w/w). In some embodiments, the buffering agent is citric acid, for example, citric acid monohydrate.

In some embodiments, the pharmaceutical spray formulation further comprises trisodium citrate or citric acid monohydrate. In some embodiments, the pharmaceutical spray formulation further comprises from about 0.01% to about 2.0% trisodium citrate or citric acid monohydrate. In some embodiments, the pharmaceutical spray formulation further comprises from about 0.1% to about 2.0% trisodium citrate or citric acid monohydrate. In some embodiments, the pharmaceutical spray formulation further comprises from about 0.1% to about 1.0% trisodium citrate or citric acid monohydrate. In some embodiments, the pharmaceutical spray formulation further comprises about 0.42% trisodium citrate or citric acid monohydrate.

Antioxidants

In an aspect provided herein, the pharmaceutical spray formulation comprises an antioxidant. Antioxidants can reduce or mitigate oxidation of the active ingredient such as epinephrine. Examples of antioxidants include sodium bisulfite, sodium metabisulfite, butylated hydroxytoluene, and tocopherol. In some embodiments, the antioxidant comprises sodium bisulfite or sodium metabisulfite. In some embodiments, the antioxidant comprises sodium bisulfite. In some embodiments, the antioxidant comprises sodium metabisulfite. In some embodiments, the antioxidant acts as a preservative. In some embodiments, the antioxidant is a preservative. In some embodiments, the preservative is sodium bisulfite or sodium metabisulfite. In some embodiments, the pharmaceutical spray formulation comprises an antioxidant that reduces oxidation of the active ingredient such that the pharmaceutical spray formulation that has no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15% impurities after storage at room temperature for at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months. Room temperature can be from about 20 degrees Celsius to about 25 degrees Celsius. In some embodiments, room temperature is about 20, 21, 22, 23, 24, or 25 degrees Celsius.

In some embodiments, the pharmaceutical spray formulation is a stable and/or pure formulation that minimizes oxidation of the active ingredient and/or the presence of impurities (w/w). In some embodiments, the pharmaceutical spray formulation has no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15% impurities after storage for at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months. In some embodiments, the pharmaceutical spray formulation is stored at a temperature of at least about 5 degrees Celsius, at least about 10 degrees Celsius, at least about 20 degrees Celsius, at least about 25 degrees Celsius, at least about 35 degrees Celsius, or at least about 40 degrees Celsius and/or a temperature of no more than about 5 degrees Celsius, no more than about 10 degrees Celsius, no more than about 20 degrees Celsius, no more than about 25 degrees Celsius, no more than about 35 degrees Celsius, no more than about 40 degrees Celsius, or no more than about 45 degrees Celsius. In some embodiments, the pharmaceutical spray formulation is stored at a temperature of about 5 degrees Celsius, about 10 degrees Celsius, about 20 degrees Celsius, about 25 degrees Celsius, about 35 degrees Celsius, or about 40 degrees Celsius. In some embodiments, the impurities content of the formulation is determined relative to an initial impurities content measured at 0 months (t=0). In some embodiments, the impurities content of the formulation is determined as an absolute percentage.

In some embodiments, the impurities include one or more of epinephrine sulfonic acid, adrenochrome, norepinephrine, or adrenalone. In some embodiments, the pharmaceutical spray formulation has an epinephrine sulfonic acid content of no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, no more than 3%, no more than 4%, no more than 5%, no more than 6%, no more than 7%, no more than 8%, or no more than 9%, after storage at about 5 degrees Celsius, about 25 degrees Celsius, or about 40 degrees Celsius for at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months.

In some embodiments, the pharmaceutical spray formulation has an adrenochrome content of no more than 0.1%, no more than 0.2%, no more than 0.3%, no more than 0.4%, or no more than 0.5% after storage at about 5 degrees Celsius, about 25 degrees Celsius, or about 40 degrees Celsius for at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months.

In some embodiments, the pharmaceutical spray formulation has a norepinephrine content of no more than 0.05%, no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, no more than 3%, or no more than 4% after storage at about 5 degrees Celsius, about 25 degrees Celsius, or about 40 degrees Celsius for at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months.

In some embodiments, the pharmaceutical spray formulation has an adrenalone content of no more than 0.05%, no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, or no more than 3% after storage at about 5 degrees Celsius, about 25 degrees Celsius, or about 40 degrees Celsius for at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months.

In some embodiments, the pharmaceutical spray formulation comprises the L-isomer of epinephrine at an enantiomeric purity of at least 95%, 96%, 97%, 98%, 99%, or 99.5%. In some embodiments, the pharmaceutical spray formulation comprises the L-isomer of epinephrine at an enantiomeric purity of at least 95%, 96%, 97%, 98%, 99%, or 99.5% after storage at about 5 degrees Celsius, about 25 degrees Celsius, or about 40 degrees Celsius for at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months.

In some embodiments, the pharmaceutical spray formulation comprises an antioxidant at a concentration of about 0.0001% (w/w) to about 0.5% (w/w). In some embodiments, the pharmaceutical spray formulation comprises an antioxidant at a concentration of at least about 0.0001% (w/w). In some embodiments, the pharmaceutical spray formulation comprises an antioxidant at a concentration of at most about 0.5% (w/w). In some embodiments, the pharmaceutical spray formulation comprises an antioxidant at a concentration of about 0.0001% (w/w) to about 0.001% (w/w), about 0.0001% (w/w) to about 0.01% (w/w), about 0.0001% (w/w) to about 0.02% (w/w), about 0.0001% (w/w) to about 0.03% (w/w), about 0.0001% (w/w) to about 0.04% (w/w), about 0.0001% (w/w) to about 0.05% (w/w), about 0.0001% (w/w) to about 0.1% (w/w), about 0.0001% (w/w) to about 0.2% (w/w), about 0.0001% (w/w) to about 0.3% (w/w), about 0.0001% (w/w) to about 0.4% (w/w), about 0.0001% (w/w) to about 0.5% (w/w), about 0.001% (w/w) to about 0.01% (w/w), about 0.001% (w/w) to about 0.02% (w/w), about 0.001% (w/w) to about 0.03% (w/w), about 0.001% (w/w) to about 0.04% (w/w), about 0.001% (w/w) to about 0.05% (w/w), about 0.001% (w/w) to about 0.1% (w/w), about 0.001% (w/w) to about 0.2% (w/w), about 0.001% (w/w) to about 0.3% (w/w), about 0.001% (w/w) to about 0.4% (w/w), about 0.001% (w/w) to about 0.5% (w/w), about 0.01% (w/w) to about 0.02% (w/w), about 0.01% (w/w) to about 0.03% (w/w), about 0.01% (w/w) to about 0.04% (w/w), about 0.01% (w/w) to about 0.05% (w/w), about 0.01% (w/w) to about 0.1% (w/w), about 0.01% (w/w) to about 0.2% (w/w), about 0.01% (w/w) to about 0.3% (w/w), about 0.01% (w/w) to about 0.4% (w/w), about 0.01% (w/w) to about 0.5% (w/w), about 0.02% (w/w) to about 0.03% (w/w), about 0.02% (w/w) to about 0.04% (w/w), about 0.02% (w/w) to about 0.05% (w/w), about 0.02% (w/w) to about 0.1% (w/w), about 0.02% (w/w) to about 0.2% (w/w), about 0.02% (w/w) to about 0.3% (w/w), about 0.02% (w/w) to about 0.4% (w/w), about 0.02% (w/w) to about 0.5% (w/w), about 0.03% (w/w) to about 0.04% (w/w), about 0.03% (w/w) to about 0.05% (w/w), about 0.03% (w/w) to about 0.1% (w/w), about 0.03% (w/w) to about 0.2% (w/w), about 0.03% (w/w) to about 0.3% (w/w), about 0.03% (w/w) to about 0.4% (w/w), about 0.03% (w/w) to about 0.5% (w/w), about 0.04% (w/w) to about 0.05% (w/w), about 0.04% (w/w) to about 0.1% (w/w), about 0.04% (w/w) to about 0.2% (w/w), about 0.04% (w/w) to about 0.3% (w/w), about 0.04% (w/w) to about 0.4% (w/w), about 0.04% (w/w) to about 0.5% (w/w), about 0.05% (w/w) to about 0.1% (w/w), about 0.05% (w/w) to about 0.2% (w/w), about 0.05% (w/w) to about 0.3% (w/w), about 0.05% (w/w) to about 0.4% (w/w), about 0.05% (w/w) to about 0.5% (w/w), about 0.1% (w/w) to about 0.2% (w/w), about 0.1% (w/w) to about 0.3% (w/w), about 0.1% (w/w) to about 0.4% (w/w), about 0.1% (w/w) to about 0.5% (w/w), about 0.2% (w/w) to about 0.3% (w/w), about 0.2% (w/w) to about 0.4% (w/w), about 0.2% (w/w) to about 0.5% (w/w), about 0.3% (w/w) to about 0.4% (w/w), about 0.3% (w/w) to about 0.5% (w/w), or about 0.4% (w/w) to about 0.5% (w/w). In some embodiments, the pharmaceutical spray formulation comprises an antioxidant at a concentration of about 0.0001% (w/w), about 0.001% (w/w), about 0.01% (w/w), about 0.02% (w/w), about 0.03% (w/w), about 0.04% (w/w), about 0.05% (w/w), about 0.1% (w/w), about 0.2% (w/w), about 0.3% (w/w), about 0.4% (w/w), or about 0.5% (w/w).

In some embodiments, the pharmaceutical spray formulation comprises sodium bisulfite at a concentration of from about 0.0001% (w/w) to about 0.05% (w/w) or sodium metabisulfite at a concentration of from about 0.0001% (w/w) to about 0.1% (w/w). In some embodiments, the pharmaceutical spray formulation comprises sodium bisulfite at a concentration of from about 0.0001% (w/w) to about 0.1% (w/w) or sodium metabisulfite at a concentration of from about 0.0001% (w/w) to about 0.1% (w/w). In some embodiments, the pharmaceutical spray formulation comprises sodium bisulfite at a concentration of from about 0.001% (w/w) to about 0.05% (w/w) or sodium metabisulfite at a concentration of from about 0.001% (w/w) to about 0.1% (w/w). In some embodiments, the pharmaceutical spray formulation comprises sodium bisulfite at a concentration of from about 0.01% (w/w) to about 0.05% (w/w) or sodium metabisulfite at a concentration of from about 0.01% (w/w) to about 0.1% (w/w).

In some embodiments, the pharmaceutical spray formulation comprises sodium bisulfite. In some embodiments, the pharmaceutical spray formulation comprises sodium bisulfite at a concentration of from about 0.0001% (w/w) to about 0.1% (w/w). In some embodiments, the pharmaceutical spray formulation comprises sodium bisulfite at a concentration of from about 0.001% (w/w) to about 0.05% (w/w). In some embodiments, the pharmaceutical spray formulation comprises sodium bisulfite at a concentration of from about 0.005% (w/w) to about 0.05% (w/w). In some embodiments, the pharmaceutical spray formulation comprises sodium bisulfite at a concentration of from about 0.001% (w/w) to about 0.05% (w/w). In some embodiments, the pharmaceutical spray formulation comprises sodium bisulfite at a concentration of from about 0.01% (w/w) to about 0.05% (w/w). In some embodiments, the pharmaceutical spray formulation comprises sodium bisulfite at a concentration of about 0.005% (w/w). In some embodiments, the pharmaceutical spray formulation comprises sodium bisulfite at a concentration of about 0.01% (w/w). In some embodiments, the pharmaceutical spray formulation comprises sodium bisulfite at a concentration of about 0.02% (w/w). In some embodiments, the pharmaceutical spray formulation comprises sodium bisulfite at a concentration of about 0.03% (w/w). In some embodiments, the pharmaceutical spray formulation comprises sodium bisulfite at a concentration of about 0.04% (w/w). In some embodiments, the pharmaceutical spray formulation comprises sodium bisulfite at a concentration of about 0.05% (w/w).

In some embodiments, the pharmaceutical spray formulation comprises sodium metabisulfite. In some embodiments, the pharmaceutical spray formulation comprises sodium metabisulfite at a concentration of from about 0.0001% (w/w) to about 0.1% (w/w). In some embodiments, the pharmaceutical spray formulation comprises sodium metabisulfite at a concentration of from about 0.001% (w/w) to about 0.1% (w/w). In some embodiments, the pharmaceutical spray formulation comprises sodium metabisulfite at a concentration of from about 0.005% (w/w) to about 0.1% (w/w). In some embodiments, the pharmaceutical spray formulation comprises sodium metabisulfite at a concentration of from about 0.01% (w/w) to about 0.1% (w/w). In some embodiments, the pharmaceutical spray formulation comprises sodium metabisulfite at a concentration of about 0.005% (w/w). In some embodiments, the pharmaceutical spray formulation comprises sodium metabisulfite at a concentration of about 0.01% (w/w). In some embodiments, the pharmaceutical spray formulation comprises sodium metabisulfite at a concentration of about 0.02% (w/w). In some embodiments, the pharmaceutical spray formulation comprises sodium metabisulfite at a concentration of about 0.03% (w/w). In some embodiments, the pharmaceutical spray formulation comprises sodium metabisulfite at a concentration of about 0.04% (w/w). In some embodiments, the pharmaceutical spray formulation comprises sodium metabisulfite at a concentration of about 0.05% (w/w). In some embodiments, the pharmaceutical spray formulation comprises sodium metabisulfite at a concentration of about 0.06% (w/w). In some embodiments, the pharmaceutical spray formulation comprises sodium metabisulfite at a concentration of about 0.07% (w/w). In some embodiments, the pharmaceutical spray formulation comprises sodium metabisulfite at a concentration of about 0.08% (w/w). In some embodiments, the pharmaceutical spray formulation comprises sodium metabisulfite at a concentration of about 0.09% (w/w). In some embodiments, the pharmaceutical spray formulation comprises sodium metabisulfite at a concentration of about 0.1% (w/w).

In some embodiments, the pharmaceutical spray formulation comprises an antioxidant at a concentration of 0.01% (w/w) to 0.3% (w/w). In some embodiments, the antioxidant is sodium metabisulfite. In some embodiments, the pharmaceutical spray formulation comprises an antioxidant at a concentration of 0.01% (w/w) to 0.02% (w/w), 0.01% (w/w) to 0.03% (w/w), 0.01% (w/w) to 0.04% (w/w), 0.01% (w/w) to 0.05% (w/w), 0.01% (w/w) to 0.06% (w/w), 0.01% (w/w) to 0.07% (w/w), 0.01% (w/w) to 0.08% (w/w), 0.01% (w/w) to 0.09% (w/w), 0.01% (w/w) to 0.1% (w/w), 0.01% (w/w) to 0.2% (w/w), 0.01% (w/w) to 0.3% (w/w), 0.02% (w/w) to 0.03% (w/w), 0.02% (w/w) to 0.04% (w/w), 0.02% (w/w) to 0.05% (w/w), 0.02% (w/w) to 0.06% (w/w), 0.02% (w/w) to 0.07% (w/w), 0.02% (w/w) to 0.08% (w/w), 0.02% (w/w) to 0.09% (w/w), 0.02% (w/w) to 0.1% (w/w), 0.02% (w/w) to 0.2% (w/w), 0.02% (w/w) to 0.3% (w/w), 0.03% (w/w) to 0.04% (w/w), 0.03% (w/w) to 0.05% (w/w), 0.03% (w/w) to 0.06% (w/w), 0.03% (w/w) to 0.07% (w/w), 0.03% (w/w) to 0.08% (w/w), 0.03% (w/w) to 0.09% (w/w), 0.03% (w/w) to 0.1% (w/w), 0.03% (w/w) to 0.2% (w/w), 0.03% (w/w) to 0.3% (w/w), 0.04% (w/w) to 0.05% (w/w), 0.04% (w/w) to 0.06% (w/w), 0.04% (w/w) to 0.07% (w/w), 0.04% (w/w) to 0.08% (w/w), 0.04% (w/w) to 0.09% (w/w), 0.04% (w/w) to 0.1% (w/w), 0.04% (w/w) to 0.2% (w/w), 0.04% (w/w) to 0.3% (w/w), 0.05% (w/w) to 0.06% (w/w), 0.05% (w/w) to 0.07% (w/w), 0.05% (w/w) to 0.08% (w/w), 0.05% (w/w) to 0.09% (w/w), 0.05% (w/w) to 0.1% (w/w), 0.05% (w/w) to 0.2% (w/w), 0.05% (w/w) to 0.3% (w/w), 0.06% (w/w) to 0.07% (w/w), 0.06% (w/w) to 0.08% (w/w), 0.06% (w/w) to 0.09% (w/w), 0.06% (w/w) to 0.1% (w/w), 0.06% (w/w) to 0.2% (w/w), 0.06% (w/w) to 0.3% (w/w), 0.07% (w/w) to 0.08% (w/w), 0.07% (w/w) to 0.09% (w/w), 0.07% (w/w) to 0.1% (w/w), 0.07% (w/w) to 0.2% (w/w), 0.07% (w/w) to 0.3% (w/w), 0.08% (w/w) to 0.09% (w/w), 0.08% (w/w) to 0.1% (w/w), 0.08% (w/w) to 0.2% (w/w), 0.08% (w/w) to 0.3% (w/w), 0.09% (w/w) to 0.1% (w/w), 0.09% (w/w) to 0.2% (w/w), 0.09% (w/w) to 0.3% (w/w), 0.1% (w/w) to 0.2% (w/w), 0.1% (w/w) to 0.3% (w/w), or 0.2% (w/w) to 0.3% (w/w). In some embodiments, the pharmaceutical spray formulation comprises an antioxidant at a concentration of 0.01% (w/w), 0.02% (w/w), 0.03% (w/w), 0.04% (w/w), 0.05% (w/w), 0.06% (w/w), 0.07% (w/w), 0.08% (w/w), 0.09% (w/w), 0.1% (w/w), 0.2% (w/w), or 0.3% (w/w). In some embodiments, the pharmaceutical spray formulation comprises an antioxidant at a concentration of at least 0.01% (w/w), 0.02% (w/w), 0.03% (w/w), 0.04% (w/w), 0.05% (w/w), 0.06% (w/w), 0.07% (w/w), 0.08% (w/w), 0.09% (w/w), 0.1% (w/w), or 0.2% (w/w). In some embodiments, the pharmaceutical spray formulation comprises an antioxidant at a concentration of at most 0.02% (w/w), 0.03% (w/w), 0.04% (w/w), 0.05% (w/w), 0.06% (w/w), 0.07% (w/w), 0.08% (w/w), 0.09% (w/w), 0.1% (w/w), 0.2% (w/w), or 0.3% (w/w).

Preservatives

In an aspect provided herein, the pharmaceutical spray formulation comprises a preservative. In some embodiments, the preservative comprises a chelating agent. In some embodiments, the chelating agent is disodium edetate (EDTA). In some embodiments, the pharmaceutical spray formulation comprises disodium edetate. In some embodiments, the pharmaceutical spray formulation comprises disodium edetate at a concentration of from about 0.0001% to about 0.01%. In some embodiments, the pharmaceutical spray formulation comprises disodium edetate at a concentration of from about 0.0005% to about 0.01%. In some embodiments, the pharmaceutical spray formulation comprises disodium edetate at a concentration of from about 0.001% to about 0.01%.

In some embodiments, the pharmaceutical spray formulation comprises a chelating agent at a concentration of about 0.0001% to about 0.05%. In some embodiments, the pharmaceutical spray formulation comprises a chelating agent at a concentration of at least about 0.0001%. In some embodiments, the pharmaceutical spray formulation comprises a chelating agent at a concentration of at most about 0.05%. In some embodiments, the pharmaceutical spray formulation comprises a chelating agent at a concentration of about 0.0001% to about 0.0002%, about 0.0001% to about 0.0003%, about 0.0001% to about 0.0004%, about 0.0001% to about 0.0005%, about 0.0001% to about 0.001%, about 0.0001% to about 0.005%, about 0.0001% to about 0.01%, about 0.0001% to about 0.02%, about 0.0001% to about 0.03%, about 0.0001% to about 0.04%, about 0.0001% to about 0.05%, about 0.0002% to about 0.0003%, about 0.0002% to about 0.0004%, about 0.0002% to about 0.0005%, about 0.0002% to about 0.001%, about 0.0002% to about 0.005%, about 0.0002% to about 0.01%, about 0.0002% to about 0.02%, about 0.0002% to about 0.03%, about 0.0002% to about 0.04%, about 0.0002% to about 0.05%, about 0.0003% to about 0.0004%, about 0.0003% to about 0.0005%, about 0.0003% to about 0.001%, about 0.0003% to about 0.005%, about 0.0003% to about 0.01%, about 0.0003% to about 0.02%, about 0.0003% to about 0.03%, about 0.0003% to about 0.04%, about 0.0003% to about 0.05%, about 0.0004% to about 0.0005%, about 0.0004% to about 0.001%, about 0.0004% to about 0.005%, about 0.0004% to about 0.01%, about 0.0004% to about 0.02%, about 0.0004% to about 0.03%, about 0.0004% to about 0.04%, about 0.0004% to about 0.05%, about 0.0005% to about 0.001%, about 0.0005% to about 0.005%, about 0.0005% to about 0.01%, about 0.0005% to about 0.02%, about 0.0005% to about 0.03%, about 0.0005% to about 0.04%, about 0.0005% to about 0.05%, about 0.001% to about 0.005%, about 0.001% to about 0.01%, about 0.001% to about 0.02%, about 0.001% to about 0.03%, about 0.001% to about 0.04%, about 0.001% to about 0.05%, about 0.005% to about 0.01%, about 0.005% to about 0.02%, about 0.005% to about 0.03%, about 0.005% to about 0.04%, about 0.005% to about 0.05%, about 0.01% to about 0.02%, about 0.01% to about 0.03%, about 0.01% to about 0.04%, about 0.01% to about 0.05%, about 0.02% to about 0.03%, about 0.02% to about 0.04%, about 0.02% to about 0.05%, about 0.03% to about 0.04%, about 0.03% to about 0.05%, or about 0.04% to about 0.05%. In some embodiments, the pharmaceutical spray formulation comprises a chelating agent at a concentration of about 0.0001%, about 0.0002%, about 0.0003%, about 0.0004%, about 0.0005%, about 0.001%, about 0.005%, about 0.01%, about 0.02%, about 0.03%, about 0.04%, or about 0.05%.

In an aspect provided herein, the pharmaceutical spray formulation comprises a preservative. Examples of preservatives include parabens, phenyl ethyl alcohol, benzalkonium chloride, EDTA, and benzoyl alcohol. In some embodiments, the preservative comprises an antimicrobial preservative. In some embodiments, the antimicrobial preservative is benzalkonium sodium or chlorobutanol. In some embodiments, the antimicrobial preservative is chlorobutanol. In some embodiments, the pharmaceutical spray formulation comprises benzalkonium sodium at a concentration of from about 0.005% (w/v) to about 1% (w/v) or chlorobutanol at a concentration of from about 0.005% (w/v) to about 1% (w/v).

In some embodiments, the pharmaceutical spray formulation comprises an antimicrobial preservative at a concentration of about 0.01% (w/w) to about 1% (w/w). In some embodiments, the antimicrobial preservative is chlorobutanol, for example, chlorobutanol hemihydrate. In some embodiments, the pharmaceutical spray formulation comprises an antimicrobial preservative at a concentration of at least about 0.01% (w/w). In some embodiments, the pharmaceutical spray formulation comprises an antimicrobial preservative at a concentration of at most about 1% (w/w). In some embodiments, the pharmaceutical spray formulation comprises an antimicrobial preservative at a concentration of about 0.01% (w/w) to about 0.05% (w/w), about 0.01% (w/w) to about 0.1% (w/w), about 0.01% (w/w) to about 0.2% (w/w), about 0.01% (w/w) to about 0.3% (w/w), about 0.01% (w/w) to about 0.4% (w/w), about 0.01% (w/w) to about 0.5% (w/w), about 0.01% (w/w) to about 0.6% (w/w), about 0.01% (w/w) to about 0.7% (w/w), about 0.01% (w/w) to about 0.8% (w/w), about 0.01% (w/w) to about 0.9% (w/w), about 0.01% (w/w) to about 1% (w/w), about 0.05% (w/w) to about 0.1% (w/w), about 0.05% (w/w) to about 0.2% (w/w), about 0.05% (w/w) to about 0.3% (w/w), about 0.05% (w/w) to about 0.4% (w/w), about 0.05% (w/w) to about 0.5% (w/w), about 0.05% (w/w) to about 0.6% (w/w), about 0.05% (w/w) to about 0.7% (w/w), about 0.05% (w/w) to about 0.8% (w/w), about 0.05% (w/w) to about 0.9% (w/w), about 0.05% (w/w) to about 1% (w/w), about 0.1% (w/w) to about 0.2% (w/w), about 0.1% (w/w) to about 0.3% (w/w), about 0.1% (w/w) to about 0.4% (w/w), about 0.1% (w/w) to about 0.5% (w/w), about 0.1% (w/w) to about 0.6% (w/w), about 0.1% (w/w) to about 0.7% (w/w), about 0.1% (w/w) to about 0.8% (w/w), about 0.1% (w/w) to about 0.9% (w/w), about 0.1% (w/w) to about 1% (w/w), about 0.2% (w/w) to about 0.3% (w/w), about 0.2% (w/w) to about 0.4% (w/w), about 0.2% (w/w) to about 0.5% (w/w), about 0.2% (w/w) to about 0.6% (w/w), about 0.2% (w/w) to about 0.7% (w/w), about 0.2% (w/w) to about 0.8% (w/w), about 0.2% (w/w) to about 0.9% (w/w), about 0.2% (w/w) to about 1% (w/w), about 0.3% (w/w) to about 0.4% (w/w), about 0.3% (w/w) to about 0.5% (w/w), about 0.3% (w/w) to about 0.6% (w/w), about 0.3% (w/w) to about 0.7% (w/w), about 0.3% (w/w) to about 0.8% (w/w), about 0.3% (w/w) to about 0.9% (w/w), about 0.3% (w/w) to about 1% (w/w), about 0.4% (w/w) to about 0.5% (w/w), about 0.4% (w/w) to about 0.6% (w/w), about 0.4% (w/w) to about 0.7% (w/w), about 0.4% (w/w) to about 0.8% (w/w), about 0.4% (w/w) to about 0.9% (w/w), about 0.4% (w/w) to about 1% (w/w), about 0.5% (w/w) to about 0.6% (w/w), about 0.5% (w/w) to about 0.7% (w/w), about 0.5% (w/w) to about 0.8% (w/w), about 0.5% (w/w) to about 0.9% (w/w), about 0.5% (w/w) to about 1% (w/w), about 0.6% (w/w) to about 0.7% (w/w), about 0.6% (w/w) to about 0.8% (w/w), about 0.6% (w/w) to about 0.9% (w/w), about 0.6% (w/w) to about 1% (w/w), about 0.7% (w/w) to about 0.8% (w/w), about 0.7% (w/w) to about 0.9% (w/w), about 0.7% (w/w) to about 1% (w/w), about 0.8% (w/w) to about 0.9% (w/w), about 0.8% (w/w) to about 1% (w/w), or about 0.9% (w/w) to about 1% (w/w). In some embodiments, the pharmaceutical spray formulation comprises an antimicrobial preservative at a concentration of about 0.01% (w/w), about 0.05% (w/w), about 0.1% (w/w), about 0.2% (w/w), about 0.3% (w/w), about 0.4% (w/w), about 0.5% (w/w), about 0.6% (w/w), about 0.7% (w/w), about 0.8% (w/w), about 0.9% (w/w), or about 1% (w/w).

In some embodiments, the pharmaceutical spray formulation comprises benzalkonium sodium. In some embodiments, the pharmaceutical spray formulation comprises benzalkonium sodium at a concentration of from about 0.005% (w/v) to about 1% (w/v). In some embodiments, the pharmaceutical spray formulation comprises benzalkonium sodium at a concentration of from about 0.01% (w/v) to about 1% (w/v). In some embodiments, the pharmaceutical spray formulation comprises benzalkonium sodium at a concentration of from about 0.05% (w/v) to about 1% (w/v). In some embodiments, the pharmaceutical spray formulation comprises benzalkonium sodium at a concentration of from about 0.1% (w/v) to about 1% (w/v).

In some embodiments, the pharmaceutical spray formulation comprises chlorobutanol. In some embodiments, the chlorobutanol is chlorobutanol hemihydrate. In some embodiments, the pharmaceutical spray formulation comprises chlorobutanol at a concentration of from about 0.005% (w/v) to about 1% (w/v) (or alternatively w/w). In some embodiments, the pharmaceutical spray formulation comprises chlorobutanol at a concentration of from about 0.01% (w/v) to about 1% (w/v). In some embodiments, the pharmaceutical spray formulation comprises chlorobutanol at a concentration of from about 0.05% (w/v) to about 1% (w/v). In some embodiments, the pharmaceutical spray formulation comprises chlorobutanol at a concentration of from about 0.1% (w/v) to about 1% (w/v). In some embodiments, the pharmaceutical spray formulation comprises chlorobutanol at a concentration of from about 0.1% (w/v) to about 0.5% (w/v). In some embodiments, the pharmaceutical spray formulation comprises chlorobutanol at a concentration of about 0.21% (w/v). In some embodiments, the pharmaceutical spray formulation comprises chlorobutanol at a concentration of about 0.2% (w/v). In some embodiments, the pharmaceutical spray formulation comprises chlorobutanol at a concentration of about 0.5% (w/v).

Isotonicity Agents

Disclosed herein are various ingredients of the pharmaceutical spray formulation. In some embodiments, the pharmaceutical spray formulation comprises an isotonicity agent. In some embodiments, an isotonicity agent is sodium chloride. An isotonicity agent can be used to adjust the tonicity of the formulation. In some embodiments, the pharmaceutical spray formulation is hypotonic. In some embodiments, the pharmaceutical spray formulation is hypertonic. In some embodiments, the pharmaceutical spray formulation is isotonic.

In some embodiments, the pharmaceutical spray formulation has an osmolality of about 550 mOsm/kg to about 800 mOsm/kg. In some embodiments, the pharmaceutical spray formulation has an osmolality of about 550 mOsm/kg to about 575 mOsm/kg, about 550 mOsm/kg to about 600 mOsm/kg, about 550 mOsm/kg to about 625 mOsm/kg, about 550 mOsm/kg to about 650 mOsm/kg, about 550 mOsm/kg to about 675 mOsm/kg, about 550 mOsm/kg to about 700 mOsm/kg, about 550 mOsm/kg to about 725 mOsm/kg, about 550 mOsm/kg to about 750 mOsm/kg, about 550 mOsm/kg to about 775 mOsm/kg, about 550 mOsm/kg to about 800 mOsm/kg, about 575 mOsm/kg to about 600 mOsm/kg, about 575 mOsm/kg to about 625 mOsm/kg, about 575 mOsm/kg to about 650 mOsm/kg, about 575 mOsm/kg to about 675 mOsm/kg, about 575 mOsm/kg to about 700 mOsm/kg, about 575 mOsm/kg to about 725 mOsm/kg, about 575 mOsm/kg to about 750 mOsm/kg, about 575 mOsm/kg to about 775 mOsm/kg, about 575 mOsm/kg to about 800 mOsm/kg, about 600 mOsm/kg to about 625 mOsm/kg, about 600 mOsm/kg to about 650 mOsm/kg, about 600 mOsm/kg to about 675 mOsm/kg, about 600 mOsm/kg to about 700 mOsm/kg, about 600 mOsm/kg to about 725 mOsm/kg, about 600 mOsm/kg to about 750 mOsm/kg, about 600 mOsm/kg to about 775 mOsm/kg, about 600 mOsm/kg to about 800 mOsm/kg, about 625 mOsm/kg to about 650 mOsm/kg, about 625 mOsm/kg to about 675 mOsm/kg, about 625 mOsm/kg to about 700 mOsm/kg, about 625 mOsm/kg to about 725 mOsm/kg, about 625 mOsm/kg to about 750 mOsm/kg, about 625 mOsm/kg to about 775 mOsm/kg, about 625 mOsm/kg to about 800 mOsm/kg, about 650 mOsm/kg to about 675 mOsm/kg, about 650 mOsm/kg to about 700 mOsm/kg, about 650 mOsm/kg to about 725 mOsm/kg, about 650 mOsm/kg to about 750 mOsm/kg, about 650 mOsm/kg to about 775 mOsm/kg, about 650 mOsm/kg to about 800 mOsm/kg, about 675 mOsm/kg to about 700 mOsm/kg, about 675 mOsm/kg to about 725 mOsm/kg, about 675 mOsm/kg to about 750 mOsm/kg, about 675 mOsm/kg to about 775 mOsm/kg, about 675 mOsm/kg to about 800 mOsm/kg, about 700 mOsm/kg to about 725 mOsm/kg, about 700 mOsm/kg to about 750 mOsm/kg, about 700 mOsm/kg to about 775 mOsm/kg, about 700 mOsm/kg to about 800 mOsm/kg, about 725 mOsm/kg to about 750 mOsm/kg, about 725 mOsm/kg to about 775 mOsm/kg, about 725 mOsm/kg to about 800 mOsm/kg, about 750 mOsm/kg to about 775 mOsm/kg, about 750 mOsm/kg to about 800 mOsm/kg, or about 775 mOsm/kg to about 800 mOsm/kg. In some embodiments, the pharmaceutical spray formulation has an osmolality of about 550 mOsm/kg, about 575 mOsm/kg, about 600 mOsm/kg, about 625 mOsm/kg, about 650 mOsm/kg, about 675 mOsm/kg, about 700 mOsm/kg, about 725 mOsm/kg, about 750 mOsm/kg, about 775 mOsm/kg, or about 800 mOsm/kg. In some embodiments, the pharmaceutical spray formulation has an osmolality of at least about 550 mOsm/kg, about 575 mOsm/kg, about 600 mOsm/kg, about 625 mOsm/kg, about 650 mOsm/kg, about 675 mOsm/kg, about 700 mOsm/kg, about 725 mOsm/kg, about 750 mOsm/kg, or about 775 mOsm/kg. In some embodiments, the pharmaceutical spray formulation has an osmolality of at most about 575 mOsm/kg, about 600 mOsm/kg, about 625 mOsm/kg, about 650 mOsm/kg, about 675 mOsm/kg, about 700 mOsm/kg, about 725 mOsm/kg, about 750 mOsm/kg, about 775 mOsm/kg, or about 800 mOsm/kg.

In some embodiments, the pharmaceutical spray formulation comprises an isotonicity agent at a concentration of about 0.1% to about 4%. In some embodiments, the pharmaceutical spray formulation comprises an isotonicity agent at a concentration of at least about 0.1%. In some embodiments, the pharmaceutical spray formulation comprises an isotonicity agent at a concentration of at most about 4%. In some embodiments, the pharmaceutical spray formulation comprises an isotonicity agent at a concentration of about 0.1% to about 0.2%, about 0.1% to about 0.4%, about 0.1% to about 0.5%, about 0.1% to about 0.6%, about 0.1% to about 0.8%, about 0.1% to about 1%, about 0.1% to about 1.5%, about 0.1% to about 2%, about 0.1% to about 2.5%, about 0.1% to about 3%, about 0.1% to about 4%, about 0.2% to about 0.4%, about 0.2% to about 0.5%, about 0.2% to about 0.6%, about 0.2% to about 0.8%, about 0.2% to about 1%, about 0.2% to about 1.5%, about 0.2% to about 2%, about 0.2% to about 2.5%, about 0.2% to about 3%, about 0.2% to about 4%, about 0.4% to about 0.5%, about 0.4% to about 0.6%, about 0.4% to about 0.8%, about 0.4% to about 1%, about 0.4% to about 1.5%, about 0.4% to about 2%, about 0.4% to about 2.5%, about 0.4% to about 3%, about 0.4% to about 4%, about 0.5% to about 0.6%, about 0.5% to about 0.8%, about 0.5% to about 1%, about 0.5% to about 1.5%, about 0.5% to about 2%, about 0.5% to about 2.5%, about 0.5% to about 3%, about 0.5% to about 4%, about 0.6% to about 0.8%, about 0.6% to about 1%, about 0.6% to about 1.5%, about 0.6% to about 2%, about 0.6% to about 2.5%, about 0.6% to about 3%, about 0.6% to about 4%, about 0.8% to about 1%, about 0.8% to about 1.5%, about 0.8% to about 2%, about 0.8% to about 2.5%, about 0.8% to about 3%, about 0.8% to about 4%, about 1% to about 1.5%, about 1% to about 2%, about 1% to about 2.5%, about 1% to about 3%, about 1% to about 4%, about 1.5% to about 2%, about 1.5% to about 2.5%, about 1.5% to about 3%, about 1.5% to about 4%, about 2% to about 2.5%, about 2% to about 3%, about 2% to about 4%, about 2.5% to about 3%, about 2.5% to about 4%, or about 3% to about 4%. In some embodiments, the pharmaceutical spray formulation comprises an isotonicity agent at a concentration of about 0.1%, about 0.2%, about 0.4%, about 0.5%, about 0.6%, about 0.8%, about 1%, about 1.5%, about 2%, about 2.5%, about 3%, or about 4%.

In an aspect provided herein, the pharmaceutical spray formulation comprises sodium chloride. In some embodiments, the pharmaceutical spray formulation comprises sodium chloride at a concentration of from about 0.1% to about 5%. In some embodiments, the pharmaceutical spray formulation comprises sodium chloride at a concentration of from about 0.1% to about 1%. In some embodiments, the pharmaceutical spray formulation comprises sodium chloride at a concentration of from about 0.5% to about 5%. In some embodiments, the pharmaceutical spray formulation comprises sodium chloride at a concentration of from about 1% to about 5%. In some embodiments, the pharmaceutical spray formulation comprises sodium chloride at a concentration of from about 2% to about 5%. In some embodiments, the pharmaceutical spray formulation comprises sodium chloride at a concentration of from about 3% to about 5%. In some embodiments, the pharmaceutical spray formulation comprises sodium chloride at a concentration of from about 4% to about 5%. In some embodiments, the pharmaceutical spray formulation comprises sodium chloride at a concentration of from about 0.1% to about 3%. In some embodiments, the pharmaceutical spray formulation comprises sodium chloride at a concentration of from about 0.1% to about 2%. In some embodiments, the pharmaceutical spray formulation comprises sodium chloride at a concentration of from about 0.1% to about 1%. In some embodiments, the pharmaceutical spray formulation comprises sodium chloride at a concentration of about 0.4%.

In some embodiments, the pharmaceutical spray formulation is a stable pharmaceutical spray formulation that has no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15% impurities after storage at room temperature for at least 1 month, at least 2 months, at least 3 months, at least 4 months, at least 5 months, at least 6 months, at least 7 months, at least 8 months, at least 9 months, at least 10 months, at least 11 months, or at least 12 months. In some embodiments, the pharmaceutical spray formulation comprises one or more buffering agents and/or preservatives to improve stability of the active ingredient (e.g., reduce oxidation or degradation of epinephrine) during storage.

Vasodilators

In an aspect provided herein, the pharmaceutical spray formulation further comprises a vasodilator. In some embodiments, the vasodilator is nitroprusside, phentolamine, or nifedipine.

In some embodiments, the pharmaceutical spray formulation further comprises nitroprusside. In some embodiments, the pharmaceutical spray formulation further comprises from about 0.05 mg to about 5 mg of nitroprusside. In some embodiments, the pharmaceutical spray formulation further comprises from about 0.1 mg to about 5 mg of nitroprusside. In some embodiments, the pharmaceutical spray formulation further comprises from about 0.5 mg to about 5 mg of nitroprusside. In some embodiments, the pharmaceutical spray formulation further comprises from about 1 mg to about 5 mg of nitroprusside. In some embodiments, the pharmaceutical spray formulation further comprises from about 1 mg to about 4 mg of nitroprusside. In some embodiments, the pharmaceutical spray formulation further comprises nitroprusside. In some embodiments, the pharmaceutical spray formulation further comprises from about 0.05 mg to about 3 mg of nitroprusside. In some embodiments, the pharmaceutical spray formulation further comprises nitroprusside. In some embodiments, the pharmaceutical spray formulation further comprises from about 0.5 mg to about 3 mg of nitroprusside. In some embodiments, the pharmaceutical spray formulation further comprises nitroprusside. In some embodiments, the pharmaceutical spray formulation further comprises from about 0.5 mg to about 2 mg of nitroprusside.

In some embodiments, the pharmaceutical spray formulation further comprises phentolamine. In some embodiments, the pharmaceutical spray formulation further comprises from about 1 mg to about 50 mg of phentolamine. In some embodiments, the pharmaceutical spray formulation further comprises phentolamine. In some embodiments, the pharmaceutical spray formulation further comprises from about 1 mg to about 40 mg of phentolamine. In some embodiments, the pharmaceutical spray formulation further comprises phentolamine. In some embodiments, the pharmaceutical spray formulation further comprises from about 1 mg to about 30 mg of phentolamine. In some embodiments, the pharmaceutical spray formulation further comprises phentolamine. In some embodiments, the pharmaceutical spray formulation further comprises from about 1 mg to about 20 mg of phentolamine. In some embodiments, the pharmaceutical spray formulation further comprises phentolamine. In some embodiments, the pharmaceutical spray formulation further comprises from about 1 mg to about 10 mg of phentolamine. In some embodiments, the pharmaceutical spray formulation further comprises phentolamine. In some embodiments, the pharmaceutical spray formulation further comprises from about 5 mg to about 50 mg of phentolamine. In some embodiments, the pharmaceutical spray formulation further comprises phentolamine. In some embodiments, the pharmaceutical spray formulation further comprises from about 10 mg to about 50 mg of phentolamine. In some embodiments, the pharmaceutical spray formulation further comprises phentolamine. In some embodiments, the pharmaceutical spray formulation further comprises from about 20 mg to about 50 mg of phentolamine. In some embodiments, the pharmaceutical spray formulation further comprises phentolamine. In some embodiments, the pharmaceutical spray formulation further comprises from about 20 mg to about 40 mg of phentolamine.

In some embodiments, the pharmaceutical spray formulation further comprises nifedipine. In some embodiments, the pharmaceutical spray formulation further comprises from about 10 mg to about 500 mg of nifedipine. In some embodiments, the pharmaceutical spray formulation further comprises nifedipine. In some embodiments, the pharmaceutical spray formulation further comprises from about 10 mg to about 450 mg of nifedipine. In some embodiments, the pharmaceutical spray formulation further comprises nifedipine. In some embodiments, the pharmaceutical spray formulation further comprises from about 10 mg to about 400 mg of nifedipine. In some embodiments, the pharmaceutical spray formulation further comprises nifedipine. In some embodiments, the pharmaceutical spray formulation further comprises from about 10 mg to about 350 mg of nifedipine. In some embodiments, the pharmaceutical spray formulation further comprises nifedipine. In some embodiments, the pharmaceutical spray formulation further comprises from about 10 mg to about 300 mg of nifedipine. In some embodiments, the pharmaceutical spray formulation further comprises nifedipine. In some embodiments, the pharmaceutical spray formulation further comprises from about 10 mg to about 250 mg of nifedipine. In some embodiments, the pharmaceutical spray formulation further comprises nifedipine. In some embodiments, the pharmaceutical spray formulation further comprises from about 10 mg to about 200 mg of nifedipine. In some embodiments, the pharmaceutical spray formulation further comprises nifedipine. In some embodiments, the pharmaceutical spray formulation further comprises from about 10 mg to about 150 mg of nifedipine. In some embodiments, the pharmaceutical spray formulation further comprises nifedipine. In some embodiments, the pharmaceutical spray formulation further comprises from about 10 mg to about 100 mg of nifedipine. In some embodiments, the pharmaceutical spray formulation further comprises nifedipine. In some embodiments, the pharmaceutical spray formulation further comprises from about 10 mg to about 75 mg of nifedipine. In some embodiments, the pharmaceutical spray formulation further comprises nifedipine. In some embodiments, the pharmaceutical spray formulation further comprises from about 10 mg to about 50 mg of nifedipine. In some embodiments, the pharmaceutical spray formulation further comprises nifedipine. In some embodiments, the pharmaceutical spray formulation further comprises from about 10 mg to about 40 mg of nifedipine. In some embodiments, the pharmaceutical spray formulation further comprises nifedipine. In some embodiments, the pharmaceutical spray formulation further comprises from about 10 mg to about 30 mg of nifedipine. In some embodiments, the pharmaceutical spray formulation further comprises nifedipine. In some embodiments, the pharmaceutical spray formulation further comprises from about 50 mg to about 500 mg of nifedipine. In some embodiments, the pharmaceutical spray formulation further comprises nifedipine. In some embodiments, the pharmaceutical spray formulation further comprises from about 100 mg to about 500 mg of nifedipine. In some embodiments, the pharmaceutical spray formulation further comprises nifedipine. In some embodiments, the pharmaceutical spray formulation further comprises from about 100 mg to about 400 mg of nifedipine. In some embodiments, the pharmaceutical spray formulation further comprises nifedipine. In some embodiments, the pharmaceutical spray formulation further comprises from about 100 mg to about 350 mg of nifedipine. In some embodiments, the pharmaceutical spray formulation further comprises nifedipine. In some embodiments, the pharmaceutical spray formulation further comprises from about 100 mg to about 300 mg of nifedipine.

Absorption Enhancers

In an aspect provided herein, the pharmaceutical spray formulation comprises an absorption enhancer. In some embodiments, the absorption enhancer comprises caprylic acid, oleic acid, polysorbate 80, menthol, EDTA, sodium edetate, cetylpyridinium chloride, sodium lauryl sulfate, citric acid, sodium desoxycholate, sodium deoxyglycolate, glyceryl oleate, L-lysine, diethylene glycol monoethyl ether, α- β- or γ-cyclodextrin, hydroxypropyl β-cyclodextrin, phosphatidylcholine, or combinations thereof. Absorption enhancers can improve the pharmacokinetics of the active ingredient(s) of the pharmaceutical spray formulation. In some embodiments, the improved pharmacokinetics includes one or more of $C_{max}$, $T_{max}$, and AUC. In some cases, the absorption enhancer comprises diethylene glycol monoethyl ether. In some cases, use of absorption enhancers can reduce $T_{max}$. Absorption enhancers may be used to increase the AUC of the active ingredient.

In some embodiments, the pharmaceutical spray formulation comprises an absorption enhancer at a concentration of about 0.1% to about 2%. In some embodiments, the pharmaceutical spray formulation comprises an absorption enhancer at a concentration of at least about 0.1%. In some embodiments, the pharmaceutical spray formulation comprises an absorption enhancer at a concentration of at most about 2%. In some embodiments, the pharmaceutical spray formulation comprises an absorption enhancer at a concentration of about 0.1% to about 0.2%, about 0.1% to about 0.3%, about 0.1% to about 0.4%, about 0.1% to about 0.5%, about 0.1% to about 0.6%, about 0.1% to about 0.7%, about 0.1% to about 0.8%, about 0.1% to about 0.9%, about 0.1% to about 1%, about 0.1% to about 1.5%, about 0.1% to about 2%, about 0.2% to about 0.3%, about 0.2% to about 0.4%, about 0.2% to about 0.5%, about 0.2% to about 0.6%, about 0.2% to about 0.7%, about 0.2% to about 0.8%, about 0.2% to about 0.9%, about 0.2% to about 1%, about 0.2% to about 1.5%, about 0.2% to about 2%, about 0.3% to about 0.4%, about 0.3% to about 0.5%, about 0.3% to about 0.6%, about 0.3% to about 0.7%, about 0.3% to about 0.8%, about 0.3% to about 0.9%, about 0.3% to about 1%, about 0.3% to about 1.5%, about 0.3% to about 2%, about 0.4% to about 0.5%, about 0.4% to about 0.6%, about 0.4% to about 0.7%, about 0.4% to about 0.8%, about 0.4% to about 0.9%, about 0.4% to about 1%, about 0.4% to about 1.5%, about 0.4% to about 2%, about 0.5% to about 0.6%, about 0.5% to about 0.7%, about 0.5% to about 0.8%, about 0.5% to about 0.9%, about 0.5% to about 1%, about 0.5% to about 1.5%, about 0.5% to about 2%, about 0.6% to about 0.7%, about 0.6% to about 0.8%, about 0.6% to about 0.9%, about 0.6% to about 1%, about 0.6% to about 1.5%, about 0.6% to about 2%, about 0.7% to about 0.8%, about 0.7% to about 0.9%, about 0.7% to about 1%, about 0.7% to about 1.5%, about 0.7% to about 2%, about 0.8% to about 0.9%, about 0.8% to about 1%, about 0.8% to about 1.5%, about 0.8% to about 2%, about 0.9% to about 1%, about 0.9% to about 1.5%, about 0.9% to about 2%, about 1% to about 1.5%, about 1% to about 2%, or about 1.5% to about 2%. In some embodiments, the pharmaceutical spray formulation comprises an absorption enhancer at a concentration of about 0.1%, about 0.2%, about 0.3%, about 0.4%, about 0.5%, about 0.6%, about 0.7%, about 0.8%, about 0.9%, about 1%, about 1.5%, or about 2%.

In some embodiments, the pharmaceutical spray formulation comprises an absorption enhancer at a concentration of at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.0%, at least about 2.5%, at least about 3.0%, at least about 4.0%, at least about 5.0%, and/or no more than about 0.1%, no more than about 0.2%, no more than about 0.3%, no more than about 0.4%, no more than about 0.5%, no more than about 0.6%, no more than about 0.7%, no more than about 0.8%, no more than about 0.9%, no more than about 1.0%, no more than about 1.1%, no more than about 1.2%, no more than about 1.3%, no more than about 1.4%, no more than about 1.5%, no more than about 1.6%, no more than about 1.7%, no more than about 1.8%, no more than about 1.9%, no more than about 2.0%, no more than about 2.5%, no more than about 3.0%, no more than about 4.0%, or no more than about 5.0%. In some embodiments, the absorption enhancer is diethylene glycol monoethyl ether. In some embodiments, the pharmaceutical spray formulation comprises 1% diethylene glycol monoethyl ether.

In an aspect provided herein, the pharmaceutical spray formulation further comprises a permeability enhancer or absorption enhancer.

In an aspect provided herein, the pharmaceutical spray formulation further comprises diethylene glycol monoethyl ether. In some embodiments, the pharmaceutical spray formulation further comprises diethylene glycol monoethyl ether at a concentration of from about 0.05% to about 15%. In some embodiments, the pharmaceutical spray formulation further comprises diethylene glycol monoethyl ether at a concentration of from about 0.5% to about 10%. In some embodiments, the pharmaceutical spray formulation further comprises diethylene glycol monoethyl ether at a concentration of from about 0.5% to about 5%. In some embodiments, the pharmaceutical spray formulation further comprises diethylene glycol monoethyl ether at a concentration of from about 0.5% to about 4%. In some embodiments, the pharmaceutical spray formulation further comprises diethylene glycol monoethyl ether at a concentration of from about 0.5% to about 3%. In some embodiments, the pharmaceutical spray formulation further comprises diethylene glycol monoethyl ether at a concentration of from about 0.5% to about 2%. In some embodiments, the pharmaceutical spray formulation further comprises diethylene glycol monoethyl ether at a concentration of about 1%.

Formulations

In some aspects, disclosed herein are pharmaceutical spray formulations comprising an active ingredient or pharmaceutically acceptable salt thereof, and one or more excipients, vehicles, emulsifiers, stabilizing agents, preservatives, mucosal adhesives, antibacterial agents, buffers, and/or other additives. In some embodiments, the pharmaceutical spray formulation comprises at least one, at least two, at least three, at least four, at least five, at least six, at least seven, or at least eight of an excipient, vehicle, emulsifier, stabilizing agent, preservative, mucosal adhesive, antibacterial agent, buffer, and/or other additive. In some embodiments, the pharmaceutical spray formulation comprises at least one, at least two, at least three, at least four, at least five, or at least six of an antioxidant, a chelating agent, an antimicrobial preservative, a viscosity modifier, a buffering agent, or an absorption enhancer. In some embodiments, the pharmaceutical spray formulation comprises at least one preservative that is an antioxidant, a chelating agent, an antimicrobial preservative, or any combination thereof. In some embodiments, the pharmaceutical spray formulation comprises an active ingredient (e.g., epinephrine), or a pharmaceutically acceptable salt thereof, and at least one, at least two, at least three, at least four, at least five, or at least six of an antioxidant, an isotonicity agent, a viscosity modifier, a buffering agent, an absorption enhancer, or an antimicrobial preservative. In some embodiments, the pharmaceutical spray formulation comprises an active ingredient (e.g., epinephrine), or a pharmaceutically acceptable salt thereof, an antioxidant, an isotonicity agent, a viscosity modifier, a buffering agent, an absorption enhancer, and an antimicrobial preservative.

In some embodiments, the pharmaceutical spray formulation comprises from about 1% to about 20% w/w of epinephrine, or a pharmaceutically acceptable salt thereof, from about 0.0001% (w/w) to about 0.1% (w/w) of an antioxidant, from about 0.1% to about 5% of an isotonicity agent, from about 0.001% to about 0.5% of a viscosity modifier, from about 0.01% to about 2.0% of a buffering agent, and from about 0.05% to about 15% of an absorption enhancer.

In some embodiments, the pharmaceutical spray formulation comprises about 2% w/w of epinephrine, or a pharmaceutically acceptable salt thereof, from about 0.0001% (w/w) to about 0.1% (w/w) of an antioxidant, from about 0.1% to about 5% of an isotonicity agent, from about 0.001% to about 0.5% of a viscosity modifier, from about 0.01% to about 2% of a buffering agent, and from about 0.05% to about 15% of an absorption enhancer.

In some embodiments, the pharmaceutical spray formulation comprises about 2% w/w of epinephrine, or a pharmaceutically acceptable salt thereof, from about 0.01% (w/w) to about 0.1% (w/w) of an antioxidant, from about 0.1% to about 1% of an isotonicity agent, from about 0.01% to about 0.2% of a viscosity modifier, from about 0.1% to about 1% of a buffering agent, and from about 0.1% to about 5% of an absorption enhancer.

In some embodiments, the pharmaceutical spray formulation comprises about 2% w/w of epinephrine, or a pharmaceutically acceptable salt thereof, about 0.05% (w/w) of an antioxidant, about 0.4% of an isotonicity agent, about 0.1% of a viscosity modifier, about 0.42% of a buffering agent, and about 1% of an absorption enhancer.

In some embodiments, the pharmaceutical spray formulation comprises about 5% w/w of epinephrine, or a pharmaceutically acceptable salt thereof, from about 0.0001% (w/w) to about 0.1% (w/w) of an antioxidant, from about 0.1% to about 5% of an isotonicity agent, from about 0.001% to about 0.5% of a viscosity modifier, from about 0.01% to about 2% of a buffering agent, and from about 0.05% to about 15% of an absorption enhancer.

In some embodiments, the pharmaceutical spray formulation comprises about 5% w/w of epinephrine, or a pharmaceutically acceptable salt thereof, from about 0.01% (w/w) to about 0.1% (w/w) of an antioxidant, from about 0.1% to about 1% of an isotonicity agent, from about 0.01% to about 0.2% of a viscosity modifier, from about 0.1% to about 1% of a buffering agent, and from about 0.1% to about 5% of an absorption enhancer.

In some embodiments, the pharmaceutical spray formulation comprises about 5% w/w of epinephrine, or a pharmaceutically acceptable salt thereof, about 0.05% (w/w) of an antioxidant, about 0.4% of an isotonicity agent, about 0.1% of a viscosity modifier, about 0.42% of a buffering agent, and about 1% of an absorption enhancer.

In some embodiments, the pharmaceutical spray formulation comprises from about 1% to about 5% w/w of epinephrine, or a pharmaceutically acceptable salt thereof, from about 0.01% (w/w) to about 0.1% (w/w) of an antioxidant, from about 0.1% to about 1.0% of an isotonicity agent, from about 0.01% to about 0.2% of a viscosity modifier, from about 0.1% to about 1.0% of a buffering agent, and from about 0.1% to about 2.0% of an absorption enhancer.

In some embodiments, the pharmaceutical spray formulation comprises from about 5% to about 20% w/w of epinephrine, or a pharmaceutically acceptable salt thereof, from about 0.01% (w/w) to about 0.1% (w/w) of an antioxidant, from about 0.1% to about 1.0% of an isotonicity agent, from about 0.05% to about 0.5% of a viscosity modifier, from about 0.1% to about 1.0% of a buffering agent, and from about 0.5% to about 5% of an absorption enhancer.

In some embodiments, the pharmaceutical spray formulation comprises about 2.4% w/w of epinephrine, or a pharmaceutically acceptable salt thereof, about 0.05% (w/w) of an antioxidant, about 0.4% of an isotonicity agent, about 0.1% of a viscosity modifier, about 0.7% of a buffering agent, and about 1% of an absorption enhancer.

In some embodiments, the pharmaceutical spray formulation comprises about 5% w/w of epinephrine, or a pharmaceutically acceptable salt thereof, about 0.05% (w/w) of an antioxidant, about 0.4% of an isotonicity agent, about 0.1% of a viscosity modifier, about 0.7% of a buffering agent, and about 1% of an absorption enhancer. In some embodiments, the pharmaceutical spray formulation comprises about 10% w/w of epinephrine, or a pharmaceutically acceptable salt thereof, about 0.05% (w/w) of an antioxidant, about 0.4% of an isotonicity agent, about 0.1% of a viscosity modifier, about 0.7% of a buffering agent, and about 1% of an absorption enhancer.

In some embodiments, the pharmaceutical spray formulation comprises about 20% w/w of epinephrine, or a pharmaceutically acceptable salt thereof, about 0.05% (w/w) of an antioxidant, about 0.4% of an isotonicity agent, about 0.1% of a viscosity modifier, about 0.7% of a buffering agent, and about 1% of an absorption enhancer.

In some embodiments, the pharmaceutical spray formulation comprises from about 1% to about 20% w/w of epinephrine, or a pharmaceutically acceptable salt thereof, from about 0.0001% (w/w) to about 0.1% (w/w) of an antioxidant, from about 0.1% to about 5% of an isotonicity agent, from about 0.001% to about 0.5% of a viscosity modifier, from about 0.01% to about 2% of a buffering agent, and from about 0.05% to about 15% of an absorption enhancer.

In some embodiments, the pharmaceutical spray formulation comprises from about 1% to about 5% w/w of epinephrine, or a pharmaceutically acceptable salt thereof, from about 0.01% (w/w) to about 0.1% (w/w) of an antioxidant, from about 0.1% to about 1% of an isotonicity agent, from about 0.01% to about 0.2% of a viscosity modifier, from about 0.1% to about 1% of a buffering agent citrate, and from about 0.1% to about 5% of an absorption enhancer.

In some embodiments, the pharmaceutical spray formulation comprises from about 5% to about 20% w/w of epinephrine, or a pharmaceutically acceptable salt thereof, from about 0.01% (w/w) to about 0.1% (w/w) of an antioxidant, from about 0.1% to about 1% of an isotonicity agent, from about 0.01% to about 0.2% of a viscosity modifier, from about 0.1% to about 1% of a buffering agent, and from about 0.1% to about 5% of an absorption enhancer.

In some embodiments, the pharmaceutical spray formulation comprises about 2% w/w of epinephrine, or a pharmaceutically acceptable salt thereof, about 0.05% (w/w) of an antioxidant, about 0.4% of an isotonicity agent, about 0.1% of a viscosity modifier, about 0.42% of a buffering agent, and about 1% of an absorption enhancer.

In some embodiments, the pharmaceutical spray formulation comprises about 5% w/w of epinephrine, or a pharmaceutically acceptable salt thereof, about 0.05% (w/w) of an antioxidant, about 0.4% of an isotonicity agent, about 0.1% of a viscosity modifier, about 0.42% of a buffering agent, and about 1% of an absorption enhancer.

In some embodiments, the pharmaceutical spray formulation comprises about 10% w/w of epinephrine, or a pharmaceutically acceptable salt thereof, about 0.05% (w/w) of an antioxidant, about 0.4% of an isotonicity agent, about 0.1% of a viscosity modifier, about 0.42% of a buffering agent, and about 1% of an absorption enhancer.

In some embodiments, the pharmaceutical spray formulation comprises about 20% w/w of epinephrine, or a pharmaceutically acceptable salt thereof, about 0.05% (w/w) of an antioxidant, about 0.4% of an isotonicity agent, about 0.1% of a viscosity modifier, about 0.42% of a buffering agent, and about 1% of an absorption enhancer.

In some embodiments, the pharmaceutical spray formulation further comprises an antimicrobial preservative at a concentration of from about 0.05% (w/v) to about 1% (w/v).

In some embodiments, the pharmaceutical spray formulation comprises about 2.4% w/w of epinephrine, or a pharmaceutically acceptable salt thereof, about 0.05% (w/w) of an antioxidant, about 0.4% of an isotonicity agent, about 0.1% of a viscosity modifier, about 0.7% of a buffering agent, about 1% of an absorption enhancer, and about 0.2% an antimicrobial preservative.

In some embodiments, the pharmaceutical spray formulation comprises about 4.6% w/w of epinephrine, or a pharmaceutically acceptable salt thereof, about 0.05% (w/w) of an antioxidant, about 0.4% of an isotonicity agent, about 0.1% of a viscosity modifier, about 0.7% of a buffering agent, about 1% of an absorption enhancer, and about 0.2% an antimicrobial preservative.

In some embodiments, the pharmaceutical spray formulation comprises about 2% w/w of epinephrine, or a pharmaceutically acceptable salt thereof, about 0.05% (w/w) of an antioxidant, about 0.4% of an isotonicity agent, about 0.1% of a viscosity modifier, about 0.42% of a buffering agent, about 1% of an absorption enhancer, and about 0.21% an antimicrobial preservative In some embodiments, the pharmaceutical spray formulation comprises about 5% w/w of epinephrine, or a pharmaceutically acceptable salt thereof, about 0.05% (w/w) of an antioxidant, about 0.4% of an isotonicity agent, about 0.1% of a viscosity modifier, about 0.42% of a buffering agent, about 1% of an absorption enhancer, and about 0.21% an antimicrobial preservative.

In some embodiments, the pharmaceutical spray formulation comprises from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2.0% trisodium citrate, and from about 0.05% to about 15% diethylene glycol monoethyl ether.

In some embodiments, the pharmaceutical spray formulation comprises about 2% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether.

In some embodiments, the pharmaceutical spray formulation comprises about 2% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether.

In some embodiments, the pharmaceutical spray formulation comprises about 2% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments, the pharmaceutical spray formulation comprises about 5% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether.

In some embodiments, the pharmaceutical spray formulation comprises about 5% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether.

In some embodiments, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments, the pharmaceutical spray formulation comprises from about 1% to about 5% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.01% to about 0.2% hypromellose, from about 0.1% to about 1.0% trisodium citrate, and from about 0.1% to about 2.0% diethylene glycol monoethyl ether.

In some embodiments, the pharmaceutical spray formulation comprises from about 5% to about 20% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.05% to about 0.5% hypromellose, from about 0.1% to about 1.0% trisodium citrate, and from about 0.5% to about 5% diethylene glycol monoethyl ether.

In some embodiments, the pharmaceutical spray formulation comprises about 2.4% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. In some embodiments, the pharmaceutical spray formulation comprises about 10% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments, the pharmaceutical spray formulation comprises about 20% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments, the pharmaceutical spray formulation comprises from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether.

In some embodiments, the pharmaceutical spray formulation comprises from about 1% to about 5% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate citrate, and from about 0.1% to about 5% diethylene glycol monoethyl ether.

In some embodiments, the pharmaceutical spray formulation comprises from about 5% to about 20% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether.

In some embodiments, the pharmaceutical spray formulation comprises about 2% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments, the pharmaceutical spray formulation comprises about 10% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments, the pharmaceutical spray formulation comprises about 20% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments, the pharmaceutical spray formulation further comprises chlorobutanol at a concentration of from about 0.05% (w/v) to about 1% (w/v).

In some embodiments, the pharmaceutical spray formulation comprises about 2.4% w/w of epinephrine, or a pharmaceutically acceptable salt thereof, about 0.05% (w/w)

of sodium metabisulfite, about 0.4% sodium chloride, about 0.1% hypromellose, about 0.7% trisodium citrate, about 1% diethylene glycol monoethyl ether, and about 0.2% chlorobutanol.

In some embodiments, the pharmaceutical spray formulation comprises about 4.6% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, about 1% diethylene glycol monoethyl ether, and about 0.2% chlorobutanol.

In some embodiments, the pharmaceutical spray formulation comprises about 2% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, about 1% diethylene glycol monoethyl ether, and about 0.21% chlorobutanol In some embodiments, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, about 1% diethylene glycol monoethyl ether, and about 0.21% chlorobutanol.

In some embodiments, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, about 1% diethylene glycol monoethyl ether, and about 0.2% of chlorobutanol.

In some embodiments, the pharmaceutical spray formulation comprises about 4% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, about 1% diethylene glycol monoethyl ether, and about 0.2% of chlorobutanol.

Intranasal Delivery

In an aspect provided herein, the pharmaceutical spray formulation has a droplet size of D50 of from about 10 microns to about 100 microns. In some embodiments, the pharmaceutical spray formulation has a droplet size of D50 of from about 10 microns to about 80 microns. In some embodiments, the pharmaceutical spray formulation has a droplet size of D50 of from about 10 microns to about 60 microns. In some embodiments, the pharmaceutical spray formulation has a droplet size of D50 of from about 10 microns to about 40 microns. In some embodiments, the pharmaceutical spray formulation has a droplet size of D50 of from about 10 microns to about 20 microns. In some embodiments, the pharmaceutical spray formulation has a droplet size of D50 of about 10 microns. In some embodiments, the pharmaceutical spray formulation has a droplet size of D50 of about 20 microns. In some embodiments, the pharmaceutical spray formulation has a droplet size of D50 of about 30 microns. In some embodiments, the pharmaceutical spray formulation has a droplet size of D50 of about 40 microns. In some embodiments, the pharmaceutical spray formulation has a droplet size of D50 of about 50 microns. In some embodiments, the pharmaceutical spray formulation has a droplet size of D50 of about 60 microns. In some embodiments, the pharmaceutical spray formulation has a droplet size of D50 of about 70 microns. In some embodiments, the pharmaceutical spray formulation has a droplet size of D50 of about 80 microns. In some embodiments, the pharmaceutical spray formulation has a droplet size of D50 of about 90 microns. In some embodiments, the pharmaceutical spray formulation has a droplet size of D50 of about 100 microns.

In some embodiments, the pharmaceutical spray formulation is delivered as one or more sprays having a droplet size distribution characterized by certain D10, D50, or D90 values. In some embodiments, the pharmaceutical spray formulation is delivered as a spray with a D10 droplet size of about 15 microns to about 30 microns. In some embodiments, the pharmaceutical spray formulation is delivered as a spray with a D10 droplet size of about 15 microns to about 16 microns, about 15 microns to about 17 microns, about 15 microns to about 18 microns, about 15 microns to about 19 microns, about 15 microns to about 20 microns, about 15 microns to about 21 microns, about 15 microns to about 22 microns, about 15 microns to about 25 microns, about 15 microns to about 30 microns, about 16 microns to about 17 microns, about 16 microns to about 18 microns, about 16 microns to about 19 microns, about 16 microns to about 20 microns, about 16 microns to about 21 microns, about 16 microns to about 22 microns, about 16 microns to about 25 microns, about 16 microns to about 30 microns, about 17 microns to about 18 microns, about 17 microns to about 19 microns, about 17 microns to about 20 microns, about 17 microns to about 21 microns, about 17 microns to about 22 microns, about 17 microns to about 25 microns, about 17 microns to about 30 microns, about 18 microns to about 19 microns, about 18 microns to about 20 microns, about 18 microns to about 21 microns, about 18 microns to about 22 microns, about 18 microns to about 25 microns, about 18 microns to about 30 microns, about 19 microns to about 20 microns, about 19 microns to about 21 microns, about 19 microns to about 22 microns, about 19 microns to about 25 microns, about 19 microns to about 30 microns, about 20 microns to about 21 microns, about 20 microns to about 22 microns, about 20 microns to about 25 microns, about 20 microns to about 30 microns, about 21 microns to about 22 microns, about 21 microns to about 25 microns, about 21 microns to about 30 microns, about 22 microns to about 25 microns, about 22 microns to about 30 microns, or about 25 microns to about 30 microns. In some embodiments, the pharmaceutical spray formulation is delivered as a spray with a D10 droplet size of about 15 microns, about 16 microns, about 17 microns, about 18 microns, about 19 microns, about 20 microns, about 21 microns, about 22 microns, about 25 microns, or about 30 microns. In some embodiments, the pharmaceutical spray formulation is delivered as a spray with a D10 droplet size of at least about 15 microns, about 16 microns, about 17 microns, about 18 microns, about 19 microns, about 20 microns, about 21 microns, about 22 microns, or about 25 microns. In some embodiments, the pharmaceutical spray formulation is delivered as a spray with a D10 droplet size of at most about 16 microns, about 17 microns, about 18 microns, about 19 microns, about 20 microns, about 21 microns, about 22 microns, about 25 microns, or about 30 microns.

In some embodiments, the pharmaceutical spray formulation is delivered as a spray with a D50 droplet size of about 35 microns to about 80 microns. In some embodiments, the pharmaceutical spray formulation is delivered as a spray with a D50 droplet size of about 35 microns to about 40 microns, about 35 microns to about 42 microns, about 35 microns to about 44 microns, about 35 microns to about 46 microns, about 35 microns to about 48 microns, about 35 microns to about 50 microns, about 35 microns to about 52 microns, about 35 microns to about 55 microns, about 35 microns to about 60 microns, about 35 microns to about 70 microns, about 35 microns to about 80 microns, about 40 microns to about 42 microns, about 40 microns to about 44 microns, about 40 microns to about 46 microns, about 40 microns to about 48 microns, about 40 microns to about 50 microns, about 40 microns to about 52 microns, about 40 microns to about 55 microns, about 40 microns to about 60 microns, about 40 microns to about 70 microns, about 40 microns to about 80 microns, about 42 microns to about 44 microns, about 42 microns to about 46 microns, about 42 microns to about 48 microns, about 42 microns to about 50 microns, about 42 microns to about 52 microns, about 42 microns to about 55 microns, about 42 microns to about 60 microns, about 42 microns to about 70 microns, about 42 microns to about 80 microns, about 44 microns to about 46 microns, about 44 microns to about 48 microns, about 44 microns to about 50 microns, about 44 microns to about 52 microns, about 44 microns to about 55 microns, about 44 microns to about 60 microns, about 44 microns to about 70 microns, about 44 microns to about 80 microns, about 46 microns to about 48 microns, about 46 microns to about 50 microns, about 46 microns to about 52 microns, about 46 microns to about 55 microns, about 46 microns to about 60 microns, about 46 microns to about 70 microns, about 46 microns to about 80 microns, about 48 microns to about 50 microns, about 48 microns to about 52 microns, about 48 microns to about 55 microns, about 48 microns to about 60 microns, about 48 microns to about 70 microns, about 48 microns to about 80 microns, about 50 microns to about 52 microns, about 50 microns to about 55 microns, about 50 microns to about 60 microns, about 50 microns to about 70 microns, about 50 microns to about 80 microns, about 52 microns to about 55 microns, about 52 microns to about 60 microns, about 52 microns to about 70 microns, about 52 microns to about 80 microns, about 55 microns to about 60 microns, about 55 microns to about 70 microns, about 55 microns to about 80 microns, about 60 microns to about 70 microns, about 60 microns to about 80 microns, or about 70 microns to about 80 microns. In some embodiments, the pharmaceutical spray formulation is delivered as a spray with a D50 droplet size of about 35 microns, about 40 microns, about 42 microns, about 44 microns, about 46 microns, about 48 microns, about 50 microns, about 52 microns, about 55 microns, about 60 microns, about 70 microns, or about 80 microns. In some embodiments, the pharmaceutical spray formulation is delivered as a spray with a D50 droplet size of at least about 35 microns, about 40 microns, about 42 microns, about 44 microns, about 46 microns, about 48 microns, about 50 microns, about 52 microns, about 55 microns, about 60 microns, or about 70 microns. In some embodiments, the pharmaceutical spray formulation is delivered as a spray with a D50 droplet size of at most about 40 microns, about 42 microns, about 44 microns, about 46 microns, about 48 microns, about 50 microns, about 52 microns, about 55 microns, about 60 microns, about 70 microns, or about 80 microns.

In some embodiments, the pharmaceutical spray formulation is delivered as a spray with a D90 droplet size of about 80 microns to about 180 microns. In some embodiments, the pharmaceutical spray formulation is delivered as a spray with a D90 droplet size of about 80 microns to about 90 microns, about 80 microns to about 100 microns, about 80 microns to about 110 microns, about 80 microns to about 115 microns, about 80 microns to about 120 microns, about 80 microns to about 130 microns, about 80 microns to about 140 microns, about 80 microns to about 150 microns, about 80 microns to about 160 microns, about 80 microns to about 170 microns, about 80 microns to about 180 microns, about 90 microns to about 100 microns, about 90 microns to about 110 microns, about 90 microns to about 115 microns, about 90 microns to about 120 microns, about 90 microns to about 130 microns, about 90 microns to about 140 microns, about 90 microns to about 150 microns, about 90 microns to about 160 microns, about 90 microns to about 170 microns, about 90 microns to about 180 microns, about 100 microns to about 110 microns, about 100 microns to about 115 microns, about 100 microns to about 120 microns, about 100 microns to about 130 microns, about 100 microns to about 140 microns, about 100 microns to about 150 microns, about 100 microns to about 160 microns, about 100 microns to about 170 microns, about 100 microns to about 180 microns, about 110 microns to about 115 microns, about 110 microns to about 120 microns, about 110 microns to about 130 microns, about 110 microns to about 140 microns, about 110 microns to about 150 microns, about 110 microns to about 160 microns, about 110 microns to about 170 microns, about 110 microns to about 180 microns, about 115 microns to about 120 microns, about 115 microns to about 130 microns, about 115 microns to about 140 microns, about 115 microns to about 150 microns, about 115 microns to about 160 microns, about 115 microns to about 170 microns, about 115 microns to about 180 microns, about 120 microns to about 130 microns, about 120 microns to about 140 microns, about 120 microns to about 150 microns, about 120 microns to about 160 microns, about 120 microns to about 170 microns, about 120 microns to about 180 microns, about 130 microns to about 140 microns, about 130 microns to about 150 microns, about 130 microns to about 160 microns, about 130 microns to about 170 microns, about 130 microns to about 180 microns, about 140 microns to about 150 microns, about 140 microns to about 160 microns, about 140 microns to about 170 microns, about 140 microns to about 180 microns, about 150 microns to about 160 microns, about 150 microns to about 170 microns, about 150 microns to about 180 microns, about 160 microns to about 170 microns, about 160 microns to about 180 microns, or about 170 microns to about 180 microns. In some embodiments, the pharmaceutical spray formulation is delivered as a spray with a D90 droplet size of about 80 microns, about 90 microns, about 100 microns, about 110 microns, about 115 microns, about 120 microns, about 130 microns, about 140 microns, about 150 microns, about 160 microns, about 170 microns, or about 180 microns. In some embodiments, the pharmaceutical spray formulation is delivered as a spray with a D90 droplet size of at least about 80 microns, about 90 microns, about 100 microns, about 110 microns, about 115 microns, about 120 microns, about 130 microns, about 140 microns, about 150 microns, about 160 microns, or about 170 microns. In some embodiments, the pharmaceutical spray formulation is delivered as a spray with a D90 droplet size of at most about 90 microns, about 100 microns, about 110 microns, about 115 microns, about 120 microns, about 130 microns, about 140 microns, about 150 microns, about 160 microns, about 170 microns, or about 180 microns.

In some embodiments, the pharmaceutical spray formulation is delivered as a spray that has a % volume<10 microns of about 0.2% to about 5%. In some embodiments, the pharmaceutical spray formulation is delivered as a spray that has a % volume<10 microns of about 0.2% to about 0.4%, about 0.2% to about 0.6%, about 0.2% to about 0.8%, about 0.2% to about 1%, about 0.2% to about 1.5%, about 0.2% to about 2%, about 0.2% to about 3%, about 0.2% to about 4%, about 0.2% to about 5%, about 0.4% to about 0.6%, about 0.4% to about 0.8%, about 0.4% to about 1%, about 0.4% to about 1.5%, about 0.4% to about 2%, about 0.4% to about 3%, about 0.4% to about 4%, about 0.4% to about 5%, about 0.6% to about 0.8%, about 0.6% to about 1%, about 0.6% to about 1.5%, about 0.6% to about 2%, about 0.6% to about 3%, about 0.6% to about 4%, about 0.6% to about 5%, about 0.8% to about 1%, about 0.8% to about 1.5%, about 0.8% to about 2%, about 0.8% to about 3%, about 0.8% to about 4%, about 0.8% to about 5%, about 1% to about 1.5%, about 1% to about 2%, about 1% to about 3%, about 1% to about 4%, about 1% to about 5%, about 1.5% to about 2%, about 1.5% to about 3%, about 1.5% to about 4%, about 1.5% to about 5%, about 2% to about 3%, about 2% to about 4%, about 2% to about 5%, about 3% to about 4%, about 3% to about 5%, or about 4% to about 5%. In some embodiments, the pharmaceutical spray formulation is delivered as a spray that has a % volume<10 microns of about 0.2%, about 0.4%, about 0.6%, about 0.8%, about 1%, about 1.5%, about 2%, about 3%, about 4%, or about 5%. In some embodiments, the pharmaceutical spray formulation is delivered as a spray that has a % volume<10 microns of at least about 0.2%, about 0.4%, about 0.6%, about 0.8%, about 1%, about 1.5%, about 2%, about 3%, or about 4%. In some embodiments, the pharmaceutical spray formulation is delivered as a spray that has a % volume<10 microns of at most about 0.4%, about 0.6%, about 0.8%, about 1%, about 1.5%, about 2%, about 3%, about 4%, or about 5%.

In some embodiments, the pharmaceutical spray formulation is delivered as a spray that has a span of about 1.5 to about 2.5. In some embodiments, the pharmaceutical spray formulation is delivered as a spray that has a span of about 1.5 to about 1.6, about 1.5 to about 1.7, about 1.5 to about 1.8, about 1.5 to about 1.9, about 1.5 to about 2, about 1.5 to about 2.1, about 1.5 to about 2.2, about 1.5 to about 2.3, about 1.5 to about 2.4, about 1.5 to about 2.5, about 1.6 to about 1.7, about 1.6 to about 1.8, about 1.6 to about 1.9, about 1.6 to about 2, about 1.6 to about 2.1, about 1.6 to about 2.2, about 1.6 to about 2.3, about 1.6 to about 2.4, about 1.6 to about 2.5, about 1.7 to about 1.8, about 1.7 to about 1.9, about 1.7 to about 2, about 1.7 to about 2.1, about 1.7 to about 2.2, about 1.7 to about 2.3, about 1.7 to about 2.4, about 1.7 to about 2.5, about 1.8 to about 1.9, about 1.8 to about 2, about 1.8 to about 2.1, about 1.8 to about 2.2, about 1.8 to about 2.3, about 1.8 to about 2.4, about 1.8 to about 2.5, about 1.9 to about 2, about 1.9 to about 2.1, about 1.9 to about 2.2, about 1.9 to about 2.3, about 1.9 to about 2.4, about 1.9 to about 2.5, about 2 to about 2.1, about 2 to about 2.2, about 2 to about 2.3, about 2 to about 2.4, about 2 to about 2.5, about 2.1 to about 2.2, about 2.1 to about 2.3, about 2.1 to about 2.4, about 2.1 to about 2.5, about 2.2 to about 2.3, about 2.2 to about 2.4, about 2.2 to about 2.5, about 2.3 to about 2.4, about 2.3 to about 2.5, or about 2.4 to about 2.5. In some embodiments, the pharmaceutical spray formulation is delivered as a spray that has a span of about 1.5, about 1.6, about 1.7, about 1.8, about 1.9, about 2, about 2.1, about 2.2, about 2.3, about 2.4, or about 2.5. In some embodiments, the pharmaceutical spray formulation is delivered as a spray that has a span of at least about 1.5, about 1.6, about 1.7, about 1.8, about 1.9, about 2, about 2.1, about 2.2, about 2.3, or about 2.4. In some embodiments, the pharmaceutical spray formulation is delivered as a spray that has a span of at most about 1.6, about 1.7, about 1.8, about 1.9, about 2, about 2.1, about 2.2, about 2.3, about 2.4, or about 2.5.

In an aspect provided herein, the pharmaceutical spray formulation is present in and/or delivered from a device. In some embodiments, the pharmaceutical spray formulation is present in and/or delivered from a pre-primed device. In some embodiments, the pharmaceutical spray formulation is present in and/or delivered from a device suitable for delivering the formulation into the nostril of a subject. In some embodiments, the device is a single-dose device. In some embodiments, the device is a bi-dose device. In some embodiments, the device has a single reservoir containing from about 50 μL to about 250 μL of the pharmaceutical formulation. In some embodiments, the device has a single reservoir containing from about 75 μL to about 250 μL of the pharmaceutical formulation. In some embodiments, the device has a single reservoir containing from about 100 μL to about 250 μL of the pharmaceutical formulation. In some embodiments, the device has a single reservoir containing from about 125 μL to about 250 μL of the pharmaceutical formulation. In some embodiments, the device has a single reservoir containing from about 150 μL to about 250 μL of the pharmaceutical formulation. In some embodiments, the device delivers two sprays of the pharmaceutical solution from a single reservoir. In some embodiments, the single-dose device delivers two sprays of the pharmaceutical solution from a single reservoir. In some embodiments, the bi-dose device delivers two sprays of the pharmaceutical solution from a single reservoir. In some embodiments, the bi-dose device has a first reservoir containing from about 50 μL to about 250 μL of the pharmaceutical formulation and a second reservoir containing from about 50 μL to about 250 μL of the pharmaceutical formulation. In some embodiments, the bi-dose device has a first reservoir containing from about 75 μL to about 250 μL of the pharmaceutical formulation and a second reservoir containing from about 75 μL to about 250 μL of the pharmaceutical formulation. In some embodiments, the bi-dose device has a first reservoir containing from about 100 μL to about 250 μL of the pharmaceutical formulation and a second reservoir containing from about 100 μL to about 250 μL of the pharmaceutical formulation. In some embodiments, the bi-dose device has a first reservoir containing from about 125 μL to about 250 μL of the pharmaceutical formulation and a second reservoir containing from about 125 μL to about 250 μL of the pharmaceutical formulation. In some embodiments, the bi-dose device has a first reservoir containing from about 50 μL to about 225 μL of the pharmaceutical formulation and a second reservoir containing from about 50 μL to about 225 μL of the pharmaceutical formulation. In some embodiments, the bi-dose device has a first reservoir containing from about 50 μL to about 200 μL of the pharmaceutical formulation and a second reservoir containing from about 50 μL to about 175 μL of the pharmaceutical formulation. In some embodiments, the bi-dose device has a first reservoir containing from about 50 μL to about 175 μL of the pharmaceutical formulation and a second reservoir containing from about 50 μL to about 175 μL of the pharmaceutical formulation. In some embodiments, the bi-dose device has a first reservoir containing from about 50 μL to about 150 μL of the pharmaceutical formulation and a second reservoir containing from about 50 μL to about 150 μL of the pharmaceutical formulation. In some embodiments, the bi-dose device delivers one spray of the pharmaceutical solution from the first reservoir and one spray of the pharmaceutical solution from the second reservoir. In some embodiments, the pharmaceutical spray formulation is present in and/or delivered from a device with an oxygen absorber or scavenger. In some embodiments, the oxygen absorber or scavenger is iron, ferrous carbonate, ascorbate, or sodium bicarbonate. In some embodiments, the pharmaceutical spray formulation is present in and/or delivered from a device wherein the device has an increased reservoir.

In some embodiments, the device comprises at least one oxygen absorber or scavenger. In some embodiments, the oxygen absorber or scavenger is iron, ferrous carbonate, ascorbate, or sodium bicarbonate, or a combination thereof.

In an aspect provided herein, the pharmaceutical spray formulation is adapted for dosing by inhalation.

In an aspect provided herein, the pharmaceutical spray formulation is adapted for intranasal dosing.

In an aspect provided herein, is a spray, comprising droplets. In an aspect provided herein, is a spray delivered from a device, comprising droplets. In an aspect provided herein, is a spray, comprising droplets, wherein the droplets comprise epinephrine, or a pharmaceutically acceptable salt thereof, an isotonicity agent, and benzalkonium chloride or chlorobutanol.

In some embodiments, the droplets comprise in aggregate from about 0.5 mg to about 100 mg of epinephrine, or a pharmaceutically acceptable salt thereof. In some embodiments, the droplets comprise in aggregate about 0.5 mg of epinephrine, or a pharmaceutically acceptable salt thereof. In some embodiments, the droplets comprise in aggregate about 1 mg of epinephrine, or a pharmaceutically acceptable salt thereof. In some embodiments, the droplets comprise in aggregate about 2 mg of epinephrine, or a pharmaceutically acceptable salt thereof. In some embodiments, the droplets comprise in aggregate about 3 mg of epinephrine, or a pharmaceutically acceptable salt thereof. In some embodiments, the droplets comprise in aggregate about 4 mg of epinephrine, or a pharmaceutically acceptable salt thereof. In some embodiments, the droplets comprise in aggregate about 5 mg of epinephrine, or a pharmaceutically acceptable salt thereof. In some embodiments, the droplets comprise in aggregate about 6 mg of epinephrine, or a pharmaceutically acceptable salt thereof. In some embodiments, the droplets comprise in aggregate about 7 mg of epinephrine, or a pharmaceutically acceptable salt thereof. In some embodiments, the droplets comprise in aggregate about 8 mg of epinephrine, or a pharmaceutically acceptable salt thereof. In some embodiments, the droplets comprise in aggregate about 9 mg of epinephrine, or a pharmaceutically acceptable salt thereof. In some embodiments, the droplets comprise in aggregate about 10 mg of epinephrine, or a pharmaceutically acceptable salt thereof. In some embodiments, the droplets comprise in aggregate about 15 mg of epinephrine, or a pharmaceutically acceptable salt thereof. In some embodiments, the droplets comprise in aggregate about 20 mg of epinephrine, or a pharmaceutically acceptable salt thereof. In some embodiments, the droplets comprise in aggregate about 25 mg of epinephrine, or a pharmaceutically acceptable salt thereof. In some embodiments, the droplets comprise in aggregate about 30 mg of epinephrine, or a pharmaceutically acceptable salt thereof. In some embodiments, the droplets comprise in aggregate about 35 mg of epinephrine, or a pharmaceutically acceptable salt thereof. In some embodiments, the droplets comprise in aggregate about 40 mg of epinephrine, or a pharmaceutically acceptable salt thereof. In some embodiments, the droplets comprise in aggregate about 45 mg of epinephrine, or a pharmaceutically acceptable salt thereof. In some embodiments, the droplets comprise in aggregate about 50 mg of epinephrine, or a pharmaceutically acceptable salt thereof. In some embodiments, the droplets comprise in aggregate about 55 mg of epinephrine, or a pharmaceutically acceptable salt thereof. In some embodiments, the droplets comprise in aggregate about 60 mg of epinephrine, or a pharmaceutically acceptable salt thereof. In some embodiments, the droplets comprise in aggregate about 65 mg of epinephrine, or a pharmaceutically acceptable salt thereof. In some embodiments, the droplets comprise in aggregate about 70 mg of epinephrine, or a pharmaceutically acceptable salt thereof. In some embodiments, the droplets comprise in aggregate about 75 mg of epinephrine, or a pharmaceutically acceptable salt thereof. In some embodiments, the droplets comprise in aggregate about 80 mg of epinephrine, or a pharmaceutically acceptable salt thereof. In some embodiments, the droplets comprise in aggregate about 85 mg of epinephrine, or a pharmaceutically acceptable salt thereof. In some embodiments, the droplets comprise in aggregate about 90 mg of epinephrine, or a pharmaceutically acceptable salt thereof. In some embodiments, the droplets comprise in aggregate about 95 mg of epinephrine, or a pharmaceutically acceptable salt thereof. In some embodiments, the droplets comprise in aggregate about 100 mg of epinephrine, or a pharmaceutically acceptable salt thereof.

In some embodiments, the epinephrine is at least about 10% bioavailable. In some embodiments, the epinephrine is at least about 20% bioavailable. In some embodiments, the epinephrine is at least about 30% bioavailable. In some embodiments, the epinephrine is at least about 40% bioavailable. In some embodiments, the epinephrine is at least about 50% bioavailable. In some embodiments, the epinephrine is at least about 60% bioavailable. In some embodiments, the epinephrine is at least about 70% bioavailable. In some embodiments, the epinephrine is at least about 80% bioavailable.

In some embodiments, the epinephrine, or a pharmaceutically acceptable salt thereof, is dissolved in water, ethanol, or propylene glycol, or a combination thereof. In some embodiments, the epinephrine, or a pharmaceutically acceptable salt thereof, is dissolved in water. In some embodiments, the epinephrine, or a pharmaceutically acceptable salt thereof, is dissolved in ethanol. In some embodiments, the epinephrine, or a pharmaceutically acceptable salt thereof, is dissolved in propylene glycol. In some embodiments, the epinephrine, or a pharmaceutically acceptable salt thereof, is dissolved in a combination of water and ethanol. In some embodiments, the epinephrine, or a pharmaceutically acceptable salt thereof, is dissolved in a combination of water and propylene glycol. In some embodiments, the epinephrine, or a pharmaceutically acceptable salt thereof, is dissolved in a combination of ethanol and propylene glycol.

In some embodiments, the droplets comprise in aggregate from about 0.005% to about 10% (w/v) of benzalkonium chloride or chlorobutanol.

In some embodiments, the droplets comprise in aggregate from about 0.005% to about 10% (w/v) of benzalkonium chloride. In some embodiments, the pharmaceutical spray formulation comprises benzalkonium chloride at a concentration of from about 0.005% (w/v) to about 1% (w/v). In some embodiments, the pharmaceutical spray formulation comprises benzalkonium chloride at a concentration of from about 0.01% (w/v) to about 1% (w/v). In some embodiments, the pharmaceutical spray formulation comprises benzalkonium chloride at a concentration of from about 0.05% (w/v) to about 1% (w/v). In some embodiments, the pharmaceutical spray formulation comprises benzalkonium chloride at a concentration of from about 0.1% (w/v) to about 1% (w/v). In some embodiments, the droplets comprise in aggregate from about 0.01% to about 10% (w/v) of benzalkonium chloride. In some embodiments, the droplets comprise in aggregate from about 0.05% to about 10% (w/v) of benzalkonium chloride. In some embodiments, the droplets comprise in aggregate from about 0.5% to about 10%

(w/v) of benzalkonium chloride. In some embodiments, the droplets comprise in aggregate from about 1% to about 10% (w/v) of benzalkonium chloride. In some embodiments, the droplets comprise in aggregate from about 0.005% to about 5% (w/v) of benzalkonium chloride. In some embodiments, the droplets comprise in aggregate from about 0.01% to about 2% (w/v) of benzalkonium chloride.

In some embodiments, the droplets comprise in aggregate from about 0.005% to about 10% (w/v) of chlorobutanol. In some embodiments, the pharmaceutical spray formulation comprises chlorobutanol at a concentration of from about 0.005% (w/v) to about 1% (w/v). In some embodiments, the pharmaceutical spray formulation comprises chlorobutanol at a concentration of from about 0.01% (w/v) to about 1% (w/v). In some embodiments, the pharmaceutical spray formulation comprises chlorobutanol at a concentration of from about 0.05% (w/v) to about 1% (w/v). In some embodiments, the pharmaceutical spray formulation comprises chlorobutanol at a concentration of from about 0.1% (w/v) to about 1% (w/v). In some embodiments, the droplets comprise in aggregate from about 0.01% to about 10% (w/v) of chlorobutanol. In some embodiments, the droplets comprise in aggregate from about 0.05% to about 10% (w/v) of chlorobutanol. In some embodiments, the droplets comprise in aggregate from about 0.5% to about 10% (w/v) of chlorobutanol. In some embodiments, the droplets comprise in aggregate from about 1% to about 10% (w/v) of chlorobutanol. In some embodiments, the droplets comprise in aggregate from about 0.005% to about 5% (w/v) of chlorobutanol. In some embodiments, the droplets comprise in aggregate from about 0.01% to about 2% (w/v) of chlorobutanol. In some embodiments, the droplets comprise in aggregate about 2.1% (w/v) of chlorobutanol.

In some embodiments, the isotonicity agent is present at a concentration of from about 0.1% to about 5% (w/v). In some embodiments, the isotonicity agent is sodium chloride.

In an aspect provided herein, the spray is delivered from a device. In some embodiments, the device is pre-primed.

In an aspect provided herein, the spray takes the shape of a round plume. In some embodiments, the spray takes the shape of a round plume with an ovality ratio less than about 2.0. In some embodiments, the spray takes the shape of a round plume with an ovality ratio less than about 1.9. In some embodiments, the spray takes the shape of a round plume with an ovality ratio less than about 1.8. In some embodiments, the spray takes the shape of a round plume with an ovality ratio less than about 1.7. In some embodiments, the spray takes the shape of a round plume with an ovality ratio less than about 1.6. In some embodiments, the spray takes the shape of a round plume with an ovality ratio less than about 1.5. In some embodiments, the spray takes the shape of a round plume with an ovality ratio less than about 1.4. In some embodiments, the spray takes the shape of a round plume with an ovality ratio less than about 1.3. In some embodiments, the spray takes the shape of a round plume with an ovality ratio less than about 1.2. In some embodiments, the spray takes the shape of a round plume with an ovality ratio less than about 1.1. In some embodiments, the spray takes the shape of a round plume with an ovality ratio less than about 1.0. In some embodiments, the spray takes the shape of a round plume with an ovality ratio of at least about 1.0, at least about 1.1, at least about 1.2, at least about 1.3, at least about 1.4, at least about 1.5, and/or no more than about 2.0, no more than about 1.9, no more than about 1.8, no more than about 1.7, no more than about 1.6, no more than about 1.5, no more than about 1.4, no more than about 1.4, no more than about 1.3, no more than about 1.2, or no more than about 1.1.

In an aspect provided herein, the ovality ratio of the spray is measured at a distance of from about 1 cm to about 10 cm from the device from which the spray is delivered. In an aspect provided herein, the ovality ratio of the spray is measured at a distance of from about 1 cm to about 5 cm from the device from which the spray is delivered. In an aspect provided herein, the ovality ratio of the spray is measured at a distance of from about 3 cm to about 6 cm from the device from which the spray is delivered. In an aspect provided herein, the ovality ratio of the spray is measured at a distance of about 3 cm from the device from which the spray is delivered. In an aspect provided herein, the ovality ratio of the spray is measured at a distance of about 5 cm from the device from which the spray is delivered. In an embodiment, the spray is measured from a nozzle, such as a spray nozzle, on the device from which the spray is delivered.

In an aspect provided herein, the droplets of the spray have a median droplet size of from about 10 μm to about 120 μm. In some embodiments, no more than about 10% of the droplets have a diameter less than about 10 μm. In some embodiments, no more than approximately 5% of the droplets have a diameter less than about 10 μm. In some embodiments, no more than approximately 2% of the droplets have a diameter less than about 10 μm. In some embodiments, approximately 50% of the droplets have a diameter of from about 10 μm to about 120 μm. In some embodiments, approximately 50% of the droplets have a diameter of from about 10 μm to about 60 μm. In some embodiments, approximately 90% of the droplets have a diameter less than about 120 μm.

In an aspect provided herein, the spray further comprises a stabilizing agent and an acid. In some embodiments, the stabilizing agent is disodium edetate. In some embodiments, the acid is hydrochloric acid or citric acid, or a combination thereof. In some embodiments, the acid is hydrochloric acid. In some embodiments, the acid is citric acid. In some embodiments, the acid is a combination of hydrochloric acid and citric acid.

In an aspect provided herein, the spray further comprises sodium bisulfite or sodium metabisulfite.

In an aspect provided herein, the spray further comprises sodium bisulfite or sodium metabisulfite. In some embodiments, the spray further comprises sodium bisulfite at a concentration of from about 0.0001% (w/w) to about 0.1% (w/w) or sodium metabisulfite at a concentration of from about 0.0001% (w/w) to about 0.1% (w/w). In some embodiments, the spray comprises sodium bisulfite at a concentration of from about 0.0001% (w/w) to about 0.05% (w/w) or sodium metabisulfite at a concentration of from about 0.0001% (w/w) to about 0.05% (w/w). In some embodiments, the spray comprises sodium bisulfite at a concentration of from about 0.001% (w/w) to about 0.05% (w/w) or sodium metabisulfite at a concentration of from about 0.001% (w/w) to about 0.05% (w/w). In some embodiments, the spray comprises sodium bisulfite at a concentration of from about 0.01% (w/w) to about 0.05% (w/w) or sodium metabisulfite at a concentration of from about 0.01% (w/w) to about 0.05% (w/w). In some embodiments, the spray further comprises sodium bisulfite at a concentration of from about 0.001% (w/w) to about 0.1% (w/w) or sodium metabisulfite at a concentration of from about 0.001% (w/w) to about 0.1% (w/w). In some embodiments, the spray further comprises sodium bisulfite at a concentration of from about 0.01% (w/w) to about 0.1% (w/w) or sodium metabisulfite at a concentration of from about 0.01% (w/w) to about 0.1% (w/w).

In some embodiments, the spray comprises sodium bisulfite. In some embodiments, the spray further comprises sodium bisulfite at a concentration of from about 0.0001% (w/w) to about 0.1% (w/w). In some embodiments, the spray comprises sodium bisulfite at a concentration of from about 0.001% to about 0.05%. In some embodiments, the spray comprises sodium bisulfite at a concentration of from about 0.01% to about 0.05%. In some embodiments, the spray comprises sodium bisulfite at a concentration of about 0.01%. In some embodiments, the spray comprises sodium bisulfite at a concentration of about 0.02%. In some embodiments, the spray comprises sodium bisulfite at a concentration of about 0.03%. In some embodiments, the spray comprises sodium bisulfite at a concentration of about 0.04%. In some embodiments, the spray comprises sodium bisulfite at a concentration of about 0.05%.

In some embodiments, the spray comprises sodium metabisulfite. In some embodiments, the spray further comprises sodium metabisulfite at a concentration of from about 0.0001% (w/w) to about 0.1% (w/w). In some embodiments, the spray comprises sodium metabisulfite at a concentration of from about 0.001% to about 0.1%. In some embodiments, the spray comprises sodium metabisulfite at a concentration of from about 0.01% to about 0.1%. In some embodiments, the spray further comprises sodium metabisulfite at a concentration of from about 0.001% (w/w) to about 0.1% (w/w). In some embodiments, the spray further comprises sodium metabisulfite at a concentration of from about 0.01% (w/w) to about 0.1% (w/w). In some embodiments, the spray comprises sodium metabisulfite at a concentration of about 0.01%. In some embodiments, the spray comprises sodium metabisulfite at a concentration of about 0.02%. In some embodiments, the spray comprises sodium metabisulfite at a concentration of about 0.03%. In some embodiments, the spray comprises sodium metabisulfite at a concentration of about 0.04%. In some embodiments, the spray comprises sodium metabisulfite at a concentration of about 0.05%. In some embodiments, the spray comprises sodium metabisulfite at a concentration of about 0.06%. In some embodiments, the spray comprises sodium metabisulfite at a concentration of about 0.07%. In some embodiments, the spray comprises sodium metabisulfite at a concentration of about 0.08%. In some embodiments, the spray comprises sodium metabisulfite at a concentration of about 0.09%. In some embodiments, the spray comprises sodium metabisulfite at a concentration of about 0.1%.

In an aspect provided herein, the spray further comprises disodium edetate. In some embodiments, the spray comprises disodium edetate at a concentration of from about 0.0001% to about 0.01%. In some embodiments, the spray comprises disodium edetate at a concentration of from about 0.001% to about 0.01%.

In an aspect provided herein, the spray further comprises an antimicrobial preservative. In some embodiments, the antimicrobial preservative is benzalkonium sodium or chlorobutanol. In some embodiments, the spray comprises benzalkonium sodium at a concentration of from about 0.005% (w/v) to about 1% (w/v) or chlorobutanol at a concentration of from about 0.005% to about 1%.

In some embodiments, the spray comprises benzalkonium sodium. In some embodiments, the spray comprises benzalkonium sodium at a concentration of from about 0.005% to about 1%.

In some embodiments, the spray comprises chlorobutanol. In some embodiments, the spray comprises chlorobutanol at a concentration of from about 0.005% to about 1%.

In an aspect provided herein, the spray further comprises sodium chloride. In some embodiments, the spray comprises sodium chloride at a concentration of from about 0.1% to about 5%. In some embodiments, the spray comprises sodium chloride at a concentration of from about 0.1% to about 1%. In some embodiments, the spray comprises sodium chloride at a concentration of from about 0.5% to about 5%. In some embodiments, the spray comprises sodium chloride at a concentration of from about 1% to about 5%. In some embodiments, the spray comprises sodium chloride at a concentration of from about 2% to about 5%. In some embodiments, the spray comprises sodium chloride at a concentration of from about 3% to about 5%. In some embodiments, the spray comprises sodium chloride at a concentration of from about 4% to about 5%.

In an aspect provided herein, the spray further comprises a vasodilator. In some embodiments, the vasodilator is nitroprusside, phentolamine, or nifedipine.

In some embodiments, the spray further comprises nitroprusside. In some embodiments, the spray further comprises from about 0.05 mg to about 5 mg of nitroprusside. In some embodiments, the spray further comprises from about 0.1 mg to about 5 mg of nitroprusside. In some embodiments, the spray further comprises from about 0.5 mg to about 5 mg of nitroprusside. In some embodiments, the spray further comprises from about 1 mg to about 5 mg of nitroprusside. In some embodiments, the spray further comprises from about 1 mg to about 4 mg of nitroprusside. In some embodiments, the spray further comprises nitroprusside. In some embodiments, the spray further comprises from about 0.05 mg to about 3 mg of nitroprusside. In some embodiments, the spray further comprises nitroprusside. In some embodiments, the spray further comprises from about 0.5 mg to about 3 mg of nitroprusside. In some embodiments, the spray further comprises nitroprusside. In some embodiments, the spray further comprises from about 0.5 mg to about 2 mg of nitroprusside.

In some embodiments, the spray further comprises phentolamine. In some embodiments, the spray further comprises from about 1 mg to about 50 mg of phentolamine. In some embodiments, the spray further comprises phentolamine. In some embodiments, the spray further comprises from about 1 mg to about 40 mg of phentolamine. In some embodiments, the spray further comprises phentolamine. In some embodiments, the spray further comprises from about 1 mg to about 30 mg of phentolamine. In some embodiments, the spray further comprises phentolamine. In some embodiments, the spray further comprises from about 1 mg to about 20 mg of phentolamine. In some embodiments, the spray further comprises phentolamine. In some embodiments, the spray further comprises from about 1 mg to about 10 mg of phentolamine. In some embodiments, the spray further comprises phentolamine. In some embodiments, the spray further comprises from about 5 mg to about 50 mg of phentolamine. In some embodiments, the spray further comprises phentolamine. In some embodiments, the spray further comprises from about 10 mg to about 50 mg of phentolamine. In some embodiments, the spray further comprises phentolamine. In some embodiments, the spray further comprises from about 20 mg to about 50 mg of phentolamine. In some embodiments, the spray further comprises phentolamine. In some embodiments, the spray further comprises from about 20 mg to about 40 mg of phentolamine.

In some embodiments, the spray further comprises nifedipine. In some embodiments, the spray further comprises from about 10 mg to about 500 mg of nifedipine. In some embodiments, the spray further comprises nifedipine. In some embodiments, the spray further comprises from about 10 mg to about 450 mg of nifedipine. In some embodiments, the spray further comprises nifedipine. In some embodiments, the spray further comprises from about 10 mg to about 400 mg of nifedipine. In some embodiments, the spray further comprises nifedipine. In some embodiments, the spray further comprises from about 10 mg to about 350 mg of nifedipine. In some embodiments, the spray further comprises nifedipine. In some embodiments, the spray further comprises from about 10 mg to about 300 mg of nifedipine. In some embodiments, the spray further comprises nifedipine. In some embodiments, the spray further comprises from about 10 mg to about 250 mg of nifedipine. In some embodiments, the spray further comprises nifedipine. In some embodiments, the spray further comprises from about 10 mg to about 200 mg of nifedipine. In some embodiments, the spray further comprises nifedipine. In some embodiments, the spray further comprises from about 10 mg to about 150 mg of nifedipine. In some embodiments, the spray further comprises nifedipine. In some embodiments, the spray further comprises from about 10 mg to about 100 mg of nifedipine. In some embodiments, the spray further comprises nifedipine. In some embodiments, the spray further comprises from about 10 mg to about 75 mg of nifedipine. In some embodiments, the spray further comprises nifedipine. In some embodiments, the spray further comprises from about 10 mg to about 50 mg of nifedipine. In some embodiments, the spray further comprises nifedipine. In some embodiments, the spray further comprises from about 10 mg to about 40 mg of nifedipine. In some embodiments, the spray further comprises nifedipine. In some embodiments, the spray further comprises from about 10 mg to about 30 mg of nifedipine. In some embodiments, the spray further comprises nifedipine. In some embodiments, the spray further comprises from about 50 mg to about 500 mg of nifedipine. In some embodiments, the spray further comprises nifedipine. In some embodiments, the spray further comprises from about 100 mg to about 500 mg of nifedipine. In some embodiments, the spray further comprises nifedipine. In some embodiments, the spray further comprises from about 100 mg to about 400 mg of nifedipine. In some embodiments, the spray further comprises nifedipine. In some embodiments, the spray further comprises from about 100 mg to about 350 mg of nifedipine. In some embodiments, the spray further comprises nifedipine. In some embodiments, the spray further comprises from about 100 mg to about 300 mg of nifedipine.

In an aspect provided herein, the spray further comprises a permeability enhancer.

In an aspect provided herein, the spray further comprises diethylene glycol monoethyl ether. In some embodiments, the spray further comprises diethylene glycol monoethyl ether at a concentration of from about 0.05% to about 15%.

In an aspect provided herein, the spray further comprises a viscosity modifier. In some embodiments, the viscosity modifier is polyethylene glycol, methylcellulose, or hypromellose.

In some embodiments, the spray further comprises polyethylene glycol. In some embodiments, the spray further comprises from about 0.5% to about 50% polyethylene glycol.

In some embodiments, the spray further comprises methylcellulose. In some embodiments, the spray further comprises from about 0.001% to about 5% methylcellulose.

In some embodiments, the spray further comprises hypromellose. In some embodiments, the spray further comprises from about 0.001% to about 0.5% hypromellose. In some embodiments, the spray further comprises from about 0.05% to about 0.5% hypromellose.

In an aspect provided herein, the spray comprises per 100 μL of solution:
  from about 0.5 mg to about 100 mg of epinephrine, or a pharmaceutically acceptable salt thereof;
  from about 0.1 mg to about 2 mg sodium chloride;
  from about 0.01 mg to about 1 mg benzalkonium chloride;
  from about 0.1 mg to about 2 mg disodium edetate; and
  hydrochloric acid or citric acid, or a combination thereof sufficient to achieve a pH of from about 3.5 to about 6.5.

In some embodiments, the pH of the spray is about 4. In some embodiments, the pH of the spray is about 4.5. In some embodiments, the pH of the spray is about 5. In some embodiments, the pH of the spray is about 5.5. In some embodiments, the pH of the spray is about 6. In some embodiments, the pH of the spray is about 6.5.

In an aspect provided herein, the spray is delivered from a spray nozzle of a pre-primed device, and wherein no more than about 10% of the droplets have a diameter less than 10 In some embodiments, the spray is measured by laser diffraction with beams measuring at both 3 cm and 6 cm from the spray nozzle.

In an aspect provided herein, the pharmaceutical spray formulation or spray is administered from a unit-dose device or delivery system. In an aspect provided herein, the pharmaceutical spray formulation or spray is administered from a bi-dose device or delivery system. In an aspect provided herein, the pharmaceutical spray formulation or spray is administered from a multi-dose device or delivery system.

Pharmacokinetics

In some aspects disclosed herein, the pharmaceutical spray formulation provides desirable pharmacokinetic profiles following administration to an individual. In some embodiments, the pharmacokinetic profile comprises a $C_{max}$, a $T_{max}$, an area under curve (AUC), or any combination thereof. In some embodiments, the administration comprises a single spray. In some embodiments, the administration comprises two sprays. In some embodiments, the pharmaceutical spray formulation comprises a spray in each nostril. In some embodiments, the administration comprises one or more sprays from a unit-dose device or delivery system. In some embodiments, the administration comprises one or more sprays from a multi-dose or bi-dose device or delivery system.

In some embodiments, the pharmaceutical spray formulation is formulated to achieve a desired pharmacokinetic profile. In some embodiments, administration of the pharmaceutical spray formulation achieves a desired pharmacokinetic profile. In some embodiments, administration of the pharmaceutical spray formulation comprises a single spray, or two or more sprays. For example, a bi-dose delivery includes a single spray in each nostrils of an individual. In some embodiments, the desired pharmacokinetic profile is achieved based on the pharmaceutical spray formulation, the delivery of the pharmaceutical spray formulation, or both. In some embodiments, the combination of the delivery device and the pharmaceutical spray formulation achieves one or more sprays that have a desired ovality ratio as described herein. The ovality ratio can affect the pharmacokinetic profile, for example, by increasing the rate of absorption of the spray(s), thereby improving pharmacokinetic parameters such as blood plasma concentration, $C_{max}$, $T_{max}$, and/or AUC of the active ingredient. The pharmaceutical spray formulation may also be formulated to improve absorption such as by including one or more absorption enhancers. In some embodiments, the pharmaceutical spray formulation comprises one or more preservatives, which can include antioxidants, chelating agents, antimicrobial preservatives, and other types of preservatives that help maintain stability and/or longevity of the formulation. In some embodiments, the pharmaceutical spray formulation comprises one or more buffering agents to maintain an appropriate pH for enhancing stability of the formulation. In some embodiments, the pharmaceutical spray formulation is formulated to provide pharmacokinetics that is substantially equivalent to that of administration through intramuscular injection.

In some embodiments, the pharmaceutical formulation is formulated to be stable. In some embodiments, at least a minimum percentage of the active ingredient (e.g., epinephrine) remains in the pharmaceutical formulation in an un-degraded state after storage. In some embodiments, a stable pharmaceutical formulation has at least 85%, at least 90%, at least 91%, at least 92%, at least 93%, at least 94%, at least 95%, at least 96%, at least 97%, at least 98%, or at least 99% or more of the active ingredient in an un-degraded state after a period of storage at a given temperature and/or humidity. In some embodiments, the period of storage is at least 1 month, at least 2 months, at least 3 months, at least 4 months, at least 5 months, at least 6 months, at least 7 months, at least 8 months, at least 9 months, at least 10 months, at least 11 months, or at least 12 months or more. In some embodiments, the humidity is at least 10%, at least 20%, at least 30%, at least 40%, at least 50%, at least 60%, at least 70%, at least 80%, or at least 90% or more. In some embodiments, a stable pharmaceutical formulation has no more than 1%, no more than 2%, no more than 3%, no more than 4%, no more than 5%, no more than 6%, no more than 7%, no more than 8%, no more than 9%, no more than 10%, no more than 15%, or no more than 20% or more impurities after a period of storage at a given temperature and/or humidity. In some embodiments, the impurities comprise degradation products of the active ingredient.

In some embodiments, the pharmaceutical spray formulation is formulated to achieve a blood plasma concentration of at least 0.1, 0.2, 0.3, 0.4, 0.5, 0.6, 0.7, 0.8, 0.9, 1, 5, 10, 15, 20, 25, 30, 35, 40, 45, or 50 ng/mL, and/or no more than 0.1, 0.2, 0.3, 0.4, 0.5, 0.6, 0.7, 0.8, 0.9, 1, 5, 10, 15, 20, 25, or 30 ng/mL within no more than 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, or 15 minutes. In some embodiments, the desired pharmacokinetic profile is achieved following administration of a single spray of the pharmaceutical spray formulation. In some embodiments, the desired pharmacokinetic profile is achieved following administration of two sprays of the pharmaceutical spray formulation. In some embodiments, the desired pharmacokinetic profile is achieved following administration of two or more sprays of the pharmaceutical spray formulation such as three sprays, four sprays, five sprays, or six sprays. In some embodiments, the pharmaceutical spray formulation is formulated to achieve a target blood plasma concentration within a minimum time period following administration.

In some embodiments, the pharmaceutical spray formulation is formulated to achieve a blood plasma concentration within a minimum time period following administration of about 0.1 ng/mL to about 1 ng/mL. In some embodiments, the minimum time period is about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, or 10 minutes. In some embodiments, the pharmaceutical spray formulation is formulated to achieve a blood plasma concentration within a minimum time period following administration of at least about 0.1 ng/mL. In some embodiments, the pharmaceutical spray formulation is formulated to achieve a blood plasma concentration within a minimum time period following administration of at most about 1 ng/mL. In some embodiments, the pharmaceutical spray formulation is formulated to achieve a blood plasma concentration within a minimum time period following administration of about 0.1 ng/mL to about 0.2 ng/mL, about 0.1 ng/mL to about 0.3 ng/mL, about 0.1 ng/mL to about 0.4 ng/mL, about 0.1 ng/mL to about 0.5 ng/mL, about 0.1 ng/mL to about 0.6 ng/mL, about 0.1 ng/mL to about 0.7 ng/mL, about 0.1 ng/mL to about 0.8 ng/mL, about 0.1 ng/mL to about 0.9 ng/mL, about 0.1 ng/mL to about 1 ng/mL, about 0.2 ng/mL to about 0.3 ng/mL, about 0.2 ng/mL to about 0.4 ng/mL, about 0.2 ng/mL to about 0.5 ng/mL, about 0.2 ng/mL to about 0.6 ng/mL, about 0.2 ng/mL to about 0.7 ng/mL, about 0.2 ng/mL to about 0.8 ng/mL, about 0.2 ng/mL to about 0.9 ng/mL, about 0.2 ng/mL to about 1 ng/mL, about 0.3 ng/mL to about 0.4 ng/mL, about 0.3 ng/mL to about 0.5 ng/mL, about 0.3 ng/mL to about 0.6 ng/mL, about 0.3 ng/mL to about 0.7 ng/mL, about 0.3 ng/mL to about 0.8 ng/mL, about 0.3 ng/mL to about 0.9 ng/mL, about 0.3 ng/mL to about 1 ng/mL, about 0.4 ng/mL to about 0.5 ng/mL, about 0.4 ng/mL to about 0.6 ng/mL, about 0.4 ng/mL to about 0.7 ng/mL, about 0.4 ng/mL to about 0.8 ng/mL, about 0.4 ng/mL to about 0.9 ng/mL, about 0.4 ng/mL to about 1 ng/mL, about 0.5 ng/mL to about 0.6 ng/mL, about 0.5 ng/mL to about 0.7 ng/mL, about 0.5 ng/mL to about 0.8 ng/mL, about 0.5 ng/mL to about 0.9 ng/mL, about 0.5 ng/mL to about 1 ng/mL, about 0.6 ng/mL to about 0.7 ng/mL, about 0.6 ng/mL to about 0.8 ng/mL, about 0.6 ng/mL to about 0.9 ng/mL, about 0.6 ng/mL to about 1 ng/mL, about 0.7 ng/mL to about 0.8 ng/mL, about 0.7 ng/mL to about 0.9 ng/mL, about 0.7 ng/mL to about 1 ng/mL, about 0.8 ng/mL to about 0.9 ng/mL, about 0.8 ng/mL to about 1 ng/mL, or about 0.9 ng/mL to about 1 ng/mL. In some embodiments, the pharmaceutical spray formulation is formulated to achieve a blood plasma concentration within a minimum time period following administration of about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 0.9 ng/mL, or about 1 ng/mL.

In some embodiments, the pharmaceutical spray formulation is formulated to achieve a blood plasma concentration within a minimum time period following administration of about 1 ng/mL to about 40 ng/mL. In some embodiments, the minimum time period is about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, or 10 minutes. In some embodiments, the pharmaceutical spray formulation is formulated to achieve a blood plasma concentration within a minimum time period following administration of at least about 1 ng/mL. In some embodiments, the pharmaceutical spray formulation is formulated to achieve a blood plasma concentration within a minimum time period following administration of at most about 40 ng/mL. In some embodiments, the pharmaceutical spray formulation is formulated to achieve a blood plasma concentration within a minimum time period following administration of about 1 ng/mL to about 2 ng/mL, about 1 ng/mL to about 3 ng/mL, about 1 ng/mL to about 4 ng/mL, about 1 ng/mL to about 5 ng/mL, about 1 ng/mL to about 6 ng/mL, about 1 ng/mL to about 7 ng/mL, about 1 ng/mL to about 8 ng/mL, about 1 ng/mL to about 9 ng/mL, about 1 ng/mL to about 10 ng/mL, about 1 ng/mL to about 20 ng/mL, about 1 ng/mL to about 40 ng/mL, about 2 ng/mL to about 3 ng/mL, about 2 ng/mL to about 4 ng/mL, about 2 ng/mL to about 5 ng/mL, about 2 ng/mL to about 6 ng/mL, about 2 ng/mL to about 7 ng/mL, about 2 ng/mL to about 8 ng/mL, about 2 ng/mL to about 9 ng/mL, about 2 ng/mL to about 10 ng/mL, about 2 ng/mL to about 20 ng/mL, about 2 ng/mL to about 40 ng/mL, about 3 ng/mL to about 4 ng/mL, about 3 ng/mL to about 5 ng/mL, about 3 ng/mL to about 6 ng/mL, about 3 ng/mL to about 7 ng/mL, about 3 ng/mL to about 8 ng/mL, about 3 ng/mL to about 9 ng/mL, about 3 ng/mL to about 10 ng/mL, about 3 ng/mL to about 20 ng/mL, about 3 ng/mL to about 40 ng/mL, about 4 ng/mL to about 5 ng/mL, about 4 ng/mL to about 6 ng/mL, about 4 ng/mL to about 7 ng/mL, about 4 ng/mL to about 8 ng/mL, about 4 ng/mL to about 9 ng/mL, about 4 ng/mL to about 10 ng/mL, about 4 ng/mL to about 20 ng/mL, about 4 ng/mL to about 40 ng/mL, about 5 ng/mL to about 6 ng/mL, about 5 ng/mL to about 7 ng/mL, about 5 ng/mL to about 8 ng/mL, about 5 ng/mL to about 9 ng/mL, about 5 ng/mL to about 10 ng/mL, about 5 ng/mL to about 20 ng/mL, about 5 ng/mL to about 40 ng/mL, about 6 ng/mL to about 7 ng/mL, about 6 ng/mL to about 8 ng/mL, about 6 ng/mL to about 9 ng/mL, about 6 ng/mL to about 10 ng/mL, about 6 ng/mL to about 20 ng/mL, about 6 ng/mL to about 40 ng/mL, about 7 ng/mL to about 8 ng/mL, about 7 ng/mL to about 9 ng/mL, about 7 ng/mL to about 10 ng/mL, about 7 ng/mL to about 20 ng/mL, about 7 ng/mL to about 40 ng/mL, about 8 ng/mL to about 9 ng/mL, about 8 ng/mL to about 10 ng/mL, about 8 ng/mL to about 20 ng/mL, about 8 ng/mL to about 40 ng/mL, about 9 ng/mL to about 10 ng/mL, about 9 ng/mL to about 20 ng/mL, about 9 ng/mL to about 40 ng/mL, about 10 ng/mL to about 20 ng/mL, about 10 ng/mL to about 40 ng/mL, or about 20 ng/mL to about 40 ng/mL. In some embodiments, the pharmaceutical spray formulation is formulated to achieve a blood plasma concentration within a minimum time period following administration of about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 20 ng/mL, or about 40 ng/mL.

In some embodiments, the pharmaceutical spray formulation is formulated to achieve a blood plasma concentration after a minimum time period following administration. In some embodiments, the minimum time period is at least 1, at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, at least 100, at least 110, at least 120, at least 130, at least 140, or at least 150 minutes.

In some embodiments, the pharmaceutical spray formulation is formulated to achieve a blood plasma concentration after a minimum time period following administration of about 1 ng/mL to about 10 ng/mL. In some embodiments, the pharmaceutical spray formulation is formulated to achieve a blood plasma concentration after a minimum time period following administration of at least about 1 ng/mL. In some embodiments, the pharmaceutical spray formulation is formulated to achieve a blood plasma concentration after a minimum time period following administration of at most about 10 ng/mL. In some embodiments, the pharmaceutical spray formulation is formulated to achieve a blood plasma concentration after a minimum time period following administration of about 1 ng/mL to about 1.5 ng/mL, about 1 ng/mL to about 2 ng/mL, about 1 ng/mL to about 2.5 ng/mL, about 1 ng/mL to about 3 ng/mL, about 1 ng/mL to about 3.5 ng/mL, about 1 ng/mL to about 4 ng/mL, about 1 ng/mL to about 4.5 ng/mL, about 1 ng/mL to about 5 ng/mL, about 1 ng/mL to about 6 ng/mL, about 1 ng/mL to about 8 ng/mL, about 1 ng/mL to about 10 ng/mL, about 1.5 ng/mL to about 2 ng/mL, about 1.5 ng/mL to about 2.5 ng/mL, about 1.5 ng/mL to about 3 ng/mL, about 1.5 ng/mL to about 3.5 ng/mL, about 1.5 ng/mL to about 4 ng/mL, about 1.5 ng/mL to about 4.5 ng/mL, about 1.5 ng/mL to about 5 ng/mL, about 1.5 ng/mL to about 6 ng/mL, about 1.5 ng/mL to about 8 ng/mL, about 1.5 ng/mL to about 10 ng/mL, about 2 ng/mL to about 2.5 ng/mL, about 2 ng/mL to about 3 ng/mL, about 2 ng/mL to about 3.5 ng/mL, about 2 ng/mL to about 4 ng/mL, about 2 ng/mL to about 4.5 ng/mL, about 2 ng/mL to about 5 ng/mL, about 2 ng/mL to about 6 ng/mL, about 2 ng/mL to about 8 ng/mL, about 2 ng/mL to about 10 ng/mL, about 2.5 ng/mL to about 3 ng/mL, about 2.5 ng/mL to about 3.5 ng/mL, about 2.5 ng/mL to about 4 ng/mL, about 2.5 ng/mL to about 4.5 ng/mL, about 2.5 ng/mL to about 5 ng/mL, about 2.5 ng/mL to about 6 ng/mL, about 2.5 ng/mL to about 8 ng/mL, about 2.5 ng/mL to about 10 ng/mL, about 3 ng/mL to about 3.5 ng/mL, about 3 ng/mL to about 4 ng/mL, about 3 ng/mL to about 4.5 ng/mL, about 3 ng/mL to about 5 ng/mL, about 3 ng/mL to about 6 ng/mL, about 3 ng/mL to about 8 ng/mL, about 3 ng/mL to about 10 ng/mL, about 3.5 ng/mL to about 4 ng/mL, about 3.5 ng/mL to about 4.5 ng/mL, about 3.5 ng/mL to about 5 ng/mL, about 3.5 ng/mL to about 6 ng/mL, about 3.5 ng/mL to about 8 ng/mL, about 3.5 ng/mL to about 10 ng/mL, about 4 ng/mL to about 4.5 ng/mL, about 4 ng/mL to about 5 ng/mL, about 4 ng/mL to about 6 ng/mL, about 4 ng/mL to about 8 ng/mL, about 4 ng/mL to about 10 ng/mL, about 4.5 ng/mL to about 5 ng/mL, about 4.5 ng/mL to about 6 ng/mL, about 4.5 ng/mL to about 8 ng/mL, about 4.5 ng/mL to about 10 ng/mL, about 5 ng/mL to about 6 ng/mL, about 5 ng/mL to about 8 ng/mL, about 5 ng/mL to about 10 ng/mL, about 6 ng/mL to about 8 ng/mL, about 6 ng/mL to about 10 ng/mL, or about 8 ng/mL to about 10 ng/mL. In some embodiments, the pharmaceutical spray formulation is formulated to achieve a blood plasma concentration after a minimum time period following administration of about 1 ng/mL, about 1.5 ng/mL, about 2 ng/mL, about 2.5 ng/mL, about 3 ng/mL, about 3.5 ng/mL, about 4 ng/mL, about 4.5 ng/mL, about 5 ng/mL, about 6 ng/mL, about 8 ng/mL, or about 10 ng/mL.

In some embodiments, the pharmaceutical spray formulation is formulated to achieve a $C_{max}$ of about 0.1 ng/mL to about 1 ng/mL. In some embodiments, the pharmaceutical spray formulation is formulated to achieve a $C_{max}$ of at least about 0.1 ng/mL. In some embodiments, the pharmaceutical spray formulation is formulated to achieve a $C_{max}$ of at most about 1 ng/mL. In some embodiments, the pharmaceutical spray formulation is formulated to achieve a $C_{max}$ of about 0.1 ng/mL to about 0.2 ng/mL, about 0.1 ng/mL to about 0.3 ng/mL, about 0.1 ng/mL to about 0.4 ng/mL, about 0.1 ng/mL to about 0.5 ng/mL, about 0.1 ng/mL to about 0.6 ng/mL, about 0.1 ng/mL to about 0.7 ng/mL, about 0.1 ng/mL to about 0.8 ng/mL, about 0.1 ng/mL to about 0.9 ng/mL, about 0.1 ng/mL to about 1 ng/mL, about 0.2 ng/mL to about 0.3 ng/mL, about 0.2 ng/mL to about 0.4 ng/mL, about 0.2 ng/mL to about 0.5 ng/mL, about 0.2 ng/mL to about 0.6 ng/mL, about 0.2 ng/mL to about 0.7 ng/mL, about 0.2 ng/mL to about 0.8 ng/mL, about 0.2 ng/mL to about 0.9 ng/mL, about 0.2 ng/mL to about 1 ng/mL, about 0.3 ng/mL to about 0.4 ng/mL, about 0.3 ng/mL to about 0.5 ng/mL, about 0.3 ng/mL to about 0.6 ng/mL, about 0.3 ng/mL to about 0.7 ng/mL, about 0.3 ng/mL to about 0.8 ng/mL, about 0.3 ng/mL to about 0.9 ng/mL, about 0.3 ng/mL to about 1 ng/mL, about 0.4 ng/mL to about 0.5 ng/mL, about 0.4 ng/mL to about 0.6 ng/mL, about 0.4 ng/mL to about 0.7 ng/mL, about 0.4 ng/mL to about 0.8 ng/mL, about 0.4 ng/mL to about 0.9 ng/mL, about 0.4 ng/mL to about 1 ng/mL, about 0.5 ng/mL to about 0.6 ng/mL, about 0.5 ng/mL to about 0.7 ng/mL, about 0.5 ng/mL to about 0.8 ng/mL, about 0.5 ng/mL to about 0.9 ng/mL, about 0.5 ng/mL to about 1 ng/mL, about 0.6 ng/mL to about 0.7 ng/mL, about 0.6 ng/mL to about 0.8 ng/mL, about 0.6 ng/mL to about 0.9 ng/mL, about 0.6 ng/mL to about 1 ng/mL, about 0.7 ng/mL to about 0.8 ng/mL, about 0.7 ng/mL to about 0.9 ng/mL, about 0.7 ng/mL to about 1 ng/mL, about 0.8 ng/mL to about 0.9 ng/mL, about 0.8 ng/mL to about 1 ng/mL, or about 0.9 ng/mL to about 1 ng/mL. In some embodiments, the pharmaceutical spray formulation is formulated to achieve a $C_{max}$ of about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 0.9 ng/mL, or about 1 ng/mL.

In some embodiments, the pharmaceutical spray formulation is formulated to achieve a $C_{max}$ of about 1 ng/mL to about 40 ng/mL. In some embodiments, the pharmaceutical spray formulation is formulated to achieve a $C_{max}$ of at least about 1 ng/mL. In some embodiments, the pharmaceutical spray formulation is formulated to achieve a $C_{max}$ of at most about 40 ng/mL. In some embodiments, the pharmaceutical spray formulation is formulated to achieve a $C_{max}$ of about 1 ng/mL to about 2 ng/mL, about 1 ng/mL to about 3 ng/mL, about 1 ng/mL to about 4 ng/mL, about 1 ng/mL to about 5 ng/mL, about 1 ng/mL to about 6 ng/mL, about 1 ng/mL to about 7 ng/mL, about 1 ng/mL to about 8 ng/mL, about 1 ng/mL to about 9 ng/mL, about 1 ng/mL to about 10 ng/mL, about 1 ng/mL to about 20 ng/mL, about 1 ng/mL to about 40 ng/mL, about 2 ng/mL to about 3 ng/mL, about 2 ng/mL to about 4 ng/mL, about 2 ng/mL to about 5 ng/mL, about 2 ng/mL to about 6 ng/mL, about 2 ng/mL to about 7 ng/mL, about 2 ng/mL to about 8 ng/mL, about 2 ng/mL to about 9 ng/mL, about 2 ng/mL to about 10 ng/mL, about 2 ng/mL to about 20 ng/mL, about 2 ng/mL to about 40 ng/mL, about 3 ng/mL to about 4 ng/mL, about 3 ng/mL to about 5 ng/mL, about 3 ng/mL to about 6 ng/mL, about 3 ng/mL to about 7 ng/mL, about 3 ng/mL to about 8 ng/mL, about 3 ng/mL to about 9 ng/mL, about 3 ng/mL to about 10 ng/mL, about 3 ng/mL to about 20 ng/mL, about 3 ng/mL to about 40 ng/mL, about 4 ng/mL to about 5 ng/mL, about 4 ng/mL to about 6 ng/mL, about 4 ng/mL to about 7 ng/mL, about 4 ng/mL to about 8 ng/mL, about 4 ng/mL to about 9 ng/mL, about 4 ng/mL to about 10 ng/mL, about 4 ng/mL to about 20 ng/mL, about 4 ng/mL to about 40 ng/mL, about 5 ng/mL to about 6 ng/mL, about 5 ng/mL to about 7 ng/mL, about 5 ng/mL to about 8 ng/mL, about 5 ng/mL to about 9 ng/mL, about 5 ng/mL to about 10 ng/mL, about 5 ng/mL to about 20 ng/mL, about 5 ng/mL to about 40 ng/mL, about 6 ng/mL to about 7 ng/mL, about 6 ng/mL to about 8 ng/mL, about 6 ng/mL to about 9 ng/mL, about 6 ng/mL to about 10 ng/mL, about 6 ng/mL to about 20 ng/mL, about 6 ng/mL to about 40 ng/mL, about 7 ng/mL to about 8 ng/mL, about 7 ng/mL to about 9 ng/mL, about 7 ng/mL to about 10 ng/mL, about 7 ng/mL to about 20 ng/mL, about 7 ng/mL to about 40 ng/mL, about 8 ng/mL to about 9 ng/mL, about 8 ng/mL to about 10 ng/mL, about 8 ng/mL to about 20 ng/mL, about 8 ng/mL to about 40 ng/mL, about 9 ng/mL to about 10 ng/mL, about 9 ng/mL to about 20 ng/mL, about 9 ng/mL to about 40 ng/mL, about 10 ng/mL to about 20 ng/mL, about 10 ng/mL to about 40 ng/mL, or about 20 ng/mL to about 40 ng/mL. In some embodiments, the pharmaceutical spray formulation is formulated to achieve a $C_{max}$ of about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 20 ng/mL, or about 40 ng/mL.

In some embodiments, the pharmaceutical spray formulation is formulated to achieve a $T_{max}$ of no more than 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, 15 minutes, or 20 minutes. In some embodiments, administration of the pharmaceutical spray formulation achieves a $T_{max}$ of at least 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, 15 minutes, or 20 minutes.

In some embodiments, the pharmaceutical spray formulation is formulated to achieve a $T_{max}$ of about 0.1 min to about 10 min. In some embodiments, the pharmaceutical spray formulation is formulated to achieve a $T_{max}$ of at least about 0.1 min. In some embodiments, the pharmaceutical spray formulation is formulated to achieve a $T_{max}$ of at most about 10 min. In some embodiments, the pharmaceutical spray formulation is formulated to achieve a $T_{max}$ of about 0.1 min to about 0.2 min, about 0.1 min to about 0.4 min, about 0.1 min to about 0.6 min, about 0.1 min to about 0.8 min, about 0.1 min to about 1 min, about 0.1 min to about 2 min, about 0.1 min to about 4 min, about 0.1 min to about 5 min, about 0.1 min to about 6 min, about 0.1 min to about 8 min, about 0.1 min to about 10 min, about 0.2 min to about 0.4 min, about 0.2 min to about 0.6 min, about 0.2 min to about 0.8 min, about 0.2 min to about 1 min, about 0.2 min to about 2 min, about 0.2 min to about 4 min, about 0.2 min to about 5 min, about 0.2 min to about 6 min, about 0.2 min to about 8 min, about 0.2 min to about 10 min, about 0.4 min to about 0.6 min, about 0.4 min to about 0.8 min, about 0.4 min to about 1 min, about 0.4 min to about 2 min, about 0.4 min to about 4 min, about 0.4 min to about 5 min, about 0.4 min to about 6 min, about 0.4 min to about 8 min, about 0.4 min to about 10 min, about 0.6 min to about 0.8 min, about 0.6 min to about 1 min, about 0.6 min to about 2 min, about 0.6 min to about 4 min, about 0.6 min to about 5 min, about 0.6 min to about 6 min, about 0.6 min to about 8 min, about 0.6 min to about 10 min, about 0.8 min to about 1 min, about 0.8 min to about 2 min, about 0.8 min to about 4 min, about 0.8 min to about 5 min, about 0.8 min to about 6 min, about 0.8 min to about 8 min, about 0.8 min to about 10 min, about 1 min to about 2 min, about 1 min to about 4 min, about 1 min to about 5 min, about 1 min to about 6 min, about 1 min to about 8 min, about 1 min to about 10 min, about 2 min to about 4 min, about 2 min to about 5 min, about 2 min to about 6 min, about 2 min to about 8 min, about 2 min to about 10 min, about 4 min to about 5 min, about 4 min to about 6 min, about 4 min to about 8 min, about 4 min to about 10 min, about 5 min to about 6 min, about 5 min to about 8 min, about 5 min to about 10 min, about 6 min to about 8 min, about 6 min to about 10 min, or about 8 min to about 10 min. In some embodiments, the pharmaceutical spray formulation is formulated to achieve a $T_{max}$ of about 0.1 min, about 0.2 min, about 0.4 min, about 0.6 min, about 0.8 min, about 1 min, about 2 min, about 4 min, about 5 min, about 6 min, about 8 min, or about 10 min.

In some embodiments, the pharmaceutical spray formulation is formulated to achieve an AUC of about 0.1 ng·h/mL to about 50 ng·h/mL. In some embodiments, the pharmaceutical spray formulation is formulated to achieve an AUC of at least about 0.1 ng·h/mL. In some embodiments, the pharmaceutical spray formulation is formulated to achieve an AUC of at most about 50 ng·h/mL. In some embodiments, the pharmaceutical spray formulation is formulated to achieve an AUC of about 0.1 ng·h/mL to about 0.5 ng·h/mL, about 0.1 ng·h/mL to about 1 ng·h/mL, about 0.1 ng·h/mL to about 2 ng·h/mL, about 0.1 ng·h/mL to about 4 ng·h/mL, about 0.1 ng·h/mL to about 6 ng·h/mL, about 0.1 ng·h/mL to about 8 ng·h/mL, about 0.1 ng·h/mL to about 10 ng·h/mL, about 0.1 ng·h/mL to about 20 ng·h/mL, about 0.1 ng·h/mL to about 30 ng·h/mL, about 0.1 ng·h/mL to about 40 ng·h/mL, about 0.1 ng·h/mL to about 50 ng·h/mL, about 0.5 ng·h/mL to about 1 ng·h/mL, about 0.5 ng·h/mL to about 2 ng·h/mL, about 0.5 ng·h/mL to about 4 ng·h/mL, about 0.5 ng·h/mL to about 6 ng·h/mL, about 0.5 ng·h/mL to about 8 ng·h/mL, about 0.5 ng·h/mL to about 10 ng·h/mL, about 0.5 ng·h/mL to about 20 ng·h/mL, about 0.5 ng·h/mL to about 30 ng·h/mL, about 0.5 ng·h/mL to about 40 ng·h/mL, about 0.5 ng·h/mL to about 50 ng·h/mL, about 1 ng·h/mL to about 2 ng·h/mL, about 1 ng·h/mL to about 4 ng·h/mL, about 1 ng·h/mL to about 6 ng·h/mL, about 1 ng·h/mL to about 8 ng·h/mL, about 1 ng·h/mL to about 10 ng·h/mL, about 1 ng·h/mL to about 20 ng·h/mL, about 1 ng·h/mL to about 30 ng·h/mL, about 1 ng·h/mL to about 40 ng·h/mL, about 1 ng·h/mL to about 50 ng·h/mL, about 2 ng·h/mL to about 4 ng·h/mL, about 2 ng·h/mL to about 6 ng·h/mL, about 2 ng·h/mL to about 8 ng·h/mL, about 2 ng·h/mL to about 10 ng·h/mL, about 2 ng·h/mL to about 20 ng·h/mL, about 2 ng·h/mL to about 30 ng·h/mL, about 2 ng·h/mL to about 40 ng·h/mL, about 2 ng·h/mL to about 50 ng·h/mL, about 4 ng·h/mL to about 6 ng·h/mL, about 4 ng·h/mL to about 8 ng·h/mL, about 4 ng·h/mL to about 10 ng·h/mL, about 4 ng·h/mL to about 20 ng·h/mL, about 4 ng·h/mL to about 30 ng·h/mL, about 4 ng·h/mL to about 40 ng·h/mL, about 4 ng·h/mL to about 50 ng·h/mL, about 6 ng·h/mL to about 8 ng·h/mL, about 6 ng·h/mL to about 10 ng·h/mL, about 6 ng·h/mL to about 20 ng·h/mL, about 6 ng·h/mL to about 30 ng·h/mL, about 6 ng·h/mL to about 40 ng·h/mL, about 6 ng·h/mL to about 50 ng·h/mL, about 8 ng·h/mL to about 10 ng·h/mL, about 8 ng·h/mL to about 20 ng·h/mL, about 8 ng·h/mL to about 30 ng·h/mL, about 8 ng·h/mL to about 40 ng·h/mL, about 8 ng·h/mL to about 50 ng·h/mL, about 10 ng·h/mL to about 20 ng·h/mL, about 10 ng·h/mL to about 30 ng·h/mL, about 10 ng·h/mL to about 40 ng·h/mL, about 10 ng·h/mL to about 50 ng·h/mL, about 20 ng·h/mL to about 30 ng·h/mL, about 20 ng·h/mL to about 40 ng·h/mL, about 20 ng·h/mL to about 50 ng·h/mL, about 30 ng·h/mL to about 40 ng·h/mL, about 30 ng·h/mL to about 50 ng·h/mL, or about 40 ng·h/mL to about 50 ng·h/mL. In some embodiments, the pharmaceutical spray formulation is formulated to achieve an AUC of about 0.1 ng·h/mL, about 0.5 ng·h/mL, about 1 ng·h/mL, about 2 ng·h/mL, about 4 ng·h/mL, about 6 ng·h/mL, about 8 ng·h/mL, about 10 ng·h/mL, about 20 ng·h/mL, about 30 ng·h/mL, about 40 ng·h/mL, or about 50 ng·h/mL.

In some embodiments, intranasal administration of the pharmaceutical spray formulation produces an epinephrine plasma concentration that is at least 5% higher, at least 10% higher, at least 15% higher, at least 20% higher, at least 25% higher, at least 30% higher, at least 35% higher, at least 40% higher, at least 45% higher, at least 50% higher, at least 60% higher, at least 70% higher, at least 80% higher, at least 90% higher, at least 100% higher, at least 150% higher, at least 200% higher, at least 250% higher, at least 300% higher, at least 350% higher, at least 400% higher, at least 450% higher, at least 500% higher, at least 600% higher, at least 700% higher, at least 800% higher, at least 900% higher, or at least 1000% higher than by injection using a commercially available delivery device (e.g., an EpiPen) after about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, or about 15 minutes following administration. In some embodiments, intranasal administration of the pharmaceutical spray formulation results in epinephrine plasma concentrations having a relative standard deviation of no more than about 10%, about 20%, about 30%, about 40%, about 50%, about 60%, about 70%, about 80%, about 90%, or no more than about 100% based on plasma concentrations measured within 15 minutes (inclusive) following administration. In some embodiments, intranasal administration of the pharmaceutical spray formulation results in epinephrine plasma concentrations having a relative standard deviation that is lower than by injection using a commercially available delivery device based on plasma concentration measured within 15 minutes (inclusive) following administration. In some embodiments, the plasma concentrations are measured at 1 minute and two or more later time points within 15 minutes (inclusive).

III. Methods of Use

In another aspect is provided a method of treating anaphylaxis, anaphylactic shock, a severe allergic reaction, and/or bronchial constriction, comprising administering to a subject in need thereof a therapeutically effective amount of a pharmaceutical spray formulation or a spray as described herein, including embodiments.

In an aspect provided herein is a method for treating at least one symptom of anaphylaxis or anaphylactic shock, comprising administering to a subject in need thereof a therapeutically effective amount of a pharmaceutical spray formulation or a spray as described herein, including embodiments.

In an aspect provided herein is a method of treating anaphylaxis- or anaphylactic shock-induced respiratory depression or distress, comprising administering to a subject in need thereof a therapeutically effective amount of a pharmaceutical spray formulation or a spray as described herein, including embodiments.

In another aspect is provided a method of treating anaphylaxis, anaphylactic shock, a severe allergic reaction, and/or bronchial constriction, comprising delivering a spray of a pharmaceutical solution from a pre-primed device into a nostril of a subject in need thereof, wherein:
(i) the device is adapted for nasal delivery;
(ii) a volume of from about 20 µL to about 250 µL of spray is delivered; and
(iii) the pharmaceutical solution comprises from about 0.5 mg to about 100 mg of epinephrine, or a pharmaceutically acceptable salt thereof, an isotonicity agent, and from about 0.005% to about 1% (w/v) of benzalkonium chloride.

In some embodiments, the pharmaceutical solution comprises from about 0.5 mg to about 100 mg of epinephrine, or a pharmaceutically acceptable salt thereof. In some embodiments, the pharmaceutical solution comprises about 0.5 mg of epinephrine, or a pharmaceutically acceptable salt thereof. In some embodiments, the pharmaceutical solution comprises about 1 mg of epinephrine, or a pharmaceutically acceptable salt thereof. In some embodiments, the pharmaceutical solution comprises about 2 mg of epinephrine, or a pharmaceutically acceptable salt thereof. In some embodiments, the pharmaceutical solution comprises about 3 mg of epinephrine, or a pharmaceutically acceptable salt thereof. In some embodiments, the pharmaceutical solution comprises about 4 mg of epinephrine, or a pharmaceutically acceptable salt thereof. In some embodiments, the pharmaceutical solution comprises about 5 mg of epinephrine, or a pharmaceutically acceptable salt thereof. In some embodiments, the pharmaceutical solution comprises about 6 mg of epinephrine, or a pharmaceutically acceptable salt thereof. In some embodiments, the pharmaceutical solution comprises about 7 mg of epinephrine, or a pharmaceutically acceptable salt thereof. In some embodiments, the pharmaceutical solution comprises about 8 mg of epinephrine, or a pharmaceutically acceptable salt thereof. In some embodiments, the pharmaceutical solution comprises about 9 mg of epinephrine, or a pharmaceutically acceptable salt thereof. In some embodiments, the pharmaceutical solution comprises about 10 mg of epinephrine, or a pharmaceutically acceptable salt thereof. In some embodiments, the pharmaceutical solution comprises about 15 mg of epinephrine, or a pharmaceutically acceptable salt thereof. In some embodiments, the pharmaceutical solution comprises about 20 mg of epinephrine, or a pharmaceutically acceptable salt thereof. In some embodiments, the pharmaceutical solution comprises about 25 mg of epinephrine, or a pharmaceutically acceptable salt thereof. In some embodiments, the pharmaceutical solution comprises about 30 mg of epinephrine, or a pharmaceutically acceptable salt thereof. In some embodiments, the pharmaceutical solution comprises about 35 mg of epinephrine, or a pharmaceutically acceptable salt thereof. In some embodiments, the pharmaceutical solution comprises about 40 mg of epinephrine, or a pharmaceutically acceptable salt thereof. In some embodiments, the pharmaceutical solution comprises about 45 mg of epinephrine, or a pharmaceutically acceptable salt thereof. In some embodiments, the pharmaceutical solution comprises about 50 mg of epinephrine, or a pharmaceutically acceptable salt thereof. In some embodiments, the pharmaceutical solution comprises about 55 mg of epinephrine, or a pharmaceutically acceptable salt thereof. In some embodiments, the pharmaceutical solution comprises about 60 mg of epinephrine, or a pharmaceutically acceptable salt thereof. In some embodiments, the pharmaceutical solution comprises about 65 mg of epinephrine, or a pharmaceutically acceptable salt thereof. In some embodiments, the pharmaceutical solution comprises about 70 mg of epinephrine, or a pharmaceutically acceptable salt thereof. In some embodiments, the pharmaceutical solution comprises about 75 mg of epinephrine, or a pharmaceutically acceptable salt thereof. In some embodiments, the pharmaceutical solution comprises about 80 mg of epinephrine, or a pharmaceutically acceptable salt thereof. In some embodiments, the pharmaceutical solution comprises about 85 mg of epinephrine, or a pharmaceutically acceptable salt thereof. In some embodiments, the pharmaceutical solution comprises about 90 mg of epinephrine, or a pharmaceutically acceptable salt thereof. In some embodiments, the pharmaceutical solution comprises about 95 mg of epinephrine, or a pharmaceutically acceptable salt thereof. In some embodiments, the pharmaceutical solution comprises about 100 mg of epinephrine, or a pharmaceutically acceptable salt thereof.

In some embodiments, the spray delivers from about 0.5 mg to about 100 mg of epinephrine, or a pharmaceutically acceptable salt thereof. In some embodiments, the pharmaceutical solution comprises from about 0.5 mg to about 100 mg of epinephrine, or a pharmaceutically acceptable salt thereof. In some embodiments, the spray delivers about 0.5 mg of epinephrine, or a pharmaceutically acceptable salt thereof. In some embodiments, the spray delivers about 1 mg of epinephrine, or a pharmaceutically acceptable salt thereof. In some embodiments, the spray delivers about 2 mg of epinephrine, or a pharmaceutically acceptable salt thereof. In some embodiments, the spray delivers about 3 mg of epinephrine, or a pharmaceutically acceptable salt thereof. In some embodiments, the spray delivers about 4 mg of epinephrine, or a pharmaceutically acceptable salt thereof. In some embodiments, the spray delivers about 5 mg of epinephrine, or a pharmaceutically acceptable salt thereof. In some embodiments, the spray delivers about 6 mg of epinephrine, or a pharmaceutically acceptable salt thereof. In some embodiments, the spray delivers about 7 mg of epinephrine, or a pharmaceutically acceptable salt thereof. In some embodiments, the spray delivers about 8 mg of epinephrine, or a pharmaceutically acceptable salt thereof. In some embodiments, the spray delivers about 9 mg of epinephrine, or a pharmaceutically acceptable salt thereof. In some embodiments, the spray delivers about 10 mg of epinephrine, or a pharmaceutically acceptable salt thereof. In some embodiments, the spray delivers about 15 mg of epinephrine, or a pharmaceutically acceptable salt thereof. In some embodiments, the spray delivers about 20 mg of epinephrine, or a pharmaceutically acceptable salt thereof. In some embodiments, the spray delivers about 25 mg of epinephrine, or a pharmaceutically acceptable salt thereof. In some embodiments, the spray delivers about 30 mg of epinephrine, or a pharmaceutically acceptable salt thereof. In some embodiments, the spray delivers about 35 mg of epinephrine, or a pharmaceutically acceptable salt thereof. In some embodiments, the spray delivers about 40 mg of epinephrine, or a pharmaceutically acceptable salt thereof. In some embodiments, the spray delivers about 45 mg of epinephrine, or a pharmaceutically acceptable salt thereof. In some embodiments, the spray delivers about 50 mg of epinephrine, or a pharmaceutically acceptable salt thereof. In some embodiments, the spray delivers about 55 mg of epinephrine, or a pharmaceutically acceptable salt thereof. In some embodiments, the spray delivers about 60 mg of epinephrine, or a pharmaceutically acceptable salt thereof. In some embodiments, the spray delivers about 65 mg of epinephrine, or a pharmaceutically acceptable salt thereof. In some embodiments, the spray delivers about 70 mg of epinephrine, or a pharmaceutically acceptable salt thereof. In some embodiments, the spray delivers about 75 mg of epinephrine, or a pharmaceutically acceptable salt thereof. In some embodiments, the spray delivers about 80 mg of epinephrine, or a pharmaceutically acceptable salt thereof. In some embodiments, the spray delivers about 85 mg of epinephrine, or a pharmaceutically acceptable salt thereof. In some embodiments, the spray delivers about 90 mg of epinephrine, or a pharmaceutically acceptable salt thereof. In some embodiments, the spray delivers about 95 mg of epinephrine, or a pharmaceutically acceptable salt thereof. In some embodiments, the spray delivers about 100 mg of epinephrine, or a pharmaceutically acceptable salt thereof.

In some embodiments, the plasma concentration versus time curve of epinephrine in the subject has a $t_{max}$ of less than from about 10 minutes to about 120 minutes. In some embodiments, the plasma concentration versus time curve of epinephrine in the subject has a $t_{max}$ of about 5 minutes to about 50 minutes. In some embodiments, the plasma concentration versus time curve of epinephrine in the subject has a $t_{max}$ of about 5 minutes to about 10 minutes, about 5 minutes to about 15 minutes, about 5 minutes to about 20 minutes, about 5 minutes to about 25 minutes, about 5 minutes to about 30 minutes, about 5 minutes to about 40 minutes, about 5 minutes to about 50 minutes, about 10 minutes to about 15 minutes, about 10 minutes to about 20 minutes, about 10 minutes to about 25 minutes, about 10 minutes to about 30 minutes, about 10 minutes to about 40 minutes, about 10 minutes to about 50 minutes, about 15 minutes to about 20 minutes, about 15 minutes to about 25 minutes, about 15 minutes to about 30 minutes, about 15 minutes to about 40 minutes, about 15 minutes to about 50 minutes, about 20 minutes to about 25 minutes, about 20 minutes to about 30 minutes, about 20 minutes to about 40 minutes, about 20 minutes to about 50 minutes, about 25 minutes to about 30 minutes, about 25 minutes to about 40 minutes, about 25 minutes to about 50 minutes, about 30 minutes to about 40 minutes, about 30 minutes to about 50 minutes, or about 40 minutes to about 50 minutes. In some embodiments, the plasma concentration versus time curve of epinephrine in the subject has a $t_{max}$ of about 5 minutes, about 10 minutes, about 15 minutes, about 20 minutes, about 25 minutes, about 30 minutes, about 40 minutes, or about 50 minutes. In some embodiments, the plasma concentration versus time curve of epinephrine in the subject has a $t_{max}$ of at least about 5 minutes, about 10 minutes, about 15 minutes, about 20 minutes, about 25 minutes, about 30 minutes, or about 40 minutes. In some embodiments, the plasma concentration versus time curve of epinephrine in the subject has a $t_{max}$ of at most about 10 minutes, about 15 minutes, about 20 minutes, about 25 minutes, about 30 minutes, about 40 minutes, or about 50 minutes.

In some embodiments, a therapeutic plasma concentration of epinephrine in the subject is achieved within 15 minutes, 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, or 1 minute following administration to the subject. In some embodiments, a therapeutic plasma concentration of epinephrine in the subject is achieved in less than 20 minutes following administration to the subject. In some embodiments, a therapeutic plasma concentration of epinephrine in the subject is achieved in less than 15 minutes following administration to the subject. In some embodiments, a therapeutic plasma concentration of epinephrine in the subject is achieved in less than 10 minutes following administration to the subject. In some embodiments, a therapeutic plasma concentration of epinephrine in the subject is achieved in less than 5 minutes following administration to the subject. In some embodiments, the therapeutic plasma concentration of epinephrine in the subject is about 500 pg/mL of epinephrine. In some embodiments, the therapeutic plasma concentration of epinephrine in the subject is about 450 pg/mL of epinephrine. In some embodiments, the therapeutic plasma concentration of epinephrine in the subject is about 400 pg/mL of epinephrine. In some embodiments, the therapeutic plasma concentration of epinephrine in the subject is about 350 pg/mL of epinephrine. In embodiments, the therapeutic plasma concentration of epinephrine in the subject is about 300 pg/mL of epinephrine. In some embodiments, the subject has a maximum plasma concentration ($C_{max}$) of from about 50 pg/mL to about 500 pg/mL of epinephrine. In some embodiments, the area under a plasma concentration-time curve of epinephrine in the subject is from about 5 ng/minute/mL to about 50 ng/minute/mL.

In some embodiments, the device comprises a plunger that houses a container closure comprising:
  (i) a vial comprising an opening;
  (ii) a cannula; and
  (iii) a rubber stopper; wherein the stopper is configured to occlude the opening of the vial, and wherein the cannula is configured such that the cannula can pierce the stopper when the plunger applies sufficient force to the cannula.

In some embodiments, the pre-primed device is actuatable with one hand. In some embodiments, the device is a single-dose device. In some embodiments, the device is a bi-dose device. In some embodiments, the volume of the reservoir is not more than about 140 µL. In some embodiments, the device has a single reservoir containing approximately 125 µL of the pharmaceutical solution. In some embodiments, approximately 100 µL of the pharmaceutical solution is delivered by one actuation of the device. In some embodiments, the device has a single reservoir containing from about 50 µL to about 250 µL of the pharmaceutical formulation. In some embodiments, the device has a single reservoir containing from about 75 µL to about 250 µL of the pharmaceutical formulation. In some embodiments, the device has a single reservoir containing from about 100 µL to about 250 µL of the pharmaceutical formulation. In some embodiments, the device has a single reservoir containing from about 125 µL to about 250 µL of the pharmaceutical formulation. In some embodiments, the device has a single reservoir containing from about 150 µL to about 250 µL of the pharmaceutical formulation. In some embodiments, the device delivers two sprays of the pharmaceutical solution from a single reservoir. In some embodiments, the single-dose device delivers two sprays of the pharmaceutical solution from a single reservoir. In some embodiments, the bi-dose device delivers two sprays of the pharmaceutical solution from a single reservoir. In some embodiments, the bi-dose device has a first reservoir containing from about 50 µL to about 250 µL of the pharmaceutical formulation and a second reservoir containing from about 50 µL to about 250 µL of the pharmaceutical formulation. In some embodiments, the bi-dose device has a first reservoir containing from about 75 µL to about 250 µL of the pharmaceutical formulation and a second reservoir containing from about 75 µL to about 250 µL of the pharmaceutical formulation. In some embodiments, the bi-dose device has a first reservoir containing from about 100 µL to about 250 µL of the pharmaceutical formulation and a second reservoir containing from about 100 µL to about 250 µL of the pharmaceutical formulation. In some embodiments, the bi-dose device has a first reservoir containing from about 125 µL to about 250 µL of the pharmaceutical formulation and a second reservoir containing from about 125 µL to about 250 µL of the pharmaceutical formulation. In some embodiments, the bi-dose device has a first reservoir containing from about 50 µL to about 225 µL of the pharmaceutical formulation and a second reservoir containing from about 50 µL to about 225 µL of the pharmaceutical formulation. In some embodiments, the bi-dose device has a first reservoir containing from about 50 µL to about 200 µL of the pharmaceutical formulation and a second reservoir containing from about 50 µL to about 175 µL of the pharmaceutical formulation. In some embodiments, the bi-dose device has a first reservoir containing from about 50 µL to about 175 µL of the pharmaceutical formulation and a second reservoir containing from about 50 µL to about 175 µL of the pharmaceutical formulation. In some embodiments, the bi-dose device has a first reservoir containing from about 50 µL to about 150 µL of the pharmaceutical formulation and a second reservoir containing from about 50 µL to about 150 µL of the pharmaceutical formulation. In some embodiments, the bi-dose device delivers one spray of the pharmaceutical solution from the first reservoir and one spray of the pharmaceutical solution from the second reservoir.

In some embodiments, delivery time of the pharmaceutical solution is less than about 25 seconds. In some embodiments, the delivery time of the pharmaceutical solution is less than about 20 seconds.

In some embodiments, less than about 20% of the pharmaceutical solution leaves the nasal cavity via drainage into the nasopharynx or externally. In some embodiments, less than about 10% of the pharmaceutical solution leaves the nasal cavity via drainage into the nasopharynx or externally. In some embodiments, less than about 5% of the pharmaceutical solution leaves the nasal cavity via drainage into the nasopharynx or externally.

In some embodiments, the subject is suffering from a severe allergic reaction from exposure or suspected exposure to an allergen. In some embodiments, the allergen is food, medication, or an insect bite or sting. In some embodiments, the allergen is an airborne allergen.

In some embodiments, the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, and vomiting. In some embodiments, the subject exhibits respiratory depression or distress, or cardiovascular depression. In some embodiments, the subject exhibits respiratory depression. In some embodiments, the subject exhibits respiratory distress. In some embodiments, the subject exhibits cardiovascular depression.

In some embodiments, the subject is free from respiratory depression or distress for at least about 1 hour following treatment comprising delivery of the therapeutically effective amount of the epinephrine, or a pharmaceutically acceptable salt thereof. In some embodiments, the subject is free from respiratory depression or distress for at least about 2 hours following treatment comprising delivery of the therapeutically effective amount of the epinephrine, or a pharmaceutically acceptable salt thereof. In some embodiments, the subject is free from respiratory depression or distress for at least about 4 hours following treatment comprising delivery of the therapeutically effective amount of the epinephrine, or a pharmaceutically acceptable salt thereof. In some embodiments, the subject is free from respiratory depression or distress for at least about 6 hours following treatment comprising delivery of the therapeutically effective amount of the epinephrine, or a pharmaceutically acceptable salt thereof. In some embodiments, the subject is in a lying, supine, or recovery position.

In some embodiments, a single spray in the nostril yields a plasma concentration of ng/mL within 2.5 minutes in the subject. In some embodiments, a single spray in the nostril yields a plasma concentration of ≥1 ng/mL within 5 minutes in the subject. In some embodiments, a single spray in the nostril yields a plasma concentration of ≥1 ng/mL within 10 minutes in the subject. In some embodiments, a single spray in the nostril yields a plasma concentration of ≥1 ng/mL within 2.5 minutes in the subject. In some embodiments, a single spray in the nostril yields a plasma concentration ≥1 ng/mL within 5 minutes in the subject. In some embodiments, a single spray in the nostril yields a plasma concentration ≥1 ng/mL within 5 minutes in the subject.

In some embodiments, the nasal spray administration described herein provides rapid absorption of epinephrine. In some embodiments, the nasal spray administration described herein provides absorption of epinephrine that is substantially equivalent to that of intramuscular or subcutaneous injection. In some embodiments, the nasal spray administration described herein provides pharmacokinetics that is substantially equivalent to that of intramuscular or subcutaneous injection. In some embodiments, described herein are methods of administration of a nasal spray to a subject having congested and/or inflamed nasal passageways, thereby providing rapid absorption of epinephrine. For example, experimental data provided herein indicate congestion enhances absorption, providing a surprising benefit. In some embodiments, a single spray in the nostril within about 1, 2, 3, 4, or 5 minutes of administration yields a plasma concentration of at least about 0.2 ng/mL to about 3 ng/mL. In some embodiments, a single spray in the nostril within about 1, 2, 3, 4, or 5 minutes of administration yields a plasma concentration of at least about 0.2 ng/mL to about 0.3 ng/mL, about 0.2 ng/mL to about 0.4 ng/mL, about 0.2 ng/mL to about 0.5 ng/mL, about 0.2 ng/mL to about 0.6 ng/mL, about 0.2 ng/mL to about 0.7 ng/mL, about 0.2 ng/mL to about 0.8 ng/mL, about 0.2 ng/mL to about 0.9 ng/mL, about 0.2 ng/mL to about 1 ng/mL, about 0.2 ng/mL to about 1.5 ng/mL, about 0.2 ng/mL to about 2 ng/mL, about 0.2 ng/mL to about 3 ng/mL, about 0.3 ng/mL to about 0.4 ng/mL, about 0.3 ng/mL to about 0.5 ng/mL, about 0.3 ng/mL to about 0.6 ng/mL, about 0.3 ng/mL to about 0.7 ng/mL, about 0.3 ng/mL to about 0.8 ng/mL, about 0.3 ng/mL to about 0.9 ng/mL, about 0.3 ng/mL to about 1 ng/mL, about 0.3 ng/mL to about 1.5 ng/mL, about 0.3 ng/mL to about 2 ng/mL, about 0.3 ng/mL to about 3 ng/mL, about 0.4 ng/mL to about 0.5 ng/mL, about 0.4 ng/mL to about 0.6 ng/mL, about 0.4 ng/mL to about 0.7 ng/mL, about 0.4 ng/mL to about 0.8 ng/mL, about 0.4 ng/mL to about 0.9 ng/mL, about 0.4 ng/mL to about 1 ng/mL, about 0.4 ng/mL to about 1.5 ng/mL, about 0.4 ng/mL to about 2 ng/mL, about 0.4 ng/mL to about 3 ng/mL, about 0.5 ng/mL to about 0.6 ng/mL, about 0.5 ng/mL to about 0.7 ng/mL, about 0.5 ng/mL to about 0.8 ng/mL, about 0.5 ng/mL to about 0.9 ng/mL, about 0.5 ng/mL to about 1 ng/mL, about 0.5 ng/mL to about 1.5 ng/mL, about 0.5 ng/mL to about 2 ng/mL, about 0.5 ng/mL to about 3 ng/mL, about 0.6 ng/mL to about 0.7 ng/mL, about 0.6 ng/mL to about 0.8 ng/mL, about 0.6 ng/mL to about 0.9 ng/mL, about 0.6 ng/mL to about 1 ng/mL, about 0.6 ng/mL to about 1.5 ng/mL, about 0.6 ng/mL to about 2 ng/mL, about 0.6 ng/mL to about 3 ng/mL, about 0.7 ng/mL to about 0.8 ng/mL, about 0.7 ng/mL to about 0.9 ng/mL, about 0.7 ng/mL to about 1 ng/mL, about 0.7 ng/mL to about 1.5 ng/mL, about 0.7 ng/mL to about 2 ng/mL, about 0.7 ng/mL to about 3 ng/mL, about 0.8 ng/mL to about 0.9 ng/mL, about 0.8 ng/mL to about 1 ng/mL, about 0.8 ng/mL to about 1.5 ng/mL, about 0.8 ng/mL to about 2 ng/mL, about 0.8 ng/mL to about 3 ng/mL, about 0.9 ng/mL to about 1 ng/mL, about 0.9 ng/mL to about 1.5 ng/mL, about 0.9 ng/mL to about 2 ng/mL, about 0.9 ng/mL to about 3 ng/mL, about 1 ng/mL to about 1.5 ng/mL, about 1 ng/mL to about 2 ng/mL, about 1 ng/mL to about 3 ng/mL, about 1.5 ng/mL to about 2 ng/mL, about 1.5 ng/mL to about 3 ng/mL, or about 2 ng/mL to about 3 ng/mL. In some embodiments, a single spray in the nostril within about 1, 2, 3, 4, or 5 minutes of administration yields a plasma concentration of at least about 0.2 ng/mL, about 0.3 ng/mL, about 0.4 ng/mL, about 0.5 ng/mL, about 0.6 ng/mL, about 0.7 ng/mL, about 0.8 ng/mL, about 0.9 ng/mL, about 1 ng/mL, about 1.5 ng/mL, about 2 ng/mL, or about 3 ng/mL. In some embodiments, a single spray in the nostril within about 1, 2, 3, 4, or 5 minutes of administration yields a plasma concentration of at least at least about 0.2 ng/mL, about 0.3 ng/mL, about 0.4 ng/mL, about 0.5 ng/mL, about 0.6 ng/mL, about 0.7 ng/mL, about 0.8 ng/mL, about 0.9 ng/mL, about 1 ng/mL, about 1.5 ng/mL, or about 2 ng/mL. In some embodiments, a single spray in the nostril within about 1, 2, 3, 4, or 5 minutes of administration yields a plasma concentration of at least at most about 0.3 ng/mL, about 0.4 ng/mL, about 0.5 ng/mL, about 0.6 ng/mL, about 0.7 ng/mL, about 0.8 ng/mL, about 0.9 ng/mL, about 1 ng/mL, about 1.5 ng/mL, about 2 ng/mL, or about 3 ng/mL. In some embodiments, the plasma concentration described herein refers to average plasma concentration (e.g., a mean or median concentration determined for multiple sprays in one or both nostrils in a subject, or sprays in multiple subjects).

In an aspect provided herein is a method of treating anaphylaxis- or anaphylactic shock-induced respiratory depression or distress, comprising delivering a spray of a pharmaceutical solution from a pre-primed device into a nostril of a subject in need thereof in a manner that delivers the pharmaceutical solution in a round spray plume with an ovality ratio less than about 2.0 when measured at a distance of from about 1 to about 10 cm from the pre-primed device, wherein:

(i) the device is adapted for nasal delivery;

(ii) a volume of from about 20 µL to about 250 µL of spray is delivered; and the pharmaceutical solution comprises from about 0.5 mg to about 100 mg of epinephrine, or a pharmaceutically acceptable salt thereof, an isotonicity agent, and from about 0.005% to about 1% (w/v) of benzalkonium chloride.

In some embodiments, the round spray plume has an ovality ratio less than about 2.0. In some embodiments, the round spray plume has an ovality ratio less than about 1.9. In some embodiments, the round spray plume has an ovality ratio less than about 1.8. In some embodiments, the round spray plume has an ovality ratio less than about 1.7. In some embodiments, the round spray plume has an ovality ratio less than about 1.6. In some embodiments, the round spray plume has an ovality ratio less than about 1.5. In some embodiments, the round spray plume has an ovality ratio less than about 1.4. In some embodiments, the round spray plume has an ovality ratio less than about 1.3. In some embodiments, the round spray plume has an ovality ratio less than about 1.2. In some embodiments, the round spray plume has an ovality ratio less than about 1.1. In some embodiments, the round spray plume has an ovality ratio less than about 1.0.

In some embodiments, the ovality ratio of the spray is measured at a distance of from about 1 cm to about 5 cm from the device from which the spray is delivered.

In an aspect provided herein is a method for treating at least one symptom of anaphylaxis or anaphylactic shock, comprising delivering a spray of a pharmaceutical solution from a device into a nostril of a subject in need thereof, wherein:

(i) the device is adapted for nasal delivery;

(ii) a volume of from about 20 µL to about 250 µL of spray is delivered; and (iii) the pharmaceutical solution comprises from about 0.5 mg to about 100 mg of epinephrine, or a pharmaceutically acceptable salt thereof, an isotonicity agent, and from about 0.005% to about 1% (w/v) of benzalkonium chloride.

In some embodiments provided herein is a method for treating at least one symptom of anaphylaxis or anaphylactic shock, comprising delivering a spray of a pharmaceutical solution from a device into a nostril of a subject in need thereof, wherein the pharmaceutical spray formulation comprises from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2.0% trisodium citrate, and from about 0.05% to about 15% diethylene glycol monoethyl ether.

In some embodiments provided herein is a method for treating at least one symptom of anaphylaxis or anaphylactic shock, comprising delivering a spray of a pharmaceutical solution from a device into a nostril of a subject in need thereof, wherein the pharmaceutical spray formulation comprises from about 5% to about 20% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.05% to about 0.5% hypromellose, from about 0.1% to about 1.0% trisodium citrate, and from about 0.5% to about 5% diethylene glycol monoethyl ether.

In some embodiments provided herein is a method for treating at least one symptom of anaphylaxis or anaphylactic shock, comprising delivering a spray of a pharmaceutical solution from a device into a nostril of a subject in need thereof, wherein the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments provided herein is a method for treating at least one symptom of anaphylaxis or anaphylactic shock, comprising delivering a spray of a pharmaceutical solution from a device into a nostril of a subject in need thereof, wherein the pharmaceutical spray formulation comprises from about 1% to about 20% w/w of epinephrine, or a pharmaceutically acceptable salt thereof, from about 0.01% (w/w) to about 0.1% (w/w) of sodium metabisulfite, from about 0.1% to about 1% sodium chloride, from about 0.05% to about 0.5% hypromellose, from about 0.1% to about 1.0% citric acid monohydrate, and from about 0.1% to about 5% diethylene glycol monoethyl ether.

In some embodiments provided herein is a method for treating at least one symptom of anaphylaxis or anaphylactic shock, comprising delivering a spray of a pharmaceutical solution from a device into a nostril of a subject in need thereof, wherein the pharmaceutical spray formulation comprises about 2% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments provided herein is a method for treating at least one symptom of anaphylaxis or anaphylactic shock, comprising delivering a spray of a pharmaceutical solution from a device into a nostril of a subject in need thereof, wherein the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments provided herein is a method for treating at least one symptom of anaphylaxis or anaphylactic shock, comprising delivering a spray of a pharmaceutical solution from a device into a nostril of a subject in need thereof, wherein the pharmaceutical spray formulation comprises about 10% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments provided herein is a method for treating at least one symptom of anaphylaxis or anaphylactic shock, comprising delivering a spray of a pharmaceutical solution from a device into a nostril of a subject in need thereof, wherein the pharmaceutical spray formulation comprises about 20% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments, the subject in need thereof is an adult. In some embodiments, the subject in need thereof is a child. In some embodiments, the subject in need thereof weighs from about 10 lbs to about 80 lbs.

IV. Device

In an aspect provided herein, the pharmaceutical solution is administered from a unit-dose device or delivery system. In an aspect provided herein, the pharmaceutical solution is administered from a bi-dose device or delivery system. In an aspect provided herein, the pharmaceutical solution is administered from a multi-dose device or delivery system.

In some embodiments, the device comprises: a reservoir containing at least two doses of fluid; a dispenser member, such as a piston, that is mounted to slide in said reservoir so as to dispense the fluid; a dispenser head that is provided with a dispenser orifice, said head being movable relative to said reservoir so as to move said actuator member in said reservoir and thus dispense the fluid through said dispenser orifice; said dispenser head including at least two viewing windows, said device including an indicator that is movable together with said reservoir, said indicator co-operating with a respective viewing window after each actuation of the device. In some embodiments, said indicator comprises at least one colored indication zone, said indication zone appearing in said first viewing window after the first dose of fluid has been dispensed, and in the second viewing window after the second dose of fluid has been dispensed. In some embodiments, said indicator is adapted to mask colored indication zones that are provided in said dispenser head, said indicator masking a colored indication zone in said first viewing window after the first dose of fluid has been dispensed, and masking a colored indication zone in said second viewing window after the second dose of fluid has been dispensed. In some embodiments, said indicator is adapted to indicate, through at least one viewing window, that an incomplete dose has been dispensed. In some embodiments, the device is held between the second and the third fingers with the thumb on the actuator. In some embodiments, a pressure point mechanism is incorporated in the device to secure reproducibility of the actuation force and emitted plume characteristics. In some embodiments, a cap is incorporated in the device. In some embodiments, a trigger guard on the actuator is incorporated in the device. In some embodiments, a window is incorporated in the device to view the fluid in the reservoir. In some embodiments, a dose meter is incorporated in the device. In some embodiments, a mechanism is incorporated in the device to lock the device and prevent a second actuation of the device. In some embodiments, a timing mechanism is incorporated in the device to lock the device and prevent a second actuation of the device after a specified period of time.

Figure 17:
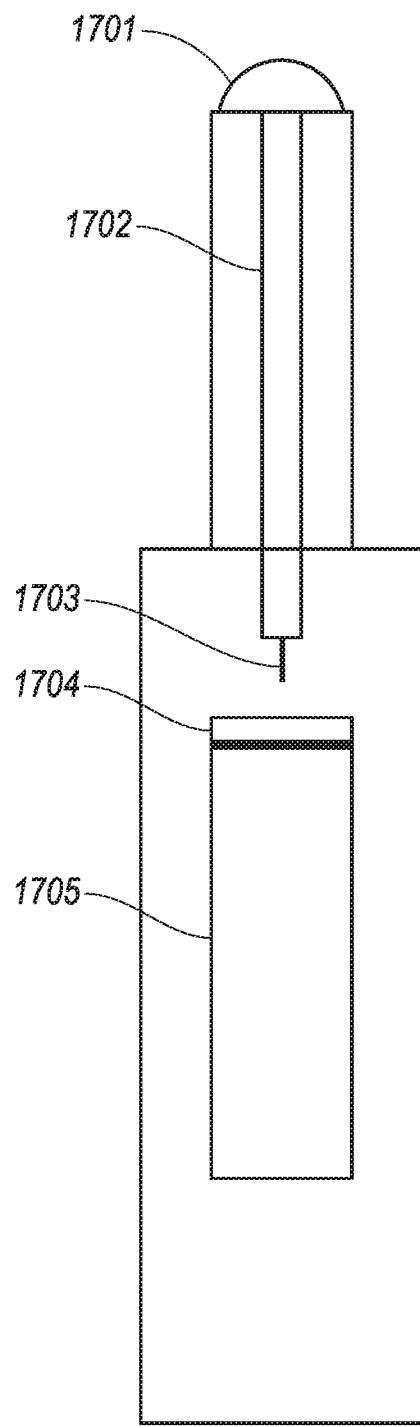
FIG. 17 shows an illustrative diagram of a nasal spray delivery device.

An illustrative diagram of a device is shown in FIG. 17. The device as shown has a tip 1701 for dispensing the pharmaceutical spray formulation, a cannula 1702 that is coupled to the tip and transports the formulation or solution from the reservoir 1705. Upon actuation of the device, a needle 1703 pierces a seal (e.g., polymeric or elastomeric seal) 1704 to enter the reservoir 1705 to access the pharmaceutical spray formulation stored as a solution within.

In some embodiments, the device is a single-dose device. In some embodiments, the device is a bi-dose device. In some embodiments, the volume of the reservoir is not more than about 140 µL. In some embodiments, the device has a single reservoir containing approximately 125 µL of the pharmaceutical solution. In some embodiments, approximately 100 µL of the pharmaceutical solution is delivered by one actuation of the device. In some embodiments, the device has a single reservoir containing from about 50 µL to about 250 µL of the pharmaceutical formulation. In some embodiments, the device has a single reservoir containing from about 75 µL to about 250 µL of the pharmaceutical formulation. In some embodiments, the device has a single reservoir containing from about 100 µL to about 250 µL of the pharmaceutical formulation. In some embodiments, the device has a single reservoir containing from about 125 µL to about 250 µL of the pharmaceutical formulation. In some embodiments, the device has a single reservoir containing from about 150 µL to about 250 µL of the pharmaceutical formulation. In some embodiments, the device delivers two sprays of the pharmaceutical solution from a single reservoir. In some embodiments, the single-dose device delivers two sprays of the pharmaceutical solution from a single reservoir. In some embodiments, the bi-dose device delivers two sprays of the pharmaceutical solution from a single reservoir. In some embodiments, the bi-dose device has a first reservoir containing from about 50 µL to about 250 µL of the pharmaceutical formulation and a second reservoir containing from about 50 µL to about 250 µL of the pharmaceutical formulation. In some embodiments, the bi-dose device has a first reservoir containing from about 75 µL to about 250 µL of the pharmaceutical formulation and a second reservoir containing from about 75 µL to about 250 µL of the pharmaceutical formulation. In some embodiments, the bi-dose device has a first reservoir containing from about 100 µL to about 250 µL of the pharmaceutical formulation and a second reservoir containing from about 100 µL to about 250 µL of the pharmaceutical formulation. In some embodiments, the bi-dose device has a first reservoir containing from about 125 µL to about 250 µL of the pharmaceutical formulation and a second reservoir containing from about 125 µL to about 250 µL of the pharmaceutical formulation. In some embodiments, the bi-dose device has a first reservoir containing from about 50 µL to about 225 µL of the pharmaceutical formulation and a second reservoir containing from about 50 µL to about 225 µL of the pharmaceutical formulation. In some embodiments, the bi-dose device has a first reservoir containing from about 50 µL to about 200 µL of the pharmaceutical formulation and a second reservoir containing from about 50 µL to about 175 µL of the pharmaceutical formulation. In some embodiments, the bi-dose device has a first reservoir containing from about 50 µL to about 175 µL of the pharmaceutical formulation and a second reservoir containing from about 50 µL to about 175 µL of the pharmaceutical formulation. In some embodiments, the bi-dose device has a first reservoir containing from about 50 µL to about 150 µL of the pharmaceutical formulation and a second reservoir containing from about 50 µL to about 150 µL of the pharmaceutical formulation. In some embodiments, the bi-dose device delivers one spray of the pharmaceutical solution from the first reservoir and one spray of the pharmaceutical solution from the second reservoir.

In some embodiments described herein, a bi-dose device adapted for nasal delivery of a pharmaceutical composition to a patient comprises a first volume of a pharmaceutical formulation in a first reservoir, and a second volume of said pharmaceutical formulation in a second reservoir, and wherein said therapeutically effective amount of said pharmaceutical formulation is delivered essentially by a first actuation of said drug delivery device from said first reservoir into a nostril of a patient and a second actuation of said drug delivery device from said second reservoir into a nostril of said patient. In some embodiments, the bi-dose device has a first reservoir containing from about 50 µL to about 250 µL of the pharmaceutical formulation and a second reservoir containing from about 50 µL to about 250 µL of the pharmaceutical formulation. In some embodiments, each reservoir of the pre-printed, bi-dose device adapted for nasal delivery of a pharmaceutical composition to a patient comprises between about 0.5 mg to about 100 mg of epinephrine.

In some embodiments of the device described herein, the pharmaceutical spray formulation comprises from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2.0% trisodium citrate, and from about 0.05% to about 15% diethylene glycol monoethyl ether.

In some embodiments of the device described herein, the pharmaceutical spray formulation comprises from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2.0% citric acid monohydrate, and from about 0.05% to about 15% diethylene glycol monoethyl ether.

In some embodiments of the device described herein, the pharmaceutical spray formulation comprises from about 5% to about 20% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.05% to about 0.5% hypromellose, from about 0.1% to about 1.0% trisodium citrate, and from about 0.5% to about 5% diethylene glycol monoethyl ether.

In some embodiments of the device described herein, the pharmaceutical spray formulation comprises from about 5% to about 20% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.01% to about 0.2% hypromellose, from about 0.1% to about 1.0% citric acid monohydrate, and from about 0.1% to about 5% diethylene glycol monoethyl ether.

In some embodiments of the device described herein, the pharmaceutical spray formulation comprises about 2% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments of the device described herein, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments of the device described herein, the pharmaceutical spray formulation comprises about 5% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments of the device described herein, the pharmaceutical spray formulation comprises about 10% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments of the device described herein, the pharmaceutical spray formulation comprises about 10% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments of the device described herein, the pharmaceutical spray formulation comprises about 20% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether.

In some embodiments of the device described herein, the pharmaceutical spray formulation comprises about 20% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether.

In some embodiments, the formulation devices and methods described herein include a digital processing device or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Mobile Application

In some embodiments, a computer program includes a mobile application provided to a digital processing device or a portable device. In some embodiments, the mobile application is provided to a mobile digital processing device at the time it is manufactured. In other embodiments, the mobile application is provided to a mobile digital processing device via the computer network described herein.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information such as geological information and administration information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

NUMBERED EMBODIMENTS

The following embodiments recite nonlimiting permutations of combinations of features disclosed herein. Other permutations of combinations of features are also contemplated. 1. A pharmaceutical spray formulation comprising from about 0.5% to about 25% w/w of epinephrine, or a pharmaceutically acceptable salt of epinephrine, in water, ethanol, propylene glycol, or a combination thereof; wherein the pH of the formulation is from about 4.0 to about 6.5. 2. The pharmaceutical spray formulation of embodiment 1, comprising from about 0.5% to about 10% w/w of epinephrine, or a pharmaceutically acceptable salt thereof 3. The pharmaceutical spray formulation of embodiment 1 or 2, wherein the pH is controlled by the addition of hydrochloric acid, citric acid, or a combination thereof 4. The pharmaceutical spray formulation of embodiment 3, wherein the pH is controlled by the addition of hydrochloric acid. 5. The pharmaceutical spray formulation of embodiment 3, wherein the pH is controlled by the addition of citric acid. 6. The pharmaceutical spray formulation of embodiment 3, wherein the pH is controlled by the addition of a combination of hydrochloric acid and citric acid. 7. The pharmaceutical spray formulation of any one of embodiments 1-6, further comprising sodium bisulfite at a concentration of from about 0.0001% (w/w) to about 0.1% (w/w) or sodium metabisulfite at a concentration of from about 0.0001% (w/w) to about 0.1% (w/w). 8. The pharmaceutical spray formulation of any one of embodiments 1-7, further comprising sodium bisulfite at a concentration of from about 0.0001% (w/w) to about 0.05% (w/w) or sodium metabisulfite at a concentration of from about 0.0001% (w/w) to about 0.05% (w/w). 9. The pharmaceutical spray formulation of any one of embodiments 1-8, further comprising sodium bisulfite at a concentration of from about 0.0001% (w/w) to about 0.05% (w/w). 10. The pharmaceutical spray formulation of any one of embodiments 1-8, further comprising sodium metabisulfite at a concentration of from about 0.0001% (w/w) to about 0.05% (w/w). 11. The pharmaceutical spray formulation of any one of embodiments 1-10, further comprising disodium edetate at a concentration of from about 0.0001% to about 0.01%. 12. The pharmaceutical spray formulation of any one of embodiments 1-11, further comprising an antimicrobial preservative. 13. The pharmaceutical spray formulation of any one of embodiments 1-12, further comprising an antimicrobial preservative selected from benzalkonium sodium at a concentration of from about 0.005% (w/v) to about 1% (w/v) and chlorobutanol at a concentration of from about 0.005% (w/v) to about 1% (w/v). 14. The pharmaceutical spray formulation of any one of embodiments 1-13, further comprising benzalkonium sodium at a concentration of from about 0.005% (w/v) to about 1% (w/v). 15. The pharmaceutical spray formulation of any one of embodiments 1-13, further comprising chlorobutanol at a concentration of from about 0.005% (w/v) to about 1% (w/v). 16. The pharmaceutical spray formulation of any one of embodiments 1-15, further comprising sodium chloride at a concentration of from about 0.1% to about 5%. 17. The pharmaceutical spray formulation of any one of embodiments 1-16, further comprising a vasodilator. 18. The pharmaceutical spray formulation of any one of embodiments 1-17, further comprising a vasodilator selected from about 0.05 mg to about 5 mg of nitroprusside, from about 1 mg to about 50 mg of phentolamine, and from about 10 mg to about 500 mg of nifedipine. 19. The pharmaceutical spray formulation of any one of embodiments 1-18, further comprising from about 0.05 mg to about 5 mg of nitroprusside. 20. The pharmaceutical spray formulation of any one of embodiments 1-18, further comprising from about 1 mg to about 50 mg of phentolamine. 21. The pharmaceutical spray formulation of any one of embodiments 1-18, further comprising from about 10 mg to about 500 mg of nifedipine. 22. The pharmaceutical spray formulation of any one of embodiments 1-21, further comprising a permeability enhancer. 23. The pharmaceutical spray formulation of any one of embodiments 1-22, further comprising diethylene glycol monoethyl ether at a concentration of from about 0.05% to about 15%. 24. The pharmaceutical spray formulation of any one of embodiments 1-23, further comprising a viscosity modifier. 25. The pharmaceutical spray formulation of embodiment 24, wherein the viscosity modifier is from about 0.5% to about 50% polyethylene glycol, from about 0.001% to about 5% methylcellulose, or from about 0.001% to about 0.5% hypromellose. 26. The pharmaceutical spray formulation of any one of embodiments 1-25, further comprising from about 0.5% to about 50% polyethylene glycol. 27. The pharmaceutical spray formulation of any one of embodiments 1-25, further comprising from about 0.001% to about 5% methylcellulose. 28. The pharmaceutical spray formulation of any one of embodiments 1-25, further comprising from about 0.001% to about 0.5% hypromellose. 29. The pharmaceutical spray formulation of any one of embodiments 1-28, further comprising from about 0.01% to about 2.0% trisodium citrate 30. The pharmaceutical spray formulation of embodiment 1 comprising from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2.0% trisodium citrate, and from about 0.05% to about 15% diethylene glycol monoethyl ether. 31. The pharmaceutical spray formulation of embodiment 30 comprising from about 1% to about 5% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.01% to about 0.2% hypromellose, from about 0.1% to about 1.0% trisodium citrate, and from about 0.1% to about 2.0% diethylene glycol monoethyl ether. 32. The pharmaceutical spray formulation of embodiment 30 comprising from about 5% to about 20% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.05% to about 0.5% hypromellose, from about 0.1% to about 1.0% trisodium citrate, and from about 0.5% to about 5% diethylene glycol monoethyl ether. 33. The pharmaceutical spray formulation of embodiment 30 comprising about 2.4% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. 34. The pharmaceutical spray formulation of embodiment 30 comprising about 5% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. 35. The pharmaceutical spray formulation of embodiment 30 comprising about 10% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. 36. The pharmaceutical spray formulation of embodiment 30 comprising about 20% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. 37. The pharmaceutical spray formulation of any one of embodiments 30-36, further comprising chlorobutanol at a concentration of from about 0.05% (w/v) to about 1% (w/v). 38. The pharmaceutical spray formulation of any one of embodiments 1-37, wherein the droplet size of D50 is from about 10 microns to about 100 microns. 39. The pharmaceutical spray formulation of any one of embodiments 1-38, wherein the formulation is present in and/or delivered from a device. 40. The pharmaceutical spray formulation of embodiment 39, wherein the device has an oxygen absorber or scavenger. 41. The pharmaceutical spray formulation of embodiment 40, wherein the oxygen absorber or scavenger is iron, ferrous carbonate, ascorbate, or sodium bicarbonate. 42. The pharmaceutical spray formulation of any one of embodiments 39-41, wherein the device has an increased reservoir. 43. The pharmaceutical spray formulation of any one of embodiments 39-41, wherein the device is a single-dose device. 44. The pharmaceutical spray formulation of any one of embodiments 39-41, wherein the device is a bi-dose device. 45. The pharmaceutical spray formulation of any one of embodiments 39-44, wherein the device has a single reservoir containing from about 125 μL to about 250 μL of the pharmaceutical formulation. 46. The pharmaceutical spray formulation of embodiment 44, wherein the device has a first reservoir containing from about 50 μL to about 250 μL of the pharmaceutical formulation and a second reservoir containing from about 50 μL to about 250 μL of the pharmaceutical formulation. 47. The pharmaceutical spray formulation of any one of embodiments 1-46, wherein the formulation is adapted for dosing by inhalation. 48. The pharmaceutical spray formulation of any one of embodiments 1-47, wherein the formulation is adapted for intranasal dosing. 49. The pharmaceutical spray formulation of any one of embodiments 1-37, wherein the formulation is adapted for parenteral dosing. 50. A method of treating anaphylaxis, anaphylactic shock, a severe allergic reaction, and/or bronchial constriction, comprising administering to a subject in need thereof a therapeutically effective amount of a pharmaceutical spray formulation of any one of embodiments 1-49. 51. A spray, comprising droplets, wherein the droplets comprise in aggregate from about 0.5 mg to about 100 mg of epinephrine, or a pharmaceutically acceptable salt thereof, an isotonicity agent, and from about 0.005% (w/v) to about 10% (w/v) of benzalkonium chloride or from about 0.005% (w/v) to about 10% (w/v) chlorobutanol. 52. The spray of embodiment 51, wherein the spray is delivered from a device. 53. The spray of embodiment 52, wherein the device is a single-dose device. 54. The spray of embodiment 52, wherein the device is a bi-dose device. 55. The spray of any one of embodiments 52-54, wherein the device has a single reservoir containing from about 125 μL to about 250 μL of the pharmaceutical formulation. 56. The spray of embodiment 54, wherein the device has a first reservoir containing from about 50 μL to about 250 μL of the pharmaceutical formulation and a second reservoir containing from about 50 μL to about 250 μL of the pharmaceutical formulation. 57. The spray of any one of embodiments 52-56, wherein the device is pre-primed. 58. The spray of any one of embodiments 51-57, wherein the isotonicity agent is present in a concentration from about 0.1% (w/w) to about 5% (w/w). 59. The spray of any one of embodiments 51-58, wherein the isotonicity agent is sodium chloride. 60. The spray of any one of embodiments 51-59, wherein the spray takes the shape of a round plume with an ovality ratio less than about 2.0. 61. The spray of any one of embodiments 51-59, wherein the spray takes the shape of a round plume with an ovality ratio less than about 1.5. 62. The spray of any one of embodiments 51-59, wherein the spray takes the shape of a round plume with an ovality ratio less than about 1.3. 63. The spray of any one of embodiments 51-59, wherein the spray takes the shape of a round plume with an ovality ratio less than about 1.2. 64. The spray of any one of embodiments 51-59, wherein the spray takes the shape of a round plume with an ovality ratio less than about 1.1. 65. The spray of any one of embodiments 60-64, wherein the ovality ratio of the spray is measured at a distance of from about 1 cm to about 10 cm from the device. 66. The spray of any one of embodiments 60-64, wherein the ovality ratio of the spray is measured at a distance of from about 1 cm to about 5 cm from the device. 67. The spray of any one of embodiments 60-64, wherein the ovality ratio of the spray is measured at a distance of about 3 cm from the device. 68. The spray of any one of embodiments 51-67, wherein the epinephrine is at least 10% bioavailable. 69. The spray of any one of embodiments 51-68, wherein the epinephrine is at least 40% bioavailable. 70. The spray of any one of embodiments 51-69, wherein the epinephrine is at least 50% bioavailable. 71. The spray of any one of embodiments 51-70, wherein the epinephrine is at least 60% bioavailable. 72. The spray of any one of embodiments 51-71, wherein the median droplet size is from about 10 μm to about 120 μm. 73. The spray of any one of embodiments 50-71, wherein no more than about 10% of the droplets have a diameter less than about 10 μm. 74. The spray of any one of embodiments 51-72, wherein no more than approximately 5% of the droplets have a diameter less than about 10 μm. 75. The spray of any one of embodiments 51-72, wherein no more than approximately 2% of the droplets have a diameter less than about 10 μm. 76. The spray of any one of embodiments 51-72, wherein approximately 50% of the droplets have a diameter of from about 10 μm to about 120 μm. 77. The spray of any one of embodiments 51-72, wherein approximately 50% of the droplets have a diameter of from about 10 μm to about 60 μm. 78. The spray of any one of embodiments 51-72, wherein approximately 90% of the droplets have a diameter less than about 120 μm. 79. The spray of any one of embodiments 51-78, further comprising a stabilizing agent and an acid. 80. The spray of embodiment 79, wherein the stabilizing agent is disodium edetate. 81. The spray of embodiment 79 or 80, wherein the acid is hydrochloric acid or citric acid, or a combination thereof 82. The spray of any one of embodiments 51-81, wherein the epinephrine, or a pharmaceutically acceptable salt thereof, is dissolved in water, ethanol, or propylene glycol, or a combination thereof. 83. The spray of any one of embodiments 51-82, further comprising sodium bisulfite at a concentration of from about 0.0001% (w/w) to about 0.05% (w/w) or sodium metabisulfite at a concentration of from about 0.0001% (w/w) to about 0.05% (w/w). 84. The spray of any one of embodiments 51-83, further comprising chlorobutanol at a concentration of from about 0.005% (w/v) to about 1% (w/v). 85. The spray of any one of embodiments 51-84, further comprising a vasodilator. 86. The spray of embodiment 85, wherein the vasodilator is nitroprusside, phentolamine, or nifedipine. 87. The spray of any one of embodiments 51-86, further comprising a permeability enhancer. 88. The spray of embodiment 87, wherein the permeability enhancer is diethylene glycol monoethyl ether. 89. The spray of any one of embodiments 51-88, further comprising a viscosity modifier. 90. The spray of embodiment 89, wherein the viscosity modifier is polyethylene glycol, methylcellulose, or hypromellose. 91. The spray of any one of embodiments 51-90, wherein the device comprises at least one oxygen absorber or scavenger. 92. The spray of embodiment 91, wherein the at least one oxygen absorber or scavenger is iron, ferrous carbonate, ascorbate, or sodium bicarbonate, or a combination thereof. 93. The spray of any one of embodiments 51-92, wherein the spray comprises per 100 μL of solution: from about 0.5 mg to about 100 mg of epinephrine, or a pharmaceutically acceptable salt thereof from about 0.1 mg to about 2 mg sodium chloride; from about 0.01 mg to about 1 mg benzalkonium chloride; from about 0.1 mg to about 2 mg disodium edetate; and hydrochloric acid or citric acid, or a combination thereof sufficient to achieve a pH of from about 3.5 to about 6.5. 94. The spray of any one of embodiments 51-93, wherein the spray is delivered from a spray nozzle of a pre-primed device, and wherein no more than about 10% of the droplets have a diameter less than 10 μm. 95. The spray of embodiment 94, wherein the spray is measured by laser diffraction with beams measuring at both 3 cm and 6 cm from the spray nozzle. 96. A method of treating anaphylaxis, anaphylactic shock, a severe allergic reaction, and/or bronchial constriction, comprising delivering a spray of a pharmaceutical solution from a pre-primed device into a nostril of a subject in need thereof, wherein: (i) the device is adapted for nasal delivery; (ii) a volume of from about 20 μL to about 250 μL of spray is delivered; and (iii) the pharmaceutical solution comprises from about 0.5 mg to about 100 mg of epinephrine, or a pharmaceutically acceptable salt thereof, an isotonicity agent, and from about 0.005% (w/v) to about 1% (w/v) of benzalkonium chloride. 97. The method of embodiment 96, wherein the device is a single-dose device. 98. The method of any one of embodiment 96, wherein the device is a bi-dose device. 99. The method of any one of embodiments 96-98, wherein the device has a single reservoir containing from about 125 μL to about 250 μL of the pharmaceutical solution. 100. The method of embodiment 99, wherein the device delivers two sprays of the pharmaceutical solution from a single reservoir. 101. The method of embodiment 98, wherein the device has a first reservoir containing from about 50 μL to about 250 μL of the pharmaceutical solution and a second reservoir containing from about 50 μL to about 250 μL of the pharmaceutical solution. 102. The method of embodiment 101, wherein the device delivers one spray of the pharmaceutical solution from the first reservoir and one spray of the pharmaceutical solution from the second reservoir. 103. The method of any one of embodiments 96-102, wherein the epinephrine, or a pharmaceutically acceptable salt thereof, is dissolved in water, ethanol, propylene glycol, or a combination thereof 104. The method of any one of embodiments 96-103, wherein the isotonicity agent is present in a concentration of from about 0.2% (w/w) to about 1.2% (w/v). 105. The method of any one of embodiments 96-104, wherein the pharmaceutical solution further comprises from about 0.1% (w/v) to about 0.5% (w/v) of a stabilizing agent. 106. The method of any one of embodiments 96-105, wherein the pharmaceutical solution further comprises an amount of an acid sufficient to achieve a pH of from about 3.5 to about 6.5. 107. The method of embodiment 106, wherein the acid is hydrochloric acid or citric acid, or a combination thereof. 108. The method of any one of embodiments 96-107, wherein: the isotonicity agent is sodium chloride; the stabilizing agent is disodium edetate; and the acid is hydrochloric acid or citric acid, or a combination thereof. 109. The method of any one of embodiments 96-108 wherein the plasma concentration versus time curve of epinephrine in the subject has a $t_{max}$ of less than from about 10 minutes to about 120 minutes. 110. The method of any one of embodiments 96-109, wherein the subject has a maximum plasma concentration ($C_{max}$) of from about 50 pg/mL to about 500 pg/mL of epinephrine. 111. The method of any one of embodiments 96-110, wherein the area under a plasma concentration-time curve of epinephrine in the subject is from about 5 ng/minute/mL to about 50 ng/minute/mL. 112. The method of any one of embodiments 96-111, wherein the device comprises a plunger that houses a container closure comprising: (i) a vial comprising an opening; (ii) a cannula; and (iii) a rubber stopper; wherein the stopper is configured to occlude the opening of the vial, and wherein the cannula is configured such that the cannula can pierce the stopper when the plunger applies sufficient force to the cannula. 113. The method of any one of embodiments 96-112, wherein the spray delivers from about 0.5 mg to about 100 mg of epinephrine, or a pharmaceutically acceptable salt thereof. 114. The method of any one of embodiments 96-113, wherein the pre-primed device is actuatable with one hand. 115. The method of any one of embodiments 96-114, wherein the pre-primed device has a single reservoir containing approximately 125 μL of the pharmaceutical solution. 116. The method of any one of embodiments 96-115, wherein approximately 100 μL of the pharmaceutical solution is delivered by one actuation of the device. 117. The method of any one of embodiments 96-116, wherein the volume of the reservoir is not more than about 140 μL. 118. The method of any one of embodiments 96-117, wherein delivery time of the pharmaceutical solution is less than about 25 seconds. 119. The method of any one of embodiments 96-117, wherein delivery time of the pharmaceutical solution is less than about 20 seconds. 120. The method of any one of embodiments 96-119, wherein less than about 20% of the pharmaceutical solution leaves the nasal cavity via drainage into the nasopharynx or externally. 121. The method of any one of embodiments 96-120, wherein less than about 10% of the pharmaceutical solution leaves the nasal cavity via drainage into the nasopharynx or externally. 122. The method of any one of embodiments 96-121, wherein less than about 5% of the pharmaceutical solution leaves the nasal cavity via drainage into the nasopharynx or externally. 123. The method of any one of embodiments 96-122, wherein the subject is suffering from a severe allergic reaction from exposure or suspected exposure to an allergen. 124. The method of embodiment 123, wherein the allergen is food, medication, or an insect bite or sting. 125. The method of any one of embodiments 96-124, wherein the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, and vomiting. 126. The method of any one of embodiments 96-125, wherein the subject exhibits respiratory depression or distress, or cardiovascular depression. 127. The method of any one of embodiments 96-126, wherein the subject is free from respiratory depression or distress for at least about 1 hour following treatment comprising delivery of the therapeutically effective amount of the epinephrine, or a pharmaceutically acceptable salt thereof. 128. The method of any one of embodiments 96-127, wherein the subject is free from respiratory depression or distress for at least about 2 hours following treatment comprising delivery of the therapeutically effective amount of the epinephrine, or a pharmaceutically acceptable salt thereof. 129. The method of any one of embodiments 96-128, wherein the subject is free from respiratory depression or distress for at least about 4 hours following treatment comprising delivery of the therapeutically effective amount of the epinephrine, or a pharmaceutically acceptable salt thereof. 130. The method of any one of embodiments 96-129, wherein the subject is free from respiratory depression or distress for at least about 6 hours following treatment comprising delivery of the therapeutically effective amount of the epinephrine, or a pharmaceutically acceptable salt thereof. 131. The method of any one of embodiments 96-130, wherein the subject is in a lying, supine, or recovery position. 132. The method of any one of embodiments 96-131, wherein a single spray in the nostril yields a plasma concentration of ≥0.2 ng/mL within 2.5 minutes in the subject. 133. The method of any one of embodiments 96-131, wherein a single spray in the nostril yields a plasma concentration of ≥1 ng/mL within 5 minutes in the subject. 134. The method of any one of embodiments 96-131, wherein a single spray in the nostril yields a plasma concentration of ng/mL within 10 minutes in the subject. 135. A method of treating anaphylaxis- or anaphylactic shock-induced respiratory depression or distress, comprising delivering a spray of a pharmaceutical solution from a pre-primed device into a nostril of a subject in need thereof in a manner that delivers the pharmaceutical solution in a round spray plume with an ovality ratio less than about 2.0 when measured at a distance of from about 1 to about 10 cm from the pre-primed device, wherein: (i) the device is adapted for nasal delivery; (ii) a volume of from about 20 µL to about 250 µL of spray is delivered; and (iii) the pharmaceutical solution comprises from about 0.5 mg to about 100 mg of epinephrine, or a pharmaceutically acceptable salt thereof, an isotonicity agent, and from about 0.005% (w/v) to about 1% (w/v) of benzalkonium chloride. 136. The method of embodiment 135, wherein the device is a single-dose device. 137. The method of any one of embodiment 135, wherein the device is a bi-dose device. 138. The method of any one of embodiments 135-137, wherein the device has a single reservoir containing from about 125 µL to about 250 µL of the pharmaceutical solution. 139. The method of embodiment 138, wherein the device delivers two sprays of the pharmaceutical solution from a single reservoir. 140. The method of embodiment 138, wherein the device has a first reservoir containing from about 50 µL to about 250 µL of the pharmaceutical solution and a second reservoir containing from about 50 µL to about 250 µL of the pharmaceutical solution. 141. The method of embodiment 140, wherein the device delivers one spray of the pharmaceutical solution from the first reservoir and one spray of the pharmaceutical solution from the second reservoir. 142. The method of any one of embodiments 135-141, wherein the ovality ratio is less than about 1.5. 143. The method of any one of embodiments 135-141, wherein the ovality ratio is less than about 1.3. 144. The method of any one of embodiments 135-141, wherein the ovality ratio is less than about 1.2. 145. The method of any one of embodiments 135-141, wherein the ovality ratio is less than about 1.1. 146. The method of any one of embodiments 135-145, wherein the ovality ratio of the spray is measured at a distance of from about 1 cm to about 5 cm from the device. 147. A method for treating at least one symptom of anaphylaxis or anaphylactic shock, comprising delivering a spray of a pharmaceutical solution from a device into a nostril of a subject in need thereof, wherein: (i) the device is adapted for nasal delivery; (ii) a volume of from about 20 µL to about 250 µL of spray is delivered; and (iii) the pharmaceutical solution comprises from about 0.5 mg to about 100 mg of epinephrine, or a pharmaceutically acceptable salt thereof, an isotonicity agent, and from about 0.005% (w/v) to about 1% (w/v) of benzalkonium chloride. 148. The method of embodiment 147, wherein the device is a single-dose device. 149. The method of any one of embodiment 147, wherein the device is a bi-dose device. 150. The method of any one of embodiments 147-149, wherein the device has a single reservoir containing from about 125 µL to about 250 µL of the pharmaceutical solution. 151. The method of embodiment 150, wherein the device delivers two sprays of the pharmaceutical solution from a single reservoir. 152. The method of embodiment 149, wherein the device has a first reservoir containing from about 50 µL to about 250 µL of the pharmaceutical solution and a second reservoir containing from about 50 µL to about 250 µL of the pharmaceutical solution. 153. The method of embodiment 152, wherein the device delivers one spray of the pharmaceutical solution from the first reservoir and one spray of the pharmaceutical solution from the second reservoir. 154. A stable pharmaceutical spray formulation, comprising: (i) from about 1% to about 25% w/w of epinephrine, or a pharmaceutically acceptable salt thereof, in water, ethanol, propylene glycol, or a combination thereof; and (ii) one or more excipients, vehicles, emulsifiers, stabilizing agents, preservatives, mucosal adhesives, antibacterial agents, buffers, and/or other additives, wherein the formulation is stable at a temperature of at least about 20° C. and at a relative humidity of at least about 30%, and wherein the formulation is stable for a period of at least about two months. 155. The pharmaceutical spray formulation of embodiment 154, comprising from about 1% to about 10% w/w of epinephrine, or a pharmaceutically acceptable salt thereof. 156. The pharmaceutical spray formulation of embodiment 154 or 155, wherein the formulation is stable at a temperature of at least about 25° C. 157. The pharmaceutical spray formulation of embodiment 154 or 155, wherein the formulation is stable at a temperature of at least about 30° C. 158. The pharmaceutical spray formulation of any one of embodiments 154-157, wherein the formulation is stable at a temperature of at least about 35° C. 159. The pharmaceutical spray formulation of any one of embodiments 154-158, wherein the formulation is stable at a temperature of at least about 40° C. 160. The pharmaceutical spray formulation of any one of embodiments 154-159, wherein the formulation is stable at a temperature of at least about 45° C. 161. The pharmaceutical spray formulation of any one of embodiments 154-160, wherein the formulation is stable at a relative humidity of at least about 40%. 162. The pharmaceutical spray formulation of any one of embodiments 154-161, wherein the formulation is stable at a relative humidity of at least about 50%. 163. The pharmaceutical spray formulation of any one of embodiments 154-162, wherein the formulation is stable at a relative humidity of at least about 60%. 164. The pharmaceutical spray formulation of any one of embodiments 154-163, wherein the formulation is stable at a relative humidity of at least about 70%. 165. The pharmaceutical spray formulation of any one of embodiments 154-164, wherein the formulation is stable at a relative humidity of at least about 80%. 166. The pharmaceutical spray formulation of any one of embodiments 154-165, wherein the formulation is stable for a period of at least about six months. 167. The pharmaceutical spray formulation of any one of embodiments 154-166, wherein the formulation is stable for a period of at least about 12 months. 168. The pharmaceutical spray formulation of any one of embodiments 154-167, wherein the formulation is stable for a period of at least about 18 months. 169. The pharmaceutical spray formulation of any one of embodiments 154-168, wherein the formulation is stable for a period of at least about 24 months. 170. The pharmaceutical spray formulation of any one of embodiments 154-169, wherein the formulation is stable for a period of at least about 36 months. 171. The pharmaceutical spray formulation of any one of embodiments 154-170, wherein the formulation has a viscosity of from about 100 to about 2,500 cP. 172. The pharmaceutical spray formulation of any one of embodiments 154-171, wherein the formulation is adapted for dosing by inhalation. 173. The pharmaceutical spray formulation of any one of embodiments 154-172, wherein the formulation is adapted for intranasal dosing. 174. The pharmaceutical spray formulation of any one of embodiments 154-171, wherein the formulation is adapted for parenteral dosing. 175. The pharmaceutical spray formulation of any one of embodiments 154-174, further comprising an isotonicity agent present in a concentration from about 0.1% (w/w) to about 5% (w/w). 176. The pharmaceutical spray formulation of embodiment 175, wherein the isotonicity agent is sodium chloride. 177. The pharmaceutical spray formulation of any one of embodiments 154-176, comprising a stabilizing agent. 178. The pharmaceutical spray formulation of embodiment 177, wherein the stabilizing agent is disodium edetate. 179. The pharmaceutical spray formulation of any one of embodiments 154-178, further comprising an acid sufficient to achieve a pH of from about 3.5 to about 6.5. 180. The pharmaceutical spray formulation of embodiment 179, wherein the acid is hydrochloric acid or citric acid, or a combination thereof. 181. The pharmaceutical spray formulation of any one of embodiments 154-180, further comprising sodium bisulfite at a concentration of from about 0.0001% (w/w) to about 0.1% (w/w) or sodium metabisulfite at a concentration of from about 0.0001% (w/w) to about 0.1% (w/w). 182. The pharmaceutical spray formulation of any one of embodiments 154-181, further comprising sodium bisulfite at a concentration of from about 0.0001% (w/w) to about 0.05% (w/w) or sodium metabisulfite at a concentration of from about 0.0001% (w/w) to about 0.05% (w/w). 183. The pharmaceutical spray formulation of any one of embodiments 154-182, further comprising chlorobutanol at a concentration of from about 0.005% (w/v) to about 1% (w/v). 184. The pharmaceutical spray formulation of any one of embodiments 154-183, further comprising further comprising a vasodilator. 185. The pharmaceutical spray formulation of embodiment 184, wherein the vasodilator is nitroprusside, phentolamine, or nifedipine. 186. The pharmaceutical spray formulation of any one of embodiments 154-185, further comprising a permeability enhancer. 187. The pharmaceutical spray formulation of embodiment 186, wherein the permeability enhancer is diethylene glycol monoethyl ether. 188. The pharmaceutical spray formulation of any one of embodiments 154-187, further comprising a viscosity modifier. 189. The pharmaceutical spray formulation of embodiment 188, wherein the viscosity modifier is polyethylene glycol, methylcellulose, or hypromellose. 190. The pharmaceutical spray formulation of any one of embodiments 154-189, further comprising trisodium citrate. 191. The pharmaceutical spray formulation of embodiment 154 comprising from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2.0% trisodium citrate, and from about 0.05% to about 15% diethylene glycol monoethyl ether. 192. The pharmaceutical spray formulation of embodiment 191 comprising from about 1% to about 5% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.01% to about 0.2% hypromellose, from about 0.1% to about 1.0% trisodium citrate, and from about 0.1% to about 2.0% diethylene glycol monoethyl ether. 193. The pharmaceutical spray formulation of embodiment 191 comprising from about 5% to about 20% w/w of epinephrine, or a pharmaceutically acceptable salt thereof, from about 0.01% (w/w) to about 0.1% (w/w) of sodium metabisulfite, from about 0.1% to about 1.0% sodium chloride, from about 0.05% to about 0.5% hypromellose, from about 0.1% to about 1.0% trisodium citrate, and from about 0.5% to about 5% diethylene glycol monoethyl ether. 194. The pharmaceutical spray formulation of embodiment 191 comprising about 2.4% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. 195. The pharmaceutical spray formulation of embodiment 191 comprising about 5% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. 196. The pharmaceutical spray formulation of embodiment 191 comprising about 10% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. 197. The pharmaceutical spray formulation of embodiment 191 comprising about 20% w/w of epinephrine, or a pharmaceutically acceptable salt thereof, about 0.05% (w/w) of sodium metabisulfite, about 0.4% sodium chloride, about 0.1% hypromellose, about 0.7% trisodium citrate, and about 1% diethylene glycol monoethyl ether. 198. The pharmaceutical spray formulation of any one of embodiments 154-197, further comprising chlorobutanol at a concentration of from about 0.05% (w/v) to about 1% (w/v). 199. The pharmaceutical spray formulation of any one of embodiments 154-198, wherein the formulation is delivered from a device. 200. The pharmaceutical spray formulation of embodiment 199, wherein the device is a single-dose device. 201. The pharmaceutical spray formulation of any one of embodiment 199, wherein the device is a bi-dose device. 202. The pharmaceutical spray formulation of any one of embodiments 199-201, wherein the device has a single reservoir containing from about 125 µL to about 250 µL of the pharmaceutical solution. 203. The pharmaceutical spray formulation of embodiment 202, wherein the device delivers two sprays of the pharmaceutical solution from a single reservoir. 204. The pharmaceutical spray formulation of embodiment 201, wherein the device has a first reservoir containing from about 50 µL to about 250 µL of the pharmaceutical solution and a second reservoir containing from about 50 µL to about 250 µL of the pharmaceutical solution. 205. The pharmaceutical spray formulation of embodiment 204, wherein the device delivers one spray of the pharmaceutical solution from the first reservoir and one spray of the pharmaceutical solution from the second reservoir. 206. The pharmaceutical spray formulation of any one of embodiments 196-205, wherein the device is pre-primed. 207. The pharmaceutical spray formulation of any one of embodiments 199-206, wherein the device is suitable for delivering the formulation into the nostril of a subject. 208. The pharmaceutical spray formulation of any one of embodiments 199-207, wherein the device comprises at least one oxygen absorber or scavenger. 209. The pharmaceutical spray formulation of embodiment 208, wherein the at least one oxygen absorber or scavenger is iron, ferrous carbonate, ascorbate, or sodium bicarbonate, or a combination thereof. 210. The pharmaceutical spray formulation of any one of embodiments 154-209, wherein the formulation is delivered as a spray. 211. The pharmaceutical spray formulation of embodiment 210, wherein the spray takes the shape of a round plume with an ovality ratio less than about 2.0. 212. The pharmaceutical spray formulation of embodiment 210 or 211, wherein the spray takes the shape of a round plume with an ovality ratio less than about 1.5. 213. The pharmaceutical spray formulation of any one of embodiments 210-212, wherein the spray takes the shape of a round plume with an ovality ratio less than about 1.3. 214. The pharmaceutical spray formulation of any one of embodiments 210-213, wherein the spray takes the shape of a round plume with an ovality ratio less than about 1.2. 215. The pharmaceutical spray formulation of any one of embodiments 210-214, wherein the spray takes the shape of a round plume with an ovality ratio less than about 1.1. 216. The pharmaceutical spray formulation of any one of embodiments 210-215, wherein the ovality ratio of the spray is measured at a distance of from about 1 cm to about 10 cm from a device from which the formulation is administered or delivered. 217. The pharmaceutical spray formulation of any one of embodiments 210-216, wherein the ovality ratio of the spray is measured at a distance of from about 1 cm to about 5 cm from a device from which the formulation is administered or delivered. 218. The pharmaceutical spray formulation of any one of embodiments 210-217, wherein the ovality ratio of the spray is measured at a distance of about 3 cm from a device from which the formulation is administered or delivered. 219. The pharmaceutical spray formulation of any one of embodiments 154-218, wherein the epinephrine is at least 10% bioavailable. 220. The pharmaceutical spray formulation of any one of embodiments 154-219, wherein the epinephrine is at least 40% bioavailable. 221. The pharmaceutical spray formulation of any one of embodiments 154-220, wherein the epinephrine is at least 50% bioavailable. 222. The pharmaceutical spray formulation of any one of embodiments 154-221, wherein the epinephrine is at least 60% bioavailable. 223. The pharmaceutical spray formulation of any one of embodiments 154-222, wherein the formulation comprises droplets with a median droplet size from about 10 µm to about 120 µm. 224. The pharmaceutical spray formulation of embodiment 223, wherein no more than about 10% of the droplets have a diameter less than about 10 µm. 225. The pharmaceutical spray formulation of embodiment 223 or 224, wherein no more than approximately 5% of the droplets have a diameter less than about 10 µm. 226. The pharmaceutical spray formulation of any one of embodiments 223-225, wherein no more than approximately 2% of the droplets have a diameter less than about 10 µm. 227. The pharmaceutical spray formulation of any one of embodiments 223-226, wherein approximately 50% of the droplets have a diameter from about 10 µm to about 120 µm. 228. The pharmaceutical spray formulation of any one of embodiments 223-227, wherein approximately 50% of the droplets have a diameter from about 10 µm to about 60 µm. 229. The pharmaceutical spray formulation of any one of embodiments 223-228, wherein approximately 90% of the droplets have a diameter less than about 120 µm. 230. A method of treating anaphylaxis, anaphylactic shock, a severe allergic reaction, and/or bronchial constriction, comprising administering or delivering to a subject in need thereof the pharmaceutical spray formulation of any one of embodiments 154-229. 231. The method of embodiment 230, wherein the pharmaceutical spray formulation is administered or delivered into a nostril of the subject from a pre-primed device adapted for nasal delivery. 232. The method of embodiment 231, wherein a volume of from about 20 µL to about 250 µL of spray is delivered. 233. The method of any one of embodiments 230-232, wherein the plasma concentration versus time curve of epinephrine in the subject has a tmax of less than from about 10 minutes to about 120 minutes. 234. The method of any one of embodiments 230-233, wherein a therapeutic plasma concentration of epinephrine in the subject is achieved in less than 20 minutes following administration to the subject. 235. The method of any one of embodiments 230-234, wherein a therapeutic plasma concentration of epinephrine in the subject is achieved in less than 15 minutes following administration to the subject. 236. The method of any one of embodiments 230-235, wherein a therapeutic plasma concentration of epinephrine in the subject is achieved in less than 10 minutes following administration to the subject. 237. The method of any one of embodiments 230-236, wherein a therapeutic plasma concentration of epinephrine in the subject is achieved in less than 5 minutes following administration to the subject. 238. The method of any one of embodiments 234-237, wherein the therapeutic plasma concentration of epinephrine in the subject is about 500 pg/mL of epinephrine. 239. The method of any one of embodiments 234-238, wherein the therapeutic plasma concentration of epinephrine in the subject is about 450 pg/mL of epinephrine. 240. The method of any one of embodiments 234-239, wherein the therapeutic plasma concentration of epinephrine in the subject is about 400 pg/mL of epinephrine. 241. The method of any one of embodiments 234-240, wherein the therapeutic plasma concentration of epinephrine in the subject is about 350 pg/mL of epinephrine. 242. The method of any one of embodiments 234-241, wherein the therapeutic plasma concentration of epinephrine in the subject is about 300 pg/mL of epinephrine. 243. The method of any one of embodiments 230-242, wherein the subject has a maximum plasma concentration ($C_{max}$) of from about 50 pg/mL to about 500 pg/mL of epinephrine. 244. The method of any one of embodiments 230-243, wherein the area under a plasma concentration-time curve of epinephrine in the subject is from about 5 ng/minute/mL to about 50 ng/minute/mL. 245. The method of any one of embodiments 231-244, wherein the pre-primed device is actuatable with one hand. 246. The method of any one of embodiments 231-245, wherein the pre-primed device is a single-dose device. 247. The method of any one of embodiments 231-245, wherein the pre-primed device is a bi-dose device. 248. The method of any one of embodiments 231-247, wherein the pre-primed device has a single reservoir containing from about 125 µL to about 250 µL of the pharmaceutical formulation. 249. The method of embodiment 248, wherein the device delivers two sprays of the pharmaceutical solution from a single reservoir. 250. The method of embodiment 247, wherein the device has a first reservoir containing from about 50 µL to about 250 µL of the pharmaceutical solution and a second reservoir containing from about 50 µL to about 250 µL of the pharmaceutical solution. 251. The method of embodiment 250, wherein the device delivers one spray of the pharmaceutical solution from the first reservoir and one spray of the pharmaceutical solution from the second reservoir. 252. The method of any one of embodiments 230-251, wherein approximately 100 µL of the pharmaceutical formulation is delivered by one actuation of the device. 253. The method of embodiment 248, wherein the volume of the reservoir is not more than about 140 µL. 254. The method of embodiment 250, wherein the volume of each reservoir is not more than about 140 µL. 255. The method of any one of embodiments 230-254, wherein delivery time is less than about 25 seconds. 256. The method of any one of embodiments 230-255, wherein delivery time is less than about 20 seconds. 257. The method of any one of embodiments 230-256, wherein less than about 20% of the formulation leaves the nasal cavity via drainage into the nasopharynx or externally. 258. The method of any one of embodiments 230-257, wherein less than about 10% of the formulation leaves the nasal cavity via drainage into the nasopharynx or externally. 259. The method of any one of embodiments 230-258, wherein less than about 5% of the formulation leaves the nasal cavity via drainage into the nasopharynx or externally. 260. The method of any one of embodiments 230-259, wherein the subject is suffering from a severe allergic reaction from exposure or suspected exposure to an allergen. 261. The method of embodiment 260, wherein the allergen is food, medication, or an insect bite or sting. 262. The method of any one of embodiments 230-261, wherein the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, and vomiting. 263. The method of any one of embodiments 230-262, wherein the subject exhibits respiratory depression or distress, or cardiovascular depression. 264. The method of any one of embodiments 230-263, wherein the subject is free from respiratory depression or distress for at least about 1 hour following treatment comprising delivery of the therapeutically effective amount of the epinephrine, or a pharmaceutically acceptable salt thereof. 265. The method of any one of embodiments 230-264, wherein the subject is free from respiratory depression or distress for at least about 2 hours following treatment comprising delivery of the therapeutically effective amount of the epinephrine, or a pharmaceutically acceptable salt thereof. 266. The method of any one of embodiments 230-265, wherein the subject is free from respiratory depression or distress for at least about 4 hours following treatment comprising delivery of the therapeutically effective amount of the epinephrine, or a pharmaceutically acceptable salt thereof. 267. The method of any one of embodiments 230-266, wherein the subject is free from respiratory depression or distress for at least about 6 hours following treatment comprising delivery of the therapeutically effective amount of the epinephrine, or a pharmaceutically acceptable salt thereof. 268. The method of any one of embodiments 230-267, wherein the subject is in a lying, supine, or recovery position. 269. The method of any one of embodiments 230-268, wherein a single spray in the nostril yields a plasma concentration of ≥0.2 ng/mL within 2.5 minutes in the subject. 270. The method of any one of embodiments 230-268, wherein a single spray in the nostril yields a plasma concentration of ≥1 ng/mL within 5 minutes in the subject. 271. The method of any one of embodiments 230-268, wherein a single spray in the nostril yields a plasma concentration of ng/mL within 10 minutes in the subject. 272. A method of treating anaphylaxis- or anaphylactic shock-induced respiratory depression or distress, comprising administering or delivering to a subject in need thereof the spray formulation of any one of embodiments 154-229 from a pre-primed device into a nostril of the subject in a manner that delivers the formulation in a round spray plume with an ovality ratio less than about 2.0 when measured at a distance of from about 1 to about 10 cm from the pre-primed device, wherein: (i) the device is adapted for nasal delivery; and (ii) a volume of from about 20 µL to about 250 µL of spray is delivered. 273. The method of embodiment 272, wherein the ovality ratio is less than about 1.5. 274. The method of embodiment 272, wherein the ovality ratio is less than about 1.3. 275. The method of embodiment 272, wherein the ovality ratio is less than about 1.2. 276. The method of embodiment 272, wherein the ovality ratio is less than about 1.1. 277. The method of any one of embodiments 272-276, wherein the ovality ratio of the spray is measured at a distance of from about 1 cm to about 5 cm from the device. 278. A method for treating at least one symptom of anaphylaxis or anaphylactic shock, comprising administering or delivering to a subject in need thereof the pharmaceutical spray formulation of any one of embodiments 154-229 from a device into a nostril of the subject, wherein: (i) the device is adapted for nasal delivery; and (ii) a volume of from about 20 µL to about 250 µL of spray is delivered. 279. The device of any one of the preceding embodiments, wherein the device comprises: at least one processor, an operating system configured to perform executable instructions, a memory, and a computer program including instructions executable by the digital processing device to create an application comprising: a) a software module sending a first notification to a portable device of a user when the device has been triggered for formulation administration; b) a software module sending a second notification to a second device of a designated third party when the device has been triggered for formulation administration; c) a software module sending a third notification to the portable device of the user when the device is outside a predetermined range from the portable device; d) a software module sending a fourth notification to the second device of the designated third party when the device is outside the predetermined range from the portable device; e) a software module collecting geographic data of the device when the device is in administration to the user or a second user; f) a software module saving geographic data of the device to a remote or cloud database; and g) a software module allowing the user or the second user to order a new device using the device or the portable device of the user. 280. The method of any one of the preceding embodiments, wherein the method comprising: a) sending a first notification to a portable device of a user when the device has been triggered for formulation administration; b) sending a second notification to a second device of a designated third party when the device has been triggered for formulation administration; c) sending a third notification to the portable device of the user when the device is outside a predetermined range from the portable device; d) sending a fourth notification to the second device of the designated third party when the device is outside the predetermined range from the portable device; e) collecting geographic data of the device when the device is in administration to the user or a second user; f) saving geographic data of the device to a remote or cloud database; and g) allowing the user or the second user to order a new device using the device or the portable device of the user. 281. The device of embodiment 279, wherein the portable device or the second device comprises one or more of: a computer, a notebook computer, a handheld computer, a mobile smartphones, a tablet computer, and a personal digital assistant. 282. The device of embodiment 279 further comprising a communications element configured to allow two-way data communication with the portable device of the user and a digital processing device using a wireless data transfer protocol. 283. The device of embodiment 279, wherein the first, second, third, or fourth notification is sent within the application. 284. The device of embodiment 279, wherein the first, second, third, or fourth notification is automatic. 285. The device of embodiment 279, wherein the first, second, third, or fourth notification comprises one or more of: text, graphic information, sound, and vibration. 286. A pharmaceutical spray formulation comprising from about 0.5% to about 25% w/w of epinephrine, or a pharmaceutically acceptable salt of epinephrine, in water, wherein the pH of the formulation is from about 4.0 to about 6.5. 287. The pharmaceutical spray formulation of embodiment 286, comprising from about 0.5% to about 10% w/w of epinephrine, or a pharmaceutically acceptable salt thereof. 288. The pharmaceutical spray formulation of embodiment 286, comprising from about 2% to about 5% w/w of epinephrine. 289. The pharmaceutical spray formulation of embodiment 286, comprising about 2% w/w of epinephrine. 290. The pharmaceutical spray formulation of embodiment 286, comprising about 5% w/w of epinephrine. 291. The pharmaceutical spray formulation of any one of embodiments 286-290, further comprising one or more of an antioxidant, an antimicrobial preservative, an isotonicity agent, an absorption enhancer, a viscosity modifier, or a buffering agent. 292. The pharmaceutical spray formulation of embodiment 291, wherein the pharmaceutical formulation comprises an antioxidant, an antimicrobial preservative, an isotonicity agent, an absorption enhancer, a viscosity modifier, and a buffering agent. 293. The pharmaceutical spray formulation of any one of embodiments 286-293, further comprising an antioxidant. 294. The pharmaceutical spray formulation of embodiment 293, wherein the antioxidant comprises sodium bisulfite or sodium metabisulfite. 295. The pharmaceutical spray formulation of embodiment 293, comprising the antioxidant at a concentration from about 0.0001% (w/w) to about 0.1% (w/w). 296. The pharmaceutical spray formulation of embodiment 293, comprising the antioxidant at a concentration from about 0.001% (w/w) to about 0.1% (w/w). 297. The pharmaceutical spray formulation of embodiment 293, comprising the antioxidant at a concentration from about 0.01% (w/w) to about 0.1% (w/w). 298. The pharmaceutical spray formulation of embodiment 293, comprising the antioxidant at a concentration of about 0.05% (w/w). 299. The pharmaceutical spray formulation of any one of embodiments 286-298, further comprising an antimicrobial preservative. 300. The pharmaceutical spray formulation of embodiment 299, wherein the antimicrobial preservative comprises chlorobutanol. 301. The pharmaceutical spray formulation of embodiment 299, comprising the antimicrobial preservative at a concentration from about 0.005% (w/v) to about 1% (w/v). 302. The pharmaceutical spray formulation of embodiment 299, comprising the antimicrobial preservative at a concentration from about 0.01% (w/v) to about 1% (w/v). 303. The pharmaceutical spray formulation of embodiment 299, comprising the antimicrobial preservative at a concentration from about 0.1% (w/v) to about 1% (w/v). 304. The pharmaceutical spray formulation of embodiment 299, comprising the antimicrobial preservative at a concentration of about 0.21% (w/v). 305. The pharmaceutical spray formulation of embodiment 286, further comprising an isotonicity agent. 306. The pharmaceutical spray formulation of embodiment 305, wherein an isotonicity agent comprises sodium chloride. 307. The pharmaceutical spray formulation of embodiment 305, comprising an isotonicity agent at a concentration from about 0.1% to about 5%. 308. The pharmaceutical spray formulation of embodiment 305, comprising an isotonicity agent at a concentration from about 0.1% to about 1%. 309. The pharmaceutical spray formulation of embodiment 305, comprising an isotonicity agent at a concentration of about 0.4%. 310. The pharmaceutical spray formulation of any one of embodiments 286-309, further comprising an absorption enhancer. 311. The pharmaceutical spray formulation of embodiment 310, wherein the absorption enhancer comprises diethylene glycol monoethyl ether. 312. The pharmaceutical spray formulation of embodiment 310, comprising the absorption enhancer at a concentration from about 0.05% to about 15%. 313. The pharmaceutical spray formulation of embodiment 310, comprising the absorption enhancer at a concentration from about 0.1% to about 5%. 314. The pharmaceutical spray formulation of embodiment 310, comprising the absorption enhancer at a concentration of about 1%. 315. The pharmaceutical spray formulation of any one of embodiments 286-314, further comprising a viscosity modifier. 316. The pharmaceutical spray formulation of embodiment 315, wherein the viscosity modifier comprises hypromellose. 317. The pharmaceutical spray formulation of embodiment 315, comprising the viscosity modifier at a concentration from about 0.001% to about 0.5%. 318. The pharmaceutical spray formulation of embodiment 315, comprising the viscosity modifier at a concentration from about 0.01% to about 0.2%. 319. The pharmaceutical spray formulation of embodiment 315, comprising the viscosity modifier at a concentration of about 0.1%. 320. The pharmaceutical spray formulation of any one of embodiments 286-319, further comprising a buffering agent. 321. The pharmaceutical spray formulation of embodiment 320, wherein the buffering agent comprises citric acid or citric acid monohydrate. 322. The pharmaceutical spray formulation of embodiment 320, comprising the buffering agent at a concentration from about 0.01% to about 2%. 323. The pharmaceutical spray formulation of embodiment 320, comprising the buffering agent at a concentration from about 0.1% to about 1%. 324. The pharmaceutical spray formulation of embodiment 320, comprising the buffering agent at a concentration of about 0.42%. 325. The pharmaceutical spray formulation of embodiment 286, further comprising sodium metabisulfite, sodium chloride, hypromellose, citric acid monohydrate, and diethylene glycol monoethyl ether. 326. The pharmaceutical spray formulation of embodiment 325, comprising from about 1% to about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. 327. The pharmaceutical spray formulation of embodiment 325, comprising from about 1% to about 20% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. 328. The pharmaceutical spray formulation of embodiment 325, comprising about 2% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. 329. The pharmaceutical spray formulation of embodiment 325, comprising about 2% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. 330. The pharmaceutical spray formulation of embodiment 325, comprising about 2% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. 331. The pharmaceutical spray formulation of embodiment 325, comprising about 5% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. 332. The pharmaceutical spray formulation of embodiment 325, comprising about 5% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. 333. The pharmaceutical spray formulation of embodiment 325, comprising about 5% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. 334. The pharmaceutical spray formulation of embodiment 325, comprising about 10% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. 335. The pharmaceutical spray formulation of embodiment 325, comprising about 10% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. 336. The pharmaceutical spray formulation of embodiment 325, comprising about 10% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. 337. The pharmaceutical spray formulation of embodiment 325, comprising about 20% w/w of epinephrine, or a pharmaceutically acceptable salt thereof, from about 0.0001% (w/w) to about 0.1% (w/w) of sodium metabisulfite, from about 0.1% to about 5% sodium chloride, from about 0.001% to about 0.5% hypromellose, from about 0.01% to about 2% citric acid monohydrate, and from about 0.05% to about 15% diethylene glycol monoethyl ether. 338. The pharmaceutical spray formulation of embodiment 325, comprising about 20% w/w of epinephrine, or a pharmaceutically acceptable salt thereof, from about 0.01% (w/w) to about 0.1% (w/w) of sodium metabisulfite, from about 0.1% to about 1% sodium chloride, from about 0.01% to about 0.2% hypromellose, from about 0.1% to about 1% citric acid monohydrate, and from about 0.1% to about 5% diethylene glycol monoethyl ether. 339. The pharmaceutical spray formulation of embodiment 325, comprising about 20% w/w of epinephrine, or a pharmaceutically acceptable salt thereof, about 0.05% (w/w) of sodium metabisulfite, about 0.4% sodium chloride, about 0.1% hypromellose, about 0.42% citric acid monohydrate, and about 1% diethylene glycol monoethyl ether. 340. The pharmaceutical spray formulation of any one of embodiments 286-339, further comprising chlorobutanol at a concentration of from about 0.005% (w/v) to about 10% (w/v). 341. The pharmaceutical spray formulation of any one of embodiments 286-339, further comprising chlorobutanol at a concentration of from about 0.01% (w/v) to about 10% (w/v). 342. The pharmaceutical spray formulation of any one of embodiments 286-339, further comprising chlorobutanol at a concentration of from about 0.1% (w/v) to about 1% (w/v). 343. The pharmaceutical spray formulation of any one of embodiments 286-339, further comprising chlorobutanol at a concentration about 0.21% (w/v). 344. A spray, comprising droplets, wherein the droplets comprise the pharmaceutical spray formulation of any one of embodiments 286-343. 345. A method of treating anaphylaxis, anaphylactic shock, a severe allergic reaction, and/or bronchial constriction, comprising delivering a spray of a pharmaceutical solution from a pre-primed device into a nostril of a subject in need thereof, wherein: (i) the device is adapted for nasal delivery; (ii) a volume of from about 20 µL to about 250 µL of spray is delivered; and (iii) the pharmaceutical solution comprises the pharmaceutical spray formulation of any one of embodiments 286-343. 346. A method of treating anaphylaxis- or anaphylactic shock-induced respiratory depression or distress, comprising delivering a spray of a pharmaceutical solution from a pre-primed device into a nostril of a subject in need thereof in a manner that delivers the pharmaceutical solution in a round spray plume with an ovality ratio less than about 2.0 when measured at a distance of from about 1 to about 10 cm from the pre-primed device, wherein: (i) the device is adapted for nasal delivery; (ii) a volume of from about 20 µL to about 250 µL of spray is delivered; and (iii) the pharmaceutical solution comprises the pharmaceutical spray formulation of any one of embodiments 286-343. 347. A method for treating at least one symptom of anaphylaxis or anaphylactic shock, comprising delivering a spray of a pharmaceutical solution from a device into a nostril of a subject in need thereof, wherein: (i) the device is adapted for nasal delivery; (ii) a volume of from about 20 µL to about 250 µL of spray is delivered; and the pharmaceutical solution comprises the pharmaceutical spray formulation of any one of embodiments 286-343. 348. The method of any one of embodiments 345-347, wherein a therapeutic plasma concentration of epinephrine in the subject is achieved in less than 20 minutes following administration to the subject. 349. The method of any one of embodiments 345-347, wherein the therapeutic plasma concentration of epinephrine in the subject is about 0.5 ng/mL of epinephrine. 350. The method of any one of embodiments 345-347, wherein the subject has a maximum plasma concentration (Cmax) of from about 0.1 ng/mL to about 1 ng/mL of epinephrine. 351. The method of any one of embodiments 345-347, wherein the area under a plasma concentration-time curve of epinephrine in the subject is from about 0.1 ng·h/mL to about 5 ng·h/mL. 352. The method of any one of embodiments 345-347, wherein the plasma concentration versus time curve of epinephrine in the subject has a tmax of less than from about 10 minutes to about 120 minutes 353. The method of any one of embodiments 345-352, wherein the device is a single-dose device. 354. The method of any one of embodiments 345-352, wherein the device is a bi-dose device. 355. The method of any one of embodiments 345-354, wherein the device delivers two sprays of the pharmaceutical solution from a single reservoir. 356. The method of any one of embodiments 345-354, wherein the device has a first reservoir containing from about 50 μL to about 250 μL of the pharmaceutical solution and a second reservoir containing from about 50 μL to about 250 μL of the pharmaceutical solution. 357. The method of any one of embodiments 345-356, wherein less than about 20% of the formulation leaves the nasal cavity via drainage into the nasopharynx or externally. 358. The method of any one of embodiments 345-357, wherein a single spray in a nostril of the subject yields a plasma concentration of at least 0.2 ng/mL within 2 minutes in the subject. 359. A stable pharmaceutical spray formulation, comprising: (i) from about 1% to about 25% w/w of epinephrine, or a pharmaceutically acceptable salt thereof, in water; and (ii) one or more excipients, vehicles, emulsifiers, stabilizing agents, preservatives, mucosal adhesives, antibacterial agents, buffers, and/or other additives, wherein the formulation is stable at a temperature of at least about 20° C. and at a relative humidity of at least about 30%, and wherein the formulation is stable for a period of at least about two months, wherein the stable pharmaceutical formulation is the pharmaceutical spray formulation from any one of embodiments 286-343. 360. A pharmaceutical spray formulation, comprising: (i) from about 1% to about 25% (w/w) of epinephrine, or a pharmaceutically acceptable salt thereof, in water, ethanol, propylene glycol, or a combination thereof; and (ii) one or more of an antioxidant, an antimicrobial preservative, an isotonicity agent, an absorption enhancer, a viscosity modifier, or a buffering agent; wherein the formulation is configured to be administered into a nostril of a subject as a nasal spray that yields a plasma concentration of at least 0.5 ng/mL within 1 minute of administration. 361. The pharmaceutical spray formulation of embodiment 360, wherein the pH of the formulation is from about 4.0 to about 6.5. 362. The pharmaceutical spray formulation of embodiment 360 or 361, wherein the antioxidant comprises sodium bisulfite or sodium metabisulfite at a concentration from about 0.01% to about 0.1% (w/w). 363. The pharmaceutical spray formulation of any one of embodiments 360-362, wherein the antimicrobial preservative comprises chlorobutanol or chlorobutanol hemihydrate at a concentration from about 0.1% to about 1% (w/w). 364. The pharmaceutical spray formulation of any one of embodiments 360-363, wherein the isotonicity agent comprises sodium chloride at a concentration from about 0.1% to about 1% (w/w). 365. The pharmaceutical spray formulation of any one of embodiments 360-364, wherein the viscosity modifier comprises hypromellose at a concentration from about 0.01% to about 0.2% (w/w). 366. The pharmaceutical spray formulation of any one of embodiments 360-365, wherein the buffering agent comprises citric acid or citric acid monohydrate at a concentration from about 0.1% to about 1% (w/w). 367. The pharmaceutical spray formulation of any one of embodiments 360-366, comprising about 2% or about 5% (w/w) of epinephrine, or a pharmaceutically acceptable salt thereof. 368. The pharmaceutical spray formulation of any one of embodiments 360-367, wherein the pharmaceutical spray formulation comprises sodium metabisulfite, sodium chloride, hypromellose, citric acid monohydrate, diethylene glycol monoethyl ether, and chlorobutanol hemihydrate. 369. The pharmaceutical spray formulation of any one of embodiments 360-367, comprising from about 1% to about 10% (w/w) of epinephrine, or a pharmaceutically acceptable salt thereof, from about 0.01% to about 0.1% (w/w) of sodium metabisulfite, from about 0.1% to about 1% (w/w) sodium chloride, from about 0.01% to about 0.2% (w/w) hypromellose, from about 0.1% to about 1% (w/w) citric acid monohydrate, from about 0.1% to about 5% (w/w) diethylene glycol monoethyl ether, and from about 0.1% to about 1% (w/w) chlorobutanol hemihydrate. 370. A stable pharmaceutical spray formulation, comprising: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the formulation is stable for a period of at least about one month at a temperature of at least about 20° C. 371. The pharmaceutical spray formulation of embodiment 370, wherein the formulation is stable for a period of at least one month at a temperature of at least about 40° C. 372. The pharmaceutical spray formulation of embodiment 370 or 371, wherein the formulation has no more than about 2% total impurities after storage for a period of at least about one month at a temperature of at least about 40° C. 373. The pharmaceutical spray formulation of any one of embodiments 370-372, wherein the antioxidant comprises sodium bisulfite or sodium metabisulfite at a concentration from about 0.01% to about 0.1% (w/w). 374. The pharmaceutical spray formulation of any one of embodiments 370-373, wherein the antimicrobial preservative comprises chlorobutanol or chlorobutanol hemihydrate at a concentration from about 0.1% to about 1% (w/w). 375. The pharmaceutical spray formulation of any one of embodiments 370-374, wherein the isotonicity agent comprises sodium chloride at a concentration from about 0.1% to about 1% (w/w). 376. The pharmaceutical spray formulation of any one of embodiments 370-375, wherein the buffering agent comprises citric acid or citric acid monohydrate at a concentration from about 0.1% to about 1% (w/w). 377. A pharmaceutical spray formulation, comprising: (i) from about 1% to about 25% (w/w) of epinephrine, or a pharmaceutically acceptable salt thereof, in water, ethanol, propylene glycol, or a combination thereof; and (ii) one or more of an antioxidant, an antimicrobial preservative, an isotonicity agent, an absorption enhancer, a viscosity modifier, or a buffering agent; wherein the absorption enhancer is diethylene glycol monoethyl ether. 378. The pharmaceutical spray formulation of embodiment 377, wherein the formulation comprises diethylene glycol monoethyl ether at a concentration from about 0.1% to about 5% (w/w). 379. The pharmaceutical spray formulation of embodiment 377 or 378, wherein the absorption enhancer comprises diethylene glycol monoethyl ether at a concentration of about 1% (w/w). 380. A method for treating at least one symptom of anaphylaxis or anaphylactic shock, comprising delivering a spray of a pharmaceutical spray formulation from a nasal spray device into a nostril of a subject in need thereof, wherein the pharmaceutical spray formulation comprises: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the formulation is configured to be administered into a nostril of a subject as a nasal spray that yields a plasma concentration of at least 0.5 ng/mL within 1 minute of administration. 381. The method of embodiment 380, wherein the subject is suffering from a severe allergic reaction from exposure or suspected exposure to an allergen. 382. The method of embodiment 381, wherein the allergen is food, medication, or an insect bite or sting. 383. The method of any one of embodiments 380-382, wherein the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, and vomiting. 384. The method of any one of embodiments 380-383, wherein the subject exhibits respiratory depression or distress, or cardiovascular depression. 385. The method of any one of embodiments 380-384, wherein the subject is free from respiratory depression or distress for at least about 1 hour following delivery of the pharmaceutical spray formulation. 386. The method of any one of embodiments 380-385, wherein the antioxidant comprises sodium bisulfite or sodium metabisulfite at a concentration from about 0.01% to about 0.1% (w/w). 387. The method of any one of embodiments 380-386, wherein the antimicrobial preservative comprises chlorobutanol or chlorobutanol hemihydrate at a concentration from about 0.1% to about 1% (w/w). 388. The method of any one of embodiments 380-387, wherein the isotonicity agent comprises sodium chloride at a concentration from about 0.1% to about 1% (w/w). 389. The method of any one of embodiments 380-388, wherein the viscosity modifier comprises hypromellose at a concentration from about 0.01% to about 0.2% (w/w). 390. The method of any one of embodiments 380-389, wherein the buffering agent comprises citric acid or citric acid monohydrate at a concentration from about 0.1% to about 1% (w/w). 391. The method of any one of embodiments 380-390, comprising about 2% or about 5% (w/w) of epinephrine, or a pharmaceutically acceptable salt thereof. 392. The method of any one of embodiments 380-391, wherein the pharmaceutical spray formulation comprises sodium metabisulfite, sodium chloride, hypromellose, citric acid monohydrate, diethylene glycol monoethyl ether, and chlorobutanol hemihydrate. 393. A method of treating at least one of anaphylaxis, anaphylactic shock, a severe allergic reaction, or bronchial constriction, comprising administering or delivering to a subject in need thereof a stable pharmaceutical spray formulation, wherein the stable pharmaceutical spray formulation comprises: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the formulation is stable for a period of at least about one month at a temperature of at least about 20° C. 394. The method of embodiment 393, wherein the formulation is stable for a period of at least one month at a temperature of at least about 40° C. 395. The method of embodiment 393 or 394, wherein the formulation comprises no more than 2% total impurities after storage for a period of at least about one month at a temperature of at least about 40° C. 396. A method of treating at least one of anaphylaxis, anaphylactic shock, a severe allergic reaction, or bronchial constriction, comprising administering or delivering to a subject in need thereof the pharmaceutical spray formulation, wherein the pharmaceutical spray formulation comprises: (c) from about 1% to about 25% (w/w) of epinephrine, or a pharmaceutically acceptable salt thereof, in water, ethanol, propylene glycol, or a combination thereof; and (d) one or more of an antioxidant, an antimicrobial preservative, an isotonicity agent, an absorption enhancer, a viscosity modifier, or a buffering agent; wherein a therapeutic plasma concentration of epinephrine in the subject is achieved in less than 15 minutes following administration to the subject. 397. The method of embodiment 396, wherein the absorption enhancer is diethylene glycol monoethyl ether. 398. The method of embodiment 396 or 397, wherein the formulation comprises diethylene glycol monoethyl ether at a concentration from about 0.1% to about 5% (w/w). 399. The method of any one of embodiments 396-398, wherein the formulation comprises diethylene glycol monoethyl ether at a concentration of about 1% (w/w). 400. A bi-dose nasal delivery device adapted for delivery of a pharmaceutical solution into a nostril of a subject, comprising: (a) the pharmaceutical solution configured as a pharmaceutical spray formulation comprising from about 1% to about 25% (w/w) of epinephrine, or a pharmaceutically acceptable salt thereof, in water, ethanol, propylene glycol, or a combination thereof; (b) a reservoir containing from about 125 μL to about 250 μL of the pharmaceutical solution; and wherein the bi-dose device is configured to administer the pharmaceutical solution into a nostril of a subject as two nasal sprays. 401. The device of embodiment 400, wherein the device is a pre-primed device that is configured to be actuatable with one hand. 402. The device of embodiment 400 or 401, wherein the device is configured to deliver about 100 μL of the pharmaceutical solution from the reservoir upon each actuation of the device. 403. The device of any one of embodiments 400-402, wherein the pH of the pharmaceutical solution is from about 4.0 to about 6.5. 404. The device of any one of embodiments 400-403, wherein one or more sprays take the shape of a round plume with an ovality ratio less than about 2.0. 405. The device of any one of embodiments 400-404, wherein the pharmaceutical solution comprises an antioxidant. 406. The device of embodiment 405, wherein the antioxidant comprises sodium bisulfite or sodium metabisulfite at a concentration from about 0.01% to about 0.1% (w/w). 407. The device of any one of embodiments 400-406, wherein the pharmaceutical solution comprises an antimicrobial preservative. 408. The device of embodiment 407, wherein the antimicrobial preservative comprises chlorobutanol or chlorobutanol hemihydrate at a concentration from about 0.1% to about 1% (w/w). 409. The device of any one of embodiments 400-408, wherein the pharmaceutical solution comprises an isotonicity agent. 410. The device of embodiment 409, wherein the isotonicity agent comprises sodium chloride at a concentration from about 0.1% to about 1% (w/w). 411. The device of any one of embodiments 400-410, wherein the pharmaceutical solution comprises a viscosity modifier. 412. The device of embodiment 411, wherein the viscosity modifier comprises hypromellose at a concentration from about 0.01% to about 0.2% (w/w). 413. The device of any one of embodiments 400-412, wherein the pharmaceutical solution comprises a buffering agent. 414. The device of embodiment 413, wherein the buffering agent comprises citric acid or citric acid monohydrate at a concentration from about 0.1% to about 1% (w/w). 415. The device of any one of embodiments 400-414, wherein the pharmaceutical solution comprises about 2% or about 5% (w/w) of epinephrine, or a pharmaceutically acceptable salt thereof. 416. A pre-primed device adapted for delivery of a pharmaceutical solution into one or both nostrils of a subject, comprising a reservoir containing from about 125 µL to about 250 µL of the pharmaceutical solution, wherein the pharmaceutical solution comprises: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the pre-primed device is configured to administer the pharmaceutical solution as one or more sprays into one or both nostrils of the subject. 417. The device of embodiment 416, wherein the formulation comprises diethylene glycol monoethyl ether at a concentration from about 0.1% to about 5% (w/w). 418. A bi-dose device adapted for delivery of a pharmaceutical solution into one or both nostrils of a subject, comprising a reservoir containing from about 125 µL to about 250 µL of the pharmaceutical solution, wherein the pharmaceutical solution comprises: (a) from about 1% to about 25% (w/w) of epinephrine, or a pharmaceutically acceptable salt thereof, in water, ethanol, propylene glycol, or a combination thereof; and (b) one or more of an antioxidant, an antimicrobial preservative, an isotonicity agent, an absorption enhancer, a viscosity modifier, or a buffering agent; wherein the pharmaceutical solution is stable for a period of at least about one month at a temperature of at least about 20° C. 419. The device of embodiment 418, wherein the pharmaceutical solution is stable for a period of at least about three months at a temperature of at least about 20° C. 420. A method of administering a pharmaceutical solution, comprising delivering a spray of the pharmaceutical solution from a device into a nostril of a subject in need thereof in a manner that delivers the pharmaceutical solution in a round spray plume with an ovality ratio less than about 1.4 when measured at a distance of from about 1 to about 10 cm from the device, wherein: (i) the device is adapted for nasal delivery; (ii) a volume of from about 20 µL to about 250 µL of spray is delivered; and (iii) the pharmaceutical solution comprises from about 0.5 mg to about 100 mg of epinephrine, or a pharmaceutically acceptable salt thereof 421. The method of embodiment 420, wherein the spray plume has a particle size distribution with a span of no more than about 2.2 when measured at a distance of from about 1 to about 10 cm from the device. 422. The method of embodiment 420 or 421, wherein the spray plume has a Dmax of less than about 28 mm when measured at a distance of from about 1 to about 10 cm from the device. 423. The method of any one of embodiments 420-422, wherein the device is a bi-dose device configured to deliver two sprays of the pharmaceutical solution. 424. The method of any one of embodiments 420-423, wherein the device has a single reservoir containing from about 125 µL to about 250 µL of the pharmaceutical solution. 425. The method of any one of embodiments 420-424, wherein the device comprises a plunger that houses a container closure comprising: (i) a vial comprising an opening; (ii) a cannula; and (iii) a rubber stopper; wherein the stopper is configured to occlude the opening of the vial, and wherein the cannula is configured such that the cannula can pierce the stopper when the plunger applies sufficient force to the cannula. 426. The method of any one of embodiments 420-426, wherein the device is a pre-primed device that is configured to be actuatable with one hand. 427. The method of any one of embodiments 420-427, wherein a delivery time of the pharmaceutical solution is less than about 25 seconds. 428. The method of any one of embodiments 420-427, wherein the subject is suffering from a severe allergic reaction from exposure or suspected exposure to an allergen. 429. The method of embodiment 428, wherein the allergen is food, medication, or an insect bite or sting. 430. The method of any one of embodiments 420-429, wherein the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, or vomiting. 431. The method of any one of embodiments 420-430, wherein the subject exhibits respiratory depression or distress, or cardiovascular depression. 432. The method of embodiment 431, wherein the subject is free from respiratory depression or distress for at least about 1 hour following treatment comprising delivery of a therapeutically effective amount of the epinephrine, or a pharmaceutically acceptable salt thereof. 433. A method of administering a pharmaceutical solution, comprising delivering a spray of the pharmaceutical solution from a device into a nostril of a subject in need thereof in a manner that delivers the pharmaceutical solution in a spray plume with a particle size distribution having a span of no more than about 2.2 when measured at a distance of from about 1 to about 10 cm from the device, wherein: (i) the device is adapted for nasal delivery; (ii) a volume of from about 20 µL to about 250 µL of spray is delivered; and (iii) the pharmaceutical solution comprises from about 0.5 mg to about 100 mg of epinephrine, or a pharmaceutically acceptable salt thereof 434. The method of embodiment 433, wherein the particle size distribution has a span of no more than about 2.0 when measured at a distance of from about 1 to about 10 cm from the device. 435. The method of embodiment 433 or 434, wherein the device has a single reservoir containing from about 125 µL to about 250 µL of the pharmaceutical solution. 436. The method of any one of embodiments 433-435, wherein the device is a bi-dose device configured to deliver two sprays of the pharmaceutical solution from a single reservoir. 437. A method for administering a pharmaceutical solution, comprising delivering a spray of the pharmaceutical solution from a device into a nostril of a subject in need thereof in a manner that delivers the pharmaceutical solution in a spray plume with a Dmax of less than about 28 mm when measured at a distance of from about 1 to about 10 cm from the device, wherein: (i) the device is adapted for nasal delivery; (ii) a volume of from about 20 µL to about 250 µL of spray is delivered; and (iii) the pharmaceutical solution comprises from about 0.5 mg to about 100 mg of epinephrine, or a pharmaceutically acceptable salt thereof 438. The method of embodiment 437, wherein the device is a bi-dose device configured to deliver two sprays of the pharmaceutical solution. 439. The method of embodiment 437 or 438, wherein the Dmax is less than about 26 mm when measured at a distance of from about 1 to about 10 cm from the device.

EXAMPLES

Example 1: Epinephrine Spray Formulation and Related Studies

TABLE 1

Epinephrine Spray Formulation

| Raw Material | Compendia | CAS # | Amount g |
|---|---|---|---|
| (−)-Epinephrine | USP | 51-43-4 | 0.05 g |
| Sodium metabisulfite | Ph. Eur., BP, or NF | 7681-57-4 | 0.001 g |
| HCl* | Ph. Eur., BP, or USP/NF | 7647-01-0 | q.s. to pH 4.7 +/− 0.2 |

TABLE 1-continued

Epinephrine Spray Formulation

| Raw Material | Compendia | CAS # | Amount g |
|---|---|---|---|
| NaCl | Ph. Eur. BP, or USP | 7647-14-5 | 0.008 g |
| Water for Injection | USP |  | q.s. to 1.000 g +/− 0.002 g |

*Diluted HCl solutions may be prepared from concentrated or fuming HCl or purchased directly from a supplier.

Viscosity

Viscosity will be varied using a viscosity modifier such as methyl cellulose. The viscosity will be adjusted within a range spray characteristics at 10, 50, and 100 centipoise will be analyzed.

Preservative

The formulation in Table 1 will be modified by using 0.05% benzalkonium chloride. The impact of surfactant on spray characteristics will be analyzed.

Vasodilator

The formulation in Table 1 will be modified by the addition of a vasodilator such as phentolamine at 20 mg/mL. The impact on spray characteristics will be analyzed.

Permeation Enhancer

The formulation in Table 1 will be modified by using a permeation enhancer such as 1% diethylene glycol monoethyl ether. The impact on spray characteristics will be analyzed.

Vitamin A

Formulation development will be conducted to support the addition of a Lecithin, tween, or other suitable surfactant to solubilize vitamin A and epinephrine, including varying the pH. Initial studies may be a visual color change after 5-7 days.

Compositions will be formulated and filled in a low $O_2$ environment. Nitrogen overlays and solution purges.

NaCl will be added to make 300 mosmol.

Compatibility with primary container components (glass and plunger) will be investigated. Options for components in parallel will be assayed (for example: different rubbers for plunger, plunger coatings, and/or glass surface treatments).

Variation of pH at time of formulation and impact on stability will be investigated. Solutions at pH 4.0, 4.5, and 5.0 will be studied.

Stability studies at 25° C., 30° C., 40° C., and 50° C. will be conducted.

The formulations will be tested for potency, impurities, pH, and osmolality

Studies will be conducted for characterization of spray.

Stability

TABLE 2

Stability at 25° C., 30° C., and 40° C.

|  | 0 | 1 wk | 3 wk | 6 wk | 10 wk | 16 wk | 26 wk |
|---|---|---|---|---|---|---|---|
| Primary Formulation 50 mg/mL | A | B | A | B | A | B | A |
| Secondary Formulation 36 mg/mL | A | B | A | B | A | B | A |
| pH low | A | B | A | B | A | B | A |
| pH high | A | B | A | B | A | B | A |
| Configuration 2 | A | B | A | B | A | B | A |
| Configuration 3 | A | B | A | B | A | B | A |

A = Assay, purity, pH, osmolality and spray characteristics.
B = Assay and purity

TABLE 3

Stability at 50° C.

|  | 0 | 1 wk | 2 wk | 3 wk | 6 wk | 10 wk |
|---|---|---|---|---|---|---|
| Primary Formulation | N/A | B | B | B | B | AB |
| pH low | N/A | B | B | B | B | A |
| pH high | N/A | B | B | B | B | A |
| Configuration 2 | N/A | B | B | B | B | A |
| Configuration 3 | N/A | B | B | B | B | A |

Example 2: Preparation of Epinephrine Formulation 1

TABLE 4

Epinephrine Formulation 1

| Component | Compendia | Composition (mg/mL) | Amount per spray (mg/spray) |
|---|---|---|---|
| (−)-Epinephrine | USP | 50.0 or 25.0 | 5.0 or 2.5 |
| Sodium metabisulfite | EP, BP or NF | 0.5 | 0.05 |
| HCl* | EP, BP or USP/NF | qs to pH 4.7 +/− 0.3 |  |
| NaCl** | USP | 4.0 | 0.4 |
| Purified Water | USP | qs |  |

*adjust pH to 4.7 ± 0.3
**target 300 mOsm

Epinephrine Formulation 1 was prepared by dissolving sodium metabisulfite in Water for Injection, USP followed by the addition of Sodium Chloride, USP. Epinephrine, USP was added as a dry powder and dissolution of the epinephrine was aided by the addition of HCl until a pH of 4.7 was achieved.

Example 3: Preparation of Epinephrine Formulation 2

TABLE 5

Epinephrine Formulation 2

| Component | Compendia | Composition (mg/mL) | Amount per spray (mg/spray) |
|---|---|---|---|
| (−)-Epinephrine | USP | 50.0 or 25.0 | 5.0 or 2.5 |
| Sodium metabisulfite | EP, BP or NF | 0.5 | 0.05 |
| HCl* | EP, BP or USP/NF | qs to pH 4.7 +/− 0.3 | |
| NaCl** | USP | 4.0 | 0.4 |
| Diethylene glycol monoethyl ether | NF | 10.0 | 1.0 |
| Sodium citrate | NF | 7.0 | 0.7 |
| Hypromellose | USP | 1.0 | 0.1 |
| Purified Water | USP | qs | |

*adjust pH to 4.7 ± 0.3
**target 300 mOsm

Water for Injection (~20% of final formulation volume) was added to a clean dry beaker. Sufficient volume of a 10 mg/mL sodium metabisulfite solution and an 80 mg/mL sodium chloride solution were added and mixed well. Sufficient volumes of 10% solutions of each trisodium citrate, hypromellose and diethylene glycol monoethyl ether were added separately and mixed between additions. Epinephrine was added as a poorly soluble powder. 1.5M HCl was added slowly until nearly all epinephrine was dissolved. 0.3M HCl was slowly added until a pH of 4.7+/−0.3 was achieved. Water was added to bring the mixture to final volume.

Example 4: Preparation of Epinephrine Formulation 3

TABLE 6

Epinephrine Formulation 3

| Component | Compendia | Composition (mg/mL) | Amount per spray (mg/spray) |
|---|---|---|---|
| (−)-Epinephrine | USP | 50.0 or 25.0 | 5.0 or 2.5 |
| Sodium metabisulfite | EP, BP or NF | 0.5 | 0.05 |
| HCl* | EP, BP or USP/NF | qs to pH 4.7 +/− 0.3 | AR |
| NaCl** | USP | 4.0 | 0.4 |
| Diethylene glycol monoethyl ether | NF | 10.0 | 1.0 |
| Chlorobutanol | NF | 2.0 | 0.2 |
| Sodium citrate | NF | 7.0 | 0.7 |
| Hypromellose | USP | 1.0 | 0.1 |
| Purified Water | USP | AR | AR |

*adjust pH to 4.7 ± 0.3
**target 300 mOsm

Water for Injection (~20% of final formulation volume) was added to a clean dry beaker. Sufficient volume of a 10 mg/mL sodium metabisulfite solution and an 80 mg/mL sodium chloride solution were added and mixed well. Sufficient volumes of 10% solutions of each trisodium citrate and hypromellose were added separately and mixed between additions. Separately, a solution of 10% diethelyene glycol monoethyl ether and 2% chlorobutanol was made in water. The diethylene glycol monoethyl ether/chlorobutanol solution was then added to the main mixing vessel and then mixed well. Epinephrine was added to the main mixing vessel as a poorly soluble powder. 1.5M HCl was added slowly until nearly all epinephrine was dissolved. 0.3M HCl was slowly added until a pH of 4.7+/−0.3 was achieved. Water was added to bring the mixture to final volume.

Example 5: Preparation of Epinephrine Formulation 4

TABLE 7

Epinephrine Formulation 4

| Component | Compendia | Composition (mg/mL) | Amount per spray (mg/spray) |
|---|---|---|---|
| (−)-Epinephrine | USP | 50.0 or 20.0 | 5.0 or 2.0 |
| Sodium metabisulfite | EP, BP or NF | 0.5 | 0.05 |
| HCl* | EP, BP or USP/NF | qs to pH 4.7 +/− 0.3 | AR |
| NaCl** | USP | 4.0 | 0.4 |
| Diethylene glycol monoethyl ether | NF | 10.0 | 1.0 |
| Chlorobutanol hemihydrate | NF | 2.1 | 0.21 |
| Citric acid monohydrate | NF | 4.2 | 0.42 |
| Hypromellose | USP | 1.0 | 0.1 |
| Purified Water | USP | AR | AR |

*adjust pH to 4.7 ± 0.3
**target 300 mOsm

Water for Injection (~20% of final formulation volume) was added to a clean dry beaker. Sufficient volume of a 10 mg/mL sodium metabisulfite solution and an 80 mg/mL sodium chloride solution were added and mixed well. Sufficient volumes of 10% solutions of each citrate acid monohydrate and hypromellose were added separately and mixed between additions. Separately, a solution of 10% diethelyene glycol monoethyl ether and 2.1% chlorobutanol hemihydrate was made in water. The diethylene glycol monoethyl ether/chlorobutanol hemihydrate solution was then added to the main mixing vessel and then mixed well. Epinephrine was added to the main mixing vessel as a poorly soluble powder. 1.5M HCl was added slowly until nearly all epinephrine was dissolved. 0.3M HCl was slowly added until a pH of 4.7+/−0.3 was achieved. Water was added to bring the mixture to final volume.

Example 6: In Vivo Study

Conscious animals that did not receive either a sedative or an anesthetic drug were used in the study. Prior to dosing, three electrode leads were placed on the animal for the continuous monitoring of the heart rate and a standard electrocardiogram by the use of telemetry in which the signal from the electrode leads were transmitted to the receiving unit by the use of Bluetooth. The cardiovascular parameters were continuously recorded throughout the entire experiment. In addition, three blood samples were obtained from the veins in the front legs between 60 and 1-minute pre-dosing for the measurement of baseline plasma epinephrine levels. A specific dose of epinephrine (Epinephrine Formulation 2) was administered into the right nostril in each of six animals. The doses of epinephrine employed in these studies ranged from 2 to 20 milligrams (mgs). The volume delivered was 100 microliters (uls) delivered in a 200 ul capacity cannula attached to a 100 ul calibrated pipette. There was no dead space in the cannula and the entire amount was delivered at a depth of approximately ¾ inch into the nostril. Following the intranasal administration of epinephrine blood samples were obtained at 1, 5 10, 15, 20, 30, 60 & 90 minutes post-dosing. The blood samples were immediately kept on ice and the tubes were centrifuged to separate the plasma from the heavier elements such as the red blood cells. Sodium metabisulfite was added to the plasma samples to prevent oxidation of epinephrine. The samples were stored at −70 degrees until they were analyzed by the use of an HPLC.

The average of the three pre-drug epinephrine samples was considered as the baseline level. This was subtracted from the epinephrine levels obtained at the specific time points ranging from 1-90 minutes post-dose. The resultant epinephrine concentrations expressed as nanograms/milliliter were considered to represent the absorption of the intranasal administration over time.

In a separate experiment, six animals received an intramuscular injection of 0.3 mg of epinephrine administered into the upper quadrant of the left leg. Plasma samples were obtained at the same time points as the intranasal experiments. The resultant plasma epinephrine time action curve was compared to those obtained by the intranasal administration.

Figure 2:
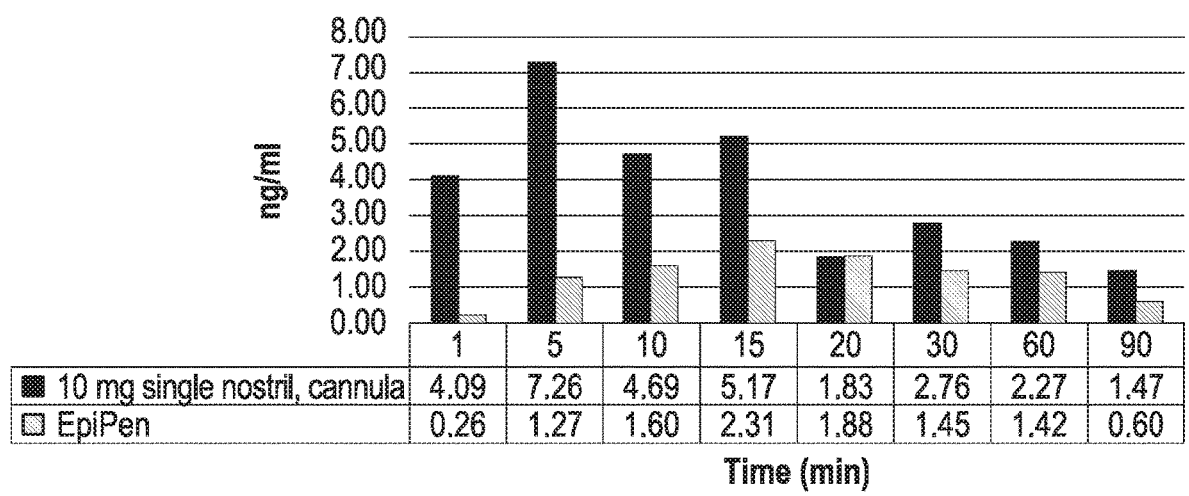
FIG. 2 depicts plasma concentrations of epinephrine in dogs dosed with 10 mg in a single nostril of a formulation described in Example 3 (Formulation 2) versus plasma concentrations of epinephrine in dogs dosed with EpiPen Adult (0.3 mg/mL).

The results of two experiments comparing the plasma levels observed following the administration of either 5 mg or 10 mg administered intranasally in comparison to the standard dose of 0.3 mg in the Adult EpiPen given by the intramuscular route are shown in FIG. 1 and FIG. 2. In all cases, the number of animals was six per group. As shown in FIG. 1, the intranasal administration of 5 mg of epinephrine produced significantly higher plasma levels than those achieved with the EpiPen at the earliest time points of 1 and 5 minutes following drug delivery. In addition, the plasma concentrations of epinephrine were maintained at virtually the same levels at the 30, 60 and 90 minute time periods. At these later time points, the levels of epinephrine resulting from the EpiPen administration had already significantly decreased from the peak observed at 15 minutes. FIG. 2 shows the comparison of the plasma epinephrine levels following the intranasal administration of 10 mg as compared to the EpiPen. As shown in FIG. 2, the plasma levels of epinephrine are much higher at the initial time periods of 1 and 5 minutes following the intranasal dosage. Indeed, the plasma levels achieved by the intranasal route of administration are higher than those observed with the EpiPen throughout the entire 90 minute post-administration.

Epinephrine is considered as the critical therapeutic treatment in acute anaphylaxis following inadvertent exposure to a triggering agent, such as nuts. This is a life threatening situation in which the rapid absorption of epinephrine following administration is essential. As can be seen in both FIG. 1 and FIG. 2, the intranasal delivery of epinephrine produces higher plasma levels during the critical first few minutes following exposure to the triggering agent than the EpiPen. Furthermore, the plasma levels of epinephrine remain elevated at higher levels throughout the entire 90 minute time-action curve at the higher dose of 10 mg intranasal epinephrine compared to the EpiPen. This data suggests that the intranasal route will provide for both a more rapid and more sustained treatment of the anaphylaxis. Finally, the plasma levels following 10 mg are greater than those of 5 mg signifying a dose-response relationship.

Example 7: A Study for Absorption of Intranasal Epinephrine Compared to Conventional Intramuscular Epinephrine The purpose of this study is to obtain pharmacokinetic data of epinephrine administered via intranasal route (IN) and compare it with intramuscular (IM) route in healthy adult volunteers Patients are reluctant to use Epipen® on emergency basis, perhaps because of improperly training, hesitancy and fear of needle. Other route of administration of epinephrine (EPI) may be more benefit such as intranasal route.

Primary Outcome Measures: Composite of Pharmacokinetics of Epinephrine

[Time Frame: predose, 5, 10, 15, 20, 30, 45, 60, 90, 120, 180 minutes post-dose]

$C_{max}$, Area Under Curve, $T_{max}$ of epinephrine compare between 0.3 mg intramuscular and 5 mg intranasal route Secondary Outcome Measures: Numbers of Participants with Adverse Events as a Measure of Safety and Tolerability

[Time Frame: 1 Year]

| | |
|---|---|
| Study Design | Allocation: Non-Randomized (12 participants) |
| | Intervention Model: Single Group Assignment |
| | Masking: None (Open Label) |
| | Primary Purpose: Treatment |
| Condition | Anaphylaxis |
| Intervention | Drug: Epinephrine |
| | 1. Intranasal epinephrine 5 mg/spray |
| | 2. Intramuscular epinephrine 0.3 mg |
| | 3. Intranasal saline spray |
| | Other Name: adrenaline |
| Study Arms | Experimental: epinephrine IN, epinephrine IM, saline IN |
| | 1. Intranasal saline |
| | 2. Intramuscular epinephrine |
| | 3. Intranasal epinephrine |
| | Intervention: Drug: Epinephrine |

Example 8: Evaluation of Efficacy and Safety in Anaphylactic Reaction Patients

This study has three primary objectives:
(1) to compare the bioavailability of aqueous formulations to that of hydro-alcoholic formulations of the company's proprietary epinephrine nasal spray at two doses (3 mg and 6 mg);
(2) to compare the bioavailability of both formulations (aqueous and hydro-alcoholic) to that of the standard intramuscular injection—specifically, EpiPen® (0.30 mg); and
(3) to evaluate the effect of an intranasal allergen challenge on the bioavailability of both intranasal epinephrine spray formulations at both doses.

Secondarily, the study will evaluate the safety and tolerability of both formulations at both doses The study will enroll a total of 60 adult patients IS-45 years of age in five 12-patient cohorts at a single clinical site. To qualify for enrollment, all study patients will be confirmed to be healthy subjects with a history of seasonal allergies; after enrollment, they will be exposed to an intranasal allergen at specific time points as part of the protocol. Subjects who use current medication that interfere with result of plasma epinephrine level (such as pseudoephedrine) will be excluded from the study.

Patients should not have had exposure to the epinephrine prior to the study entry. Patients must not have received treatment for their allergies/anaphylaxis within 2 weeks of beginning the trial. Treatments include epinephrine I.V. or I.M. injections and/or immunotherapy.

All subjects are evaluated for safety and all blood collections for pharmacokinetic analysis are collected as scheduled. All studies are performed with institutional ethics committee approval and patient consent.

Example 9: Assessment of the Impact of Pre-Existing Nasal Congestion on the Systemic Absorption of Intranasally Administered Epinephrine in Beagle Dogs This study evaluated epinephrine absorption during congestion or no congestion and the effect of epinephrine on congestion following aerosolized histamine exposure.

This study consisted of two dosing groups (Group 1—histamine and Group 2—saline) with three male and three female beagle dogs per group (n=6/group). This study was conducted over four days (Study Days 0-3) with three dogs being tested per day. On Study Day (SD) 0 and SD 2, three dogs from Group 1 were anesthetized and administered a single dose of 5% histamine (dissolved in saline) via a nebulizer over a period of 5 minutes. Epinephrine (4 mg/100 mL) was given in the same nostril, 15 minutes post-histamine administration. On SD 1 and SD 3, three dogs from Group 2 were anesthetized and administered saline via a nebulizer over a period of 5 minutes. Epinephrine (4 mg/100 mL) was given in the same nostril, 15 minutes post-saline administration. A complete outline of the study design is provided in Table 8.

TABLE 8

Study Design

| Group | Histamine | Saline (mL) | Administration of Epinephrine | Sex Males | Females |
|---|---|---|---|---|---|
| 1 | 5% | 0 | 4 mg IN into congested nostril | 3 | 3 |
| 2 | 0% | 0.4-0.7$^a$ | 4 mg IN into saline exposed nostril | 3 | 3 |

$^a$See Table 11 for individual values

Epinephrine Formulation

Vehicle for the test article (epinephrine) was composed of sterile water injection containing 5 mg/10 mL of Na metabisulfite, 40 mg/10 mL of sodium chloride, 0.7% trisodium citrate, 0.1% hypromellose, 0.05% chlorobutanol and 1% diethylene glycol monoethyl ether with a final pH of 5.0±0.5. For information regarding final concentration of each chemical in the formulated test article, see Table 9.

TABLE 9

Test Article Formulation

| Compound | Final Concentration | Final pH |
|---|---|---|
| Epinephrine | 4 mg/100 μL | 5.18 |
| Sodium Chloride | 0.4 mg/100 μL | |
| Sodium Metabisulfite | 0.05 mg/100 μL | |
| Trisodium citrate | 0.7% | |
| Chlorobutanol | 0.2% | |
| Hypromellose | 0.1% | |
| Diethylene glycol monoethyl ether | 1% | |

Intranasal Aerosol Delivery and Pressure Measurement System

Figure 3:
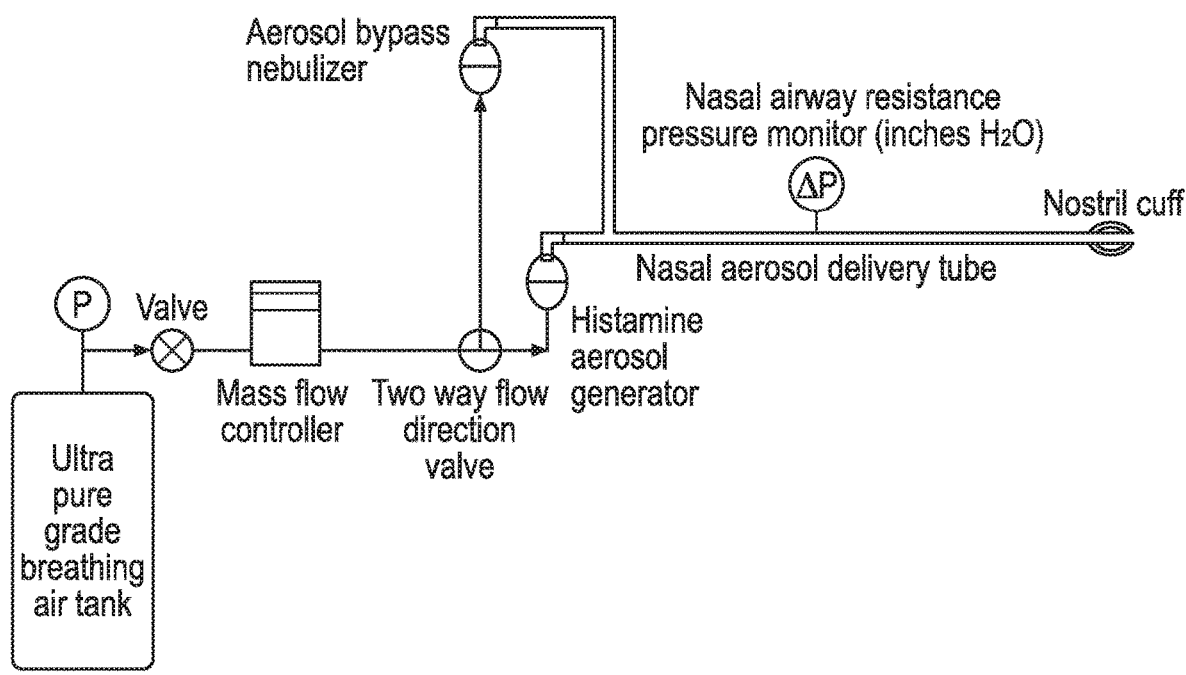
FIG. 3 shows a diagram of a congestion test system.

A test system was designed and constructed for the intranasal delivery of histamine and saline aerosols, and for measurement of nasal congestion restriction in real time. The system and methods used are similar to those conducted by Tiniakov et. al, 2003. The system delivered aerosolized histamine at concentrations sufficient to elicit congestion in the dog model via a conventional patient drug delivery nebulizer. A diagram of the congestion test system is depicted in FIG. 3.

Histamine Nasal Exposures

Preceding each test, baseline ambient pressures of the test system at the 3 L/min flow condition were recorded. The histamine generation nebulizer was filled with approximately 5 mL of 5% histamine solution or 0.9% saline solution. The nebulizer was weighed prior to and after each exposure to determine the generated histamine/saline (see Table 11). Dogs were anesthetized, and a cannula was lubricated with saline and inserted into the left nostril. The air flow was slowly increased to provide 3 L/min of fresh air into the dog's nostril and pressure measurements were taken every five minutes while the cannula was in place (see Table 10). Approximately 10 minutes post-cannula insertion, 5% histamine (5 mg/mL) or 0.9% saline was administered via aerosol for 5 minutes.

The nasal cannula was removed 5 minutes after cessation of histamine/saline administration (T=20 min) to facilitate the intranasal administration of epinephrine. Approximately 10 min following the removal of the nasal cannula, intranasal epinephrine (4 mg/100 μL) was administered (T=30 min). The nasal cannula was re-inserted into the nose 60 min post-epinephrine administration (T=90 min). The cannula remained in the nose for 40 minutes during which time nasal restriction pressures were monitored. Blood draws were taken multiple times over the course of each test for analysis of epinephrine plasma levels in the histamine and saline exposed dog groups. Table 10 shows the test matrix time course in minutes with the measurements/samples taken at each time point.

TABLE 10

Aerosol Exposure Test Matrix
Epinephrine study minute time and task test matrix

| T = −5 | 1$^{st}$ blood draw |
|---|---|
| T = 0 | Insert nasal cannula & baseline ΔP reading |
| T = 5 | 2$^{nd}$ blood draw & nasal restriction ΔP reading |
| T = 10 | Histamine or saline aerosol start & nasal restriction ΔP reading |
| T = 15 | Histamine or saline aerosol stop & nasal restriction ΔP reading |
| T = 20 | Nasal restriction ΔP reading & removal of nasal cannula |
| T = 25 | 3$^{rd}$ blood draw |
| T = 30 | Epinephrine nasal administration |
| T = 31, 35, 40, 45, 50, 55, 60, 90 | Blood draws |
| T = 91, 100, 105, 110, 115 | Reinsert nasal cannula & nasal ΔP readings |
| T = 120 | Blood draw & nasal cannula ΔP readings |
| T = 122, 124, 126, 128, 130 | Nasal cannula ΔP readings |

Bioanalytical Analysis

Heart rate data was collected and recorded every 5 minutes throughout the experiment. Plasma samples were analyzed by liquid chromatography tandem-mass spectrometry (LC-MS/MS) using a C18-PFP column. LC-MS/MS analysis was performed in positive electrospray ionization (ESI+) mode using multiple reaction monitoring (MRM) ionization.

Pharmacokinetic Analysis

Epinephrine plasma concentrations were adjusted to account for the plasma epinephrine baseline by using average concentrations of the three pre-dose samples and subtracting that value from the post-dose values for each dog. If baseline-subtraction resulted in negative values, these samples were assigned a value of zero. In addition, epinephrine concentrations were considered as outliers and removed from analysis if they exceeded two times standard deviation from the mean of baseline-subtracted post-dose epinephrine plasma concentrations of each animal over the course of blood sampling (i.e., 1-90 min post-dose).

Histamine-Induced Nasal Congestion

Histamine administration induced congestion in all animals to varying degrees. The data was plotted to show the effect of histamine- and saline-induced congestion effects following aerosol administration, and the effect of epinephrine administration in reducing nasal congestion. A plot including a pilot study with baseline histamine congestion results (leftmost bar at each time-point), histamine with epinephrine administration test results (center bar), and saline with epinephrine administration test results (rightmost bar) are shown in FIG. 4.

Figure 4:
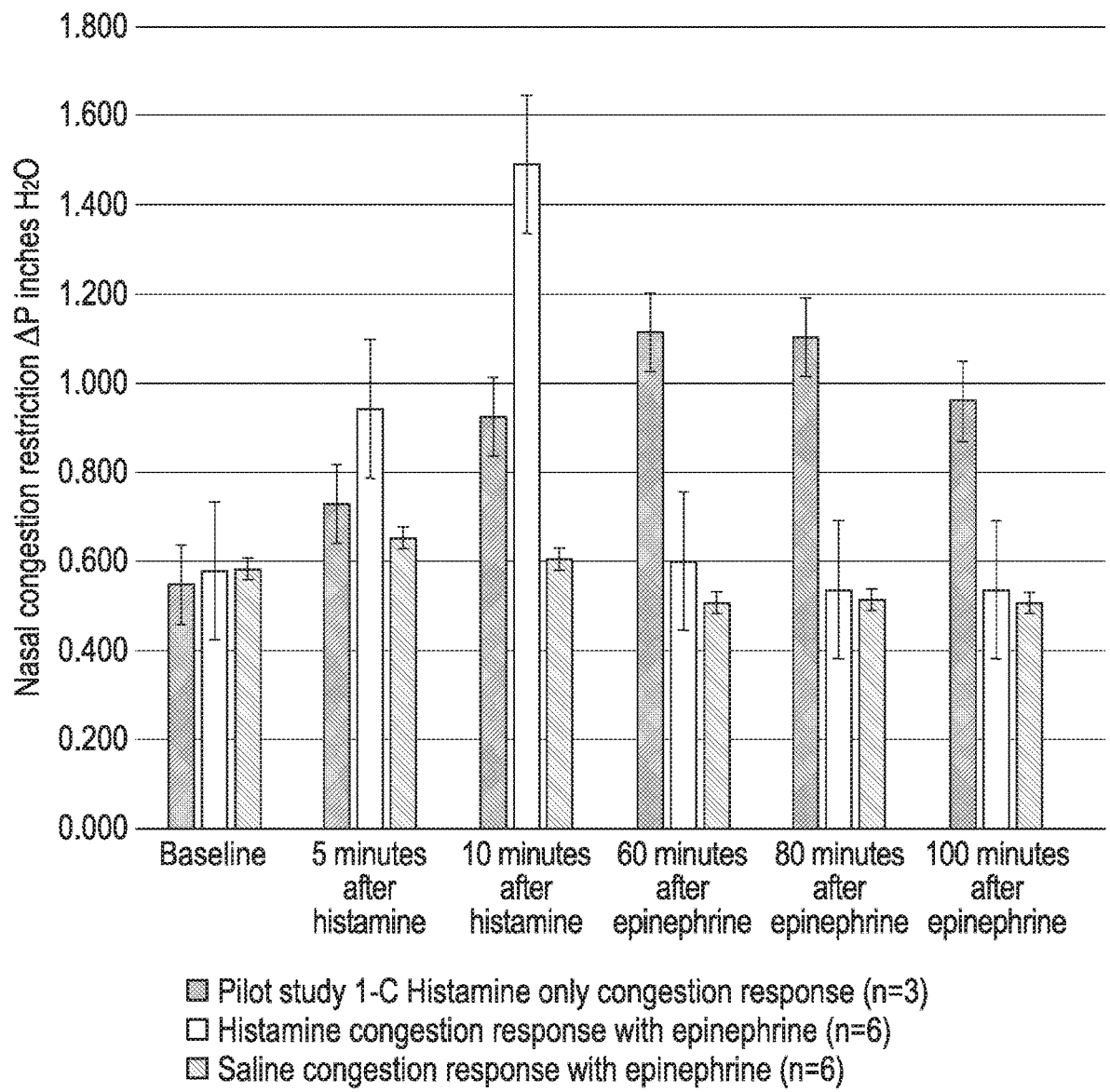
FIG. 4 shows the results of epinephrine inhibition of histamine induced nasal congestion.

The average nasal pressure restriction levels in Groups 1 and 2, as well as in the pilot study are plotted in FIG. 4. The restriction levels are shown at key time points: baseline, post-histamine/saline aerosol administration, and post-epinephrine administration. The data indicate a progressive increase in nasal congestion and flow restriction pressure at 5 and 10 minutes post-histamine exposure (Group 1). In contrast, no increase in flow restriction pressure was observed following saline aerosol administration at these same time points. Epinephrine was administered via a micropipette in the left nostril 15 minutes following the cessation of histamine or saline aerosol administration. The data indicate that epinephrine administration had a significant effect in reducing nasal congestion induced by histamine at the 60, 80, and 100 minute time points with the nasal restriction pressures reduced to baseline levels. This data shows that epinephrine has a significant anti-congestion effect. The pilot study data shows that without epinephrine administration, histamine induced congestion remains elevated at significant levels out to the 60, 80, and 100 minute time points.

Telemetry

Group 1 (5% Histamine+4 mg/100 μL Epinephrine)

Figure 5:
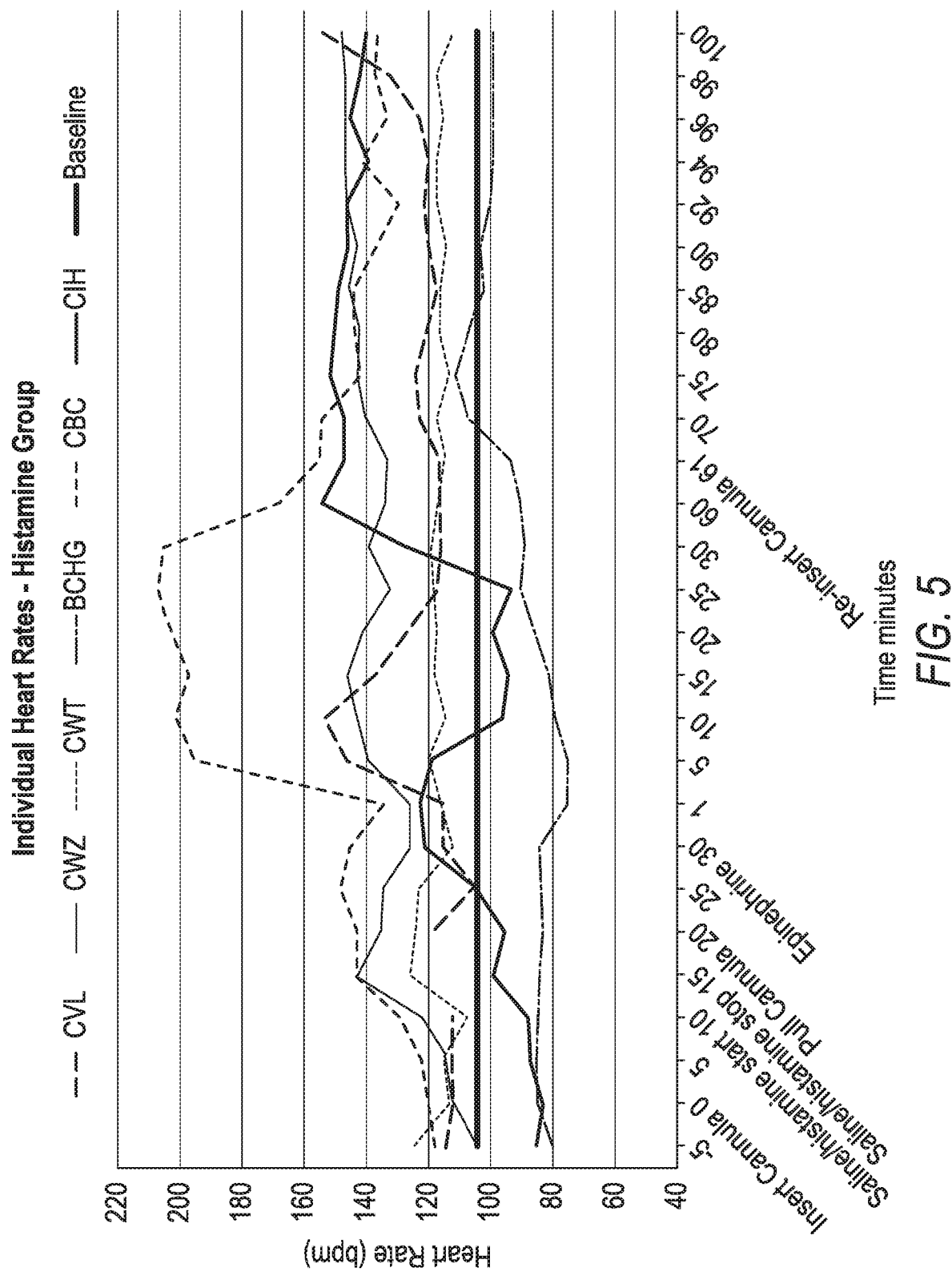
FIG. 5 shows a chart of individual heart rates for beagles exposed to histamine and treated with epinephrine.

Test article-related increases in heart rate were observed following intranasal (IN) administration of epinephrine and typically stayed above baseline following epinephrine administration. The baseline heart rate (red line, FIG. 5) was set at 104 bpm based on the mean of the pre-dose measurements. A summary of the individual and mean heart rates of Group 1 animals is provided in Table 12.

TABLE 11

Histamine-induced Congestion

| Test number | Nostril size[b] (cm) | Dog ID/sex | Cannula pressure (in H₂O) | | Aerosol exposure | Nebulizer net use (g) |
|---|---|---|---|---|---|---|
| | | | Pre-exposure[c] | Post-exposure[d] | | |
| 1 (Pilot)[a] | 7.5 | CPK/M | 0.530 | 0.714 | Histamine | NA |
| 2 (Pilot)[a] | 6.5 | CGV/F | 0.730 | 1.626 | Histamine | 0.63 |
| 3 (Pilot)[a] | 8 | CXV/M | 0.336 | 0.414 | Histamine | 0.56 |
| 1 | 8 | CVL/M | 0.692 | 1.232 | Histamine | 0.43 |
| 2 | 8 | CWZ/M | 0.399 | 0.653 | Histamine | 0.43 |
| 3 | 9 | CWT/M | 0.406 | 0.752 | Histamine | 0.43 |
| 4 | 7 | CWP/F | 0.460 | 0.433 | Saline | 0.63 |
| 5 | 7 | CFI/F | 0.522 | 0.535 | Saline | 0.44 |
| 6 | 7 | CSW/F | 0.580 | 0.701 | Saline | 0.48 |
| 7 | 8 | BCHG/F | 0.420 | 0.531 | Histamine | 0.44 |
| 8 | 7 | CBC/F | 0.735 | 3.411 | Histamine | 0.49 |
| 9 | 7.5 | CIH/F | 0.606 | 2.372 | Histamine | 0.46 |
| 10 | 8 | CXU/M | 0.530 | 0.688 | Saline | 0.47 |
| 11 | 7.5 | CUU/M | 0.543 | 0.636 | Saline | 0.52 |
| 12 | 7.5 | CYA/M | 0.657 | 0.636 | Saline | 0.57 |

[a]Intranasal epinephrine not administered.
[b]nostril measurement taken as average of vertical and horizontal nostril diameters.
[c]pre-exposure nasal pressure taken 5 minutes after cannula insertion into left nostril
[d]nasal pressure taken at 5 minutes post aerosol exposure end

TABLE 12

Individual and Mean Heart Rates of Dogs in Group 1 - 5% Histamine + 4 mg/100 μL Epinephrine Histamine (Group 1) individual and mean heart rates (bpm)

| Event/Time(min) | CVL | CWZ | CWT | BCHG | CBC | CIH | Mean | Mean STDEV |
|---|---|---|---|---|---|---|---|---|
| BD/-5 | 114 | 105 | 124 | 80 | 118 | 85 | 104 | 18.1 |
| Insert Cannula/0 | 112 | 111 | 113 | 85 | 120 | 83 | 104 | 15.8 |
| ΔP, BD/5 | 112 | 113 | 115 | 85 | 122 | 87 | 106 | 15.6 |
| ΔP, saline start/10 | 112 | 122 | 108 | 84 | 129 | 88 | 107 | 18.0 |
| ΔP, saline stop/15 | NA | 143 | 126 | 84 | 143 | 99 | 119 | 26.6 |

TABLE 12-continued

Individual and Mean Heart Rates of Dogs in Group 1 - 5% Histamine + 4 mg/100 μL Epinephrine
Histamine (Group 1) individual and mean heart rates (bpm)

| Event/Time(min) | CVL | CWZ | CWT | BCHG | CBC | CIH | Mean | Mean STDEV |
|---|---|---|---|---|---|---|---|---|
| ΔP, Pull Cannula/20 | 119 | 135 | 124 | 83 | 143 | 95 | 117 | 23.2 |
| BD/25 | 105 | 134 | 123 | 84 | 148 | 104 | 116 | 23.2 |
| Epinephrine 30 | 115 | 126 | 112 | 84 | 145 | 121 | 117 | 20.0 |
| BD/1 | 115 | 126 | 116 | 75 | 134 | 123 | 115 | 20.7 |
| BD/5 | 146 | 139 | 120 | 75 | 195 | 119 | 132 | 39.4 |
| BD/10 | 153 | 143 | 114 | 79 | 201 | 96 | 131 | 44.1 |
| BD/15 | 137 | 146 | 118 | 81 | 197 | 94 | 129 | 41.5 |
| BD/20 | 127 | 141 | 117 | 86 | 203 | 99 | 129 | 41.3 |
| BD/25 | 117 | 132 | 119 | 90 | 207 | 93 | 126 | 42.7 |
| BD/30 | 116 | 139 | 119 | 89 | 205 | 127 | 133 | 39.2 |
| BD/60 | 116 | 134 | 117 | 90 | 168 | 154 | 130 | 28.3 |
| Re-insert Cannula 61 | 116 | 133 | 114 | 93 | 155 | 147 | 126 | 23.1 |
| ΔP, 70 | 123 | 140 | 117 | 107 | 154 | 147 | 131 | 18.4 |
| ΔP, 75 | 124 | 143 | 113 | 111 | 142 | 151 | 131 | 17.0 |
| ΔP, 80 | 121 | 142 | 116 | 107 | 144 | 150 | 130 | 17.6 |
| ΔP, 85 | 117 | 146 | 116 | 102 | 144 | 149 | 129 | 19.8 |
| ΔP, BD, 90 | 120 | 143 | 114 | 103 | 137 | 146 | 127 | 17.4 |
| ΔP, 92 | 121 | 146 | 117 | 100 | 129 | 146 | 127 | 17.8 |
| ΔP, 94 | 120 | 147 | 117 | 99 | 141 | 139 | 127 | 18.3 |
| ΔP, 96 | 123 | 147 | 115 | 99 | 133 | 145 | 127 | 18.5 |
| ΔP, 98 | 132 | 147 | 117 | 99 | 137 | 142 | 129 | 17.9 |
| ΔP, 100 | 153 | 148 | 112 | 99 | 136 | 140 | 131 | 21.3 |

Group 2 (Saline+4 mg/100 μL Epinephrine)

Figure 6:
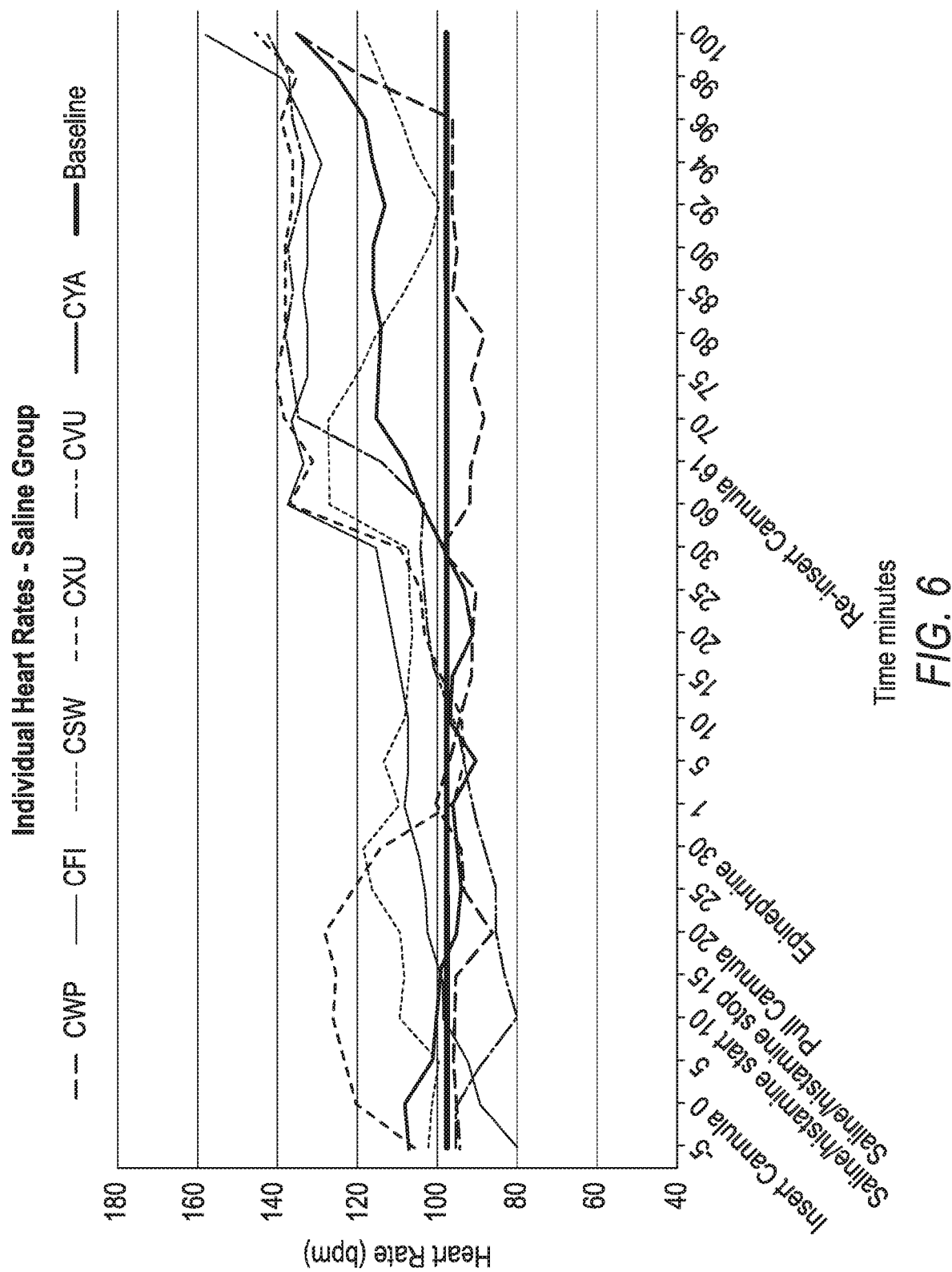
FIG. 6 shows a chart of individual heart rates for beagles exposed to saline (control) and treated with epinephrine.
Figure 7:
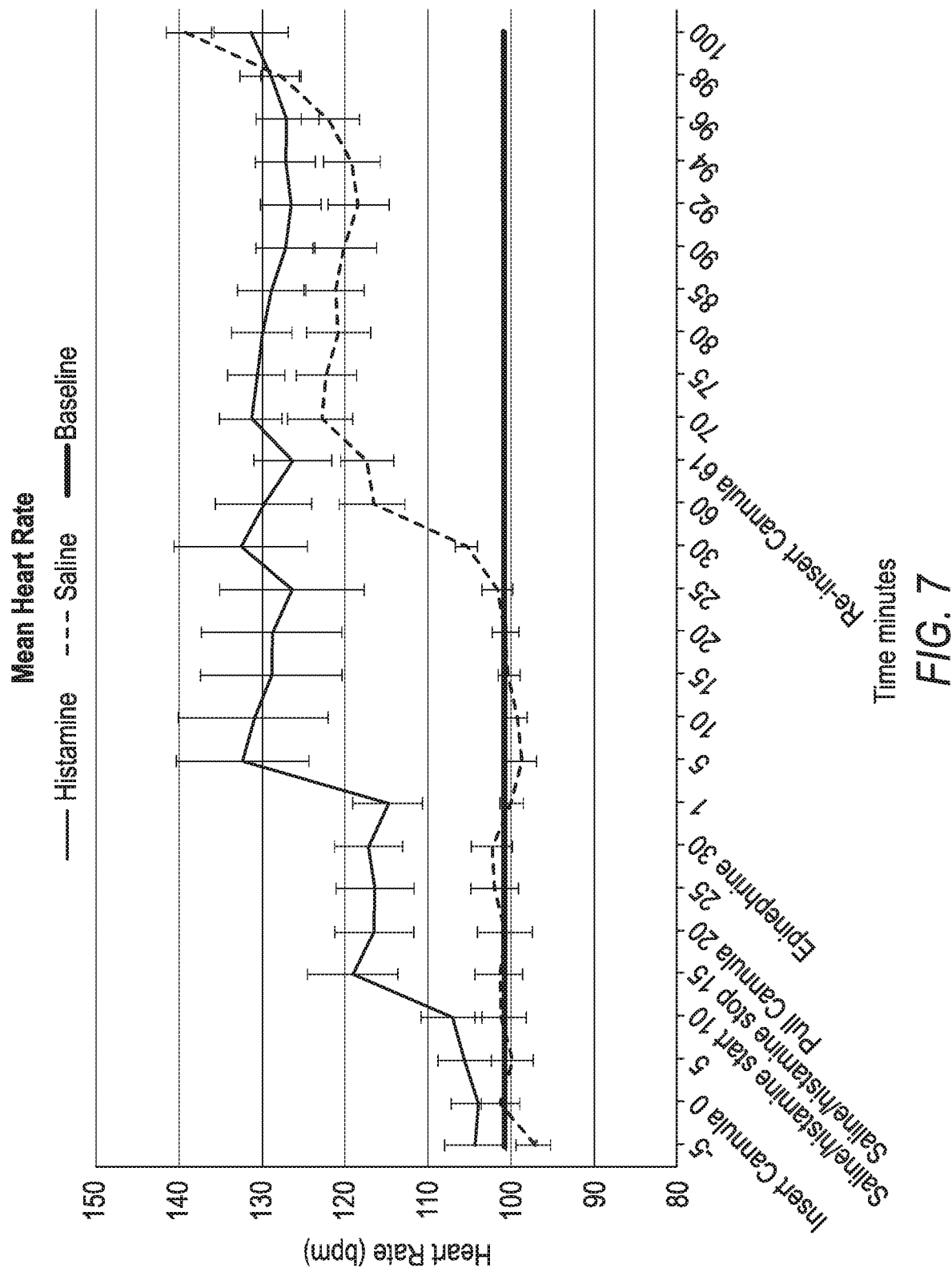
FIG. 7 shows a chart of mean heart rates comparing exposure to histamine and saline.

Test-article related increases in HR were noted in Group 2 (FIG. 6), but the pattern was significantly different from Group 1. The baseline heart rate (red line, FIG. 6) was set at 97 bpm based on the mean of the pre-dose measurements. While the initial changes in HR (pertaining to stabilizing the anesthetic plane) were present in Group 2, an evident increase in HR was not observed until 30-60 minutes post-epinephrine administration. This mirrors the rise in epinephrine blood plasma levels in Group 1, but with a delayed effect in Group 2 at the 30-60 minute mark (this is discussed further, below). Once the HR increased in Group 2 animals, it typically remained elevated until the end of the experiment. A summary of the individual and mean heart rates of Group 2 animals is provided in Table 13.

TABLE 13

Individual and Mean Heart Rate of Dogs in Group 2 - Saline + 4 mg/100 μL Epinephrine
Saline (Group 2) individual and mean heart rate (bpm)

| Event/Time(min) | CWP | CFI | CSW | CXU | CVU | CYA | Mean | Mean STDEV |
|---|---|---|---|---|---|---|---|---|
| BD/−5 | 94 | 80 | 102 | 106 | 95 | 107 | 97 | 10.1 |
| Insert Cannula/0 | 95 | 89 | 101 | 120 | 95 | 108 | 101 | 11.2 |
| ΔP, BD/5 | 96 | 92 | 99 | 123 | 88 | 101 | 100 | 12.3 |
| ΔP, saline start/10 | 95 | 98 | 109 | 126 | 80 | 100 | 101 | 15.3 |
| ΔP, saline stop/15 | 95 | 99 | 108 | 125 | 83 | 99 | 102 | 14.1 |
| ΔP, Pull Cannula/20 | 86 | 102 | 109 | 128 | 85 | 95 | 101 | 16.2 |
| BD/25 | 93 | 103 | 116 | 121 | 85 | 94 | 102 | 14.1 |
| Epinephrine 30 | 94 | 105 | 118 | 114 | 88 | 95 | 102 | 12.0 |
| BD/1 | 100 | 108 | 109 | 96 | 91 | 96 | 100 | 7.2 |
| BD/5 | 97 | 107 | 113 | 93 | 93 | 90 | 99 | 9.1 |
| BD/10 | 94 | 107 | 108 | 94 | 96 | 97 | 99 | 6.4 |
| BD/15 | 91 | 109 | 107 | 99 | 100 | 96 | 100 | 6.7 |
| BD/20 | 91 | 111 | 106 | 103 | 102 | 91 | 101 | 8.1 |
| BD/25 | 90 | 113 | 107 | 104 | 103 | 93 | 102 | 8.7 |
| BD/30 | 99 | 115 | 107 | 109 | 104 | 98 | 105 | 6.4 |
| BD/60 | 92 | 137 | 127 | 137 | 103 | 104 | 117 | 19.4 |
| Re-insert Cannula 61 | 91 | 133 | 127 | 131 | 114 | 108 | 117 | 16.2 |
| ΔP, 70 | 88 | 136 | 127 | 138 | 134 | 115 | 123 | 19.1 |
| ΔP, 75 | 91 | 132 | 120 | 140 | 136 | 115 | 122 | 18.1 |
| ΔP, 80 | 88 | 132 | 115 | 138 | 138 | 114 | 121 | 19.4 |
| ΔP, 85 | 96 | 133 | 108 | 138 | 136 | 116 | 121 | 17.2 |
| ΔP, BD, 90 | 95 | 132 | 102 | 138 | 137 | 116 | 120 | 18.6 |
| ΔP, 92 | 96 | 132 | 99 | 136 | 134 | 113 | 118 | 18.1 |
| ΔP, 94 | 96 | 129 | 105 | 136 | 133 | 116 | 119 | 16.2 |
| ΔP, 96 | 96 | 133 | 109 | 139 | 136 | 118 | 122 | 17.1 |
| ΔP, 98 | 118 | 139 | 113 | 135 | 137 | 125 | 128 | 10.8 |
| ΔP, 100 | 135 | 158 | 118 | 145 | 142 | 135 | 139 | 13.3 |

Pharmacokinetic Results

Figure 8:
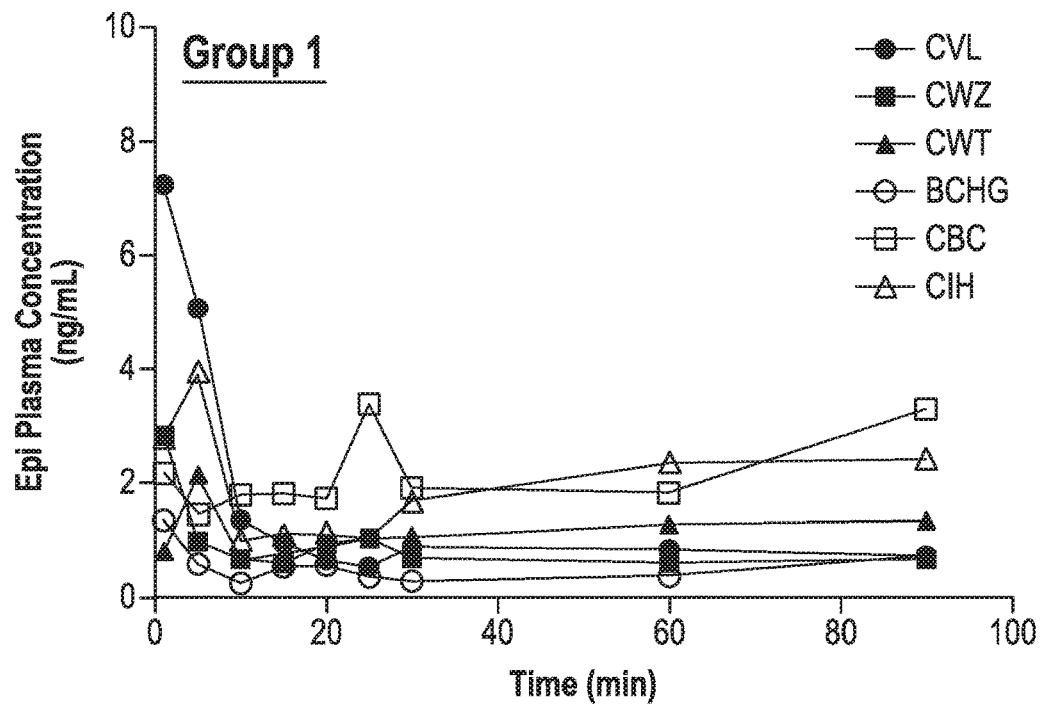
FIG. 8 shows plasma epinephrine concentration profiles over time for individual animals within group 1.
Figure 9:
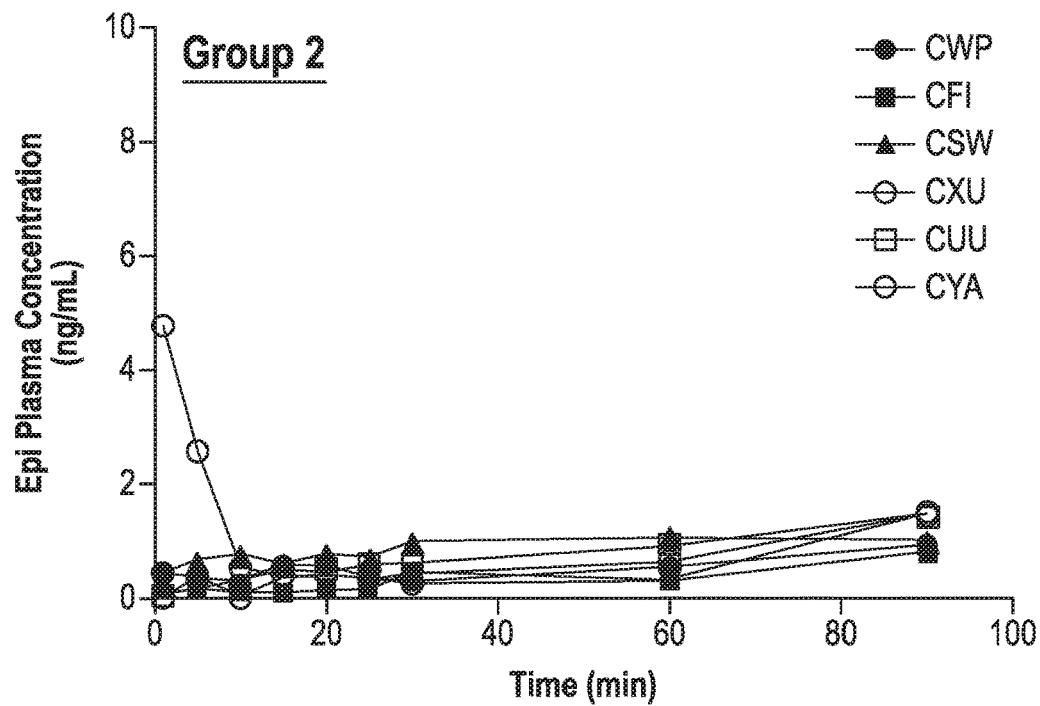
FIG. 9 shows plasma epinephrine concentration profiles over time for individual animals within group 2.

Plasma samples were collected at the indicated time points and analyzed. Plasma epinephrine concentration profiles over time are plotted for individual animals within a group (FIG. 8, FIG. 9). AUC, $T_{max}$ and $C_{max}$ were calculated using post-dose baseline-subtracted epinephrine concentrations for each individual animal and the trapezoid rule (Tables 14-15).

TABLE 14

AUC and $C_{max}$ of epinephrine in dogs from Group 1

| Parameter[a] | Group 1 | | | | | | | |
|---|---|---|---|---|---|---|---|---|
| | BCHG | CBC | CIH | CVL | CWT | CMZ | Average | SD |
| Dose, mg | 4 | 4 | 4 | 4 | 4 | 4 | — | — |
| $T_{max}$, min | 1 | 25 | 5 | 1 | 5 | 1 | 6 | 9 |
| $C_{max}$, mg/mL | 1.4 | 3.4 | 4.0 | 7.2 | 2.2 | 2.9 | 3.5 | 2.1 |
| $AUC_{1-90\ min}$, ng/mL · min | 42 | 194 | 182 | 109 | 106 | 68 | 117 | 61 |

[a]Abbreviations: $C_{max}$, maximum plasma concentration before baseline subtraction; $T_{max}$, time to reach $C_{max}$; $AUC_{1-90\ min}$, area under the plasma concentration time curve from time 1 min to 90 min after baseline subtraction

TABLE 15

AUC and $C_{max}$ of epinephrine in dogs from Group 2

| Parameter[a] | Group 2 | | | | | | | |
|---|---|---|---|---|---|---|---|---|
| | CFI | CSW | CUU | CWP | CXU | CYA | Average | SD |
| Dose, mg | 4 | 4 | 4 | 4 | 4 | 4 | — | — |
| $T_{max}$, min | 90 | 60 | 90 | 90 | 1 | 90 | 70 | 36 |
| $C_{max}$, mg/mL | 0.8 | 1.1 | 1.4 | 0.9 | 4.8 | 1.4 | 1.7 | 1.5 |
| $AUC_{1-90\ min}$, ng/mL · min | 33 | 83 | 71 | 478 | 67 | 56 | 59 | 18 |

[a]Abbreviations: Cmax, maximum plasma concentration before baseline subtraction; $T_{max}$, time to reach $C_{max}$; $AUC_{1-90\ min}$, area under the plasma concentration time curve from time 1 min to 90 min after baseline subtraction In Tables 14 and 15, plasma concentration vs. time data were first analyzed for the individual animal and then PK measurements (AUC, $C_{max}$, $T_{max}$) from the individual animals were averaged within a group.

Figure 10:
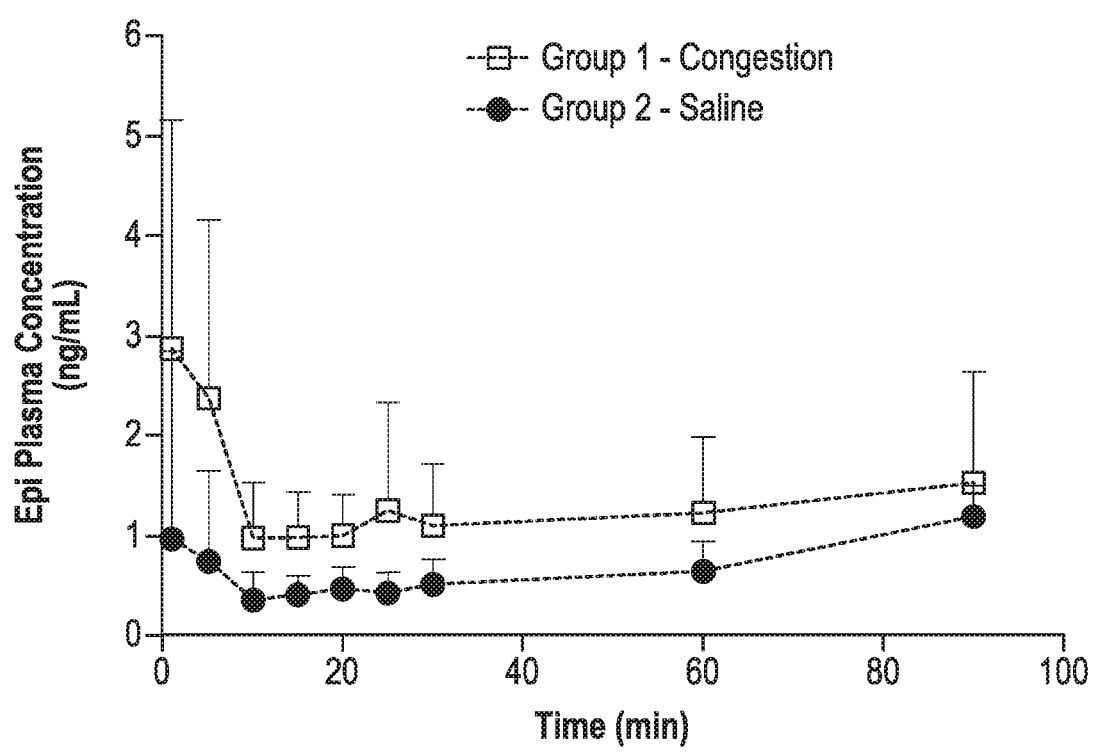
FIG. 10 shows group average epinephrine concentration profiles over time for the two study groups.

Furthermore, group average epinephrine concentration profiles over time are plotted for the two study groups (FIG. 10). AUC, $T_{max}$ and $C_{max}$ calculated using the trapezoid rule are shown in Table 16.

TABLE 16

AUC, $T_{max}$ and $C_{max}$ of epinephrine after administration in dogs (average plasma concentrations from all dogs in the same group)

| | Study - congestion vs saline | |
|---|---|---|
| Parameter[a, b], unit | Group 1 - Congestion (4 mg × 1 nostril) | Group 2 - Saline (4 mg × 1 nostril) |
| Dose, mg | 4 | 4 |
| $T_{max}$, min | 1 | 90 |
| $C_{max}$, ng/mL | 2.9 | 1.2 |
| $AUC_{1-last}$, ng/mL · min | 117 | 60 |
| $t_{1/2}$ | NC | NC |

[a]Abbreviations: $C_{max}$, maximum plasma concentration before baseline subtraction; $T_{max}$, time to reach $C_{max}$; $AUC_{1-90\ min}$, area under the plasma concentration time curve from time 1 min to 90 min after baseline subtraction; NC, not calculated due to pre-dose concentration higher than post-dose concentration of failed to establish elimination phase.
[b]Values were obtained from NCA by WinNonlin (Build 8.1.0.3530)

In Table 16, plasma concentration vs. time data were first averaged for all animals within the same group and then PK measurements were obtained from the averaged data. As compared to values reported in Tables 14 and 15 where individual $T_{max}$ varied from one animal to another, this resulted in different $T_{max}$ and $C_{max}$ values between the two types of analyses (Tables 14/15 vs Table 16). AUC, on the other hand, remained essentially same for both of these analyses.

In the congestion model (Table 16), the $T_{max}$ was 1 min vs 90 min for the congested dogs vs the saline dogs, respectively. The $C_{max}$ was 2.9 ng/mL vs 1.2 ng/mL for the congested dogs vs the saline dogs, respectively. Finally, the AUC was 117 ng/mL-min vs 60 ng/mL-min for the congested dogs vs the saline dogs, respectively. For all of these aforementioned values, an IN dose of epinephrine at 4 mg/100 □L was administered to the same nostril where either histamine (congested dogs) or saline (control) was previously administered. Clearly, the epinephrine when delivered intranasally to the congested dogs was absorbed faster, leading to higher plasma levels as compared to dogs with no congestion that received saline alone. This was an unexpected and surprising result since the assumption would be that dogs with congestion would have constricted nasal passageways that reduce absorption efficiency. Upon further investigation, it is noted that Bleske et al. demonstrated in dogs that epinephrine plasma levels, following intranasal administration, were enhanced by the concomitant intranasal administration of the alpha blocker, phentolamine. The explanation was that phentolamine prevented the epinephrine induced vasoconstriction thus increasing the mucosal absorption of epinephrine. Nasal congestion associated with allergy is due to the release of histamine from mast cells which causes a profound vasodilation in the nasal tissue. Therefore, it is likely that the histamine induced vasodilation offset the vasoconstrictive properties of the intranasal epinephrine resulting in enhanced absorption. Finally, there was a difference in heart rate levels in the congested, epinephrine administered dogs as compared to the saline epinephrine administration where the heart rates were clearly elevated, due to increased plasma epinephrine levels in the congested dogs versus the saline administered dogs.

Figure 11A:
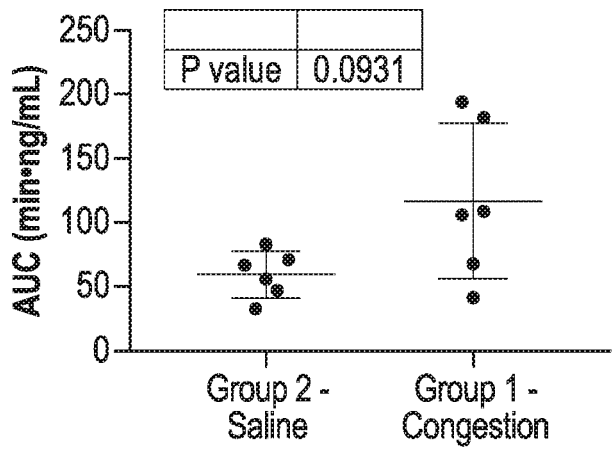
FIG. 11 shows Student's t-test comparing: A) AUC, B) $C_{max}$, and C) $T_{max}$ between two study groups.
Figure 11B:
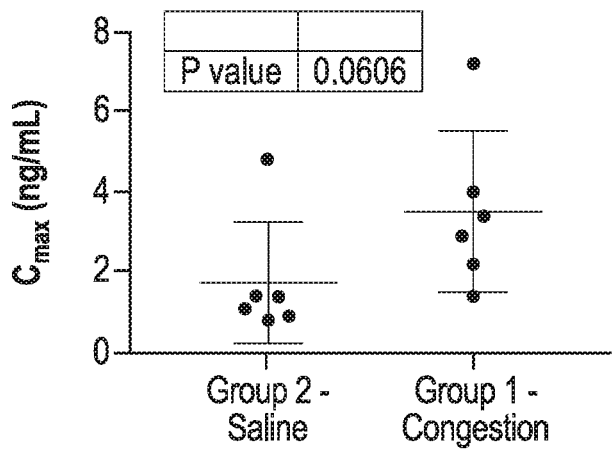
Figure 11C:
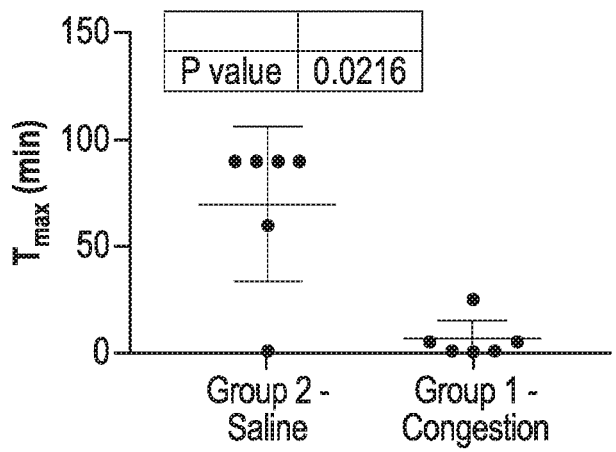

To determine if nasal congestion affects the systemic absorption of IN administered epinephrine, Student's t-test was first used to compare AUC, $T_{max}$ and $C_{max}$ between two study groups (FIG. 11). The Group 1 and Group 2 AUC and $C_{max}$ were not significantly different whereas the $T_{max}$ of the Group 1 animals was significantly lower than that of the Group 2 animals.

Furthermore, bioequivalence was assessed using Ln-transformed AUC, $C_{max}$ and $T_{max}$ of individual animals (Table 17). Bioequivalence is defined as when the 90% confidence intervals [CI] of the geometric mean ratio between the test (Group 1—Congestion) and reference (Group 2—Saline) fall within 80-125%. Results show that intranasal (IN) administered epinephrine does not demonstrate bioequivalence between Group 1 and Group 2 animals, as ratios deviate from 100% and CI (90%) values fall well outside of the 80-125% range. In addition, bioequivalence analysis indicates that the study is under-powered (Power<80%), likely due to large inter-individual variability and small number of animals in each group.

TABLE 17

Bioequivalence analysis of epinephrine after a single IN dose to saline (reference) and congestion (test) dogs

| Parameter[a, b], unit | NCA PK | | |
|---|---|---|---|
| | Ratio of geometric mean (% of reference) | 90% CI | Power of Study at 20% (80/20 Rule)[b] |
| Dose, mg per animal | | 4 | |
| $T_{max}$, min | 7.4 | 1.4-3.9 | 0.107 |
| $C_{max}$, ng/mL | 217 | 115-408 | 0.151 |
| $AUC_{1-last}$, ng/mL · min | 180 | 109-296 | 0.182 |

[a]Abbreviations: $C_{max}$, maximum plasma concentration before baseline subtraction; $T_{max}$, time to reach $C_{max}$; $AUC_{0-\infty}$, area under the plasma concentration time curve from time 0 min to infinite time; CI, confidence interval.
[b]the power to detect a difference in least square means equal to 20% of the reference least squares mean and the desired result is that the power is greater than 0.8 or 80%.

Blood samples were collected up to 35 min prior to and up to 90 min post drug administration to determine epinephrine plasma concentrations (see Table 18). The results show that a spike in epinephrine plasma concentration was often achieved within 1 or 5 minutes of intranasal administration.

TABLE 18

Epinephrine plasma concentration.

| Animal ID | Sex | Dose Amount (mg) | Collection Time (min) | Determined Matrix Conc. (ng/mL) |
|---|---|---|---|---|
| CVL | M | 4 | Pre 35 | 0.148 |
| CVL | M | 4 | Pre 25 | 0.192 |
| CVL | M | 4 | Pre 5 | 0.347 |
| CVL | M | 4 | 1 | 7.469 |
| CVL | M | 4 | 5 | 5.314 |
| CVL | M | 4 | 10 | 1.595 |
| CVL | M | 4 | 15 | 1.192 |
| CVL | M | 4 | 20 | 0.883 |
| CVL | M | 4 | 25 | 0.786 |
| CVL | M | 4 | 30 | 1.139 |
| CVL | M | 4 | 60 | 1.076 |
| CVL | M | 4 | 90 | 0.96 |
| CWZ | M | 4 | Pre 35 | ND |
| CWZ | M | 4 | Pre 25 | 0.139 |
| CWZ | M | 4 | Pre 5 | 0.161 |
| CWZ | M | 4 | 1 | 3.002 |

TABLE 18-continued

Epinephrine plasma concentration.

| Animal ID | Sex | Dose Amount (mg) | Collection Time (min) | Determined Matrix Conc. (ng/mL) |
|---|---|---|---|---|
| CWZ | M | 4 | 5 | 1.137 |
| CWZ | M | 4 | 10 | 0.843 |
| CWZ | M | 4 | 15 | 0.773 |
| CWZ | M | 4 | 20 | 1.092 |
| CWZ | M | 4 | 25 | 1.213 |
| CWZ | M | 4 | 30 | 0.852 |
| CWZ | M | 4 | 60 | 0.74 |
| CWZ | M | 4 | 90 | 0.83 |
| CWT | M | 4 | Pre 35 | ND |
| CWT | M | 4 | Pre 25 | 0.125 |
| CWT | M | 4 | Pre 5 | 0.493 |
| CWT | M | 4 | 1 | 1.153 |
| CWT | M | 4 | 5 | 2.465 |
| CWT | M | 4 | 10 | 0.976 |
| CWT | M | 4 | 15 | 1.091 |
| CWT | M | 4 | 20 | 1.211 |
| CWT | M | 4 | 25 | 1.378 |
| CWT | M | 4 | 30 | 1.387 |
| CWT | M | 4 | 60 | 1.605 |
| CWT | M | 4 | 90 | 1.663 |
| BCHG | F | 4 | Pre 35 | 0.147 |
| BCHG | F | 4 | Pre 25 | 0.147 |
| BCHG | F | 4 | Pre 5 | 0.144 |
| BCHG | F | 4 | 1 | 1.507 |
| BCHG | F | 4 | 5 | 0.736 |
| BCHG | F | 4 | 10 | 0.405 |
| BCHG | F | 4 | 15 | 0.697 |
| BCHG | F | 4 | 20 | 0.718 |
| BCHG | F | 4 | 25 | 0.503 |
| BCHG | F | 4 | 30 | 0.445 |
| BCHG | F | 4 | 60 | 0.527 |
| BCHG | F | 4 | 90 | 0.846 |
| CBC | F | 4 | Pre 35 | ND |
| CBC | F | 4 | Pre 25 | ND |
| CBC | F | 4 | Pre 5 | ND |
| CBC | F | 4 | 1 | 2.171 |
| CBC | F | 4 | 5 | 1.459 |
| CBC | F | 4 | 10 | 1.81 |
| CBC | F | 4 | 15 | 1.833 |
| CBC | F | 4 | 20 | 1.731 |
| CBC | F | 4 | 25 | 3.385 |
| CBC | F | 4 | 30 | 1.926 |
| CBC | F | 4 | 60 | 1.839 |
| CBC | F | 4 | 90 | 3.313 |
| CIH | F | 4 | Pre 35 | ND |
| CIH | F | 4 | Pre 25 | ND |
| CIH | F | 4 | Pre 5 | ND |
| CIH | F | 4 | 1 | 2.801 |
| CIH | F | 4 | 5 | 3.969 |
| CIH | F | 4 | 10 | 1.014 |
| CIH | F | 4 | 15 | 1.099 |
| CIH | F | 4 | 20 | 1.144 |
| CIH | F | 4 | 25 | 1.04 |
| CIH | F | 4 | 30 | 1.694 |
| CIH | F | 4 | 60 | 2.356 |
| CIH | F | 4 | 90 | 2.439 |
| CWP | F | 4 | Pre 35 | ND |
| CWP | F | 4 | Pre 25 | ND |
| CWP | F | 4 | Pre 5 | 0.125 |
| CWP | F | 4 | 1 | 0.575 |
| CWP | F | 4 | 5 | 0.512 |
| CWP | F | 4 | 10 | 0.385 |
| CWP | F | 4 | 15 | 0.686 |
| CWP | F | 4 | 20 | 0.721 |
| CWP | F | 4 | 25 | 0.463 |
| CWP | F | 4 | 30 | 0.415 |
| CWP | F | 4 | 60 | 0.682 |
| CWP | F | 4 | 90 | 1.067 |
| CFI | F | 4 | Pre 35 | 0.263 |
| CFI | F | 4 | Pre 25 | 0.418 |
| CFI | F | 4 | Pre 5 | 0.327 |
| CFI | F | 4 | 1 | 0.407 |
| CFI | F | 4 | 5 | 0.545 |
| CFI | F | 4 | 10 | 0.427 |

TABLE 18-continued

Epinephrine plasma concentration.

| Animal ID | Sex | Dose Amount (mg) | Collection Time (min) | Determined Matrix Conc. (ng/mL) |
|---|---|---|---|---|
| CFI | F | 4 | 15 | 0.44 |
| CFI | F | 4 | 20 | 0.453 |
| CFI | F | 4 | 25 | 0.5 |
| CFI | F | 4 | 30 | 0.799 |
| CFI | F | 4 | 60 | 0.642 |
| CFI | F | 4 | 90 | 1.141 |
| CSW | F | 4 | Pre 35 | 0.147 |
| CSW | F | 4 | Pre 25 | 0.127 |
| CSW | F | 4 | Pre 5 | 0.166 |
| CSW | F | 4 | 1 | 0.577 |
| CSW | F | 4 | 5 | 0.82 |
| CSW | F | 4 | 10 | 0.927 |
| CSW | F | 4 | 15 | 0.761 |
| CSW | F | 4 | 20 | 0.922 |
| CSW | F | 4 | 25 | 0.867 |
| CSW | F | 4 | 30 | 1.133 |
| CSW | F | 4 | 60 | 1.202 |
| CSW | F | 4 | 90 | 1.166 |
| CXU | M | 4 | Pre 35 | 0.461 |
| CXU | M | 4 | Pre 25 | ND |
| CXU | M | 4 | Pre 5 | ND |
| CXU | M | 4 | 1 | 5.229 |
| CXU | M | 4 | 5 | 3.036 |
| CXU | M | 4 | 10 | 1.009 |
| CXU | M | 4 | 15 | 0.787 |
| CXU | M | 4 | 20 | 0.856 |
| CXU | M | 4 | 25 | 0.906 |
| CXU | M | 4 | 30 | 0.703 |
| CXU | M | 4 | 60 | 0.801 |
| CXU | M | 4 | 90 | 1.969 |
| CUU | M | 4 | Pre 35 | ND |
| CUU | M | 4 | Pre 25 | 0.263 |
| CUU | M | 4 | Pre 5 | 0.317 |
| CUU | M | 4 | 1 | 0.32 |
| CUU | M | 4 | 5 | 0.434 |
| CUU | M | 4 | 10 | 0.662 |
| CUU | M | 4 | 15 | 0.749 |
| CUU | M | 4 | 20 | 0.789 |
| CUU | M | 4 | 25 | 0.881 |
| CUU | M | 4 | 30 | 0.9 |
| CUU | M | 4 | 60 | 1.222 |
| CUU | M | 4 | 90 | 1.729 |
| CYA | M | 4 | Pre 35 | ND |
| CYA | M | 4 | Pre 25 | 0.234 |
| CYA | M | 4 | Pre 5 | 0.732 |
| CYA | M | 4 | 1 | 0.433 |
| CYA | M | 4 | 5 | 0.903 |
| CYA | M | 4 | 10 | 0.422 |
| CYA | M | 4 | 15 | 0.872 |
| CYA | M | 4 | 20 | 0.917 |
| CYA | M | 4 | 25 | 0.781 |
| CYA | M | 4 | 30 | 0.9 |
| CYA | M | 4 | 60 | 1.125 |
| CYA | M | 4 | 90 | 1.92 |

Example 10: Assessment of Whether Epinephrine Crosses the Blood Brain Barrier Pre- and post-IN epinephrine (4 mg/0.1 mL IN) samples of plasma and CSF were collected at just prior to pre-dose (0 min) and 15 min post-dose for the study in Example 9. Blood samples were processed to plasma; plasma and CSF samples were stabilized. Samples were assayed for epinephrine levels.

Figure 12:
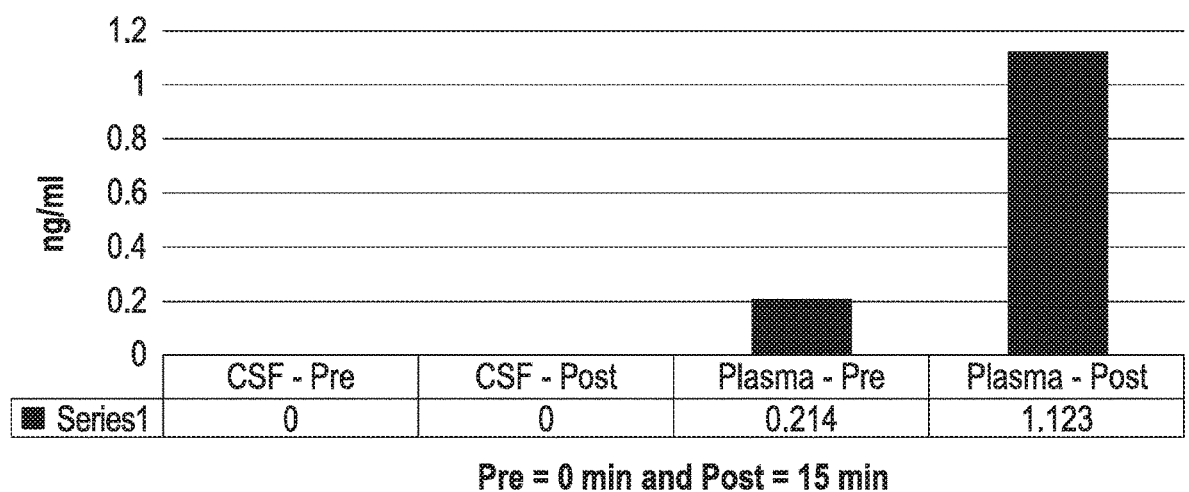
FIG. 12 shows pre- and post-dose plasma levels of epinephrine in CSF.

As shown in FIG. 12, pre- and post-dose plasma levels of epinephrine were at a pre-dose average of 0.214 ng/mL and at 15 min post-epinephrine levels were 1.123 ng/mL. For both pre- and post-dose time points, no epinephrine was detected in CSF (see Table 19).

TABLE 19

Epinephrine blood plasma concentration.

| Animal ID | Sex | Dose Amount (mg) | Collection Time and Type | Matrix Concentration (ng/mL) |
|---|---|---|---|---|
| CVX | M | 4 | Pre-CSF | ND |
| CVX | M | 4 | 15 min CSF | ND |
| CVX | M | 4 | Pre-Plasma | 0.360 |
| CVX | M | 4 | 15 min Plasma | 1.060 |
| CWD | M | 4 | Pre-CSF | ND |
| CWD | M | 4 | 15 min CSF | ND |
| CWD | M | 4 | Pre-Plasma | 0.276 |
| CWD | M | 4 | 15 min Plasma | 0.369 |
| CWP | F | 4 | Pre-CSF | ND |
| CWP | F | 4 | 15 min CSF | ND |
| CWP | F | 4 | Pre-Plasma | 0.218 |
| CWP | F | 4 | 15 min Plasma | 2.151 |
| BCHG | F | 4 | Pre-CSF | ND |
| BCHG | F | 4 | 15 min CSF | ND |
| BCHG | F | 4 | Pre-Plasma | ND |
| BCHG | F | 4 | 15 min Plasma | 0.910 |

The IN administration of epinephrine to dogs did not result in detection of epinephrine in CSF samples at 15 min post-dose administration, while plasma levels did increase at this same time point. Therefore, IN administration of epinephrine to dogs does not result in epinephrine crossing the blood brain barrier.

Example 11—A GLP Pharmacokinetic Comparison of Intranasal Application Vs Current Therapeutic Approach in Beagle Dogs In this GLP study, which was based on previous studies that optimized the pharmacokinetics (PK) of intranasal epinephrine in terms of delivery and dose selection, the down-selected dose was tested for a PK assessment as a primary endpoint in dogs with heart rate also assessed to demonstrate the effect of epinephrine on the cardiovascular system.

The epinephrine formulation was composed of sterile injection water containing 5 mg/10 mL of Na metabisulfite, 40 mg/10 mL of sodium chloride, 0.7% Trisodium citrate, 0.1% hypromellose, 0.2% chlorobutanol and 1% Diethylene glycol monoethyl ether with a final pH of 5.0±0.5. Epinephrine was included at the concentrations as shown in Table 20. For information regarding vendor, lot number, and final concentration of each chemical in the formulated test formulation, see Table 20.

TABLE 20

Chemicals Used in Test Formulation

| Compound | Vendor | Lot Number | Final Concentration |
|---|---|---|---|
| (−) Epinephrine | Spectrum | 2HD0281 | 4 mg/100 μl (Group 1) 5 mg/100 μl (Group 2) |
| Sodium Chloride | Spectrum | 1FIO675 | 0.4 mg/100 μL |
| Sodium Metabisulfite | Spectrum | 1GC1002 | 0.05 mg/100 μL |
| Trisodium citrate | Sigma | BCBV1682 | 0.7% |
| Hypromellose | Sigma | SLBR5196V | 0.1% |
| Diethylene glycol monoethyl ether | Sigma | O4508HEV | 1% |
| Chlorobutanol | Spectrum | 1FF0469 | 0.2% |
| Hydrochloric Acid | Spectrum | 2GJ0228 | NA |
| Sterile water for Injection | Spectrum | A1705131 | NA |

Two dosing concentrations (4 mg/100 μL and 5 mg/100 μL) were formulated 2 times during the course of this study.

Complete information regarding the date of formulation, batch ID associated with each formulated test article, amount of epinephrine (grams) used in each formulation, and the final pH of each formulated test article used for dose administration are included in Table 21.

TABLE 21

Test Article Formulation Batches

| Date of Formulation | Dose Concentration (Pre-dose) | Amount of Epinephrine used | Final pH | Study Day | Dose Concentration (Post-Dose) |
|---|---|---|---|---|---|
| Aug. 21, 2018 | 4.4 mg/100 μL | 0.8008 g | 5.207 | 16-17 | 4.4 mg/100 μL |
| Aug. 21, 2018 | 5.4 mg/100 μL | 1.0033 g | 5.202 | 16-17 | 5.4 mg/100 μL |
| Aug. 31, 2018 | 4.1 mg/100 μL | 0.8004 g | 4.729 | 29-30 | 4.0 mg/100 μL |
| Aug. 31, 2018 | 5.3 mg/100 μL | 1.0010 g | 4.814 | 29-30 | 5.1 mg/100 μL |

The EpiPen® Auto-Injector 0.3 mg (Mylan Specialty, L.P., USP Grade) was utilized as a control article in this study. Individual EpiPens® were procured from local pharmacies and stored at room temperature (20°-25° C.) protected from light.

A total of 48 dogs participated in this study with 16 dogs (8/sex) per treatment group. Table 22 outlines the study design.

TABLE 22

Study Design

| Group | Epinephrine (mg) Total | Administration Route | Sex Male | Female |
|---|---|---|---|---|
| 1 | 4 mg in 100 μl volume of vehicle | IN via pipette tip into the right nostril | 8 | 8 |
| 2 | 5 mg in 100 μl volume of vehicle | IN via pipette tip into the right nostril | 8 | 8 |
| 3 | 0.3 mg in 0.3 mL (EpiPen® Adult) | IM single injection to thigh muscle | 8 | 8 |

Two dogs/sex/group received a single administration of either IN epinephrine at 4 mg or 5 mg (Groups 1 and 2) or a single EpiPen® IM injection (Group 3) on Study Days 0, 1, 16, and 17. Note that individual dogs within each group were only dosed a single time during the course of this study.

Telemetry measurements were collected from all animals during the treatment phase of this study. Prior to dose administration, telemetric collection jackets were placed on animals. Data collection points occurred 60 min prior to dose administration (baseline) through the 120 minute endpoint for a total collection time of 180 min. The parameters that were evaluated included: EKG (PR, QRS, QT, and RR; a continuous collection). Heart rate values were collected prior to dose administration at 60, 12, and 2-3 minutes before epinephrine administration and at the following intervals post-epinephrine administration: 1, 5, 10, 15, 20, 25, 30, 60, 90, and 120 minutes. A six second EKG was reported at the $C_{max}$ for epinephrine for each dog to evaluate the EKG parameters listed above.

Approximately 2 mL of whole blood was collected at the following time points: prior to dosing (60, mins, 15 mins, 2-3 mins pre-dose) and at 1, 5, 10, 15, 20, 25, 30, 60, 90, and 120 mins post-dose administration (±10% of target time point).

Prior to PK data analysis, the three prior to dosing time points (60 mins, 15 mins, 2-3 mins pre-dose) epinephrine plasma values for each dog were averaged, then this average subtracted from the post-dose epinephrine plasma values reported at time points 1, 5, 10, 15, 20, 25, 30, 60, 90 and 120 mins post-dose administration for all animals on study. Should one or more of the pre-dose samples fall beneath the limit of quantification (BLQ), the mean of the remaining quantifiable values was used for baseline correction. If all three pre-dose samples fell under the limit of detection (i.e., values not determined), no baseline correction was performed on the post-dose samples. If, after baseline correction, the post-dose values are negative (i.e., >0) these values were changed to 0 for subsequent PK analysis.

Pharmacokinetic (PK) data analysis and evaluation of plasma concentration-time curves was performed. Individual epinephrine plasma concentration time profiles from epinephrine treated animals were analyzed using model-independent methods. Pharmacokinetic parameters were obtained for each animal following a single intranasal administration of epinephrine to animals in Groups 1 and 2 or following a single IM injection of epinephrine to animals in Group 3. Concentrations less than the lower limit of quantitation (LLOQ<0.4 ng/mL) were set to 0 for pharmacokinetic analysis.

Figure 13:
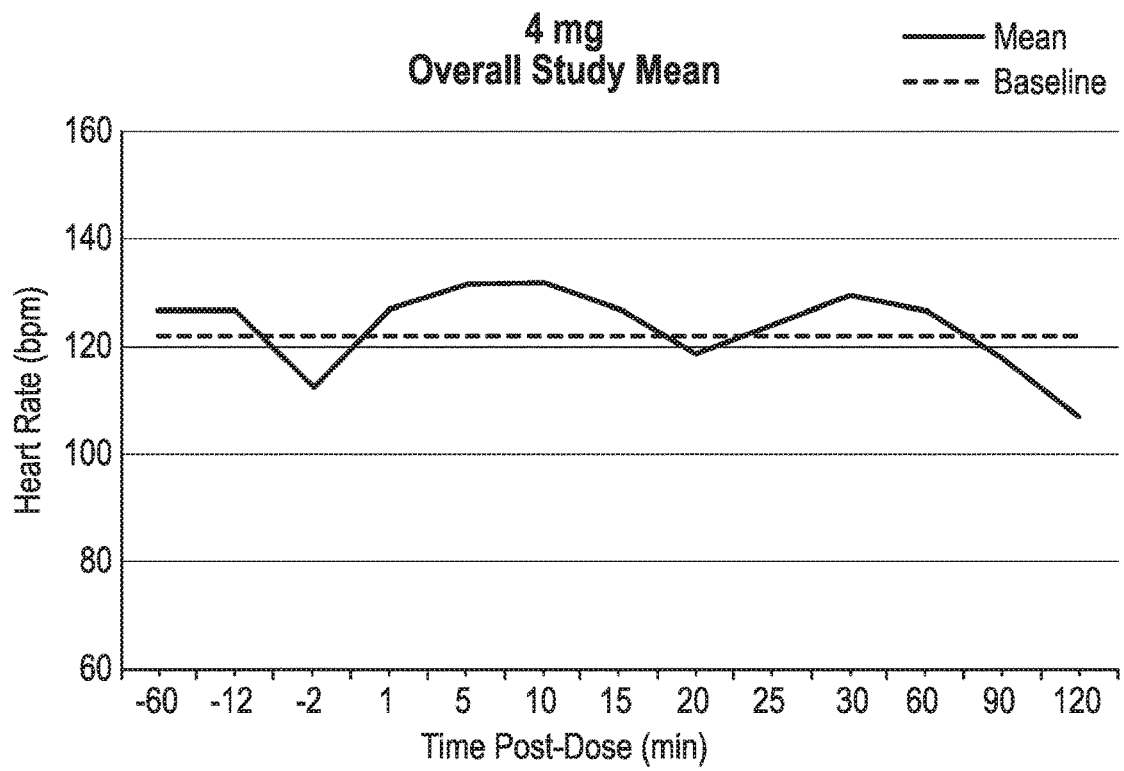
FIG. 13 shows mean heart rates over time before and after 4 mg epinephrine dose compared to baseline for SD29-30 for the overall study (intranasal administration).

For each animal, the following pharmacokinetic parameters were determined: maximum observed plasma concentration ($C_{max}$), time of maximum observed plasma concentration ($T_{max}$), and area under the plasma concentration time curve (AUC). The AUC from time 0 to 120 minutes ($AUC_{0-120}$ min) and the AUC from time 0 to infinity ($AUC_{INF}$) were calculated by the linear trapezoidal method for all animals with at least 3 consecutive quantifiable concentrations. For Day 1, 0 was used as an estimate of the 0 hr concentration. Half-life values ($T_{1/2}$) were reported for each plasma concentration time profile that had sufficient plasma concentrations in the terminal elimination phase (at least 3 samples not including Tmax), an adjusted $R^2$ of ≥0.9, and were determined from at least 3 half-lives of data. Additional pharmacokinetic parameters calculated were clearance divided by fraction of dose absorbed (Cl/F), volume of distribution divided by the fraction of dose absorbed (Vz/F), and mean residence time (MRTlast). The female to male exposure ratio (F:M) was calculated for each dose group using the following formula: F:M=Mean $AUC_{0-120\ min\ Female}$÷Mean $AUC_{0-120\ min\ Male}$ The % AUC extrapolated (% AUCExtrap) was calculated as: % AUCExtrap=$[(AUC_{INF}-AUC_{Tlast})/AUC_{INF}]\times 100$ Group 1-4 mg IN Epinephrine Test formulation-related increases in heart rate were observed following intranasal (IN) administration of Epinephrine (4 mg) on Study Day (SD) 0-1 and SD 16-17. All animals were administered IN Epinephrine (4 mg, 100 μL) via a cannula. The mean heart rate through time of all animals dosed with 4 mg epinephrine is provided in FIG. 13.

On SD 16-17, heart rates increased following dose administration with the max heart rate measurement (181 bpm) occurring 25 min post-dose. At 120 min post-dose the heart rate of 2 animals had returned to a normal baseline range while the heart rates of the remaining 6 animals remained elevated (Table 23).

On SD 29-30, heart rates increased following dose administration with the max heart rate measurement (226 bpm) occurring 15 min post-dose. At 120 min post-dose the heart rate of seven dogs had returned to a normal baseline range while the heart rate of one animal remained elevated slightly above the baseline value (Table 23).

TABLE 23

Individual and Mean Heart Rate of Dogs in Group 1-4 mg IN Epinephrine
Individual and Mean Heart Rates (bpm) - 4 mg IN Epinephrine

Study Days 16-17

| Time | CVR | CLB | CWB | CNB | CWD | CXX | CWZ | CYN | Mean |
|---|---|---|---|---|---|---|---|---|---|
| −60 | 137 | 155 | 111 | 146 | 90 | 154 | 134 | 109 | 130 |
| −12 | 117 | 135 | 117 | 154 | 160 | 139 | 129 | 106 | 132 |
| −2 | 102 | 152 | 81 | 151 | 108 | 170 | 119 | 92 | 122 |
| 1 | 106 | 144 | 166 | 156 | 85 | 135 | 125 | 115 | 129 |
| 5 | 157 | 137 | 105 | 156 | 125 | 144 | 136 | 119 | 135 |
| 10 | 116 | 158 | 123 | 164 | 116 | 151 | 122 | 126 | 135 |
| 15 | 124 | 163 | 117 | 143 | 129 | 131 | 130 | 99 | 130 |
| 20 | 137 | 146 | 98 | 130 | 76 | 142 | 128 | 114 | 121 |
| 25 | 120 | 174 | 87 | 145 | 126 | 181 | 118 | 132 | 135 |
| 30 | 122 | 157 | 83 | 158 | 115 | 138 | 137 | 153 | 133 |
| 60 | 171 | 159 | 119 | 122 | 153 | 127 | 153 | 117 | 140 |
| 90 | 97 | 157 | 112 | 155 | 105 | 135 | 124 | 127 | 127 |
| 120 | 74 | 129 | 140 | 139 | 108 | 121 | 150 | 141 | 125 |

Study Days 29-30

| Time | CGR | ACHG | CPK | CBC | CUD | CFU | CUE | CJE | Mean |
|---|---|---|---|---|---|---|---|---|---|
| −60 | 181 | 92 | 106 | 131 | 106 | 132 | 111 | 135 | 124 |
| −12 | 139 | 141 | 130 | 141 | 109 | 95 | 83 | 138 | 122 |
| −2 | 117 | 99 | 98 | 123 | 135 | 95 | 57 | 103 | 103 |
| 1 | 132 | 125 | 120 | 126 | 142 | 114 | 119 | 128 | 126 |
| 5 | 122 | 126 | 113 | 135 | 158 | 105 | 154 | 118 | 129 |
| 10 | 182 | 156 | 113 | 146 | 97 | 95 | 119 | 130 | 130 |
| 15 | 226 | 100 | 101 | 138 | 134 | 103 | 65 | 135 | 125 |
| 20 | 116 | 122 | 118 | 129 | 168 | 72 | 77 | 126 | 116 |
| 25 | 119 | 120 | 112 | 139 | 144 | 76 | 73 | 121 | 113 |
| 30 | 150 | 134 | 112 | 140 | 162 | 112 | 86 | 114 | 126 |
| 60 | 114 | 122 | 94 | 137 | 98 | 125 | 93 | 128 | 114 |
| 90 | 222 | 99 | 91 | 131 | 86 | 85 | 67 | 99 | 110 |
| 120 | 89 | 100 | 88 | 125 | 76 | 71 | 70 | 97 | 90 |

Group 2-5 mg IN Epinephrine

Figure 14:
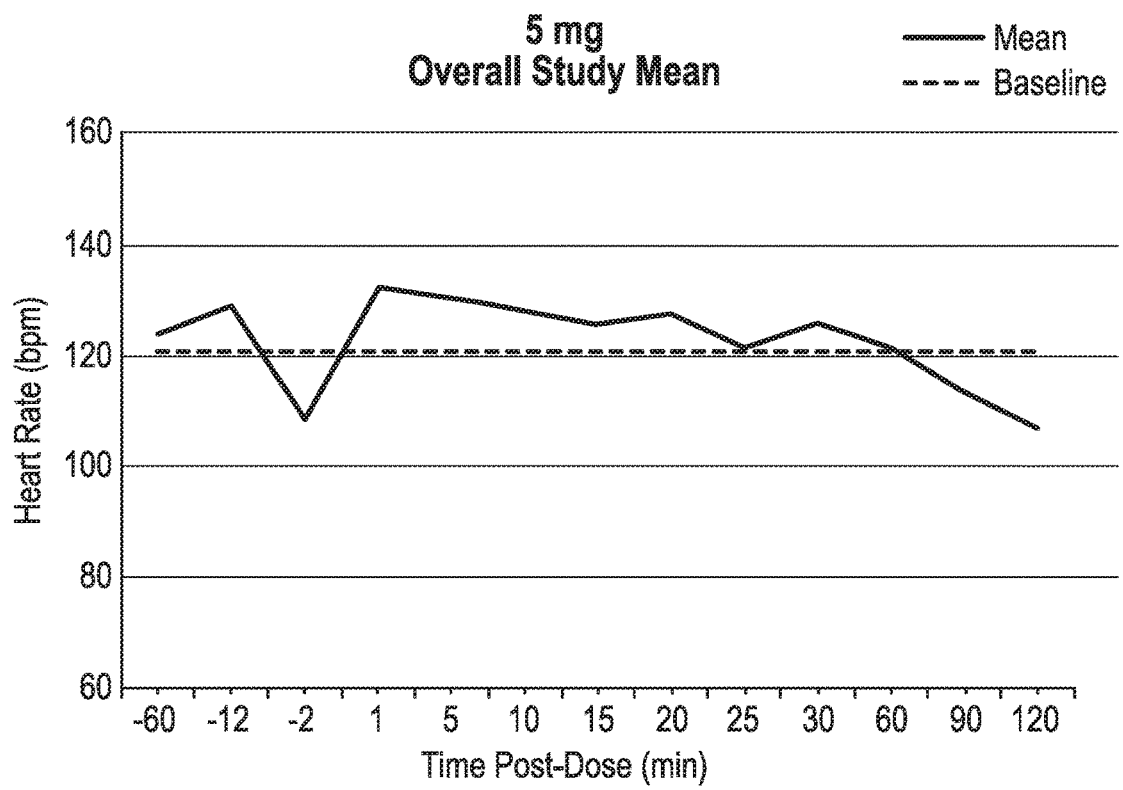
FIG. 14 shows mean heart rates over time before and after 5 mg epinephrine dose compared to baseline for SD29-30 for the overall study (intranasal administration).

Test article-related increases in heart rate were observed following intranasal (IN) administration of Epinephrine (5 mg) on Study Day (SD) 0-1 and SD 16-17. All animals were administered IN Epinephrine (5 mg, 100 μL) via a cannula. The mean heart rate through time of all animals dosed with 5 mg epinephrine is provided in FIG. 14.

On SD 16-17, heart rates increased following dose administration with the max heart rate measurement (174 bpm) occurring 60 min post-dose. At 90 min post-dose the heart rates of all 8 animals had returned to a normal baseline range (Table 24).

On SD 29-30, heart rates increased following dose administration with the max heart rate measurement (220 bpm) occurring 1 min post-dose. At 120 min post-dose the heart rates of five animals had returned to a normal baseline range while the heart rates of three animals remained elevated above the normal baseline range (Table 24).

TABLE 24

Individual and Mean Heart Rate of Dogs in Group 2-5 mg IN Epinephrine
Individual and Mean Heart Rates (bpm)-5 mg IN Epinephrine

Study Days 16-17

| Min | CVL | CSW | CVX | CTZ | CWT | CWF | CXV | CGF | Mean |
|---|---|---|---|---|---|---|---|---|---|
| −60 | 93 | 128 | 138 | 158 | 103 | 112 | 119 | 149 | 125 |
| −12 | 163 | 118 | 129 | 152 | 104 | 145 | 116 | 124 | 131 |
| −2 | 65 | 128 | 73 | 145 | 86 | 133 | 104 | 124 | 107 |
| 1 | 121 | 126 | 120 | 151 | 129 | 113 | 100 | 137 | 125 |
| 5 | 146 | 141 | 88 | 132 | 111 | 131 | 129 | 146 | 128 |
| 10 | 145 | 130 | 128 | 144 | 105 | 130 | 123 | 128 | 129 |
| 15 | 135 | 132 | 140 | 147 | 95 | 140 | 122 | 113 | 128 |
| 20 | 147 | 145 | 122 | 129 | 137 | 124 | 130 | 137 | 134 |
| 25 | 115 | 139 | 121 | 139 | 124 | 109 | 138 | 135 | 128 |
| 30 | 168 | 128 | 125 | 123 | 128 | 101 | 118 | 136 | 128 |
| 60 | 174 | 133 | 149 | 134 | 139 | 102 | 124 | 128 | 135 |
| 90 | 120 | 109 | 105 | 118 | 113 | 120 | 90 | 117 | 112 |
| 120 | 92 | 108 | 125 | 113 | 84 | 105 | 116 | 109 | 107 |

Study Days 29-30

| Time | CNE | BCHG | CRA | CTZ | CUF | CIH | CUU | CRF | Mean |
|---|---|---|---|---|---|---|---|---|---|
| −60 | 146 | 108 | 127 | 142 | 85 | 133 | 122 | 116 | 122 |
| −12 | 126 | 132 | 135 | 137 | 96 | 116 | 115 | 151 | 126 |
| −2 | 126 | 72 | 127 | 110 | 84 | 133 | 99 | 122 | 109 |
| 1 | 181 | 140 | 220 | 119 | 91 | 122 | 102 | 142 | 140 |
| 5 | 172 | 109 | 153 | 123 | 103 | 173 | 113 | 119 | 133 |
| 10 | 144 | 109 | 143 | 125 | 113 | 156 | 106 | 118 | 127 |
| 15 | 125 | 113 | 160 | 114 | 111 | 130 | 109 | 124 | 123 |
| 20 | 125 | 100 | 149 | 127 | 101 | 114 | 106 | 149 | 121 |
| 25 | 129 | 84 | 142 | 117 | 98 | 130 | 104 | 119 | 115 |
| 30 | 113 | 133 | 155 | 120 | 116 | 133 | 103 | 112 | 123 |
| 60 | 130 | 92 | 122 | 97 | 108 | 127 | 86 | 96 | 107 |
| 90 | 106 | 92 | 124 | 128 | 73 | 140 | 133 | 127 | 115 |
| 120 | 105 | 90 | 125 | 129 | 63 | 116 | 88 | 142 | 107 |

Group—EpiPen® 0.3 mg IM Injection

Figure 15:
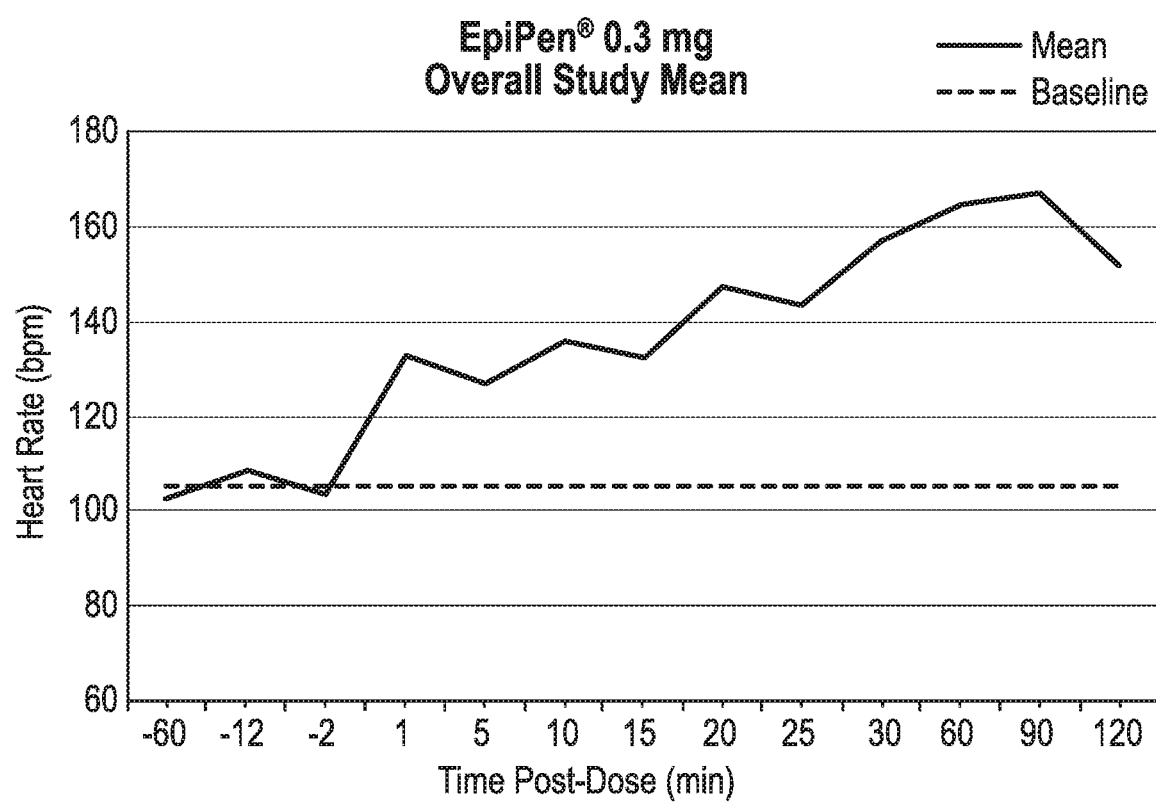
FIG. 15 shows mean heart rates over time before and after 0.3 mg epinephrine dose compared to baseline for SD29-30 for the overall study (intramuscular administration).

Intramuscular (IM) injection of EpiPen® 0.3 mg resulted in overall increased heart rates in all animals. All animals were administered an EpiPen® 0.3 mg IM injection on the right hind leg. The mean heart rate through time of all animals dosed with EpiPen® Adult is provided in FIG. 15.

On SD 16-17, heart rates increased following dose administration with the max heart rate measurement (222 bpm) occurring 20 min post-dose. Consistent with results from SD 0-1, the heart rates of all eight dogs remained elevated above the normal baseline range at 120 min post dose administration (Table 25).

On SD 29-30, heart rates increased following dose administration with the max heart rate measurement (222 bpm) occurring 20 min post-dose. Consistent with results from SD 0-1, the heart rates of all eight dogs remained elevated above the normal baseline range at 120 min post dose administration (Table 25).

TABLE 25

Individual and Mean Heart Rate of Dogs in Group 3 - EpiPen® 0.3 mg Injection
Individual and Mean Heart Rates (bpm) - EpiPen® 0.3 mg Injection

Study Days 16-17

| Min | CWU | CHT | CXU | CLZ | CYA | CPL | CYR | CPN | Mean |
|---|---|---|---|---|---|---|---|---|---|
| −60 | 112 | 122 | 121 | 117 | 152 | 106 | 106 | 110 | 118 |
| −12 | 124 | 87 | 100 | 87 | 107 | 109 | 153 | 149 | 115 |
| −2 | 105 | 145 | 123 | 111 | 135 | 83 | 85 | 107 | 112 |
| 1 | 123 | 194 | 143 | 147 | 157 | 133 | 174 | 108 | 147 |
| 5 | 142 | 144 | 144 | 103 | 172 | 137 | 148 | 112 | 138 |
| 10 | 182 | 137 | 157 | 127 | 124 | 153 | 112 | 147 | 142 |
| 15 | 169 | 148 | 127 | 121 | 101 | 153 | 119 | 124 | 133 |
| 20 | 222 | 145 | 158 | 107 | 157 | 153 | 179 | 151 | 159 |
| 25 | 212 | 167 | 142 | 120 | 144 | 156 | 157 | 134 | 154 |
| 30 | 205 | 144 | 190 | 154 | 131 | 191 | 147 | 176 | 167 |

TABLE 25-continued

Individual and Mean Heart Rate of Dogs in Group 3 - EpiPen ® 0.3 mg Injection
Individual and Mean Heart Rates (bpm) - EpiPen ® 0.3 mg Injection

| 60  | 160 | 186 | 211 | 144 | 148 | 180 | 188 | 162 | 172 |
| 90  | 151 | 173 | 199 | 204 | 159 | 178 | 165 | 151 | 173 |
| 120 | 163 | 151 | 193 | 123 | 153 | 167 | 151 | 145 | 156 |

Study Days 29-30

| Time | CPJ | CBE | CTE | CEU | CUT | CFI | CUZ | CGV | Mean |
|---|---|---|---|---|---|---|---|---|---|
| −60 | 61  | 113 | 124 | 103 | 66  | 73  | 80  | 84  | 88  |
| −12 | 71  | 130 | 127 | 113 | 70  | 120 | 112 | 82  | 103 |
| −2  | 121 | 108 | 108 | 98  | 74  | 73  | 96  | 91  | 96  |
| 1   | 104 | 156 | 127 | 125 | 94  | 151 | 107 | 89  | 119 |
| 5   | 115 | 132 | 107 | 113 | 86  | 162 | 110 | 109 | 117 |
| 10  | 103 | 131 | 138 | 116 | 178 | 107 | 161 | 103 | 130 |
| 15  | 142 | 131 | 136 | 137 | 134 | 184 | 93  | 103 | 133 |
| 20  | 166 | 136 | 138 | 139 | 163 | 124 | 108 | 118 | 137 |
| 25  | 165 | 139 | 140 | 146 | 155 | 113 | 98  | 111 | 133 |
| 30  | 179 | 175 | 122 | 142 | 192 | 130 | 110 | 125 | 147 |
| 60  | 154 | 173 | 130 | 179 | 201 | 148 | 129 | 146 | 158 |
| 90  | 155 | 182 | 151 | 173 | 189 | 179 | 144 | 125 | 162 |
| 120 | 155 | 182 | 114 | 151 | 162 | 132 | 154 | 133 | 148 |

Pharmacokinetic Analysis

All epinephrine plasma concentrations were baseline corrected for endogenous epinephrine levels using the mean predose concentrations; therefore, the following discussion of epinephrine systemic exposure is based on the data in excess of endogenous levels.

Systemic exposure to epinephrine was independent of sex. There were no consistent differences in individual plasma concentration time profiles, $C_{max}$, and AUC values between males and females (the F:M $AUC_{0-24\ hr}$ ratios following intranasal administration were 0.711 and 1.20 for Groups 1 and 2, respectively, and the F:M $AUC_{0-24\ hr}$ ratio following intramuscular administration was 1.27 for Group 3); therefore, the following discussion is based on data for males and females combined.

The variability in mean epinephrine plasma concentrations, as measured by CV values, ranged from 53.4% to 170% following a single IN administration of epinephrine to dogs in Groups 1 and 2 and from 48.7% to 174% following a single IM injection of 0.3 mg epinephrine to dogs in Group 3. Epinephrine was quantifiable up to 120 minutes post-dose for Group 1 (4 mg), up to 30 or 120 minutes post-dose for Group 2 (5 mg), and up to 120 minutes post-dose for Group 3 (0.3 mg). Individual peak epinephrine plasma concentrations were observed between 1 and 30 minutes post-dose for Group 1 (4 mg), between 1 and 90 minutes post-dose for Group 2 (5 mg), and between 5 and 60 minutes post-dose for Group 3 (0.3 mg).

Following a single IN administration of epinephrine to dogs, mean $C_{max}$ and $AUC_{0-120\ min}$ values for epinephrine increased slightly with increasing dose from 4 to 5 mg. A 1.25-fold increase in epinephrine dose resulted in an approximate 1.22-fold increase in mean epinephrine $C_{max}$ values (2.48 and 3.01 ng/mL at 4 and 5 mg, respectively) and an approximate 1.09-fold increase in mean epinephrine $AUC_{0-120\ min}$ values (75.0 and 81.8 min*ng/mL at 4 and 5 mg, respectively). Following a single IM injection of 0.3 mg epinephrine to dogs, mean $C_{max}$ and $AUC_{0-120\ min}$ values for epinephrine were 2.76 ng/mL and 110 min*ng/mL, respectively.

Mean $MRT_{last}$ values for epinephrine following IN administration were 51.1 and 53.9 minutes at 4 and 5 mg, respectively. The mean $MRT_{last}$ value for epinephrine following IM injection was 50.4 minutes. A complete summary of the pharmacokinetic aforementioned pharmacokinetic parameters are provided in Table 26.

Figure 16:
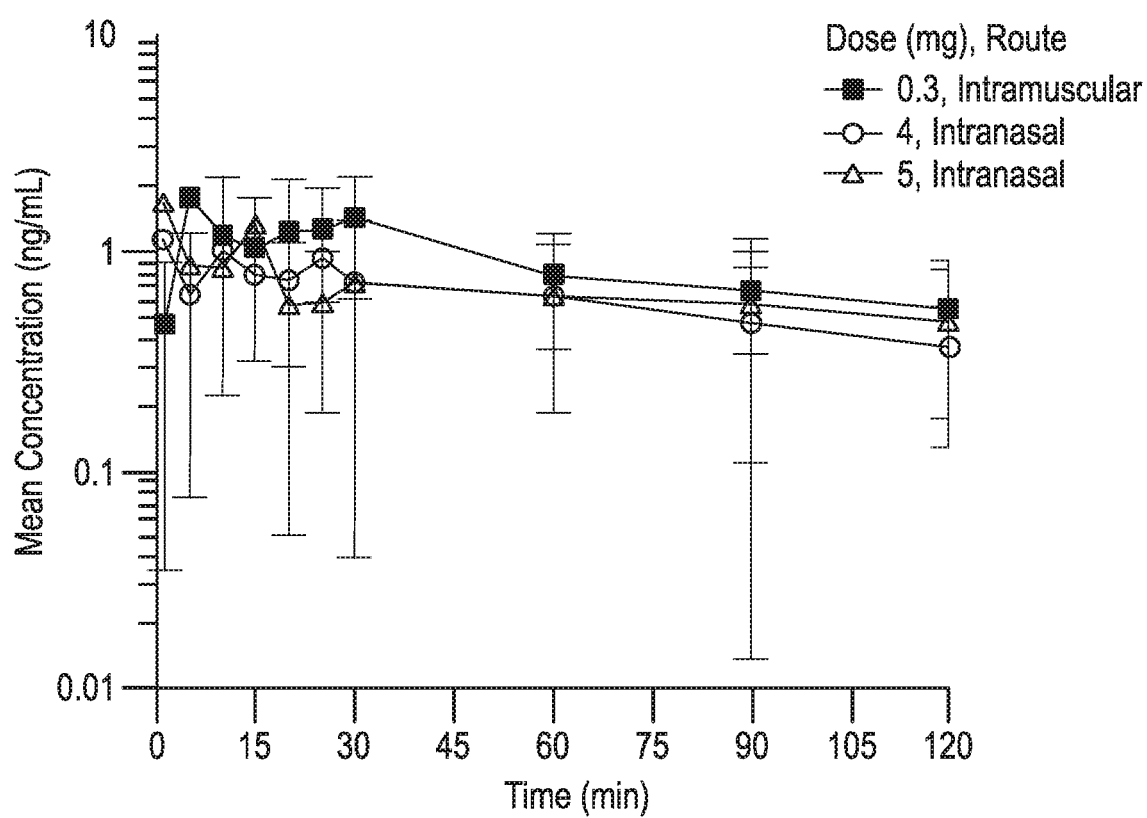
FIG. 16 shows individual plasma concentration-time profiles comparing animals treated with epinephrine via intranasal administration and animals treated with epinephrine via intramuscular injection.

Overall, the individual plasma concentration-time profiles were generally similar between animals treated with epinephrine via IN administration when compared to animals treated with epinephrine via IM injection (FIG. 16).

TABLE 26

Epinephrine Pharmacokinetic Parameters Following a Single IN Administration of 4 or 5 mg Epinephrine or a Single IM Injection of 0.3 mg Epinephrine to Dogs (Males and Females Combined)

| Group | Route | Dose (mg) | Statistic | $C_{max}$ (ng/mL) | $C_{max}$/Dose (ng/mL/mg) | $T_{max}^a$ (min) | $T_{last}^a$ (min) | $AUC_{0-120\ min}$ (min*ng/mL) | $AUC_{0-120\ min}$/Dose (min*ng/mL/mg) | $MRT_{last}$ (min) |
|---|---|---|---|---|---|---|---|---|---|---|
| 1 | IN | 4 | N | 16 | 16 | 16 | 16 | 16 | 16 | 16 |
|   |    |   | Mean | 2.48 | 0.619 | 20 | 120 | 75.0 | 18.7 | 51.1 |
|   |    |   | SD | 2.27 | 0.568 | (1-30) | (120-120) | 53.8 | 13.5 | 11.3 |
|   |    |   | CV % | 91.7 | 91.7 | NA | NA | 71.8 | 71.8 | 22.2 |
| 2 | IN | 5 | N | 16 | 16 | 16 | 16 | 15 | 15 | 15 |
|   |    |   | Mean | 3.01 | 0.602 | 15 | 120 | 81.8 | 16.4 | 53.9 |
|   |    |   | SD | 2.96 | 0.592 | (1-90) | (30-120) | 46.3 | 9.26 | 12.9 |
|   |    |   | CV % | 98.3 | 98.3 | NA | NA | 56.6 | 56.6 | 23.8 |
| 3 | IM | 0.3 | N | 16 | 16 | 16 | 16 | 16 | 16 | 16 |
|   |    |   | Mean | 2.76 | 9.22 | 25 | 120 | 110 | 365 | 50.4 |
|   |    |   | SD | 2.78 | 9.25 | (5-60) | (120-120) | 42.1 | 140 | 9.39 |
|   |    |   | CV % | 100 | 100 | NA | NA | 38.4 | 38.4 | 18.6 |

NA—Not applicable.
[a]Median (minimum-maximum), median value only reported if actual collection interval.

Three groups of 8 male and 8 female Beagle dogs each were administered 4 mg/100 µL IN epinephrine to the right nostril (Group 1), 5 mg/100 µL IN epinephrine to the right nostril (Group 2), or 0.3 mg in 0.3 mL EpiPen® (adult) IM to the thigh muscle (Group 3), followed by timed blood draws for this PK study. Additionally, dogs were telemetrized to monitor their heart rate pre- and post-dose administration.

Heart rate data was comparable in the 4 and 5 mg IN Group 1 and 2 (respectively) dogs with an increase in mean heart rate occurring at approximately 5-10 min post-dose in Group 1 dogs and at approximately 1 min post-dose in Group 2 dogs. The peak increase in mean heart rate was 132 bpm at 10 min and 132 bpm at 1 min post-IN administration for Group 1 and 2 dogs, respectively. The heart rate in the Group 3 EpiPen® administered dogs began to increase at 1 min post-dose with a peak increase in mean heart rate (167 bpm) occurring at approximately 90 min post-dose administration.

Systemic exposure to epinephrine was independent of sex. Individual peak epinephrine plasma concentrations were observed between 1 and 30 minutes post-dose for Group 1 (4 mg), between 1 and 90 minutes post-dose for Group 2 (5 mg), and between 5 and 60 minutes post-dose for Group 3 (0.3 mg). Following a single IN administration of epinephrine to dogs, mean $C_{max}$ and $AUC_{0-120\ min}$ values for epinephrine increased slightly with increasing dose from 4 to 5 mg. A 1.25-fold increase in epinephrine dose resulted in an approximate 1.22-fold increase in mean epinephrine $C_{max}$ values (2.48 and 3.01 ng/mL at 4 and 5 mg, respectively) and an approximate 1.09-fold increase in mean epinephrine $AUC_{0-120\ min}$ values (75.0 and 81.8 min*ng/mL at 4 and 5 mg, respectively). Following a single IM injection of 0.3 mg epinephrine to dogs, mean $C_{max}$ and $AUC_{0-120\ min}$ values for epinephrine were 2.76 ng/mL and 110 min*ng/mL, respectively.

Mean $MRT_{last}$ values for epinephrine following IN administration were 51.1 and 53.9 minutes at 4 and 5 mg, respectively. The mean $MRT_{last}$ value for epinephrine following IM injection was 50.4 minutes.

Overall, the individual plasma concentration-time profiles were generally similar between animals treated with epinephrine via IN administration when compared to animals treated with epinephrine via IM injection.

Example 12—Dose Administration of Epinephrine Via One or Two Nostrils

This study investigated intranasal administration of Epinephrine in a Beagle dogs to evaluate if one or two nostril administrations of epinephrine produces the optimal plasma levels.

The epinephrine formulation used is defined in Table 27. The study consisted of three male and three female beagle dogs per group (Table 28). Groups 1-4 were administered epinephrine through a 100 µl intranasal device intranasally. Following dose administration, all animals had serial blood samples collected for pharmacokinetic analysis.

TABLE 27

Test Article Formulation

| Compound | Final Concentration | Final pH |
|---|---|---|
| Epinephrine | 5 mg/100 µl | 5.35 |
| Sodium Chloride | 0.4 mg/100 µl | |
| Sodium Metabisulfite | 0.05 mg/100 µl | |
| Trisodium citrate | 0.7% | |
| Hypromellose | 0.1% | |
| Diethylene glycol monoethyl ether | 1% | |
| Epinephrine | 10 mg/100 µl | 4.90 |
| Sodium Chloride | 0.4 mg/100 µl | |
| Sodium Metabisulfite | 0.05 mg/100 µl | |
| Trisodium citrate | 0.7% | |
| Hypromellose | 0.1% | |
| Diethylene glycol monoethyl ether | 1% | |

TABLE 28

Study Design

| Groups | Total Dose Level (mg) of Epinephrine | Dose Volume (µl) | Nostril Administration | Males | Females |
|---|---|---|---|---|---|
| 1 | 5 | 100 | One | 3[a] | 3[a] |
| 2 | 10 (two nostrils with 5 mg/nostril) | 100 | Both | 3[b] | 3[b] |
| 3 | 10 | 100 | One | 3[a] | 3[a] |
| 4[c] | 20 (two nostrils with 10 mg/nostril) | 100 | Both | 3[b] | 3[b] |

264 PK samples total from Groups 1, 2, 3, and 4 were analyzed by liquid chromatography tandem-mass spectrometry (LC-MS/MS) using a C18-PFP column. LC-MS/MS analysis was performed in positive electrospray ionization (ESI+) mode using multiple reaction monitoring (MRM) ionization.

Epinephrine plasma concentrations were baseline-subtracted using average concentrations of the three pre-dose samples. If baseline-subtraction resulted in negative values, these samples were assigned a value of zero. In some cases (e.g., low dose groups 1 and 3), post-dose epinephrine concentrations of several animals were all below pre-dose baseline concentrations. In addition, epinephrine concentrations were considered as outliers if they exceeded two times standard deviation from the mean of baseline-subtracted post-dose epinephrine plasma concentrations of each animal over the course of blood sampling (i.e., 1-90 min post-dose).

AUC, Tmax and Cmax were calculated using the trapezoid rule (GraphPad Prism 7.0c) and the post-dose baseline-subtracted outlier-removed epinephrine concentrations for each individual animal (Tables 29-32).

TABLE 29

AUC and Cmax of epinephrine in dogs from group 1 (5 mg × 1 nostril)

| Parameter, unit | Group 1 (5 mg × 1 nostrils) | | | | | | | |
|---|---|---|---|---|---|---|---|---|
| | 1 | 2 | 3 | 4 | 5 | 6 | Average | SD |
| Dose, mg | 5 | 5 | 5 | 5 | 5 | 5 | | |
| Cmax, ng/mL | NC | NC | 0.1 | 0.7 | 0.1 | NC | 0.3 | 0.3 |
| Tmax, min | NC | NC | 90 | 90 | 7 | NC | 62 | 48 |
| AUC1-90 min, ng/mL*min | NC | NC | 2 | 13 | 6 | NC | 7 | 6 |

TABLE 30

AUC and Cmax of epinephrine in dogs from group 2 (5 mg × 2 nostril)

| Parameter, unit | Group 2 (5 mg × 2 nostrils) | | | | | | | |
|---|---|---|---|---|---|---|---|---|
| | 1 | 2 | 3 | 4 | 5 | 6 | Average | SD |
| Dose, mg | 10 | 10 | 10 | 10 | 10 | 10 | | |
| Cmax, ng/mL | 1.4 | 1.7 | 4.2 | 2 | 4.7 | 0.3 | 2.4 | 1.7 |
| Tmax, min | 15 | 10 | 90 | 22 | 5 | 30 | 29 | 31 |
| AUC1-90 min, ng/mL*min | 23 | 38 | 117 | 76 | 166 | 5 | 71 | 62 |

TABLE 31

AUC and Cmax of epinephrine in dogs from group 3 (10 mg × 1 nostril)

| Parameter, unit | Group 3 (10 mg × 1 nostrils) | | | | | | | |
|---|---|---|---|---|---|---|---|---|
| | 1 | 2 | 3 | 4 | 5 | 6 | Average | SD |
| Dose, mg | 10 | 10 | 10 | 10 | 10 | 10 | | |
| Cmax, ng/mL | NC | NC | 8.7 | 0.8 | NC | NC | 4.8 | 5.6 |
| Tmax, min | NC | NC | 12 | 85 | NC | NC | 51 | 54 |
| AUC1-90 min, ng/mL*min | NC | NC | 378 | 20 | NC | NC | 199 | 253 |

TABLE 32

AUC and Cmax of epinephrine in dogs from group 4 (10 mg × 2 nostril)

| Parameter, unit | Group 4 (10 mg × 2 nostrils) | | | | | | | |
|---|---|---|---|---|---|---|---|---|
| | 1 | 2 | 3 | 4 | 5 | 6 | Average | SD |
| Dose, mg | 20 | 20 | 20 | 20 | 20 | 20 | | |
| Cmax, ng/mL | 2.8 | 3.1 | 2.5 | 2 | 6.7 | 3.4 | 3.4 | 1.7 |
| Tmax, min | 60 | 15 | 10 | 90 | 63 | 90 | 55 | 35 |
| AUC1-90 min, ng/mL*min | 178 | 96 | 80 | 62 | 241 | 151 | 135 | 68 |

Example 13—an Intranasal and Intramuscular Dose Range-Finding Administration of Epinephrine in Beagle Dogs This study investigated intranasal administration of Epinephrine at various dose levels in a Beagle dogs. In addition, the Adult and JR Epi-Pens were administered via intramuscular injection to provide pharmacokinetic profiles for comparison.

The epinephrine formulation used is defined in Table 33. The study consisted of three male and three female beagle dogs per group (Table 34). Groups 1-4 were administered 100 µl of epinephrine at varying concentrations. Dose formulation was administered intranasally using a cannula. Groups 5 and 6 were administered epinephrine via intramuscular injection using and Adult EpiPen or Jr. EpiPen, respectively. Following dose administration, all animals had serial blood samples collected.

TABLE 33

| Test Article Formulation | | |
|---|---|---|
| Compound | Final Concentration | Final pH |
| Epinephrine | 5 mg/100 µl | 4.94 |
| Sodium Chloride | 0.4 mg/100 µl | |
| Sodium Metabisulfite | 0.05 mg/100 µl | |
| Trisodium citrate | 0.7% | |
| Hypromellose | 0.1% | |
| Diethylene glycol monoethyl ether | 1% | |
| Epinephrine | 10 mg/100 µl | 4.85 |
| Sodium Chloride | 0.4 mg/100 µl | |
| Sodium Metabisulfite | 0.05 mg/100 µl | |
| Trisodium citrate | 0.7% | |
| Hypromellose | 0.1% | |
| Diethylene glycol monoethyl ether | 1% | |
| Epinephrine | 20 mg/100 µl | 4.50 |
| Sodium Chloride | 0.4 mg/100 µl | |
| Sodium Metabisulfite | 0.05 mg/100 µl | |
| Trisodium citrate | 0.7% | |
| Hypromellose | 0.1% | |
| Diethylene glycol monoethyl ether | 1% | |

TABLE 34

| Study Design | | | | | |
|---|---|---|---|---|---|
| Groups | Total Dose Level (mg) of Epinephrine | Dose Volume (µl) | Administration Route | Males | Females |
| 1 | 10 | 100 | Nostril, Both | 3[a] | 3[a] |
| 2 | 20 | 100 | Nostril, One | 3[b] | 3[b] |
| 3 | 5 | 100 | Nostril, One | 3[a] | 3[a] |
| 4 | 10 | 100 | Nostril, One | 3[b] | 3[b] |
| 5 | Adult EpiPen (0.3) | 300 | IM | 3[a] | 3[a] |
| 6 | Jr EpiPen (0.15) | 300 | IM | 3[b] | 3[b] |

PK samples were analyzed by liquid chromatography tandem-mass spectrometry (LC-MS/MS) using a C18-PFP column. LC-MS/MS analysis was performed in positive electrospray ionization (ESI+) mode using multiple reaction monitoring (MRM) ionization.

AUC, Tmax and Cmax were calculated using the trapezoid rule (GraphPad Prism 7.0c) and the post-dose baseline-subtracted outlier-removed epinephrine concentrations for each individual animal (Tables 35-40). For Groups 5 and 6 (EpiPen groups), AUC, Tmax and Cmax were also calculated using the post-dose baseline-subtracted epinephrine concentrations (without removing outliers) for comparison (number in parentheses in Tables 39 and 40).

TABLE 35

AUC and Cmax of epinephrine in dogs from group 1 (10 mg × 2 nostril)

| Parameter, unit | Group 1 (10 mg × 2 nostrils) | | | | | | | |
|---|---|---|---|---|---|---|---|---|
| | 1 | 2 | 3 | 4 | 5 | 6 | Average | SD |
| Dose, mg | 20 | 20 | 20 | 20 | 20 | 20 | | |
| Cmax, ng/mL | 1.8 | 7.2 | 2.2 | 3.2 | 6.8 | 7.4 | 4.8 | 2.7 |
| Tmax, min | 1 | 5 | 60 | 60 | 90 | 90 | 51 | 40 |
| AUC1-90 min, ng/mL*min | 59 | 249 | 72 | 134 | 284 | 485 | 214 | 161 |

TABLE 36

AUC and Cmax of epinephrine in dogs from group 2 (10 mg × 1 nostril)

| Parameter, unit | Group 2 (10 mg × 1 nostrils) | | | | | | | |
|---|---|---|---|---|---|---|---|---|
| | 1 | 2 | 3 | 4 | 5 | N/A | Average | SD |
| Dose, mg | 20 | 20 | 20 | 20 | 20 | | | |
| Cmax, ng/mL | 15.7 | 53 | 4.7 | 32.3 | 10.8 | | 23.3 | 19.5 |
| Tmax, min | 5 | 5 | 1 | 60 | 5 | | 15 | 25 |
| AUC1-90 min, ng/mL*min | 769 | 1875 | 201 | 1700 | 495 | | 1008 | 742 |

TABLE 37

AUC and Cmax of epinephrine in dogs from group 3 (5 mg × 1 nostril)

| Parameter, unit | Group 3 (5 mg × 1 nostrils) | | | | | | | |
|---|---|---|---|---|---|---|---|---|
| | 1 | 2 | 3 | 4 | 5 | 6 | Average | SD |
| Dose, mg | 5 | 5 | 5 | 5 | 5 | 5 | | |
| Cmax, ng/mL | 1.3 | 3.5 | 2.7 | 6 | 3 | 4.1 | 3.4 | 1.6 |
| Tmax, min | 90 | 5 | 30 | 30 | 5 | 90 | 42 | 39 |
| AUC1-90 min, ng/mL*min | 67 | 185 | 117 | 177 | 131 | 205 | 147 | 51 |

TABLE 38

AUC and Cmax of epinephrine in dogs from group 4 (10 mg × 1 nostril)

| Parameter, unit | Group 4 (10 mg × 1 nostrils) | | | | | | | |
|---|---|---|---|---|---|---|---|---|
| | 1 | 2 | 3 | 4 | 5 | 6 | Average | SD |
| Dose, mg | 10 | 10 | 10 | 10 | 10 | 10 | | |
| Cmax, ng/mL | 4.1 | 13.9 | 5.7 | 10.6 | 17.8 | 2.4 | 9.1 | 6 |
| Tmax, min | 28 | 5 | 15 | 15 | 4 | 10 | 13 | 9 |
| AUC1-90 min, ng/mL*min | 228 | 339 | 94 | 259 | 491 | 85 | 249 | 154 |

TABLE 39

AUC and Cmax of epinephrine in dogs from group 5 (EpiPen Adult 0.3 mg IM)

| Parameter, unit | Group 5 (EpiPen Adult 0.3 mg IM) | | | | | | | |
|---|---|---|---|---|---|---|---|---|
| | 1 | 2 | 3 | 4 | 5 | 6 | Average | SD |
| Dose, mg | 0.3 | 0.3 | 0.3 | 0.3 | 0.3 | 0.3 | | |
| Cmax, ng/mL | 1.4 | 3 | 1.6 | 1.3 | 2.1 (4.1) | 7.5 | 2.8 (3.1) | 2.4 (2.4) |
| Tmax, min | 60 | 60 | 30 | 15 | 10 (14) | 15 | 32 (32) | 23 (22) |
| AUC1-90 min, ng/mL*min | 94 | 158 | 101 | 62 | 111 (123) | 193 | 120 (122) | 47 (47) |

TABLE 40

AUC and Cmax of epinephrine in dogs from group 6 (EpiPen Junior 0.15 mg IM)

| Parameter, unit | Group 6 (EpiPen Junior 0.15 mg IM) | | | | | | | |
|---|---|---|---|---|---|---|---|---|
| | 1 | 2 | 3 | 4 | 5 | 6 | Average | SD |
| Dose, mg | 0.15 | 0.15 | 0.15 | 0.15 | 0.15 | 0.15 | | |
| Cmax, ng/mL | 0.9 | 1.1 (2.5) | 1.2 (3.8) | 2.2 (4.6) | 1.1 | 1.1 (3.0) | 1.3 (2.7) | 0.5 (1.4) |
| Tmax, min | 1 | 5 (10) | 60 (20) | 10 (5) | 20 | 30 (20) | 21 (13) | 22 (9) |
| AUC1-90 min, ng/mL*min | 33 | 56 (65) | 77 (101) | 50 (63) | 74 | 66 (80) | 59 (69) | 16 (22) |

Example 14—an Intranasal Low Dose Range-Finding Administration of Epinephrine in Beagle Dogs This is a study investigating intranasal administration of Epinephrine at various dose levels and dosing intervals in Beagle dogs. This non-GLP PK study utilized the Adult EpiPen® administered via intramuscular injection to provide a pharmacokinetic profile for comparison.

The plasma levels and heart rate changes produced by intranasal administration of increasing epinephrine concentrations (2 mg/100 μL, 3 mg/100 and 4 mg/100 μL) were assessed (Groups 1-3). In addition, plasma epinephrine concentrations and changes in heart rate were assessed following intranasal administration of 2 doses of epinephrine (4 mg/100 μL) in the same or opposite nostril (Group 4 and Group 8B) with a 20 minute interval between doses. Dual intramuscular injection of the EpiPen® Adult 0.3 mg with a 20 minute interval between doses was used for pharmacokinetic comparison (Group 5/8A).

Serial blood samples were collected for bioanalytical and pharmacokinetic (PK) analysis and several pre- and post-dose time points.

Part I—Assessment of Plasma Epinephrine Concentration Following 2 mg, 3 mg, and 4 mg Intranasal Epinephrine Administration Each group in Part I of Study 4 consisted of three male and three female dogs (n=six/group). Each dog was administered one dose of epinephrine in the right nostril using a cannula. An overview of the Part I Study Design is provided in Table 41. Plasma samples were obtained at the following time points post-epinephrine administration: 1, 5, 10, 15, 20, 30, 60 & 90 minutes.

TABLE 41

Study Design

| Group | Epinephrine (mg) per Dose | Dose Volume (μl) | Nostril Administration | Administration | Males | Females |
|---|---|---|---|---|---|---|
| 1 | 2 | 100 | One | IN | 3A | 3A |
| 2 | 3 | 100 | One | IN | 3B | 3B |
| 3 | 4 | 100 | One | IN | 3C | 3C |

Vehicle for the test article was composed of sterile injection water containing 5 mg/10 mL of Na metabisulfite, 40 mg/10 mL of sodium chloride, 0.7% trisodium citrate, 0.1% hypromellose, 0.2% chlorobutanol and 1% Diethylene glycol monoethyl ether with a final pH of 5.0±0.5 (see Table 42).

TABLE 42

Test Article Formulation

| Compound | Final Concentration | Final pH |
|---|---|---|
| Epinephrine | 2 mg/100 μl | 5.30 |
| Sodium Chloride | 0.4 mg/100 μl | |
| Sodium Metabisulfite | 0.05 mg/100 μl | |
| Trisodium citrate | 0.7% | |
| Chlorobutanol | 0.2% | |
| Hypromellose | 0.1% | |
| Diethylene glycol monoethyl ether | 1% | |
| Epinephrine | 3 mg/100 μl | 5.08 |
| Sodium Chloride | 0.4 mg/100 μl | |
| Sodium Metabisulfite | 0.05 mg/100 μl | |
| Trisodium citrate | 0.7% | |
| Chlorobutanol | 0.2% | |
| Hypromellose | 0.1% | |
| Diethylene glycol monoethyl ether | 1% | |
| Epinephrine | 4 mg/100 μl | 5.32 |
| Sodium Chloride | 0.4 mg/100 μl | |
| Sodium Metabisulfite | 0.05 mg/100 μl | |
| Trisodium citrate | 0.7% | |
| Chlorobutanol | 0.2% | |
| Hypromellose | 0.1% | |
| Diethylene glycol monoethyl ether | 1% | |

Epinephrine plasma concentrations were adjusted to account for the plasma epinephrine baseline by using average concentrations of the three pre-dose samples and subtracting that value from the post-dose values for each dog. If baseline-subtraction resulted in negative values, these samples were assigned a value of zero. In addition, per the sponsor's instruction, epinephrine concentrations were considered as outliers and removed from analysis if they exceeded two times standard deviation from the mean of baseline-subtracted post-dose epinephrine plasma concentrations of each animal over the course of blood sampling (i.e., 1-90 min post-dose).

TABLE 43

AUC and Cmax of epinephrine in dogs from Group 1

| Parameter, unit | Group 1 (2 mg × 1 nostril) | | | | | | Average | SD |
|---|---|---|---|---|---|---|---|---|
| | 1 | 2 | 3 | 4 | 5 | 6 | | |
| Dose, g | 2 | 2 | 2 | 2 | 2 | 2 | — | — |
| $T_{max}$, min | 1 | 60 | 90 | 1 | 60 | 1 | 36 | 39 |
| $C_{max}$, ng/mL | 1.0 | 0.7 | 6.2 | 0.6 | 5.1 | 2.8 | 2.7 | 2.4 |
| $AUC_{1-90\ min}$, ng/mL · min | 47 | 43 | 237 | 13 | 209 | 25 | 96 | 100 |

TABLE 44

AUC and Cmax of epinephrine in dogs from Group 2

| Parameter, unit | Group 2 (3 mg × 1 nostril) | | | | | | Average | SD |
|---|---|---|---|---|---|---|---|---|
| | 1 | 2 | 3 | 4 | 5 | 6 | | |
| Dose, g | 3 | 3 | 3 | 3 | 3 | 3 | — | — |
| $T_{max}$, min | 90 | 5 | 1 | 15 | 5 | 5 | 20 | 35 |
| $C_{max}$, ng/mL | 0.7 | 1.5 | 8.2 | 0.2 | 3.4 | 0.3 | 2.4 | 3.1 |
| $AUC_{1-90\ min}$, ng/mL · min | 25 | 64 | 227 | 14 | 167 | 18 | 86 | 90 |

TABLE 45

AUC and Cmax of epinephrine in dogs from Group 3

| Parameter[a], unit | Group 3 (4 mg × 1 nostril) | | | | | | Average | SD |
|---|---|---|---|---|---|---|---|---|
| | 1 | 2 | 3 | 4 | 5 | 6 | | |
| Dose, g | 4 | 4 | 4 | 4 | 4 | 4 | — | — |
| $T_{max}$, min | 60 | 60 | 1 | 20 | 60 | 90 | 49 | 32 |
| $C_{max}$, ng/mL | 2.9 | 1.7 | 2.1 | 2.2 | 12.2 | 1.4 | 3.7 | 4.2 |
| $AUC_{1-90\ min}$, ng/mL · min | 84 | 112 | 98 | 88 | 688 | 59 | 188 | 246 |

Three doses of epinephrine, 2, 3, and 4 mg IN (100 µL volume each) were evaluated and the lowest dose compared to the PK and heart rate results of the EpiPen Jr. The Cmax of the 2, 3, and 4 were 2.7, 2.4 and 3.7 ng/mL, respectively while the AUC was 96, 86, and 188 ng/mL·min, respectively. It appears that the two lower doses of IN epinephrine exhibited similar pharmacokinetics, while the higher dose of 4 mg IN increased in a dose-dependent manner.

The 2 mg/100 µL dose, produced comparable epinephrine plasma levels to the EpiPen® Junior. Lastly, the 4 mg IN epinephrine PK results were comparable to the adult EpiPen® PK results (EpiPen® results reported in Study 3 as compared to 4 mg IN PK values from Group 3 of this report; Cmax values of 3.7 and 2.8 ng/mL and AUC of 188 and 120 ng/mL·min for the 4 mg IN vs EpiPen®, respectively). Most importantly, the 4 mg IN epinephrine resulted in an elevated plasma concentration much faster (within 1 min post-dose administration) as compared to the EpiPen IM administration, where plasma epinephrine concentrations did not begin to increase until 5-10 min post-administration.

Part II: Assessment of Plasma Epinephrine Concentration Following Repeated Intranasal Administration of 4 mg Epinephrine This study compared the plasma levels and heart rate changes observed following a second dose of epinephrine administered either intranasally or intramuscularly 20 minutes following the first dose. One potential pitfall of repeated intranasal dosing is that the first intranasal administration may result in intense vasoconstriction of the nasal epithelium thus significantly and adversely impacting the absorption of the second dose. Therefore, this study also evaluated this possibility by administering the second intranasal dose of epinephrine in the opposite nostril. Similar to the first intranasal paradigm (2 doses, same nostril), repeated intramuscular injection of the EpiPen® was used for pharmacokinetic comparison.

Groups 4 and 5 consisted of three dogs/sex (n=six/group) while Group 8A consisted of one dog/sex (n=2 dogs) and Group 8B consisted of two dogs per sex (n=4 dogs). Each dog in Group 4 and 8B was administered two doses of epinephrine (4 mg/100 µL) with a 21 min interval between doses. All intranasal doses were administered using a cannula. Dose 1 was administered in the right nostril followed by a second intranasal dose in the right (Group 4, same nostril) or left (Group 8B, opposite nostril) nostril. Dogs in Group 5 and 8A were administered two intramuscular injections of the EpiPen® Adult (0.3 mg) with a 21 min interval between injections. Injections were administered in opposite thighs with the first dose being administered in the right thigh and the second dose being administered in the left thigh. A complete overview of the study design is provided in Table 46.

TABLE 46

Study Design

| Group | Epinephrine (mg) per Dose | Dose Volume (µl) | Nostril Administration | Administration | Males | Females |
|---|---|---|---|---|---|---|
| 4 | 4 + 4 | 100 + 100 | Twice (same nostril) | IN | 3 | 3 |
| 5 | 1 Adult EpiPen® (0.3) + 1 Adult EpiPen® (0.3) | 300 + 300 | — | IM, one in each thigh muscle | 3 | 3 |
| 8A | 1 Adult EpiPen® (0.3) + 1 Adult EpiPen® (0.3) | 300 + 300 | — | IM, one in each thigh muscle | 1 | 1 |
| 8B | 4 + 4 | 100 + 100 | Twice (opposite nostril) | IN | 2 | 2 |

The test article used was formulated as described in Part I of this study (see Table 47). The EpiPen® Adult (0.3 mg) Auto-injector was used as a control article for pharmacokinetic comparison in this part.

TABLE 47

Test Article Formulation

| Compound | Final Concentration | Final pH |
|---|---|---|
| Epinephrine | 4 mg/100 µl | 5.04[2] |
| Sodium Chloride | 0.4 mg/100 µl | 5.18[3] |
| Sodium Metabisulfite | 0.05 mg/100 µl | |
| Trisodium citrate | 0.7% | |
| Hypromellose | 0.1% | |
| Diethylene glycol monoethyl ether | 1% | |

[2] Formulation for Groups 4, 6, and 7
[3] Formulation for Group 8B

Epinephrine plasma concentrations were adjusted for each dog's plasma epinephrine baseline by using average concentrations of the three pre-dose samples and subtracting that average from the subsequent post-dose plasma epinephrine values. If this adjustment resulted in negative values, these samples were assigned a value of zero. In addition, epinephrine concentrations were considered as outliers and removed from analysis if they exceeded two times standard deviation from the mean of baseline-subtracted post-dose epinephrine plasma concentrations of each animal over the course of blood sampling (i.e., 1-120 min post-dose).

AUC, Tmax and Cmax were calculated using the trapezoid rule (GraphPad Prism 7.0c) and post-dose baseline-subtracted outliers-removed epinephrine concentrations for each individual animal (Tables 48-50).

For Group 5/8A, the elimination phase could be defined, therefore the AUC, $T_{max}$, $C_{max}$, and half-life ($t_{1/2}$) were also calculated using NCA for comparison (AUC=740 ng/mL·min; $T_{max}$=30 min; $C_{max}$=15 ng/mL; $t_{1/2}$=38 min).

TABLE 48

AUC and Cmax of epinephrine in dogs from Group 5 and Group 8A

| Parameter, unit | Group 5 (EpiPen Adult 0.3 mg × 2 injections) | | | | | | | | | |
|---|---|---|---|---|---|---|---|---|---|---|
| | 1 | 2 | 3 | 4 | 5 | 6 | CRA[1] | CXX[1] | Average | SD |
| Dose, g | 0.3 + 0.3 | 0.3 + 0.3 | 0.3 + 0.3 | 0.3 + 0.3 | 0.3 + 0.3 | 0.3 + 0.3 | 0.3 + 0.3 | 0.3 + 0.3 | — | — |
| $T_{max}$, min | 10 | 30 | 10 | 30 | 25 | 30 | 30 | 60 | 28 | 16 |
| $C_{max}$, ng/mL | 17.0 | 22.7 | 9.9 | 27.3 | 54.9 | 24.5 | 3.2 | 5.0 | 20.6 | 16.6 |
| $AUC_{1-90\ min}$, ng/mL·min | 713 | 737 | 785 | 1067 | 1218 | 1014 | 208 | 375 | 765 | 343 |

[1]Animals run in Group 8A.

TABLE 49

AUC and Cmax of epinephrine in dogs from Group 4

| Parameter, unit | Group 4 (4 mg × 2 doses × 1 nostril) | | | | | | Average | SD |
|---|---|---|---|---|---|---|---|---|
| | 1 | 2 | 3 | 4 | 5 | 6 | | |
| Dose, g | 4 + 4 | 4 + 4 | 4 + 4 | 4 + 4 | 4 + 4 | 4 + 4 | — | — |
| $T_{max}$, min | 60 | 10 | 60 | 5 | 25 | 25 | 31 | 24 |
| $C_{max}$, ng/mL | 2.3 | 2.6 | 38.1 | 18.6 | 1.5 | 1.2 | 10.7 | 15.0 |
| $AUC_{1-90\ min}$, ng/mL·min | 107 | 88 | 1324 | 811 | 50 | 62 | 407 | 537 |

TABLE 50

AUC and Cmax of epinephrine in dogs from Group 8B

| Parameter, unit | Group 8B (4 mg × 2 doses × 2 nostrils) | | | | | | Average | SD |
|---|---|---|---|---|---|---|---|---|
| | 1 | 2 | 3 | 4 | — | — | | |
| Dose, g | 4 + 4 | 4 + 4 | 4 + 4 | 4 + 4 | — | — | — | — |
| $T_{max}$, min | 90 | 1 | 25 | 60 | — | — | 44 | 39 |
| $C_{max}$, ng/mL | 2.6 | 2.7 | 3.1 | 6.5 | — | — | 3.7 | 1.9 |
| $AUC_{1-90\ min}$, ng/mL·min | 161 | 135 | 151 | 372 | — | — | 205 | 112 |

The plasma levels and heart rate changes were evaluated following a second dose of epinephrine administered either intranasally (to the same nostril), intranasally (in opposite nostrils) or intramuscularly 21 minutes following the first dose. As compared to a single dose of epinephrine at 4 mg IN (see part 1 Group 3) the Cmax and AUC of the Group 4 dogs (two IN doses of epinephrine in the same nostril) was 10.7 ng/mL and 407 ng/mL·min, respectively. The two EpiPen® doses also delivered 21 min apart also resulted in higher Cmax and AUC of 20.6 ng/mL and 765 ng/mL·min as compared to a single dose.

Example 15—Stability Testing of Pharmaceutical Spray Formulations

The pharmaceutical spray formulation was quantified and monitored by high pressure liquid chromatography (HPLC). The impurities detected include epinephrine sulfonic acid, adrenochrome, norepinephrine, and adrenalone. The following Tables 51-58 show the test results for epinephrine spray formulations at varying dosages, storage temperatures, and storage lengths.

TABLE 51

20 mg/mL or 2 mg/dose pH 4.7, 0.5% Chlorobutanol at 5 C., 25 C., and 40 C.

| Test | Specification (Stability) | T0 | 5 C. T = 2.27 | 25 C. T = 1 | 40 C. T = 1 |
|---|---|---|---|---|---|
| pH | 4.2-5.2 | 4.614 | 4.593 | 4.615 | 4.607 |
| Osmolality | 300-500 mOsm/kg | 394 | | 403 | 405 |
| Weight Loss | Max ≤ 2.2%, Av ≤ 1.1% | | | 0.00% | |
| Assay | 95.0%-110.0% | 95.85% | 97.47% | 96.44% | 96.35% |
| Epinephrine Sulfonic Acid | NMT 9.0% | 0.46% | 0.20% | 1.09% | 3.69% |
| Adrenochrome | NMT 0.5% | 0.08% | 0.05% | 0.11% | 0.23% |
| Norepinephrine | NMT 4.0% | ND | ND | ND | ND |
| Adrenalone | NMT 3.0% | ND | ND | ND | ND |
| Total Impurities | ≤12.0% | 0.60% | 0.44% | 1.44% | 4.17% |
| Enantiomeric Purity | | 99.14% | | 99.19% | 99.01% |
| Chlorobutanol Assay | | 3.94 mg/mL | | | |
| Sodium Metabisulfite Assay | | 0.345 mg/mL | | 0.206 mg/mL | 0.014 mg/mL |

TABLE 52

60 mg/mL or 6 mg/dose pH 4.7, 0.5% Chlorobutanol at 5 C., 25 C., and 40 C.

| Test | Specification (Stability) | T0 | 5 C. T = 1.6 | 25 C. T = 1 | 40 C. T = 1 |
|---|---|---|---|---|---|
| pH | 4.2-5.2 | 4.644 | 4.649 | 4.622 | 4.585 |
| Osmolality | 600-1000 mOsm/kg | 797 | | 790 | 793 |
| Weight Loss | Max ≤ 2.2%, Av ≤ 1.1% | | | | |
| Assay | 95.0%-110.0% | 100.60% | 100.80% | 100.60% | 98.60% |
| Epinephrine Sulfonic Acid | NMT 3.0% | 0.42% | 0.20% | 0.81% | 1.74% |
| Adrenochrome | NMT 0.2% | 0.06% | ND | ND | 0.05% |
| Norepinephrine | NMT 4.0% | ND | ND | ND | ND |
| Adrenalone | NMT 1.2% | ND | ND | ND | ND |
| Total Impurities | ≤12.0% | 0.54% | 0.30% | 0.95% | 2.38% |
| Enantiomeric Purity | | 99.01% | | 99.77% | 98.42% |
| Chlorobutanol Assay | | 4.41 mg/mL | | | |
| Sodium Metabisulfite Assay | | .019 mg/mL | | .013 mg/mL | ND |

TABLE 53

20 mg/mL or 2 mg/dose pH 4.7, 0.2% Chlorobutanol at 25 C.

| Test | Specification (Stability) | T0 | 28 | 56 | 84 |
|---|---|---|---|---|---|
| pH | | 4.662 | 4.587 | 4.591 | 4.545 |
| Osmolality | | 428 | | | |
| Assay | 95.0%-110.0% | 101.55% | 97.58% | 99.05% | 98.51% |
| Epinephrine Sulfonic Acid | NMT 3.0% | 0.00% | 1.05% | 1.74% | 2.08% |
| Adrenochrome | NMT 0.5% | 0.09% | 0.22% | 0.36% | 0.53% |
| Norepinephrine | NMT 4.0% | ND | ND | ND | ND |
| Adrenalone | NMT 3.0% | ND | ND | ND | ND |
| Total Impurities | ≤12.0% | 0.34% | 1.70% | 2.29% | 3.30% |
| Chlorobutanol Assay | | 1.56 mg/mL | 1.46 mg/mL | 1.36 mg/mL | 1.37 mg/mL |

TABLE 54

20 mg/mL or 2 mg/dose pH 4.7, 0.2% Chlorobutanol at 40 C.

| Test | Specification (Stability) | T0 | 28 | 56 | 84 |
|---|---|---|---|---|---|
| pH | | 4.662 | 4.556 | 4.537 | 4.474 |
| Osmolality | | 428 | | | |
| Assay | 95.0%-110.0% | 101.55% | 97.90% | 97.31% | 96.96% |
| Epinephrine Sulfonic Acid | NMT 3.0% | 0.00% | 2.52% | 2.65% | 2.57% |
| Adrenochrome | NMT 0.5% | 0.09% | 0.45% | 0.41% | 0.43% |
| Norepinephrine | NMT 4.0% | ND | ND | ND | ND |
| Adrenalone | NMT 3.0% | ND | ND | ND | 0.47% |
| Total Impurities | ≤12.0% | 1.27% | 3.76% | 3.86% | 4.41% |
| Chlorobutanol Assay | | 1.56 mg/mL | 1.25 mg/mL | 1.16 mg/mL | 1.07 mg/mL |

TABLE 55

50 mg/mL or 5 mg/dose pH 4.7, 0.2% Chlorobutanol at 25 C.

| Test | Specification (Stability) | Time points (days), 25 C. | | | |
|---|---|---|---|---|---|
| | | T0 | 28 | 56 | 84 |
| pH | | 4.667 | 4.63 | 4.598 | 4.525 |
| Osmolality | | 689 | | | |
| Assay | 95.0%-110.0% | 101.69% | 98.46% | 98.73% | 99.61% |
| Epinephrine Sulfonic Acid | NMT 3.0% | 0.29% | 0.85% | 1.08% | 1.07% |
| Adrenochrome | NMT 0.5% | 0.04% | 0.13% | 0.17% | 0.18% |
| Norepinephrine | NMT 4.0% | ND | ND | ND | ND |
| Adrenalone | NMT 3.0% | ND | ND | ND | ND |
| Total Impurities | ≤12.0% | 0.47% | 1.09% | 1.73% | 2.01% |
| Chlorobutanol Assay | | 1.55 mg/mL | 1.47 mg/mL | 1.36 mg/mL | 1.35 mg/mL |

TABLE 56

50 mg/mL or 5 mg/dose pH 4.7, 0.2% Chlorobutanol at 40 C.

| Test | Specification (Stability) | Time points (days), 40 C. | | | |
|---|---|---|---|---|---|
| | | T0 | 28 | 56 | 84 |
| pH | | 4.667 | 4.586 | 4.524 | 4.47 |
| Osmolality | | 689 | | | |
| Assay | 95.0%-110.0% | 101.69% | 100.14% | 97.42% | 98.92% |
| Epinephrine Sulfonic Acid | NMT 3.0% | 0.29% | 1.19% | 1.34% | 1.19% |
| Adrenochrome | NMT 0.5% | 0.04% | 0.17% | 0.10% | 0.15% |
| Norepinephrine | NMT 4.0% | ND | ND | ND | ND |
| Adrenalone | NMT 3.0% | ND | ND | ND | 0.05% |
| Total Impurities | ≤12.0% | 0.47% | 2.45% | 2.54% | 3.53% |
| Chlorobutanol Assay | | 1.55 mg/mL | 1.25 mg/mL | 1.08 mg/mL | 1.07 mg/mL |

TABLE 57

6 mg/mL or 6 mg/dose pH 4.7, 0.2% Chlorobutanol at 25 C.

| Test | Specification (Stability) | Time points (days), 25 C. | | | |
|---|---|---|---|---|---|
| | | T0 | 28 | 56 | 84 |
| pH | | 4.684 | 4.643 | 4.592 | 4.598 |
| Osmolality | | 777 | | | |
| Assay | 95.0%-110.0% | 101.96% | 99.59% | 98.91% | 100.95% |
| Epinephrine Sulfonic Acid | NMT 3.0% | 0.30% | 0.59% | 0.59% | 0.60% |
| Adrenochrome | NMT 0.5% | 0.06% | 0.13% | 0.14% | 0.15% |
| Norepinephrine | NMT 4.0% | ND | ND | ND | ND |
| Adrenalone | NMT 3.0% | ND | ND | ND | ND |
| Total Impurities | ≤12.0% | 0.47% | 1.03% | 1.48% | 1.75% |
| Chlorobutanol Assay | | 1.42 mg/mL | 1.36 mg/mL | 1.25 mg/mL | 1.26 mg/mL |

TABLE 58

6 mg/mL or 6 mg/dose pH 4.7, 0.2% Chlorobutanol at 40 C.

| Test | Specification (Stability) | Time points (days), 40 C. | | | |
|---|---|---|---|---|---|
| | | T0 | 28 | 56 | 84 |
| pH | | 4.684 | 4.581 | 4.526 | 4.448 |
| Osmolality | | 777 | | | |
| Assay | 95.0%-110.0% | 101.96% | 99.11% | 98.43% | 98.67% |

TABLE 58-continued 6 mg/mL or 6 mg/dose pH 4.7, 0.2% Chlorobutanol at 40 C.

| Test | Specification (Stability) | Time points (days), 40 C. | | | |
|---|---|---|---|---|---|
| | | T0 | 28 | 56 | 84 |
| Epinephrine Sulfonic Acid | NMT 3.0% | 0.30% | 0.70% | 0.70% | 0.67% |
| Adrenochrome | NMT 0.5% | 0.06% | 0.10% | 0.10% | 0.11% |
| Norepinephrine | NMT 4.0% | ND | ND | ND | ND |
| Adrenalone | NMT 3.0% | ND | ND | ND | 0.06% |
| Total Impurities | ≤12.0% | 0.47% | 1.97% | 2.23% | 3.14% |
| Chlorobutanol Assay | | 1.42 mg/mL | 1.21 mg/mL | 1.02 mg/mL | 1.01 mg/mL |

Example 16—Spray Characteristics

Administration of the epinephrine spray formulation using a nasal delivery device was tested for spray characteristics including Dmax, ovality, D10, D50, D90, % volume<10 microns, and span. The results of the testing are shown in Table 59.

TABLE 59

Spray Characteristics

| Test | Results | Results |
|---|---|---|
| Spray Pattern (n = 5 at 30 mm) | Epinephine 2 mg bi-dose | Epinephrine 5 mg bi-dose |
| First Spray | | |
| Shape | Ellipsoidal | Ellipsoidal |
| Density | Relative uniform density | Relative uniform density |
| Dmax | 26.9 mm | 24.0 mm |
| Ovality | 1.454 | 1.327 |
| Second Spray | | |
| Shape | Ellipsoidal | Ellipsoidal |
| Density | Relative uniform density | Relative uniform density |
| Dmax | 26.2 mm | 24.6 |
| Ovality | 1.378 | 1.377 |
| Droplet Size Distribution (n = 5 at 30 mm) | | |
| First Spray | | |
| D10 | 21.80 microns | 19.79 microns |
| D50 | 53.69 microns | 47.73 microns |
| D90 | 126.3 microns | 112.0 microns |
| % Volume < 10 microns | 0.52% | 0.75% |
| Span | 1.945 | 1.928 |
| Second Spray | | |
| D10 | 20.58 microns | 19.92 microns |
| D50 | 50.51 microns | 47.82 microns |
| D90 | 119.0 microns | 112.0 microns |
| % Volume < 10 microns | 0.57% | 0.45% |
| Span | 1.941 | 1.925 |
| Particulates | ≥10 microns: 98 particles/container ≥25 microns: 1 particle/container | ≥10 microns: 28 particles/container ≥25 microns: 1 particle/container |
| pH | 4.6 | 4.7 |
| Osmolality (mOsm/kg) | 425 | 693 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of administering a pharmaceutical solution, comprising delivering a spray of the pharmaceutical solution from a device into a nostril of a subject in need thereof in a manner that delivers the pharmaceutical solution in a spray plume, wherein:
    (i) the device is adapted for nasal delivery;
    (ii) a volume of from about 20 μL to about 250 μL of spray is delivered;
    (iii) the pharmaceutical solution comprises water and from about 1% to about 10% (w/w) of epinephrine, or a pharmaceutically acceptable salt thereof, chlorobutanol hemihydrate; sodium bisulfite or sodium metabisulfite, hypromellose, citric acid or citric acid monohydrate, sodium chloride, and diethylene glycol monoethyl ether; and
    wherein the pharmaceutical solution has a weight ratio of epinephrine to chlorobutanol hemihydrate of about 12:1 to about 30:1.

2. The method of claim 1, wherein the spray plume has a particle size distribution with a span of no more than about 2.2 when measured at a distance of from about 1 to about 10 cm from the device.

3. The method of claim 1, wherein the spray plume has a Dmax of less than about 28 mm when measured at a distance of from about 1 to about 10 cm from the device.

4. The method of claim 1, wherein the device is a bi-dose device configured to deliver two sprays of the pharmaceutical solution.

5. The method of claim 1, wherein the device has a single reservoir containing from about 125 μL to about 250 μL of the pharmaceutical solution.

6. The method of claim 1, wherein the device comprises:
    (i) a vial comprising an opening;
    (ii) a cannula; and
    (iii) a rubber stopper;
    wherein the rubber stopper is configured to occlude the opening of the vial, and wherein the cannula is configured to pierce the rubber stopper when a plunger applies sufficient force to the cannula.

7. The method of claim 1, wherein the device is a pre-primed device that is configured to be actuatable with one hand.

8. The method of claim 1, wherein a delivery time of the pharmaceutical solution is less than about 25 seconds.

9. The method of claim 1, wherein the subject is suffering from a severe allergic reaction from exposure or suspected exposure to an allergen.

10. The method of claim 9, wherein the allergen is food, medication, or an insect bite or sting.

11. The method of claim 9, wherein the subject exhibits one or more symptoms chosen from: respiratory depression or distress, airway constriction, wheezing, tingling hands, feet, mouth, or scalp, shortness of breath, swelling or inflammation of the face, eyes, lips, tongue, or throat, hives, central nervous system depression, cardiovascular depression, altered level consciousness, mydriatic pupils, hypoxemia, hypotension, unresponsiveness to stimulus, unconsciousness, stopped breathing, erratic or stopped pulse, or vomiting.

12. The method of claim 1, wherein the subject exhibits respiratory depression or distress, or cardiovascular depression.

13. The method of claim 12, wherein the subject is free from respiratory depression or distress for at least about 1 hour following the delivery of the pharmaceutical solution into the nostril of the subject.

14. The method of claim 1, wherein the spray comprises about 1 mg to about 10 mg of the epinephrine or a pharmaceutically acceptable salt thereof.

15. The method of claim 14, wherein the spray comprises about 6 mg of the epinephrine or a pharmaceutically acceptable salt thereof.

16. A method of administering a pharmaceutical solution, comprising delivering a spray of the pharmaceutical solution from a device into a nostril of a subject in need thereof in a manner that delivers the pharmaceutical solution in a spray plume, wherein:
(i) the device is adapted for nasal delivery;
(ii) a volume of from about 20 μL to about 250 μL of spray is delivered; and
(iii) the pharmaceutical solution comprises water and from about 1% to about 10% (w/w) of epinephrine, or a pharmaceutically acceptable salt thereof, about 0.1 to about 1.0% of chlorobutanol hemihydrate, sodium bisulfite or sodium metabisulfite, hypromellose, citric acid or citric acid monohydrate, sodium chloride, and diethylene glycol monoethyl ether; and
wherein the pharmaceutical solution has a weight ratio of epinephrine to chlorobutanol hemihydrate of about 12:1 to about 30:1.

17. The method of claim 16, wherein the spray plume has a particle size distribution having a span of no more than about 2.0 when measured at a distance of from about 1 to about 10 cm from the device.

18. The method of claim 16, wherein the device has a single reservoir containing from about 125 μL to about 250 μL of the pharmaceutical solution.

19. The method of claim 16, wherein the device is a bi-dose device configured to deliver two sprays of the pharmaceutical solution from a single reservoir.

20. The method of claim 16, wherein the spray comprises about 1 mg to about 10 mg of the epinephrine or a pharmaceutically acceptable salt thereof.

21. The method of claim 20, wherein the spray comprises about 6 mg of the epinephrine or a pharmaceutically acceptable salt thereof.

22. The method of claim 16, wherein the device is a pre-primed device that is configured to be actuatable with one hand.

23. A method for administering a pharmaceutical solution, comprising delivering a spray of the pharmaceutical solution from a device into a nostril of a subject in need thereof, wherein:
(i) the device is adapted for nasal delivery;
(ii) a volume of from about 20 μL to about 250 μL of spray is delivered; and
(iv) the pharmaceutical solution comprises water and from about 1% to about 10% (w/w) of epinephrine, or a pharmaceutically acceptable salt thereof, about 0.1% to about 1.0% of chlorobutanol hemihydrate; about 0.01% to about 0.1% of sodium bisulfite or sodium metabisulfite, about 0.01% to about 0.2% of hypromellose; about 0.1% to about 1% of citric acid or citric acid monohydrate; about 0.1% to about 1% of sodium chloride, and about 0.1% to about 5% of diethylene glycol monoethyl ether; and
wherein the pharmaceutical solution has a weight ratio of epinephrine to chlorobutanol hemihydrate of about 12:1 to about 30:1.

24. The method of claim 23, wherein the device is a bi-dose device configured to deliver two sprays of the pharmaceutical solution.

25. The method of claim 23, wherein the device delivers the pharmaceutical solution in a spray plume with a Dmax less than about 26 mm when measured at a distance of from about 1 to about 10 cm from the device.

26. The method of claim 23, wherein the spray comprises about 1 mg to about 10 mg of the epinephrine or a pharmaceutically acceptable salt thereof.

27. The method of claim 26, wherein the spray comprises about 6 mg of the epinephrine or a pharmaceutically acceptable salt thereof.

28. The method of claim 23, wherein the device is a pre-primed device that is configured to be actuatable with one hand.

* * * * *